US010662138B2

United States Patent
Scutt et al.

(10) Patent No.: US 10,662,138 B2
(45) Date of Patent: May 26, 2020

(54) HERBICIDAL PROPYNYL-PHENYL COMPOUNDS

(71) Applicant: Syngenta Participations AG, Basel (CH)

(72) Inventors: James Nicholas Scutt, Bracknell (GB); Nigel James Willets, Bracknell (GB)

(73) Assignee: Syngenta Participations AG, Basel (CH)

( * ) Notice: Subject to any disclaimer, the term of this patent is extended or adjusted under 35 U.S.C. 154(b) by 10 days.

(21) Appl. No.: 15/312,898

(22) PCT Filed: Jun. 18, 2015

(86) PCT No.: PCT/EP2015/063744
§ 371 (c)(1),
(2) Date: Nov. 21, 2016

(87) PCT Pub. No.: WO2015/197468
PCT Pub. Date: Dec. 30, 2015

(65) Prior Publication Data
US 2017/0183281 A1  Jun. 29, 2017

(30) Foreign Application Priority Data
Jun. 26, 2014 (GB) .................. 1411418.5

(51) Int. Cl.
*A01N 25/32* (2006.01)
*C07C 49/603* (2006.01)
*C07D 309/32* (2006.01)
*C07C 49/653* (2006.01)
*C07C 49/697* (2006.01)
*C07C 49/753* (2006.01)
*A01N 35/06* (2006.01)
*A01N 37/06* (2006.01)
*A01N 41/12* (2006.01)
*A01N 43/16* (2006.01)
*C07C 321/10* (2006.01)

(52) U.S. Cl.
CPC ............ *C07C 49/603* (2013.01); *A01N 35/06* (2013.01); *A01N 37/06* (2013.01); *A01N 41/12* (2013.01); *A01N 43/16* (2013.01); *C07C 49/653* (2013.01); *C07C 49/697* (2013.01); *C07C 49/753* (2013.01); *C07C 321/10* (2013.01); *C07D 309/32* (2013.01); *C07C 2601/14* (2017.05); *C07C 2602/22* (2017.05)

(58) Field of Classification Search
None
See application file for complete search history.

(56) References Cited
U.S. PATENT DOCUMENTS
2010/0216638 A1 * 8/2010 Mathews ............... A01N 35/06
504/103

FOREIGN PATENT DOCUMENTS

| CN | 101730688 A | 6/2010 |
| CN | 102186834 A | 9/2011 |
| JP | 2004537570 A | 12/2004 |
| JP | 2010520866 A | 6/2010 |
| JP | 2010520867 A | 6/2010 |
| JP | 2010528074 A | 8/2010 |
| JP | 2012505848 A | 3/2012 |
| JP | 2013147484 A | 8/2013 |
| JP | 2016506403 A | 3/2016 |
| JP | 2016524615 A | 8/2016 |
| WO | 03013249 A1 | 2/2003 |
| WO | 2008110307 A1 | 9/2008 |
| WO | 2008110308 A2 | 9/2008 |
| WO | WO 2008/110307 * | 9/2008 |
| WO | 2008145336 A1 | 12/2008 |

(Continued)

OTHER PUBLICATIONS

International Search Report issued in Applicaiton No. PCT/EP2015/063744, dated Aug. 5, 2015.

*Primary Examiner* — David Browe
(74) *Attorney, Agent, or Firm* — Baker & Hostetler, LLP; Toni-Junell Herbert

(57) ABSTRACT

The present invention relates to a compound of formula (I) wherein: $R^1$ is $C_1$-$C_3$alkoxy, $C_1$-$C_2$alkoxy-$C_1$-$C_3$alkoxy, $C_1$-$C_2$fluoroalkoxy, ethyl, n-propyl, n-butyl, cyclopropyl or ethynyl; $R^2$ is hydrogen, ethyl, n-propyl, cyclopropyl, vinyl, ethynyl, $C_1$-$C_3$alkoxy, $C_1$-$C_3$fluoroalkyl, $C_1$-$C_2$fluoroalkoxy, $C_1$-$C_2$alkoxy-$C_1$-$C_3$alkoxy-, or $C_1$fluoroalkoxy-$C_1$-$C_3$alkoxy-; provided that when $R^1$ is ethyl, n-propyl, n-butyl, cyclopropyl or ethynyl, then $R^2$ is hydrogen, ethyl, n-propyl, cyclopropyl, vinyl or ethynyl; and Y is O, S, S(O), S(O)$_2$, N($C_1$-$C_2$alkyl), N($C_1$-$C_2$alkoxy), C(O), $CR^8R^9$ or —$CR^{10}R^{11}CR^{12}R^{13}$—; and G, $R^3$, $R^4$, $R^5$ and $R^6$ are as defined herein; wherein the compound of formula (I) is optionally present as an agrochemically acceptable salt thereof. These compounds are suitable for use as herbicides. The invention therefore also relates to a method of controlling weeds, especially grassy monocotyledonous weeds, in crops of useful plants, comprising applying a compound of formula (I), or a herbicidal composition comprising such a compound, to the plants or to the locus thereof.

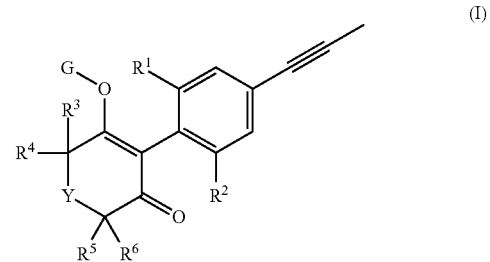

(I)

14 Claims, No Drawings

(56) References Cited

FOREIGN PATENT DOCUMENTS

| WO | 2010046194 A1 | 4/2010 |
| WO | 2010081755 A1 | 7/2010 |
| WO | 2013079708 A1 | 6/2013 |
| WO | 2014096289 A2 | 6/2014 |
| WO | 2014191535 A1 | 12/2014 |

* cited by examiner

HERBICIDAL PROPYNYL-PHENYL COMPOUNDS

RELATED APPLICATION INFORMATION

This application is a 371 of International Application No. PCT/EP2015/063744, filed Jun. 18, 2015, which claims priority to GB1411418.5, filed Jun. 26, 2014, the contents of which are incorporated herein by reference herein.

The present invention relates to herbicidally active cyclic diones, in particular pyrandione, thiopyrandione, cyclohexanedione, alkanediyl-bridged cyclohexanedione, cyclohexanetrione or cycloheptanedione compounds, or derivatives thereof (e.g. enol ketone tautomer derivatives thereof), to processes for their preparation, to herbicidal compositions comprising those compounds, and to their use in controlling weeds such as grassy monocotyledonous weeds, especially in crops of useful plants, or in inhibiting undesired plant growth. In particular, the present invention relates to herbicidally active cyclic dione compounds, or derivatives thereof (e.g. enol ketone tautomer derivatives thereof), which are substituted by a phenyl which has an alkynyl-containing substituent.

WO 01/17972 discloses phenyl-substituted (such as 4-methyl-2,6-diethyl-phenyl-substituted) heterocycles suitable for use as herbicides.

WO 03/013249 disclose selective herbicidal compositions comprising (a) a (substituted-phenyl)-substituted cyclic ketoenol and (b) a compound which improves crop plant compatibility, in particular cloquintocet-mexyl or mefenpyr-diethyl.

WO 2007/068427 disclose a composition comprising (a) a (substituted-phenyl)-substituted cyclic ketoenol as a herbicide, and (b) an ammonium or phosphonium salt to boost activity.

WO 2008/071405 and WO 2009/074314 each disclose herbicidally active pyran-3,5-diones, thiopyran-3,5-diones and cyclohexane-1,3,5-triones, each substituted at the 4-position of the cyclic dione or trione by an aryl-substituted-phenyl or by a heteroaryl-substituted-phenyl.

WO 2010/081755 and WO 2010/089211 each disclose herbicidally active pyran-3,5-diones, thiopyran-3,5-diones, cyclohexanediones, cycloheptanediones and cyclohexanetriones, each substituted by an aryloxy-substituted-phenyl or by a heteroaryloxy-substituted-phenyl.

WO 2008/110308 discloses 2-(substituted-phenyl)-cyclohexane-1,3-dione compounds and derivatives, containing a $R^8$—X—$(CR^6R^7)_n$— substituent (wherein X is O, S, S(O) or $S(O)_2$) or a heteroatom-containing-spirocyle at the 5-position of the cyclohexane-1,3-dione, and having herbicidal properties. WO 2008/110307 A1 discloses 2-(substituted-phenyl)-5-heterocyclyl-cyclohexane-1,3-dione compounds and derivatives, and their use as herbicides. WO 2010/046194 discloses 2-(substituted-phenyl)-cyclohexane-1,3-dione compounds and derivatives, containing a Q-$CR^6R^7$— substituent at the 5-position of the cyclohexane-1,3-dione (wherein Q is a saturated or mono-unsaturated heterocycle), and having herbicidal properties.

WO 2008/145336 disclose herbicidally active phenyl-substituted bicyclic (carbon-bridged, e.g. alkanediyl-bridged) 1,3-dione compounds, such as 3-(substituted-phenyl)-bicyclo[3.2.1]octane-2,4-diones.

WO 2013/079672 discloses that certain substituted spiro-heterocyclic pyrrolidine dione compounds, having an alkynyl-phenyl-headgroup, have herbicidal properties.

WO 2013/079708 discloses cyclopentane-1,3-dione compounds and derivatives (e.g. fused and/or spirocyclic bicyclic derivatives) thereof, which are substituted at the 2-position of the cyclopentane-1,3-dione by a phenyl which itself is substituted at the 4-position by (specifically) either prop-1-ynyl or chloroethynyl and at the 2-position by (specifically) methyl or chlorine, and derivatives of the enol ketone tautomer of such cyclopentanediones, which have herbicidal activity and/or plant-growth-inhibiting properties, especially in the control of grassy monocotyledonous weeds and/or when used post-emergence.

WO 2014/096289 discloses cyclic dione compounds, more particularly pyran-3,5-dione, thiopyran-3,5-dione, cyclohexane-1,3-dione, alkanediyl-bridged cyclohexane-1,3-dione, cyclohexane-1,3,5-trione or cycloheptane-1,3-dione compounds, which are substituted, at the ring-carbon atom of the cyclic dione which is between the two oxo-substituted ring-carbons of the cyclic dione, by a phenyl which itself is substituted at the 4-position by (specifically) either prop-1-ynyl or chloroethynyl and at the 2-position by (specifically) methyl or chlorine, or derivatives of the enol ketone tautomer of such cyclic diones, which have herbicidal activity and/or plant-growth-inhibiting properties, in particular in the control of grassy monocotyledonous weeds.

Novel cyclic dione compounds, more particularly pyran-3,5-dione, thiopyran-3,5-dione, cyclohexane-1,3-dione, alkanediyl-bridged cyclohexane-1,3-dione, cyclohexane-1,3,5-trione or cycloheptane-1,3-dione compounds, which are substituted, at the ring-carbon atom of the cyclic dione which is between the two oxo-substituted ring-carbons of the cyclic dione, by a phenyl which itself is substituted at the 4-position by (specifically) prop-1-ynyl and at the 2-position by (specifically) certain $C_2$ or greater alkyl groups or certain alkoxy or fluoroalkoxy groups, or derivatives of the enol ketone tautomer of such cyclic diones, which have herbicidal activity and/or plant-growth-inhibiting properties, in particular in the control of grassy monocotyledonous weeds.

Therefore, in a first aspect of the present invention, there is provided a compound of formula (I):

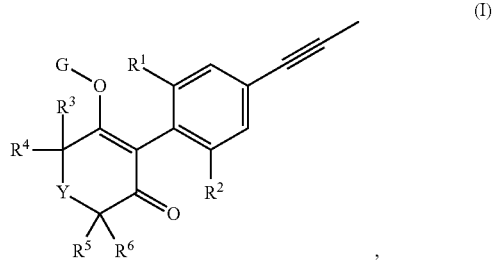

wherein:

$R^1$ is $C_1$-$C_3$alkoxy, $C_1$-$C_2$alkoxy-$C_1$-$C_3$alkoxy, $C_1$-$C_2$fluoroalkoxy, ethyl, n-propyl, n-butyl, cyclopropyl or ethynyl;

$R^2$ is hydrogen, ethyl, n-propyl, cyclopropyl, vinyl, ethynyl, $C_1$-$C_3$alkoxy, $C_1$-$C_3$fluoroalkyl, $C_1$-$C_2$fluoroalkoxy, $C_1$-$C_2$alkoxy-$C_1$-$C_3$alkoxy-, or $C_1$fluoroalkoxy-$C_1$-$C_3$alkoxy-;

provided that when $R^1$ is ethyl, n-propyl, n-butyl, cyclopropyl or ethynyl, then $R^2$ is hydrogen, ethyl, n-propyl, cyclopropyl, vinyl or ethynyl; and $R^3$, $R^4$, $R^5$ and $R^6$, independently of each other, are hydrogen, $C_1$-$C_5$alkyl (in particular $C_1$-$C_4$alkyl, e.g. $C_1$-$C_2$alkyl), $C_2$-$C_4$alkenyl (in particular $C_2$-$C_3$alkenyl-$CH_2$—, e.g. ethenyl-$CH_2$—), $C_2$-$C_4$alkynyl (in particular $C_2$-$C_3$alkynyl-$CH_2$—, e.g. ethynyl-$CH_2$—), $C_1$-$C_2$fluoroalkyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, $C_1$-$C_3$alkylsulfonyl$C_1$-$C_3$alkyl; $C_3$-$C_4$cycloalkyl (in particular cyclopropyl); or an unsubstituted 4, 5 or 6 (e.g. 4 or 5) membered monocyclic heterocyclyl having one ring heteroatom independently selected from oxygen, sulfur and nitrogen, and attached at a ring carbon atom within the heterocyclyl (in particular tetrahydrofuranyl such as tetrahydrofuran-3-yl, or tetrahydropyranyl such as tetrahydropyran-4-yl);

provided that no more than one (in particular none) of $R^3$, $R^4$, $R^5$ and $R^6$ is alkenyl, alkynyl, alkoxyalkyl, alkylthioalkyl, alkylsulfinylalkyl, alkylsulfonylalkyl, cycloalkyl or heterocyclyl;

or $R^3$ and $R^4$ taken together are —$(CH_2)_{n1}$— or —$(CH_2)_{n2}$—$X^1$—$(CH_2)_{n3}$— and $R^5$ and $R^6$ are as defined herein (e.g. hereinabove), or $R^5$ and $R^6$ taken together are —$(CH_2)_{n1}$— or —$(CH_2)_{n2}$—$X^1$—$(CH_2)_{n3}$— and $R^3$ and $R^4$ are as defined herein (e.g. hereinabove); wherein $X^1$ is O, S, S(O), S(O)$_2$, NH, N($C_1$-$C_2$alkyl), N($C_1$-$C_2$alkoxy), C(H)($C_1$-$C_2$alkyl), C($C_1$-$C_2$alkyl)$_2$ or C(H)($C_1$-$C_2$alkoxy);

n1 is 2, 3, 4 or 5 (in particular 4 or 5); and n2 and n3 are independently 1, 2 or 3 provided that n2+n3 is 2, 3 or 4 (in particular 3 or 4);

or $R^4$ and $R^5$ taken together are —$(CH_2)_{n4}$— or —$(CH_2)_{n5}$—C($R^{7a}$)($R^{7b}$)—$(CH_2)_{n6}$— or —C($R^{7c}$)=C($R^{7d}$)—; wherein $R^{7a}$ is $C_1$-$C_2$alkyl or $C_1$-$C_2$alkoxy; and $R^{7b}$ is hydrogen or $C_1$-$C_2$alkyl provided that $R^{7b}$ is hydrogen when $R^{7a}$ is $C_1$-$C_2$alkoxy;

n4 is 1, 2 or 3; and n5 and n6 are independently 0, 1 or 2 provided that n5+n6 is 0, 1 or 2;

and $R^{7c}$ and $R^{7d}$ independently are hydrogen or $C_1$-$C_2$alkyl; and

Y is O, S, S(O), S(O)$_2$, N($C_1$-$C_2$alkyl), N($C_1$-$C_2$alkoxy), C(O), C$R^8R^9$ or —C$R^{10}R^{11}$C$R^{12}R^{13}$—; and $R^8$ and $R^9$ are, independently of each other:

hydrogen, $C_1$-$C_6$alkyl (in particular $C_1$-$C_4$alkyl, e.g. $C_1$-$C_2$alkyl), $C_2$-$C_4$alkenyl (in particular $C_2$-$C_3$alkenyl-CH$_2$—, e.g. ethenyl-CH$_2$—), $C_2$-$C_4$alkynyl (in particular $C_2$-$C_3$alkynyl-CH$_2$—, e.g. ethynyl-CH$_2$—), $C_1$-$C_2$fluoroalkyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, or $C_1$-$C_3$alkylsulfonyl$C_1$-$C_3$alkyl;

$C_3$-$C_6$cycloalkyl or $C_3$-$C_6$cycloalkyl substituted by one or two substituents which independently are $C_1$-$C_3$alkyl (in particular methyl or ethyl) or $C_1$-$C_2$fluoroalkyl; and in which one ring CH$_2$ moiety of a $C_4$-$C_6$cycloalkyl is optionally (e.g. preferably) replaced by an oxygen or sulfur atom or by a S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety;

$C_3$-$C_6$cycloalkyl substituted by one substituent being $C_1$-$C_3$alkoxy (in particular $C_1$-$C_2$alkoxy) and optionally further substituted by one substituent being $C_1$-$C_2$alkyl (in particular methyl);

$C_5$-$C_6$cycloalkenyl or $C_5$-$C_6$cycloalkenyl substituted by one or two $C_1$-$C_3$alkyl (in particular methyl) substituents;

$C_3$-$C_6$cycloalkyl$C_1$-$C_2$alkyl- (in particular $C_3$-$C_6$cycloalkylmethyl-) or $C_3$-$C_6$cycloalkyl$C_1$-$C_2$alkyl- (in particular $C_3$-$C_6$cycloalkylmethyl-) substituted by one or two ring substituents which independently are $C_1$-$C_3$alkyl or $C_1$-$C_2$fluoroalkyl; and in which one ring CH$_2$ moiety of a $C_4$-$C_6$cycloalkyl$C_1$-$C_2$alkyl- (in particular $C_4$-$C_6$cycloalkylmethyl-) is optionally (e.g. preferably) replaced by an oxygen or sulfur atom or by a S(O), S(O)$_2$, NH, N($C_1$-$C_2$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety;

$C_3$-$C_6$cycloalkyl$C_1$-$C_2$alkyl- (in particular $C_3$-$C_6$cycloalkylmethyl-) substituted by one ring substituent being $C_1$-$C_3$alkoxy (in particular $C_1$-$C_2$alkoxy) and optionally further substituted by one ring substituent being $C_1$-$C_2$alkyl (in particular methyl); or Het or Het-CH$_2$—, wherein Het is a heteroaryl, attached at a ring-carbon, which is optionally substituted by 1, 2 or 3 (in particular 1 or 2, e.g. 1) ring-carbon substituents independently being $C_1$-$C_3$alkyl (e.g. $C_1$-$C_2$alkyl), $C_1$-$C_2$fluoroalkyl, $C_1$-$C_3$alkyl-C(O)—, $C_1$-$C_2$fluoroalkyl-C(O)—, hydroxy (including any oxo tautomer), $C_2$-$C_3$alkenyl (e.g. ethenyl or prop-1-enyl), $C_2$-$C_3$alkynyl (e.g. ethynyl or prop-1-ynyl), $C_1$-$C_3$alkoxy (e.g. $C_1$-$C_2$alkoxy), $C_1$-$C_2$fluoroalkoxy, halogen (e.g. fluorine or chlorine), cyano or nitro, provided that any non-fluorine halogen, alkoxy or fluoroalkoxy is not substituted at any ring-carbon bonded directly to a ring-nitrogen of the heteroaryl; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent;

provided that no more than one of $R^8$ and $R^9$ is an optionally substituted cycloalkyl; an optionally substituted cycloalkyl in which one ring CH$_2$ moiety has been replaced by an oxygen or sulfur atom or by a S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; an optionally substituted cycloalkenyl; an optionally substituted cycloalkyl-alkyl-; an optionally substituted cycloalkyl-alkyl- in which one ring CH$_2$ moiety has been replaced by an oxygen or sulfur atom or by a S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; or Het or Het-CH$_2$—;

or $R^8$ is hydrogen or $C_1$-$C_2$alkyl (in particular H or Me), and $R^9$ is $C_1$-$C_2$alkoxy (in particular methoxy);

or $R^8$ and $R^9$ taken together are —$(CH_2)_{n7}$— or —$(CH_2)_{n8}$—$X^2$—$(CH_2)_{n9}$—;

wherein $X^2$ is O, S, S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl], N($C_1$-$C_2$alkoxy), C(H)($C_1$-$C_3$alkyl), C($C_1$-$C_2$alkyl)$_2$ or C(H)($C_1$-$C_3$alkoxy);

n7 is 2, 3, 4, 5 or 6 (in particular 4 or 5); and n8 and n9 are independently 0, 1, 2 or 3 provided that n8+n9 is 2, 3, 4 or 5 (in particular 3 or 4); and $R^{10}$, $R^{11}$, $R^{12}$ and $R^{13}$ are independently of each other hydrogen or $C_1$-$C_4$alkyl (in particular $C_1$-$C_2$alkyl) provided that no more than one of $R^{10}$, $R^{11}$, $R^{12}$ and $R^{13}$ is $C_3$-$C_4$alkyl; and and wherein:

G is hydrogen; an agriculturally acceptable metal, or an agriculturally acceptable sulfonium or ammonium group; or G is —C($X^a$)—$R^a$, —C($X^b$)—$X^c$—$R^b$, —C($X^d$)—N($R^c$)—$R^d$, —SO$_2$—$R^e$, —P($X^e$)($R^f$)—$R^g$, —CH$_2$—$X^f$—$R^h$; or phenyl-CH$_2$— or phenyl-CH($C_1$-$C_2$alkyl)- (in each of which the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or heteroaryl-CH$_2$— or heteroaryl-CH($C_1$-$C_2$alkyl)- (in each of which the heteroaryl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or phenyl-C(O)—CH$_2$— (wherein the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro); or $C_1$-$C_6$alkoxy-C(O)—CH$_2$—, $C_1$-$C_6$alkoxy-C(O)—CH=CH—, $C_2$-$C_7$alken-1-yl-CH$_2$—, $C_2$-$C_7$alken-1-yl-CH($C_1$-$C_2$alkyl)-, $C_2$-$C_4$fluoroalken-1-yl-CH$_2$—, $C_2$-$C_7$alkyn-1-yl-CH$_2$—, or $C_2$-$C_7$alkyn-1-yl-CH($C_1$-$C_2$alkyl)-;

wherein $X^a$, $X^b$, $X^c$, $X^d$, $X^e$ and $X^f$ are independently of each other oxygen or sulfur (in particular oxygen); and wherein $R^a$ is H, $C_1$-$C_{21}$alkyl, $C_2$-$C_{21}$alkenyl, $C_2$-$C_{18}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy ($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy ($C_1$-$C_5$)alkyl, $C_1$-$C_5$alkylcarbonyl($C_1$—$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkyl-carbonyl-N—($C_2$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy ($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$) alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkyl-carbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl$C_1$-$C_5$alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkyl-thio, $C_1$-$C_3$alkylsulfinyl, $C_1$-$C_3$alkylsulfonyl, halogen, cyano, or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy ($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$) alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkyl-carbonyl-N—($C_2$-$C_5$)alkylaminoalkyl, $C_3$-$C_6$trialkylsilyl ($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or by nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino or $C_3$-$C_7$cycloalkoxy;

or $R^c$ and $R^d$, together with the nitrogen to which they are bonded, to form an unsubstituted 4, 5, 6 or 7 (e.g. 5 or 6) membered ring, optionally containing one heteroatom selected from O or S; and $R^e$ is $C_1$-$C_{10}$alkyl, $C_2$-$C_{10}$alkenyl, $C_2$-$C_{10}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy ($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$) alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$alkoxy, $C_1$-$C_{10}$fluoroalkoxy, $C_1$-$C_5$alkylamino or di($C_1$-$C_4$alkyl)amino; $R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$) alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$fluoroalkoxy, $C_1$-$C_5$alkylamino or di($C_1$-$C_4$alkyl)amino; or benzyloxy or phenoxy, wherein the benzyl and phenyl groups are in turn optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$) alkyl, $C_1$-$C_5$alkoxy($C_1$-$C_5$)alkyl, $C_3$-$C_5$alkenyloxy($C_1$-$C_5$) alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_8$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$) alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryl ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), phenoxy($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryloxy ($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; $C_1$-$C_6$alkyl-C (O)—; or phenyl-C(O)— wherein the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine, bromine, cyano or nitro;

wherein "heteroaryl" means an aromatic ring system containing at least one ring heteroatom and consisting either of a single ring or of two fused rings;

and wherein the compound of formula (I) is optionally present (e.g. where chemically possible) as an agrochemically acceptable salt thereof.

In the substituent definitions of the compounds of the formula I, each alkyl moiety either alone or as part of a larger group (such as alkoxy, alkylthio, alkoxycarbonyl, alkylcarbonyl, alkylaminocarbonyl, or dialkylaminocarbonyl, et al.) can be straight-chained or branched. Typically, the alkyl is, for example, methyl, ethyl, n-propyl, isopropyl, n-butyl, sec-butyl, isobutyl, tert-butyl, n-pentyl, neopentyl, or n-hexyl. The alkyl groups can e.g. be $C_1$-$C_6$alkyl groups (except where already defined more narrowly), but are preferably $C_1$-$C_4$alkyl or $C_1$-$C_3$alkyl groups (except where already defined more narrowly), and, more preferably, are $C_1$-$C_2$alkyl groups such as methyl.

Alkenyl and alkynyl moieties can be in the form of straight or branched chains, and the alkenyl moieties, where appropriate, can be of either the (E)- or (Z)-configuration. The alkenyl or alkynyl are typically $C_2$-$C_3$alkenyl or $C_2$-$C_3$alkynyl such as vinyl, allyl, ethynyl, propargyl or prop-1-ynyl. Alkenyl and alkynyl moieties can contain one or more double and/or triple bonds in any combination; but preferably contain only one double bond (for alkenyl) or only one triple bond (for alkynyl).

Halogen is fluorine, chlorine, bromine or iodine. Preferred halogens are fluorine, chlorine or bromine.

Fluoroalkyl groups are alkyl groups which are substituted with one or more (e.g. 1, 2, 3, 4 or 5; in particular 1, 2 or 3; e.g. 1 or 2) fluorine atoms. Fluoroalkyl is typically $C_1$-$C_3$fluoroalkyl or $C_1$-$C_2$fluoroalkyl (preferably $C_1$fluoroalkyl), such as $CF_3$, $CHF_2$, $CH_2F$, $CH_3CHF$—, $CF_3CH_2$—, $CHF_2CH_2$—, $CH_2FCH_2$—, $CHF_2CF_2$— or $(CH_3)_2CF$—. Fluoroalkoxy is typically $C_1$-$C_3$fluoroalkoxy or $C_1$-$C_2$fluoroalkoxy (preferably $C_1$fluoroalkoxy), such as $CF_3O$, $CHF_2O$, $CH_2FO$, $CH_3CHFO$—, $CF_3CH_2O$—, $CHF_2CH_2O$— or $CH_2FCH_2O$—.

In the context of the present specification the term "aryl" means phenyl or naphthyl. A preferred aryl group is phenyl.

The term "heteroaryl" as used herein means an aromatic ring system containing at least one ring heteroatom and consisting either of a single ring or of two fused rings. Preferably, single rings will contain 1, 2 or 3 ring heteroatoms and bicyclic systems 1, 2, 3 or 4 ring heteroatoms which will preferably be selected from nitrogen, oxygen and sulfur. Typically, a "heteroaryl" is furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl or indolizinyl; optionally present, where chemically possible, as an agrochemically acceptable salt thereof.

The term "heterocyclyl" as used herein, except where explicitly stated otherwise, means a 4, 5, 6 or 7 (in particular 5, 6 or 7) membered monocyclic organic ring or a 8, 9, 10 or 11 (in particular 8, 9 or 10) membered fused bicyclic organic ring system, which is fully saturated, and which has one or two (preferably one) ring heteroatoms independently selected from oxygen, sulfur and nitrogen. Where the heterocyclyl has two ring heteroatoms, preferably, the two ring heteroatoms are separated by at least two ring carbon atoms. Preferably, the heterocyclyl is attached at a ring carbon atom within the heterocyclyl. In particular, the heterocyclyl can be tetrahydrofuranyl, tetrahydropyranyl, tetrahydrothiophenyl, 1,4-dioxanyl, 1,4-dithianyl, morpholinyl, thiomorpholinyl, pyrrolidinyl, piperidinyl or piperazinyl; more particularly tetrahydrofuranyl (e.g. tetrahydrofuran-2-yl or particularly tetrahydrofuran-3-yl), tetrahydropyranyl (e.g. tetrahydropyran-2-yl, tetrahydropyran-3-yl or particularly tetrahydropyran-4-yl), morpholinyl, pyrrolidinyl (e.g. pyrrolidin-2-yl or particularly pyrrolidin-3-yl), piperidinyl (e.g. piperidin-2-yl, piperidin-3-yl or particularly piperidin-4-yl) or piperazinyl. In a particular embodiment, the heterocyclyl, when optionally substituted, is optionally substituted by 1 or 2 (e.g. 1) ring-carbon substituents independently being $C_1$-$C_3$alkyl (e.g. $C_1$-$C_2$alkyl), $C_1$-$C_2$fluoroalkyl or oxo (=O), and/or is optionally substituted by one $C_1$-$C_3$alkyl (e.g. $C_1$-$C_2$alkyl), $C_1$-$C_2$fluoroalkyl or $C_1$-$C_3$alkoxy (e.g. $C_1$-$C_2$alkyl or $C_1$-$C_2$fluoroalkyl) substituent on a ring nitrogen if present, and/or is optionally substituted by one or two oxo (=O) substituents on a ring sulfur if present.

Preferably, a cycloalkyl is cyclopropyl, cyclobutyl, cyclopentyl or cyclohexyl. (Cycloalkyl)alkyl is preferably (cycloalkyl)methyl such as ($C_3$-$C_6$cycloalkyl)methyl in particular cyclopropylmethyl. Preferably, cycloalkenyl is cyclopentenyl or cyclohexenyl.

The invention relates also to the agriculturally acceptable salts which the compounds of formula I are able to form with transition metal, alkali metal and alkaline earth metal bases, amines, quaternary ammonium bases or tertiary sulfonium bases.

Among the transition metal, alkali metal and alkaline earth metal salt formers, special mention should be made of the hydroxides of copper, iron, lithium, sodium, potassium, magnesium and calcium, and preferably the hydroxides, bicarbonates and carbonates of sodium and potassium. Accordingly, in one particular embodiment of the invention, G is an agriculturally acceptable metal such as copper, iron, lithium, sodium, potassium, magnesium or calcium (more particularly an agriculturally acceptable alkali metal or alkaline earth metal).

Examples of amines suitable for ammonium salt formation include ammonia as well as primary, secondary and tertiary $C_1$-$C_{18}$alkylamines, $C_1$-$C_4$hydroxyalkylamines and $C_2$-$C_4$alkoxyalkyl-amines, for example methylamine, ethylamine, n-propylamine, isopropylamine, the four butylamine isomers, n-amylamine, isoamylamine, hexylamine, heptylamine, octylamine, nonylamine, decylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, di-isopropylamine, di-n-butylamine, di-n-amylamine, di-isoamylamine, dihexylamine, diheptylamine, dioctylamine, ethanolamine, n-propanolamine, isopropanolamine, N,N-diethanolamine, N-ethylpropanolamine, N-butylethanolamine, allylamine, n-but-2-enylamine, n-pent-2-enylamine, 2,3-dimethylbut-2-enylamine, dibut-2-enylamine, n-hex-2-enylamine, propylenediamine, trimethylamine, triethylamine, tri-n-propylamine, tri-isopropylamine, tri-n-butylamine, tri-isobutylamine, tri-sec-butylamine, tri-n-amylamine, methoxyethylamine and ethoxyethylamine; heterocyclic amines, for example pyridine, quinoline, isoquinoline, morpholine, piperidine, pyrrolidine, indoline, quinuclidine and azepine; primary arylamines, for example anilines, methoxyanilines, ethoxyanilines, o-, m- and p-toluidines, phenylenediamines, benzidines, naphthylamines and o-, m- and p-chloroanilines; but especially triethylamine, isopropylamine and di-isopropylamine. Accordingly, in one particular embodiment of the invention, G is an agriculturally acceptable ammonium group, wherein the compound of formula (I) is an ammonium salt formed from: ammonia, a primary, secondary or tertiary $C_1$-$C_{18}$alkylamine, a $C_1$-$C_4$hydroxyalkylamine, or a $C_2$-$C_4$alkoxyalkyl-amine.

Preferred quaternary ammonium bases suitable for salt formation correspond, for example, to the formula $[N(R^{aa}R^{bb}R^{cc}R^{dd})]OH$, wherein $R^{aa}$, $R^{bb}$, $R^{cc}$ and $R^{dd}$ are each independently of the others hydrogen or $C_1$-$C_4$alkyl. Further suitable tetraalkylammonium bases with other anions can be obtained, for example, by anion exchange reactions. Accordingly, in one particular embodiment of the invention, G is an agriculturally acceptable ammonium group, wherein the compound of formula (I) is a salt formed from a quaternary ammonium base of formula $[N(R^{aa}R^{b}{}_{b}R^{cc}R^{dd})]OH$, wherein $R^{aa}$, $R^{bb}$, $R^{cc}$ and $R^{dd}$ are each independently of the others hydrogen or $C_1$-$C_4$alkyl.

Preferred tertiary sulfonium bases suitable for salt formation correspond, for example, to the formula $[SR^{ee}R^{ff}R^{gg}]OH$, wherein $R^{ee}$, $R^{ff}$ and $R^{gg}$ are each independently of the others $C_1$-$C_4$ alkyl. Trimethylsulfonium hydroxide is especially preferred. Suitable sulfonium bases may be obtained from the reaction of thioethers, in particular dialkylsulfides, with alkylhalides, followed by conversion to a suitable base, for example a hydroxide, by anion exchange reactions. Accordingly, in one particular embodiment of the invention, G is an agriculturally acceptable sulfonium group, wherein the compound of formula (I) is a salt formed from a tertiary sulfonium base of formula $[SR^{ee}R^{ff}R^{gg}]OH$, wherein $R^{ee}$, $R^{ff}$ and $R^{gg}$ are each independently of the others $C_1$-$C_4$ alkyl.

It should be understood that in those compounds of formula I, where G is a metal, ammonium group or sulfonium group as mentioned above, and as such represents a cation, the corresponding negative charge is largely delocalised across the O=C=C=C=O unit within formula (I).

The compounds of formula I according to the invention also include hydrates which may be formed during the salt formation.

When G is —C($X^a$)—$R^a$, —C($X^b$)—$X^c$—$R^b$, —C($X^d$)—N($R^c$)—$R^d$, —SO$_2$—$R^e$, —P($X^e$)($R^f$)—$R^g$, —CH$_2$—$X^f$—$R^h$; or phenyl-CH$_2$— or phenyl-CH($C_1$-$C_2$alkyl)- (in each of which the phenyl is optionally substituted), or heteroaryl-CH$_2$— or heteroaryl-CH($C_1$-$C_2$alkyl)- (in each of which the heteroaryl is optionally substituted), or phenyl-C(O)—CH$_2$— (wherein the phenyl is optionally substituted); or $C_1$-$C_6$alkoxy-C(O)—CH$_2$—, $C_1$-$C_6$alkoxy-C(O)—CH=CH—, $C_2$-$C_7$alken-1-yl-CH$_2$—, $C_2$-$C_7$alken-1-yl-CH($C_1$-$C_2$alkyl)-, $C_2$-$C_4$fluoroalken-1-yl-CH$_2$—, $C_2$-$C_7$alkyn-1-yl-CH$_2$—, or $C_2$-$C_7$alkyn-1-yl-CH($C_1$-$C_2$alkyl)-; generally these G groups are latentiating groups (i.e. leaving or removable groups), which are generally selected to allow their removal, typically by one or a combination of biochemical, chemical or physical processes, to afford the corresponding compound of formula (I) where G is H, before, during or following (preferably during or following, more preferably following) application of the compound of formula (I) to the treated area (e.g. field) or to plants. Examples of these processes include enzymatic cleavage or other in/on-plant cleavage (e.g. cleavage of ester and/or carbonate moieties), chemical hydrolysis, and/or photolysis. Some compounds bearing such groups G occasionally offer certain advantages or different technical properties, such as improved and/or more consistent and/or different penetration of the cuticula of the plants treated, increased and/or different tolerance of certain crops, improved and/or different compatibility or stability in formulated mixtures containing other herbicides, herbicide safeners, plant growth regulators, fungicides or insecticides, or reduced and/or different leaching properties in soils.

The preferred, suitable and/or particular values of the substituents in or other features of the compound of formula (I), in particular G, X, $R^1$, $R^2$, $R^{2A}$, $R^{2B}$, $R^{2C}$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^a$, $R^b$, $R^c$, $R^d$, $R^e$, $R^f$, $R^g$, $R^h$, $X^a$, $X^b$, $X^c$, $X^d$, $X^e$, $X^f$, Q, Het, $X^1$, n1, n2 and/or n3, are set out below (and/or generally herein), and can be either taken alone or taken together with one or more of any other preferred, suitable and/or particular features in any combination(s) thereof. In this paragraph, "preferred" is intended to encompass more preferred, even or still or yet more preferred, particularly or highly preferred, most preferred and all similar terms.

In a particular embodiment, G is hydrogen; an agriculturally acceptable metal (e.g. an agriculturally acceptable alkali metal or alkaline earth metal, e.g. lithium, sodium, potassium, magnesium or calcium), or an agriculturally acceptable sulfonium or ammonium group; or G is —C($X^a$)—$R^a$, —C($X^b$)—$X^c$—$R^b$ or —SO$_2$—$R^e$, wherein $X^a$, $R^a$, $X^b$, $X^c$, $R^b$ and $R^e$ are as defined herein.

In one preferred embodiment, G is hydrogen; an agriculturally acceptable metal (e.g. an agriculturally acceptable alkali metal or alkaline earth metal, e.g. lithium, sodium, potassium, magnesium or calcium), or an agriculturally acceptable sulfonium or ammonium group; or G is —C($X^a$)—$R^a$ or —C($X^b$)—$X^c$—$R^b$, wherein $X^a$, $R^a$, $X^b$, $X^c$ and $R^b$ are as defined herein.

In a particular embodiment, G is a group —C($X^a$)—$R^a$ or —C($X^b$)—$X^c$—$R^b$, wherein $X^a$, $R^a$, $X^b$, $X^c$ and $R^b$ are as defined herein.

Preferably, $X^a$, $X^b$, $X^c$, $X^d$, $X^e$ and/or $X^f$ are oxygen. Alternatively, preferably, $X^c$ is sulfur.

More preferably, $X^a$, $X^b$, $X^c$, $X^d$, $X^e$ and $X^f$ are oxygen.

Preferably, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl or $C_1$-$C_4$alkoxy$C_1$-$C_4$alkyl. Alternatively, preferably, $R^a$ is $C_3$-$C_7$cycloalkyl($C_1$-$C_5$) alkyl, or phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro.

Preferably, $R^b$ is $C_1$-$C_{10}$alkyl (e.g. $C_1$-$C_6$alkyl), $C_2$-$C_5$alkenyl-CH$_2$— (e.g. $C_2$-$C_3$alkenyl-CH$_2$—), $C_2$-$C_4$alkenyl-CH(Me)- (e.g. $C_2$-$C_3$alkenyl-CH(Me)-), $C_2$-$C_5$alkynyl-CH$_2$— (e.g. $C_2$-$C_3$alkynyl-CH$_2$—), $C_2$-$C_4$alkynyl-CH(Me)- (e.g. $C_2$-$C_3$alkynyl-CH(Me)-), $C_3$-$C_6$cycloalkyl or $C_1$-$C_4$alkoxy$C_1$-$C_4$alkyl. Alternatively, preferably, $R^b$ is $C_3$-$C_7$cycloalkyl($C_1$-$C_5$)alkyl, or phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro.

Preferably, $R^e$ is $C_1$-$C_{10}$alkyl (e.g. $C_1$-$C_6$alkyl or $C_1$-$C_4$alkyl) or $C_1$-$C_{10}$fluoroalkyl (e.g. $C_1$-$C_3$fluoroalkyl). In particular, $R^e$ is $C_1$-$C_{10}$alkyl (e.g. $C_1$-$C_6$alkyl or $C_1$-$C_4$alkyl).

When G is —C($X^a$)—$R^a$ or —C($X^b$)—$X^c$—$R^b$, then preferably $X^a$, $X^b$ and $X^c$ are oxygen, $R^a$ is $C_1$-$C_{10}$alkyl (e.g. $C_1$-$C_6$alkyl), $C_2$-$C_6$alkenyl (e.g. $C_2$-$C_4$alkenyl), $C_2$-$C_6$alkynyl (e.g. $C_2$-$C_4$alkynyl), $C_3$-$C_6$cycloalkyl or $C_1$-$C_4$alkoxy$C_1$-$C_4$alkyl; and $R^b$ is $C_1$-$C_{10}$alkyl (e.g. $C_1$-$C_6$alkyl), $C_2$-$C_5$alkenyl-CH$_2$— (e.g. $C_2$-$C_3$alkenyl-CH$_2$—), $C_2$-$C_4$alkenyl-CH(Me)- (e.g. $C_2$-$C_3$alkenyl-CH(Me)-), $C_2$-$C_5$alkynyl-CH$_2$— (e.g. $C_2$-$C_3$alkynyl-CH$_2$—), $C_2$-$C_4$alkynyl-CH(Me)- (e.g. $C_2$-$C_3$alkynyl-CH(Me)-), $C_3$-$C_6$cycloalkyl or $C_1$-$C_4$alkoxy$C_1$-$C_4$alkyl.

In a preferable embodiment, G is hydrogen, or an agriculturally acceptable alkali metal or alkaline earth metal, or an agriculturally acceptable sulfonium or ammonium group. More preferably, G is hydrogen, or an agriculturally acceptable alkali metal or alkaline earth metal.

In a preferable embodiment, G is hydrogen, —C($X^a$)—$R^a$ or —C($X^b$)—$X^c$—$R^b$.

Most preferably G is hydrogen.

In one aspect of the present invention, in the Compound of Formula (I) $R^1$ is preferably $C_1$-$C_2$alkoxy or $C_1$-$C_2$fluoroalkoxy, more preferably methoxy or $C_1$fluoroalkoxy, and even more preferably methoxy.

In another aspect of the present invention, in the compound of Formula (I) $R^1$ is preferably ethyl, n-propyl, n-butyl, cyclopropyl or ethynyl, more preferably ethyl, n-propyl or n-butyl, and even more preferably ethyl or n-propyl.

Preferably, when $R^2$ is $C_1$-$C_2$alkoxy-$C_1$-$C_3$alkoxy- or $C_1$fluoroalkoxy-$C_1$-$C_3$alkoxy-, then $R^2$ is $R^{2A}$O—CH($R^{2B}$)—CH($R^{2C}$)—O—;

wherein $R^{2A}$ is $C_1$-$C_2$alkyl (in particular methyl) or $C_1$fluoroalkyl; and $R^{2B}$ and $R^{2C}$ are independently hydrogen or methyl, provided that one or both of $R^{2B}$ and $R^{2C}$ are hydrogen.

Preferably, $R^{2A}$ is methyl or $C_1$fluoroalkyl, more preferably methyl.

Preferably, both of $R^{2B}$ and $R^{2C}$ are hydrogen.

More preferably, when $R^2$ is $C_1$-$C_2$alkoxy-$C_1$-$C_3$alkoxy- or $C_1$fluoroalkoxy-$C_1$-$C_3$alkoxy- (in particular when $R^2$ is $R^{2A}$O—CH($R^{2B}$)—CH($R^{2C}$)—O—), then $R^2$ is MeO—$CH_2$—$CH_2$—O—.

Preferably, e.g. in all aspects and/or embodiments of the invention, $R^1$ is $C_1$-$C_2$alkoxy or $C_1$-$C_2$fluoroalkoxy. In this case, then more preferably, $R^1$ is methoxy or $C_1$fluoroalkoxy, most preferably methoxy.

Alternatively, preferably, e.g. in all aspects and/or embodiments of the invention, $R^1$ is ethyl, n-propyl, n-butyl, cyclopropyl or ethynyl. In this case, then more preferably, $R^1$ is ethyl, n-propyl or n-butyl, most preferably ethyl or n-propyl.

Preferably, e.g. in all aspects and/or embodiments of the invention, $R^2$ is hydrogen, ethyl, n-propyl, cyclopropyl, vinyl, ethynyl, methoxy, ethoxy or fluoromethoxy.

More preferably, e.g. in all aspects and/or embodiments of the invention, $R^2$ is hydrogen, ethyl, ethynyl, methoxy, fluoromethoxy or ethoxy.

Even more preferably, e.g. in all aspects and/or embodiments of the invention, $R^2$ is hydrogen or methoxy.

Particularly preferably, e.g. in all aspects and/or embodiments of the invention, $R^1$ is methoxy, and $R^2$ is hydrogen or methoxy.

Particularly preferably, e.g. in all aspects and/or embodiments of the invention:

$R^1$ is ethyl, and $R^2$ is hydrogen or ethyl, or $R^1$ is n-propyl or n-butyl, and $R^2$ is hydrogen.

Preferably, e.g. in all aspects and/or embodiments of the invention, when $R^4$ and $R^5$ are taken together, then $R^4$ and $R^5$ taken together are —$(CH_2)_{n4}$— or —$(CH_2)_{n5}$—C($R^{7a}$)($R^{7b}$)—$(CH_2)_{n6}$—.

Preferably, $R^{7a}$ is $C_1$-$C_2$alkyl; and $R^{7b}$ is hydrogen or $C_1$-$C_2$alkyl.

Preferably, n4 is 2 or 3.

Preferably, n5 and n6 are independently 0, 1 or 2 provided that n5+n6 is 1 or 2.

Preferably, e.g. in all aspects and/or embodiments of the invention, when $R^4$ and $R^5$ are taken together (which is preferable), then $R^4$ and $R^5$ taken together are —$(CH_2)_{n4}$— or —$(CH_2)_{n5}$—C($R^{7a}$)($R^{7b}$)—$(CH_2)_{n6}$—;

wherein $R^{7a}$ is $C_1$-$C_2$alkyl; $R^{7b}$ is hydrogen or $C_1$-$C_2$alkyl;

n4 is 1, 2 or 3 (preferably 2 or 3); and n5 and n6 are independently 0, 1 or 2 provided that n5+n6 is 0, 1 or 2 (preferably 1 or 2).

Preferably, e.g. in all aspects and/or embodiments of the invention, $R^3$, $R^4$, $R^5$ and/or $R^6$, independently of each other, are hydrogen, $C_1$-$C_4$alkyl (e.g. $C_1$-$C_2$alkyl), $C_2$-$C_4$alkynyl (in particular $C_2$-$C_3$alkynyl-$CH_2$—, e.g. ethynyl-$CH_2$—), $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, $C_1$-$C_3$alkylsulfonyl$C_1$-$C_3$alkyl; $C_3$-$C_4$cycloalkyl (in particular cyclopropyl); or an unsubstituted 4, 5 or 6 (e.g. 4 or 5) membered monocyclic heterocyclyl having one ring heteroatom independently selected from oxygen, sulfur and nitrogen, and attached at a ring carbon atom within the heterocyclyl (in particular tetrahydrofuranyl such as tetrahydrofuran-3-yl, or tetrahydropyranyl such as tetrahydropyran-4-yl);

provided that no more than one (in particular none) of $R^3$, $R^4$, $R^5$ and $R^6$ is alkenyl, alkynyl, alkoxyalkyl, alkylthioalkyl, alkylsulfinylalkyl, alkylsulfonylalkyl, cycloalkyl or heterocyclyl;

or $R^3$ and $R^4$ taken together are —$(CH_2)_{n1}$— or —$(CH_2)_{n2}$—$X^1$—$(CH_2)_{n3}$— and $R^5$ and $R^6$ are as defined herein (e.g. hereinabove), or $R^5$ and $R^6$ taken together are —$(CH_2)_{n1}$— or —$(CH_2)_{n2}$—$X^1$—$(CH_2)_{n3}$— and $R^3$ and $R^4$ are as defined herein (e.g. hereinabove); wherein $X^1$ is O, S, S(O), S(O)$_2$, NH, N($C_1$-$C_2$alkyl), N($C_1$-$C_2$alkoxy), C(H)($C_1$-$C_2$alkyl), C($C_1$-$C_2$alkyl)$_2$ or C(H)($C_1$-$C_2$alkoxy);

n1 is 4 or 5; and n2 and n3 are independently 1, 2 or 3 provided that n2+n3 is 3 or 4;

and/or $R^4$ and $R^5$ taken together are —$(CH_2)_{n4}$— or —$(CH_2)_{n5}$—C($R^{7a}$)($R^{7b}$)—$(CH_2)_{n6}$—;

wherein $R^{7a}$ is $C_1$-$C_2$alkyl; $R^{7b}$ is hydrogen or $C_1$-$C_2$alkyl;

n4 is 1, 2 or 3 (in particular 2 or 3); and n5 and n6 are independently 0, 1 or 2 provided that n5+n6 is 0, 1 or 2 (in particular 1 or 2).

More preferably, e.g. in all aspects and/or embodiments of the invention, $R^3$, $R^4$, $R^5$ and/or $R^6$, independently of each other, are hydrogen, $C_1$-$C_4$alkyl (e.g. $C_1$-$C_2$alkyl), $C_2$-$C_4$alkynyl (in particular $C_2$-$C_3$alkynyl-$CH_2$—, e.g. ethynyl-$CH_2$—), $C_1$-$C_3$alkoxy$C_1$-$C_3$alkyl (in particular $C_1$-$C_2$alkoxy$C_1$-$C_2$alkyl), $C_1$-$C_3$alkylthio$C_1$-$C_3$alkyl (in particular $C_1$-$C_2$alkylthio$C_1$-$C_2$alkyl), $C_1$-$C_3$alkylsulfinyl$C_1$-$C_3$alkyl (in particular $C_1$-$C_2$alkylsulfinyl$C_1$-$C_2$alkyl), $C_1$-$C_3$alkylsulfonyl$C_1$-$C_3$alkyl (in particular $C_1$-$C_2$alkylsulfonyl$C_1$-$C_2$alkyl); $C_3$-$C_4$cycloalkyl (in particular cyclopropyl); or an unsubstituted 4, 5 or 6 (e.g. 4 or 5) membered monocyclic heterocyclyl having one ring heteroatom independently selected from oxygen, sulfur and nitrogen, and attached at a ring carbon atom within the heterocyclyl (in particular tetrahydrofuranyl such as tetrahydrofuran-3-yl, or tetrahydropyranyl such as tetrahydropyran-4-yl);

provided that no more than one (in particular none) of $R^3$, $R^4$, $R^5$ and $R^6$ is alkenyl, alkynyl, alkoxyalkyl, alkylthioalkyl, alkylsulfinylalkyl, alkylsulfonylalkyl, cycloalkyl or heterocyclyl;

and/or $R^4$ and $R^5$ taken together are —$(CH_2)_{n4}$— or —$(CH_2)_{n5}$—C($R^{7a}$)($R^{7b}$)—$(CH_2)_{n6}$—;

wherein $R^{7a}$ is $C_1$-$C_2$alkyl; $R^{7b}$ is hydrogen or $C_1$-$C_2$alkyl;

n4 is 2 or 3; and n5 and n6 are independently 0, 1 or 2 provided that n5+n6 is 1 or 2.

Still more preferably, $R^3$, $R^4$, $R^5$ and/or $R^6$, independently of each other, are hydrogen, $C_1$-$C_3$alkyl (in particular $C_1$-$C_2$alkyl such as methyl) or $C_1$-$C_3$alkoxy$C_1$-$C_3$alkyl (in particular $C_1$-$C_2$alkoxy$C_1$-$C_2$alkyl); provided that no more than one (in particular none) of $R^3$, $R^4$, $R^5$ and $R^6$ is alkoxyalkyl;

and/or $R^4$ and $R^5$ taken together are —$(CH_2)_{n4}$— or —$(CH_2)_{n5}$—$C(R^{7a})(R^{7b})$—$(CH_2)_{n6}$—;

wherein $R^{7a}$ is $C_1$-$C_2$alkyl; $R^{7b}$ is hydrogen or $C_1$-$C_2$alkyl;

n4 is 2 or 3; and n5 and n6 are independently 0, 1 or 2 provided that n5+n6 is 1 or 2.

Even more preferably, $R^3$, $R^4$, $R^5$ and/or $R^6$, independently of each other, are hydrogen or $C_1$-$C_2$alkyl (preferably hydrogen or methyl); and/or $R^4$ and $R^5$ taken together are —$(CH_2)_{n4}$— wherein n4 is 2 or 3.

Most preferably (especially when Y is $CR^8R^9$ or —$CR^{10}R^{11}CR^{12}R^{13}$—), $R^3$, $R^4$, $R^5$ and $R^6$ are hydrogen; or $R^4$ and $R^5$ taken together are —$(CH_2)_{n4}$— wherein n4 is 2 or 3, and $R^3$ and $R^6$ are hydrogen.

Preferably, e.g. in all aspects and/or embodiments of the invention, at least one (more preferably 2, 3 or 4, still more preferably 3 or 4, most preferably all four) of $R^3$, $R^4$, $R^5$ and $R^6$, independently of each other, are hydrogen or $C_1$-$C_4$alkyl (e.g. H or $C_1$-$C_3$alkyl, or H or $C_1$-$C_2$alkyl);

or $R^4$ and $R^5$ are taken together as described herein.

Preferably, e.g. in all aspects and/or embodiments of the invention, Y is O, S, S(O), $S(O)_2$, C(O), $CR^8R^9$ or —$CR^{10}R^{11}CR^{12}R^{13}$—.

More preferably, Y is O, C(O), $CR^8R^9$ or —$CR^{10}R^{11}CR^{12}R^{13}$—.

Even more preferably, Y is O or $CR^8R^9$, in particular O or $CH_2$.

Most preferably, Y is $CR^8R^9$, in particular $CH_2$.

Preferably, e.g. in all aspects and/or embodiments of the invention, in $R^8$ and $R^9$, one or both of $R^8$ and $R^9$ is or are hydrogen; or $R^8$ and $R^9$ taken together are —$(CH_2)_{n7}$— or preferably —$(CH_2)_{n8}$—$X^2$—$(CH_2)_{n9}$—. In this embodiment, preferably Y is $CR^8R^9$ and/or preferably $X^2$ is O.

In one particular embodiment, $R^8$ and $R^9$ are taken together and are —$(CH_2)_{n7}$— or preferably —$(CH_2)_{n8}$—$X^2$—$(CH_2)_{n9}$—. In this embodiment, preferably Y is $CR^8R^9$ and/or preferably $X^2$ is O.

Preferably, e.g. in all aspects and/or embodiments of the invention, $X^2$ is O, S, S(O), $S(O)_2$, $C(H)(C_1$-$C_3$alkyl), $C(C_1$-$C_2$alkyl$)_2$ or $C(H)(C_1$-$C_3$alkoxy). Most preferably, $X^2$ is O.

Preferably, n7 is 2, 3, 4 or 5, more preferably 4 or 5.

Preferably, n8 and n9 are independently 1, 2 or 3 provided that n8+n9 is 2, 3 or 4.

Preferably, n8+n9 is 3 or 4. Most preferably, n8 is 2 and n9 is 2 (in which case, preferably, $X^2$ is O).

Preferably, e.g. in all aspects and/or embodiments of the invention, $R^8$ and $R^9$ are, independently of each other:

hydrogen, $C_1$-$C_4$alkyl (in particular $C_1$-$C_2$alkyl), $C_2$-$C_3$alkenyl-$CH_2$— (in particular ethenyl-$CH_2$—), $C_2$-$C_3$alkynyl-$CH_2$— (in particular ethynyl-$CH_2$—), $C_1$-$C_2$fluoroalkyl (in particular $C_1$fluoroalkyl), $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, or $C_1$-$C_3$alkylsulfonyl$C_1$-$C_3$alkyl;

$C_3$-$C_6$cycloalkyl or $C_3$-$C_6$cycloalkyl substituted by one or two substituents which independently are $C_1$-$C_3$alkyl (in particular methyl or ethyl) or $C_1$-$C_2$fluoroalkyl; and in which one ring $CH_2$ moiety of a $C_4$-$C_6$cycloalkyl is optionally (e.g. preferably) replaced by an oxygen or sulfur atom or by a S(O), $S(O)_2$, NH, $N(C_1$-$C_3$alkyl), $N(C_1$-$C_2$fluoroalkyl), $N[C(O)C_1$-$C_3$alkyl], $N[C(O)C_1$-$C_2$fluoroalkyl] or $N(C_1$-$C_2$alkoxy) moiety;

$C_3$-$C_6$cycloalkyl substituted by one substituent being $C_1$-$C_3$alkoxy (in particular $C_1$-$C_2$alkoxy) and optionally further substituted by one substituent being $C_1$-$C_2$alkyl (in particular methyl);

$C_3$-$C_6$cycloalkyl$C_1$-$C_2$alkyl- (in particular $C_3$-$C_6$cycloalkylmethyl-) or $C_3$-$C_6$cycloalkyl$C_1$-$C_2$alkyl- (in particular $C_3$-$C_6$cycloalkylmethyl-) substituted by one or two ring substituents which independently are $C_1$-$C_3$alkyl or $C_1$-$C_2$fluoroalkyl; and in which one ring $CH_2$ moiety of a $C_4$-$C_6$cycloalkyl$C_1$-$C_2$alkyl- (in particular $C_4$-$C_6$cycloalkylmethyl-) is optionally (e.g. preferably) replaced by an oxygen or sulfur atom or by a S(O), $S(O)_2$, NH, $N(C_1$-$C_2$alkyl), $N(C_1$-$C_2$fluoroalkyl), $N[C(O)C_1$-$C_3$alkyl], $N[C(O)C_1$-$C_2$fluoroalkyl] or $N(C_1$-$C_2$alkoxy) moiety;

$C_3$-$C_6$cycloalkyl$C_1$-$C_2$alkyl- (in particular $C_3$-$C_6$cycloalkylmethyl-) substituted by one ring substituent being $C_1$-$C_3$alkoxy (in particular $C_1$-$C_2$alkoxy) and optionally further substituted by one ring substituent being $C_1$-$C_2$alkyl (in particular methyl); or Het or Het-$CH_2$—, wherein Het is a heteroaryl, attached at a ring-carbon, which is optionally substituted by 1, 2 or 3 (in particular 1 or 2, e.g. 1) ring-carbon substituents independently being $C_1$-$C_3$alkyl (e.g. $C_1$-$C_2$alkyl), $C_1$-$C_2$fluoroalkyl, $C_1$-$C_3$alkyl-C(O)—, $C_1$-$C_2$fluoroalkyl-C(O)—, hydroxy (including any oxo tautomer), $C_2$-$C_3$alkenyl (e.g. ethenyl or prop-1-enyl), $C_2$-$C_3$alkynyl (e.g. ethynyl or prop-1-ynyl), $C_1$-$C_3$alkoxy (e.g. $C_1$-$C_2$alkoxy), $C_1$-$C_2$fluoroalkoxy, halogen (e.g. fluorine or chlorine), cyano or nitro, provided that any non-fluorine halogen, alkoxy or fluoroalkoxy is not substituted at any ring-carbon bonded directly to a ring-nitrogen of the heteroaryl; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-$S(O)_2$— substituent;

provided that no more than one of $R^8$ and $R^9$ is an optionally substituted cycloalkyl; an optionally substituted cycloalkyl in which one ring $CH_2$ moiety has been replaced by an oxygen or sulfur atom or by a S(O), $S(O)_2$, NH, $N(C_1$-$C_3$alkyl), $N(C_1$-$C_2$fluoroalkyl), $N[C(O)C_1$-$C_3$alkyl], $N[C(O)C_1$-$C_2$fluoroalkyl] or $N(C_1$-$C_2$alkoxy) moiety; an optionally substituted cycloalkenyl; an optionally substituted cycloalkyl-alkyl-; an optionally substituted cycloalkyl-alkyl- in which one ring $CH_2$ moiety has been replaced by an oxygen or sulfur atom or by a S(O), $S(O)_2$, NH, $N(C_1$-$C_3$alkyl), $N(C_1$-$C_2$fluoroalkyl), $N[C(O)C_1$-$C_3$alkyl], $N[C(O)C_1$-$C_2$fluoroalkyl] or $N(C_1$-$C_2$alkoxy) moiety; or Het or Het-$CH_2$—;

or $R^8$ is hydrogen or $C_1$-$C_2$alkyl (in particular H or Me), and $R^9$ is $C_1$-$C_2$alkoxy (in particular methoxy);

or $R^8$ and $R^9$ taken together are —$(CH_2)_{n7}$— or —$(CH_2)_{n8}$—$X^2$—$(CH_2)_{n9}$—.

In the above preferred embodiment, preferably Y is $CR^8R^9$ and/or preferably $X^2$ is O.

More preferably, e.g. in all aspects and/or embodiments of the invention:

$R^8$ is hydrogen or $C_1$-$C_2$alkyl (preferably H or Me, more preferably hydrogen); and $R^9$ is:

$C_1$-$C_2$alkoxy (in particular methoxy);

$C_2$-$C_3$alkynyl-$CH_2$— (in particular ethynyl-$CH_2$—);

$C_1$-$C_3$alkoxy$C_1$-$C_3$alkyl;

$C_1$-$C_3$alkylthio$C_1$-$C_3$alkyl (preferably $C_1$-$C_2$alkylthio-$CH_2CH_2$— or more preferably $C_1$-$C_2$alkylthio-CH(Me)$CH_2$—);

$C_1$-$C_3$alkylsulfinyl$C_1$-$C_3$alkyl;

$C_1$-$C_3$alkylsulfonyl$C_1$-$C_3$alkyl;

$C_3$-$C_6$cycloalkyl or $C_3$-$C_6$cycloalkyl substituted by one or two substituents which independently are $C_1$-$C_3$alkyl (in particular methyl or ethyl) or $C_1$-$C_2$fluoroalkyl; and in which one ring $CH_2$ moiety of a $C_4$-$C_6$cycloalkyl is optionally (e.g. preferably) replaced by an oxygen or sulfur atom or by a S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety (or more preferably is replaced by an oxygen or sulfur atom or by a S(O), S(O)$_2$, NH, N($C_1$-$C_3$alkyl) or N($C_1$-$C_2$alkoxy) moiety; or still more preferably is replaced by an oxygen or sulfur atom);

$C_3$-$C_6$cycloalkyl substituted by one substituent being $C_1$-$C_3$alkoxy (in particular $C_1$-$C_2$alkoxy) and optionally further substituted by one substituent being $C_1$-$C_2$alkyl (in particular methyl);

$C_3$-$C_6$cycloalkylmethyl- or $C_3$-$C_6$cycloalkylmethyl- substituted by one or two ring substituents which independently are $C_1$-$C_3$alkyl (in particular $C_1$-$C_2$alkyl) or $C_1$-$C_2$fluoroalkyl; and in which one ring $CH_2$ moiety of a $C_4$-$C_6$cycloalkylmethyl- is optionally (e.g. preferably) replaced by an oxygen or sulfur atom or by a S(O), S(O)$_2$, NH, N($C_1$-$C_2$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety (or more preferably is replaced by an oxygen or sulfur atom or by a N[C(O)$C_1$-$C_3$alkyl] or N[C(O)$C_1$-$C_2$fluoroalkyl] moiety);

$C_3$-$C_6$cycloalkylmethyl- substituted by one ring substituent being $C_1$-$C_3$alkoxy (in particular $C_1$-$C_2$alkoxy) and optionally further substituted by one ring substituent being $C_1$-$C_2$alkyl (in particular methyl); or Het or Het-$CH_2$—, wherein Het is a heteroaryl, attached at a ring-carbon, which is optionally substituted by 1, 2 or 3 (in particular 1 or 2, e.g. 1) ring-carbon substituents independently being $C_1$-$C_3$alkyl (in particular $C_1$-$C_2$alkyl), $C_1$-$C_2$fluoroalkyl (in particular $C_1$fluoroalkyl), $C_1$-$C_3$alkyl-C(O)—, $C_1$-$C_2$fluoroalkyl-C(O)—, hydroxy (including any oxo tautomer), $C_2$-$C_3$alkenyl (in particular ethenyl or prop-1-enyl), $C_2$-$C_3$alkynyl (in particular ethynyl or prop-1-ynyl), $C_1$-$C_3$alkoxy (in particular $C_1$-$C_2$alkoxy), $C_1$-$C_2$fluoroalkoxy (in particular $C_1$fluoroalkoxy), halogen (in particular fluorine or chlorine), cyano or nitro, provided that any non-fluorine halogen, alkoxy or fluoroalkoxy is not substituted at any ring-carbon bonded directly to a ring-nitrogen of the heteroaryl; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent;

or $R^8$ and $R^9$ taken together are —(CH$_2$)$_{n7}$— or —(CH$_2$)$_{n8}$—X$^2$—(CH$_2$)$_{n9}$—.

In the above more preferred embodiment, preferably Y is CR$^8$R$^9$ and/or preferably X$^2$ is O.

Even more preferably, e.g. in all aspects and/or embodiments of the invention:

$R^8$ is hydrogen or $C_1$-$C_2$alkyl (preferably H or Me, more preferably hydrogen); and $R^9$ is:

$C_1$-$C_3$alkylthio$C_1$-$C_3$alkyl (preferably $C_1$-$C_2$alkylthio-$CH_2CH_2$— or more preferably $C_1$-$C_2$alkylthio-CH(Me)$CH_2$—);

$C_3$-$C_6$cycloalkyl or $C_3$-$C_6$cycloalkyl substituted by one or two substituents which independently are $C_1$-$C_3$alkyl (in particular methyl or ethyl) or $C_1$-$C_2$fluoroalkyl; and in which one ring $CH_2$ moiety of a $C_4$-$C_6$cycloalkyl is replaced by an oxygen or sulfur atom or by a S(O), S(O)$_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety (or preferably is replaced by an oxygen or sulfur atom or by a S(O), S(O)$_2$, NH, N($C_1$-$C_3$alkyl) or N($C_1$-$C_2$alkoxy) moiety; or more preferably is replaced by an oxygen or sulfur atom);

$C_3$-$C_6$cycloalkylmethyl- or $C_3$-$C_6$cycloalkylmethyl- substituted by one or two ring substituents which independently are $C_1$-$C_3$alkyl (in particular $C_1$-$C_2$alkyl) or $C_1$-$C_2$fluoroalkyl; and in which one ring $CH_2$ moiety of a $C_4$-$C_6$cycloalkylmethyl- is replaced by an oxygen or sulfur atom or by a S(O), S(O)$_2$, NH, N($C_1$-$C_2$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety (or preferably is replaced by an oxygen or sulfur atom or by a N[C(O)$C_1$-$C_3$alkyl] or N[C(O)$C_1$-$C_2$fluoroalkyl] moiety); or Het or Het-$CH_2$—, wherein Het is a heteroaryl, attached at a ring-carbon, which is optionally substituted by 1, 2 or 3 (in particular 1 or 2, e.g. 1) ring-carbon substituents independently being $C_1$-$C_3$alkyl (in particular $C_1$-$C_2$alkyl), $C_1$-$C_2$fluoroalkyl (in particular $C_1$fluoroalkyl), $C_1$-$C_3$alkyl-C(O)—, $C_1$-$C_2$fluoroalkyl-C(O)—, hydroxy (including any oxo tautomer), $C_2$-$C_3$alkenyl (in particular ethenyl or prop-1-enyl), $C_2$-$C_3$alkynyl (in particular ethynyl or prop-1-ynyl), $C_1$-$C_3$alkoxy (in particular $C_1$-$C_2$alkoxy), $C_1$-$C_2$fluoroalkoxy (in particular $C_1$fluoroalkoxy), halogen (in particular fluorine or chlorine), cyano or nitro, provided that any non-fluorine halogen, alkoxy or fluoroalkoxy is not substituted at any ring-carbon bonded directly to a ring-nitrogen of the heteroaryl; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent;

or $R^8$ and $R^9$ taken together are —(CH$_2$)$_{n7}$— or —(CH$_2$)$_{n8}$—X$^2$—(CH$_2$)$_{n9}$—.

In the above even more preferred embodiment, preferably Y is CR$^8$R$^9$ and/or preferably X$^2$ is O.

In one preferable embodiment (which e.g. can apply to all aspects and/or embodiments of the invention), $R^8$ and $R^9$ are, independently of each other, hydrogen or $C_1$-$C_3$alkyl (preferably hydrogen or $C_1$-$C_2$alkyl, such as hydrogen or methyl). In this embodiment, preferably, Y is CR$^8$R$^9$.

In another preferable embodiment (which e.g. can apply to all aspects and/or embodiments of the invention), $R^8$ is hydrogen, and $R^9$ is $C_1$-$C_3$alkylthio$C_1$-$C_3$alkyl. In this embodiment, $R^9$ preferably is $C_1$-$C_2$alkylthio-$CH_2CH_2$— or more preferably is $C_1$-$C_2$alkylthio-CH(Me)$CH_2$—. In this embodiment, preferably, Y is CR$^8$R$^9$.

In another preferable embodiment (which e.g. can apply to all aspects and/or embodiments of the invention), $R^8$ is hydrogen and R⁹ is C₄-C₆cycloalkylmethyl- or C₄-C₆cycloalkylmethyl- substituted by one or two ring substituents which independently are C₁-C₃alkyl (in particular C₁-C₂alkyl) or C₁-C₂fluoroalkyl, and in which one ring CH₂ moiety is replaced by an oxygen or sulfur atom or by a S(O), S(O)₂, NH, N(C₁-C₂alkyl), N(C₁-C₂fluoroalkyl), N[C(O)C₁-C₃alkyl], N[C(O)C₁-C₂fluoroalkyl] or N(C₁-C₂alkoxy) moiety (or more preferably is replaced by an oxygen or sulfur atom or by a N[C(O)C₁-C₃alkyl] or N[C(O)C₁-C₂fluoroalkyl] moiety). In this embodiment, preferably, Y is CR⁸R⁹.

In this preferable embodiment, then more preferably R⁸ is hydrogen and R⁹ is a heterocyclyl-methyl-, wherein the heterocyclyl is Q, wherein Q is one of the following sub-formulae Q₁, Q₂, Q₃, Q₄, Q₅, Q₆, Q₇, Q₃₃, Q₃₄, Q₃₇, Q₃₈, Q₄₁, Q₄₂, Q₄₃, Q₄₄, Q₄₇, Q₈₇, Q₈₉, Q₉₀ or Q₁₀₇:

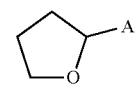
Q₁

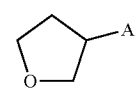
Q₂

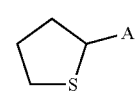
Q₃

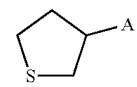
Q₄

Q₅

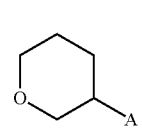
Q₆

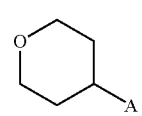
Q₇

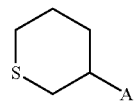
Q₃₃

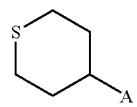
Q₃₄

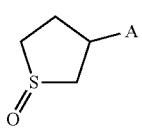
Q₃₇

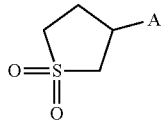
Q₃₈

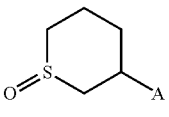
Q₄₁

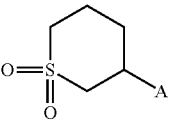
Q₄₂

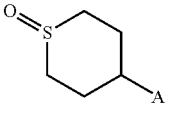
Q₄₃

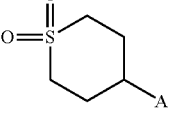
Q₄₄

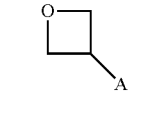
Q₄₇

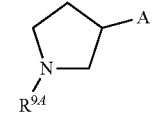
Q₈₇

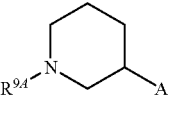
Q₈₉

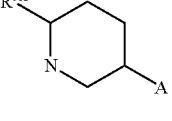
Q₉₀

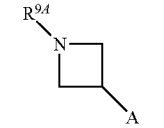
Q₁₀₇ wherein:

A is the position of attachment to the -methyl- moiety; and

R⁹ᴬ is hydrogen, C₁-C₂alkyl (e.g. methyl), C₁-C₂fluoroalkyl (e.g. C₁fluoroalkyl), —C(O)C₁-C₃alkyl (e.g. —C(O)methyl), —C(O)C₁-C₂fluoroalkyl (e.g. —C(O)C₁fluoroalkyl) or C₁-C₂alkoxy.

More preferably, Q is one of the sub-formulae Q¹, Q₂, Q₄, Q₆, Q₇, Q₃₃, Q₃₄, Q₄₁, Q₄₂, Q₄₃, Q₄₄, Q₈₇, Q₈₉ or Q₉₀. Even more preferably, Q is one of the sub-formulae Q₂, Q₆, Q₇, Q₃₃, Q₃₄, Q₄₁, Q₄₂, Q₄₃, Q₄₄, Q₈₇, Q₈₉ or Q₉₀.

Yet more preferably, Q is one of the sub-formulae $Q_2$, $Q_7$, $Q_{87}$ or $Q_{90}$. Furthermore preferably, Q is one of the sub-formulae $Q_2$, $Q_7$ or Qgo.

Most preferably, Q is sub-formula $Q_7$.

Preferably, $R^{9A}$ is —C(O)$C_1$-$C_3$alkyl (e.g. —C(O)methyl) or —C(O)$C_1$-$C_2$fluoroalkyl (e.g. —C(O)$C_1$fluoroalkyl).

In one preferable embodiment of the invention (which e.g. can apply to all aspects and/or embodiments of the invention), $R^8$ is hydrogen, and $R^9$ is tetrahydro-2H-pyran-4-yl

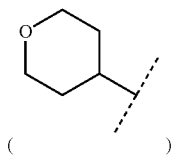

or (tetrahydro-2H-pyran-4-yl)-methyl-. In this embodiment, preferably, Y is $CR^8R^9$. When $R^9$ is (tetrahydro-2H-pyran-4-yl)-methyl-, then $R^9$ is $Q_7$-methyl- wherein $Q_7$ is

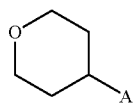

A wherein A is the position of attachment to the -methyl-moiety.

In another preferable embodiment (which e.g. can apply to all aspects and/or embodiments of the invention), $R^8$ is hydrogen and $R^9$ is Het or Het-$CH_2$— as defined herein. In this embodiment, more preferably, $R^8$ is hydrogen and $R^9$ is Het as defined herein. In this embodiment, preferably, Y is $CR^8R^9$.

Preferably, e.g. in all aspects and/or embodiments of the invention, Het is a heteroaryl (in particular monocyclic heteroaryl), attached at a ring-carbon, which is optionally substituted by 1, 2 or 3 (in particular 1 or 2, e.g. 1) ring-carbon substituents independently being $C_1$-$C_2$alkyl, $C_1$fluoroalkyl, $C_1$-$C_2$alkyl-C(O)—, $C_1$fluoroalkyl-C(O)—, hydroxy (including any oxo tautomer), ethynyl, prop-1-ynyl, $C_1$-$C_2$alkoxy, $C_1$fluoroalkoxy, fluorine, chlorine, bromine, cyano or nitro, provided that any chlorine, bromine, alkoxy or fluoroalkoxy is not substituted at any ring-carbon bonded directly to a ring-nitrogen of the heteroaryl;

and/or, in the case of a 5-membered heteroaryl ring containing a ring-nitrogen atom not partaking in a C═N ring double bond, the heteroaryl is optionally substituted on the ring-nitrogen atom not partaking in a C═N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-S(O)$_2$— substituent.

More preferably, e.g. in all aspects and/or embodiments of the invention, Het is a heteroaryl (in particular monocyclic heteroaryl), attached at a ring-carbon, which is optionally substituted by 1 or 2 (in particular 1) ring-carbon substituents independently being $C_1$-$C_2$alkyl (in particular methyl), $C_1$fluoroalkyl (in particular $CF_3$), $C_1$-$C_2$alkyl-C(O)— (in particular Me-C(O)—), $C_1$fluoroalkyl-C(O)—, ethynyl, prop-1-ynyl, fluorine or cyano;

and/or, in the case of a 5-membered heteroaryl ring containing a ring-nitrogen atom not partaking in a C═N ring double bond, the heteroaryl is optionally substituted on the ring-nitrogen atom not partaking in a C═N ring double bond by one $C_1$-$C_2$alkyl (e.g. methyl), $C_1$fluoroalkyl, methyl-C(O)— or $C_1$fluoroalkyl-C(O)— substituent.

More preferably, e.g. in all aspects and/or embodiments of the invention, Het is a heteroaryl (in particular monocyclic heteroaryl), attached at a ring-carbon, which is optionally substituted by 1 or 2 (in particular 1) ring-carbon substituents independently being $C_1$-$C_2$alkyl (in particular methyl), $C_1$fluoroalkyl (in particular $CF_3$), fluorine or cyano;

and/or, in the case of a 5-membered heteroaryl ring containing a ring-nitrogen atom not partaking in a C═N ring double bond, the heteroaryl is optionally substituted on the ring-nitrogen atom not partaking in a C═N ring double bond by one methyl substituent.

Preferably, e.g. in all aspects and/or embodiments of the invention, Het is an optionally substituted monocyclic heteroaryl, attached at a ring-carbon. Such as monocyclic heteroaryl can be 5-membered or 6-membered monocyclic heteroaryl.

More preferably, e.g. in all aspects and/or embodiments of the invention, Het is an optionally substituted monocyclic heteroaryl, attached at a ring-carbon, which is:

pyridinyl (preferably pyridin-3-yl or most preferably pyridin-2-yl), pyrazolyl (preferably pyrazol-5-yl or pyrazol-4-yl, or most preferably pyrazol-3-yl), imidazolyl (preferably imidazol-2-yl), pyrazinyl, pyrimidinyl (preferably pyrimidin-4-yl), pyridazinyl (preferably pyridazin-3-yl), triazolyl (e.g. 1,2,3-triazolyl), tetrazol-5-yl, oxazolyl, thiazolyl, isoxazolyl, isothiazolyl or oxadiazolyl; optionally present (e.g. where chemically possible) as an agrochemically acceptable salt thereof (such as an agrochemically acceptable acid addition salt thereof).

Even more preferably, e.g. in all aspects and/or embodiments of the invention, Het is an optionally substituted monocyclic heteroaryl, attached at a ring-carbon, which is: pyridinyl (preferably pyridin-3-yl or most preferably pyridin-2-yl), pyrazolyl (preferably pyrazol-5-yl or pyrazol-4-yl, or most preferably pyrazol-3-yl), imidazolyl (preferably imidazol-2-yl), pyrazinyl, pyrimidinyl (preferably pyrimidin-4-yl), pyridazinyl (preferably pyridazin-3-yl), triazolyl (e.g. 1,2,3-triazolyl), or tetrazol-5-yl; optionally present (e.g. where chemically possible) as an agrochemically acceptable salt thereof (such as an agrochemically acceptable acid addition salt thereof).

Still more preferably, e.g. in all aspects and/or embodiments of the invention, Het is an optionally substituted monocyclic heteroaryl, attached at a ring-carbon, which is: pyridinyl (preferably pyridin-3-yl or most preferably pyridin-2-yl), pyrazolyl (preferably pyrazol-5-yl or pyrazol-4-yl, or most preferably pyrazol-3-yl), imidazolyl (preferably imidazol-2-yl), pyrazinyl, pyrimidinyl (preferably pyrimidin-4-yl), or pyridazinyl (preferably pyridazin-3-yl); optionally present (e.g. where chemically possible) as an agrochemically acceptable salt thereof (such as an agrochemically acceptable acid addition salt thereof).

Yet more preferably, e.g. in all aspects and/or embodiments of the invention, Het is an optionally substituted monocyclic heteroaryl, attached at a ring-carbon, which is: pyridin-3-yl, pyridin-2-yl, or pyrazolyl (preferably pyrazol-5-yl or pyrazol-4-yl, or most preferably pyrazol-3-yl); optionally present (e.g. where chemically possible) as an agrochemically acceptable salt thereof (such as an agrochemically acceptable acid addition salt thereof).

Most preferably, e.g. in all aspects and/or embodiments of the invention, Het is an optionally substituted monocyclic heteroaryl, attached at a ring-carbon, which is: pyridin-2-yl or pyrazol-3-yl; optionally present (e.g. where chemically possible) as an agrochemically acceptable salt thereof (such as an agrochemically acceptable acid addition salt thereof).

It is particularly preferred (e.g. in all aspects and/or embodiments of the invention) that, in Het, any ring-carbon atom, which is directly bonded to the ring-carbon atom which is the point of attachment (e.g. or i.e. which is the point of attachment to the central carbon atom within the $Y=CR^8R^9$ moiety (for Het), or which is the point of attachment to the —$CH_2$— moiety (for Het-$CH_2$—), is unsubstituted. Therefore, for example, preferably, when Het is an optionally substituted pyridin-2-yl (optionally present as an agrochemically acceptable salt thereof), then the ring-carbon atom at the 3-position of the ring (calculated with respect to the pyridine ring nitrogen atom) is unsubstituted.

Preferably, e.g. in all aspects and/or embodiments of the invention, $R^{10}$, $R^{11}$, $R^{12}$ and/or $R^{13}$ are, independently of each other, hydrogen or $C_1$-$C_2$alkyl (in particular hydrogen or methyl).

Preferably, two, three or all of $R^{10}$, $R^{11}$, $R^{12}$ and $R^{13}$ are hydrogen.

Most preferably, $R^{10}$, $R^{11}$, $R^{12}$ and $R^{13}$ are hydrogen.

In a particularly preferable embodiment of the invention (which e.g. can apply to all aspects and/or embodiments of the invention):

Y is O or $CR^8R^9$ (preferably $CR^8R^9$); and $R^4$ and $R^5$ are taken together and are —$(CH_2)_{n4}$— or —$(CH_2)_{n5}$—$C(R^{7a})(R^{7b})$—$(CH_2)_{n6}$—;
wherein $R^{7a}$ is $C_1$-$C_2$alkyl; $R^{7b}$ is hydrogen or $C_1$-$C_2$alkyl;

n4 is 2 or 3; and n5 and n6 are independently 0, 1 or 2 provided that n5+n6 is 1 or 2.

In this particularly preferable embodiment, more preferably, Y is O or $CR^8R^9$ (preferably $CR^8R^9$) wherein $R^8$ and $R^9$ are, independently of each other, hydrogen or $C_1$-$C_3$alkyl (in particular, this $C_1$-$C_3$alkyl can be $C_1$-$C_2$alkyl such as methyl).

In this particularly preferable embodiment, even more preferably Y is O or $CH_2$; or, most preferably, Y is $CH_2$.

In this particularly preferable embodiment, more preferably, $R^3$ and $R^6$, independently of each other, are hydrogen, $C_1$-$C_3$alkyl (in particular $C_1$-$C_2$alkyl such as methyl) or $C_1$-$C_3$alkoxy$C_1$-$C_3$alkyl (in particular $C_1$-$C_2$alkoxy$C_1$-$C_2$alkyl); provided that no more than one (in particular none) of $R^3$ and $R^6$ is alkoxyalkyl.

In this particularly preferable embodiment, even more preferably, $R^3$ and $R^6$, independently of each other, are hydrogen or $C_1$-$C_2$alkyl (preferably hydrogen or methyl); and $R^4$ and $R^5$ taken together are —$(CH_2)_{n4}$— wherein n4 is 2 or 3.

In a particularly preferable embodiment of the invention (which e.g. can apply to all aspects and/or embodiments of the invention), the compound of formula (I) is a compound described in any of Tables 1 to 25, as described and/or illustrated herein, optionally present (e.g. where chemically possible) as an agrochemically acceptable salt thereof. In an alternative particularly preferable embodiment of the invention (which e.g. can apply to all aspects and/or embodiments of the invention), the compound of formula (I) is a compound described Table 26 or 27, as described and/or illustrated herein, optionally present (e.g. where chemically possible) as an agrochemically acceptable salt thereof. More preferably (e.g. in all aspects and/or embodiments of the invention), the compound of formula (I) is a compound described in any of Tables 1, 3, 5, 8, 9, 10, 11, 12, 14, 15, 16, 17, 18, 19, 20, 21, 22, 23, 24 or 25 (or alternatively in Table 26 or 27), as described and/or illustrated herein, optionally present (e.g. where chemically possible) as an agrochemically acceptable salt thereof. Even more preferably (e.g. in all aspects and/or embodiments of the invention), the compound of formula (I) is a compound described in any of Tables 1, 3, 5, 8, 9, 10, 11, 12, 14, 15, 16 or 25 (or alternatively in Table 26 or 27), as described and/or illustrated herein, optionally present (e.g. where chemically possible) as an agrochemically acceptable salt thereof.

In one more particularly preferable embodiment of the invention (which e.g. can apply to all aspects and/or embodiments of the invention), the compound of formula (I) is compound A-1, A-2, A-3, A-4, A-5, A-6, A-7, A-8, A-9, A-10, A-11, A-12, A-13, A-14 or A-15, as described and/or illustrated herein, optionally present (e.g. where chemically possible) as an agrochemically acceptable salt thereof. In an alternative more particularly preferable embodiment of the invention (which e.g. can apply to all aspects and/or embodiments of the invention), the compound of formula (I) is compound A-16, A-17 or A-18, as described and/or illustrated herein, optionally present (e.g. where chemically possible) as an agrochemically acceptable salt thereof. In a further alternative more particularly preferable embodiment of the invention (which e.g. can apply to all aspects and/or embodiments of the invention), the compound of formula (I) is compound A-20 (=compound 11.10), A-22 (=compound 1.10), A-25 (=compound 14.23), A-27 (=compound 12.02), A-28 (=compound 12.10), A-30 (=compound 12.15), A-31 (=compound 9.02), A-32 (=compound 9.10), A-33 (=compound 1.02), A-34 (=compound 1.15), A-35 (=compound 5.02), A-36 (=compound 5.10), A-37 (=compound 5.15), A-38 (=compound 11.02), A-39 (=compound 11.15), A-40 (=compound 25.10) or A-41 (=compound 14.06), as described and/or illustrated herein, optionally present (e.g. where chemically possible) as an agrochemically acceptable salt thereof. In a further alternative more particularly preferable embodiment of the invention (which e.g. can apply to all aspects and/or embodiments of the invention), the compound of formula (I) is compound A-19, A-21, A-23, A-24, A-26, A-29, P-3, P-4, P-5 or P-7, as described and/or illustrated herein, optionally present (e.g. where chemically possible) as an agrochemically acceptable salt thereof.

In a yet more particularly preferable embodiment of the invention (which e.g. can apply to all aspects and/or embodiments of the invention), the compound of formula (I) is compound A-2, A-3, A-4, A-5, A-8, A-9, A-10, A-12, A-13, A-14, A-15, A-16, A-17 or A-18, as described and/or illustrated herein, optionally present (e.g. where chemically possible) as an agrochemically acceptable salt thereof; or alternatively is compound A-6, as described and/or illustrated herein, optionally present as an agrochemically acceptable salt thereof. In an alternative yet more particularly preferable embodiment of the invention (which e.g. can apply to all aspects and/or embodiments of the invention), the compound of formula (I) is compound A-20, A-22, A-27, A-28, A-33, A-34, A-35, A-36, A-38, A-39, A-40 or A-41, as described and/or illustrated herein, optionally present (e.g. where chemically possible) as an agrochemically acceptable salt thereof. In a further alternative yet more particularly preferable embodiment of the invention (which e.g. can apply to all aspects and/or embodiments of the invention), the compound of formula (I) is compound A-19, A-21, A-23, A-24, A-26, P-3, P-5 or P-7, as described and/or illustrated herein, optionally present (e.g. where chemically possible) as an agrochemically acceptable salt thereof.

Depending on the nature of the substituents G, $R^1$, $R^2$, $R^3$, $R^4$, $R^5$, $R^6$, $R^7$ and $R^8$, compounds of formula (I) may exist in different isomeric forms. When G is hydrogen, for example, compounds of formula (I) may exist in different tautomeric forms:

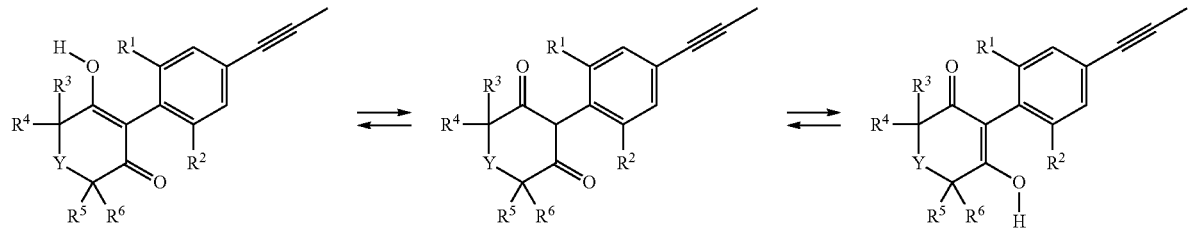

Also, when substituents contain double bonds, cis- and trans-isomers can exist. This invention covers all such isomers and tautomers and mixtures thereof in all proportions. These isomers, too, are within the scope of the claimed compounds of the formula (I).

Processes for preparation of compounds, e.g. compounds of formula (I)

Processes for preparation of compounds, e.g. a compound of formula (I) (which optionally can be an agrochemically acceptable salt thereof), are now described, and form further aspects of the present invention.

A compound of formula I, wherein G is:
—C($X^a$)—$R^a$, —C($X^b$)—$X^c$—$R^b$, —C($X^d$)—N($R^c$)—$R^d$, —$SO_2$—$R^e$, —P($X^e$)($R^f$)—$R^g$, —$CH_2$—$X^f$—$R^h$; or phenyl-$CH_2$— or phenyl-CH($C_1$-$C_2$alkyl)- (in each of which the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or heteroaryl-$CH_2$— or heteroaryl-CH($C_1$-$C_2$alkyl)- (in each of which the heteroaryl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or phenyl-C(O)—$CH_2$— (wherein the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro); or $C_1$-$C_6$alkoxy-C(O)—$CH_2$—, $C_1$-$C_6$alkoxy-C(O)—CH=CH—, $C_2$-$C_7$alken-1-yl-$CH_2$—, $C_2$-$C_7$alken-1-yl-CH($C_1$-$C_2$alkyl)-, $C_2$-$C_4$fluoroalken-1-yl-$CH_2$—, $C_2$-$C_7$alkyn-1-yl-$CH_2$—, or $C_2$-$C_7$alkyn-1-yl-CH($C_1$-$C_2$alkyl)-;

may be prepared by treating a compound of formula (A), which is a compound of formula I wherein G is H, (a) with a reagent G1-Z, wherein G1-Z is an alkylating agent (wherein G1 is an organic group according to G within the compound of formula (I) and which is linked by a non-carbonyl, non-thiocarbonyl carbon atom) such as an organic halide (in which Z=halogen such as chlorine, bromine or iodine); wherein the organic halide (e.g. chloride) can typically be a substituted alkyl halide (e.g. chloride) such as a chloromethyl alkyl ether Cl—$CH_2$—$X^f$—$R^h$ wherein $X^f$ is oxygen, a chloromethyl alkyl sulfide Cl—$CH_2$—$X^f$—$R^h$ wherein $X^f$ is sulphur, a suitable optionally substituted benzyl halide (e.g. chloride) such as Cl—$CH_2$-[optionally substituted phenyl], [optionally substituted phenyl]-C(O)—$CH_2$-[halogen e.g. Cl], $C_1$-$C_6$alkoxy-C(O)—$CH_2$-[halogen e.g. Cl], $C_1$-$C_6$alkoxy-C(O)—CH=CH-[halogen e.g. Cl], a suitable alkenyl or alkynyl halide (e.g. chloride) such as $C_2$-$C_7$alken-1-yl-$CH_2$-[halogen e.g. Cl] or $C_2$-$C_7$alkyn-1-yl-$CH_2$-[halogen e.g. Cl], or another organic halide suitable for preparing a (non-carbonyl, non-thiocarbonyl carbon)-linked G (or G1) group; or (b) [e.g. to prepare carbonyl-carbon-linked or thiocarbonyl-carbon-linked G groups] with an acylating agent such as a carboxylic acid, HO—C($X^a$)$R^a$, wherein $X^a$ is oxygen, an acid chloride, Cl—C($X^a$)$R^a$, wherein $X^a$ is oxygen, or an acid anhydride, [$R^aC(X^a)$]$_2$O, wherein $X^a$ is oxygen, or an isocyanate, $R^c$N=C=O, or a carbamoyl chloride, Cl—C($X^d$)—N($R^c$)—$R^d$ (wherein $X^d$ is oxygen and with the proviso that neither $R^c$ or $R^d$ is hydrogen), or a thiocarbamoyl chloride Cl—($X^d$)—N($R^c$)—$R^d$ (wherein $X^d$ is sulfur and with the proviso that neither $R^c$ or $R^d$ is hydrogen), or a chloroformate, Cl—C($X^b$)—$X^c$—$R^b$ (wherein $X^b$ and $X^c$ are oxygen), or a chlorothioformate Cl—C($X^b$)—$X^c$—$R^b$ (wherein $X^b$ is oxygen and $X^c$ is sulfur), or a chlorodithioformate Cl—C($X^b$)—$X^c$—$R^b$ (wherein $X^b$ and $X^c$ are sulfur), or an isothiocyanate, RcN=C=S; or (c) by sequential treatment with carbon disulfide and an alkylating agent; or (d) with a phosphorylating agent such as a phosphoryl chloride, Cl—P($X^e$)($R^f$)—$R^g$; or (e) with a sulfonylating agent such as a sulfonyl chloride Cl—$SO_2$—$R^e$, preferably in the presence of at least one equivalent of base.

Where substituents $R^4$ and $R^5$ are not equal to substituents $R^6$ and $R^7$, these reactions may produce, in addition to a compound of formula I, a second compound of formula (IA).

This invention covers both a compound of formula (I) and a compound of formula (IA), together with mixtures of these compounds in any ratio, as shown below.

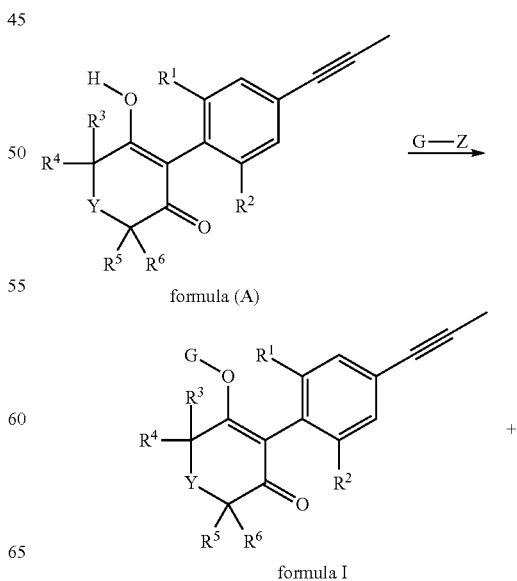

formula (A)

formula I

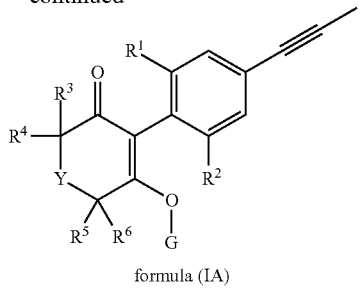

formula (IA)

The O-alkylation of cyclic 1,3-diones is known; suitable methods are described, for example, by T. Wheeler, U.S. Pat. No. 4,436,666. Alternative procedures have been reported by M. Pizzorno and S. Albonico, Chem. Ind. (London), (1972), 425-426; H. Born et al., J. Chem. Soc., (1953), 1779-1782; M. G. Constantino et al., Synth. Commun., (1992), 22 (19), 2859-2864; Y. Tian et al., Synth. Commun., (1997), 27 (9), 1577-1582; S. Chandra Roy et al., Chem. Letters, (2006), 35 (1), 16-17; P. K. Zubaidha et al., Tetrahedron Lett., (2004), 45, 7187-7188.

The O-acylation of cyclic 1,3-diones may be effected e.g. by procedures similar to those described, for example, by R. Haines, U.S. Pat. No. 4,175,135, and by T. Wheeler, U.S. Pat. Nos. 4,422,870, 4,659,372 and 4,436,666. Typically diones of formula (A) may be treated with an acylating agent preferably in the presence of at least one equivalent of a suitable base, and optionally in the presence of a suitable solvent. The base may be inorganic, such as an alkali metal carbonate or hydroxide, or a metal hydride, or an organic base such as a tertiary amine or metal alkoxide. Examples of suitable inorganic bases include sodium carbonate, sodium or potassium hydroxide, sodium hydride, and suitable organic bases include trialkylamines, such as trimethylamine and triethylamine, pyridines or other amine bases such as 1,4-diazobicyclo[2.2.2]-octane and 1,8-diazabicyclo[5.4.0]undec-7-ene. Preferred bases include triethylamine and pyridine. Suitable solvents for this reaction are selected to be compatible with the reagents and include ethers such as tetrahydrofuran and 1,2-dimethoxyethane and halogenated solvents such as dichloromethane and chloroform.

Certain bases, such as pyridine and triethylamine, may be employed successfully as both base and solvent. For cases where the acylating agent is a carboxylic acid, acylation is preferably effected in the presence of a known coupling agent such as 2-chloro-1-methylpyridinium iodide, N,N'-dicyclohexylcarbodiimide, 1-(3-dimethylaminopropyl)-3-ethylcarbodiimide and N,N'-carbodiimidazole, and optionally in the presence of a base such as triethylamine or pyridine in a suitable solvent such as tetrahydrofuran, dichloromethane or acetonitrile. Suitable procedures are described, for example, by W. Zhang and G. Pugh, Tetrahedron Lett., (1999), 40 (43), 7595-7598; T. Isobe and T. Ishikawa, J. Org. Chem., (1999), 64 (19), 6984-6988 and K. Nicolaou, T. Montagnon, G. Vassilikogiannakis, C. Mathison, J. Am. Chem. Soc., (2005), 127(24), 8872-8888.

Phosphorylation of a compound of formula (A) may be effected e.g. using a phosphoryl halide or thiophosphoryl halide and a base e.g. by procedures analogous to those described by L. Hodakowski, U.S. Pat. No. 4,409,153.

Sulfonylation of a compound of formula (A) may be achieved e.g. using an alkyl or aryl sulfonyl halide, preferably in the presence of at least one equivalent of base, for example by the procedure of C. Kowalski and K. Fields, J. Org. Chem., (1981), 46, 197-201.

Compounds of formula (A), wherein Y is S(O) or S(O)$_2$ may be prepared from compounds of formula (A) wherein Y is S by oxidation, e.g. according to a procedure analogous to that of E. Fehnel and A. Paul, J. Am. Chem. Soc., (1955), 77, 4241-4244.

A compound of formula (A), wherein Y is O, S, C(O) or $CR^8R^9$ may be prepared via the cyclisation of a compound of formula (B), preferably in the presence of an acid or base, and optionally in the presence of a suitable solvent, e.g. by analogous methods to those described by T. Wheeler, U.S. Pat. No. 4,209,532. The compounds of the formula (B) have been particularly designed as intermediates in the synthesis of the compounds of the formula I. Compounds of formula (B) wherein R is hydrogen or $C_1$-$C_4$alkyl, (especially methyl, ethyl and tert-butyl) may be cyclised under acidic conditions, preferably in the presence of a strong acid such as sulfuric acid, polyphosphoric acid or Eaton's reagent, optionally in the presence of a suitable solvent such as acetic acid, toluene or dichloromethane. A compound of formula (B) wherein R is alkyl (preferably methyl or ethyl) may also be cyclised under basic conditions in the presence of at least one equivalent of a strong base in a solvent such as tetrahydrofuran, toluene, dimethylsulfoxide or N,N-dimethylformamide. Suitable bases include potassium tert-butoxide, lithium diisopropylamide, sodium bis(trimethylsilyl)amide or sodium hydride. A compound of formula (B), wherein R is alkyl, may be produced from a compound of formula (B), wherein R is H, by esterification under known conditions (for example by treatment with an alcohol, R—OH, in the presence of an acid catalyst).

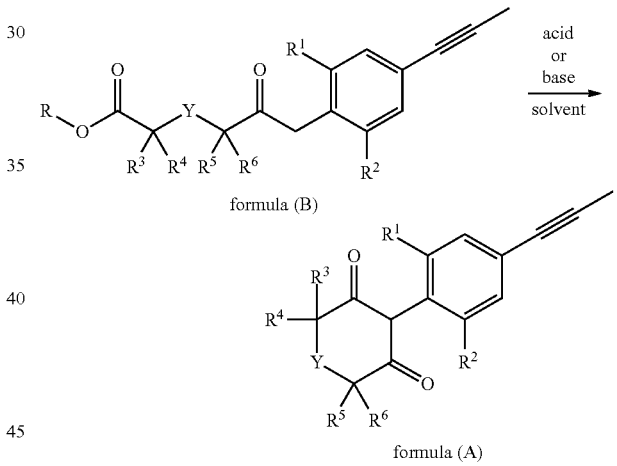

formula (B)

formula (A)

A compound of formula (B), wherein R is H may be prepared by hydrolysis of a compound of formula (C) wherein R is H or alkyl and R' is alkyl (preferably methyl or ethyl), followed by acidification of the reaction mixture to effect decarboxylation, e.g. by similar processes to those described by, for example, T. Wheeler, U.S. Pat. No. 4,209,532. Alternatively, a compound of formula (B), wherein R is alkyl or H may be prepared from a compound of formula (C), wherein R' is alkyl (preferably methyl), through a Krapcho decarboxylation procedure, e.g. under known conditions using known reagents (see for example G. Quallich, P. Morrissey, Synthesis, (1993), (1), 51-53).

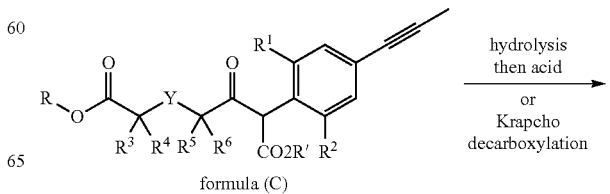

formula (C)

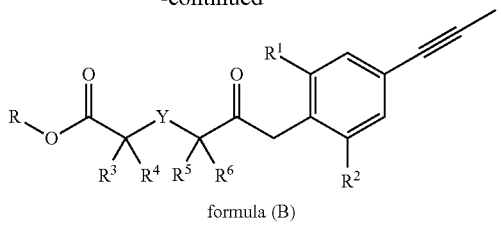

formula (B)

A compound of formula (C) wherein R is alkyl may be prepared by treating a compound of formula (D) with a suitable carboxylic acid chloride of formula (E), wherein R is alkyl, under basic conditions. Suitable bases include potassium tert-butoxide, sodium bis(trimethyl-silyl)amide and lithium diisopropylamide and the reaction is preferably conducted in a suitable solvent (such as tetrahydrofuran or toluene) at a temperature between −78° C. and 30° C. Under similar conditions, a compound of formula (C), wherein R is H, may be prepared from a suitable anhydride of formula (F).

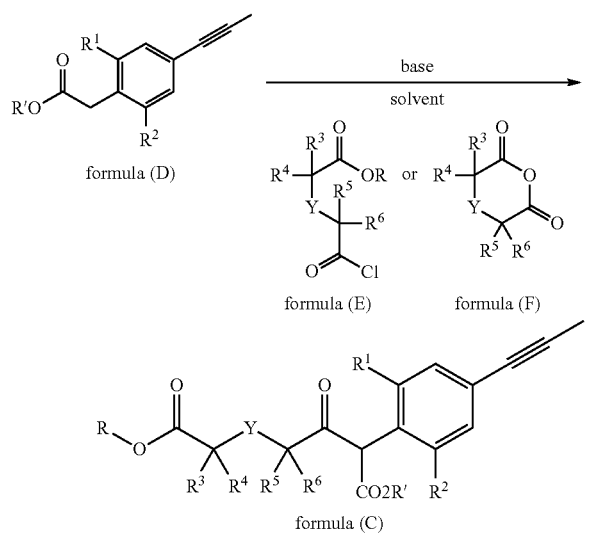

Compounds of formula (E) and formula (F) are known (see, for example T. Terasawa and T. Okada, J. Org. Chem., (1977), 42 (7), 1163-1169; G. Bennett, W. Houlihan, R. Mason; R. Engstrom, J. Med. Chem., (1976), 19 (5), 709-14; L. J. J. Hronowski, Lucjan W. A. Szarek, Canadian Journal of Chemistry (1988), 66(1), 61-70; S. F. Birch, V. E. Gripp, D. T. McAllan, W. S. Nathan, Journal of the Chemical Society (1952), 1363-8; S. Kitamura, T. D. Aicher, Gonzales, Steve; Y. Le Huerou, S. A. Pratt, Y. Nakada, WO 2008011130; O. Jentzer, M. Guglieri, WO 2009092795), or may be made by similar methods from commercially available starting materials.

Compounds of formula (D), wherein R' is $C_1$-$C_4$alkyl, can be prepared by reacting compounds of formula (G) with propyne in the presence of a suitable catalyst, optionally a suitable additive, optionally in a suitable solvent at a suitable temperature. Suitable catalysts include transition metal salts or complexes of transition metal salts (for example palladium acetate, bis(triphenylphosphine) palladium(II) dichloride, tetrakis(triphenylphosphine)palladium(O), bis(triphenylphosphine) nickel(II) dichloride and tris(acetylacetonato) iron(III)), in an amount typically 0.001-25% with respect to a compound of formula (G). Suitable additives include copper salts (for example copper(I) iodide in an amount typically 0.001-50% with respect to a compound of formula (G)), and tetraalkyl ammonium salts. Suitable bases include diethylamine, triethylamine, piperidine and pyrrolidine, and suitable solvents include 1,4-dioxane, N,N-dimethylacetamide or N,N-dimethylformamide. Preferably the reaction is carried out using 0.05-10% bis(triphenylphosphine) palladium(II) dichloride (with respect to a compound of formula (G)), 0.05-10% triphenylphosphine (with respect to a compound of formula (G)), 0.05-25% copper(I) iodide (with respect to a compound of formula (G)), 5-200% tetrabutyl ammonium iodide (with respect to a compound of formula (G)), triethylamine and N,N-dimethylformamide at a temperature between 25° C. to 150° C. Such a reaction is an example of a Sonogashira coupling and similar reactions are known in the literature (see for example F. Labrie, S. Gauthier, J. Cloutier, J. Mailhot, S. Potvin, S. Dion, J.-Y. Sanceau, WO 2008124922; M. S. Viciu, S. P. Nolan, Modern Arylation Methods (2009), 183-220; R. Chinchilla, C. Najera, Chemical Reviews (2007), 107(3), 874-922; I. P. Beletskaya, G. V. Latyshev, A. V. Tsvetkov, N. V. Lukashev, Tetrahedron Letters (2003), 44(27), 5011-5013 and J. Mao, G. Xie, M. Wu, J. Guo, S. Ji, Advanced Synthesis & Catalysis (2008), 350(16), 2477-2482). In an alternative approach a compound of formula (D) may be prepared from a compound of formula (G) by reaction with a propynyl transfer reagent such as 1-propynyllithium, 1-propynylmagnesium bromide, 1-propynylmagnesium chloride, 1-propynylmagnesium iodide, 1-propynylzinc chloride, 1-propynylzinc bromide, 1-propynylzinc iodide, tributylpropynylstannane, 1-propyne-1-boronic acid (or ester thereof), 2-butynoic acid or 1-(trimethylsilyl)propyne, with a transition metal catalyst system under suitable conditions (see for example P. Wessig, G. Mueller, C. Pick, A. Matthes, Synthesis (2007), (3), 464-477; J. H. Chaplin, G. S. Gill, D. W. Grobelny, B. L. Flynn, G. Kremmidiotis, WO07087684; A. Akao, T. Tsuritani, S. Kii, K. Sato, N. Nonoyama, T. Mase, N. Yasuda, Synlett (2007), (1), 31-36. A. Coelho Coton, E. Sotelo Perez, F. Guitian Rivera, A. Gil Gonzalez, WO 2011048247; C. H. Oh, S. H. Jung, Tetrahedron Letters (2000), 41(44), 8513-8516; D. Zhao, C. Gao, X. Su, Y. He, J. You, Y. Xue, Chemical Communications (2010), 46(47), 9049-9051; C. Yang, S. P. Nolan, Organometallics (2002), 21(6), 1020-1022). In another set of preferred conditions a compound of formula (G) is reacted with 1-propynylmagnesium bromide in the presence of 0.05-10% bis(triphenylphosphine) palladium(II) dichloride (with respect to a compound of formula (G)), in tetrahydrofuran at a temperature between 25° C. and 100° C., as described by J. H. Chaplin, G. S. Gill, D. W. Grobelny, B. L. Flynn, G. Kremmidiotis, WO 07087684. Compounds of formula (G) are known, or can be prepared by known methods using known reagents.

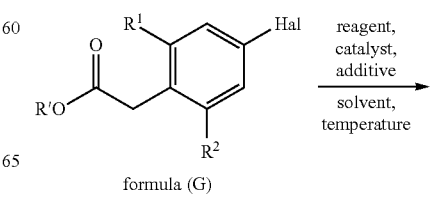

formula (G)

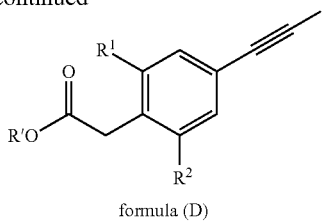

formula (D)

In a further approach a compound of formula (A) can be prepared directly from a compound of formula (L), under similar conditions described previously to convert a compound of formula (G) to a compound of formula (D).

In an alternative approach a compound of formula I, wherein G is preferably methyl or ethyl, may be prepared from a boronic acid of formula (H) or boronic ester of formula (S) by treatment with either 1-bromo-1-propyne or 1-iodo-1-propyne, preferably in the presence of a suitable catalyst system, a suitable base and/or a suitable solvent and/or at a suitable temperature. Similar reactions are known in the literature, and preferred conditions involve reacting a compound of formula (S) with 1-iodo-propyne in the presence of 0.005-25% palladium(II) chloride (with respect to a compound of formula (S)) and 1-10 equivalents potassium carbonate, preferably in a mixture of toluene, water and methanol at a temperature between 50° C.-150° C., as described by Y. Shi, X. Li, J. Liu, W. Jiang, L. Sun, Tetrahedron Letters (2010), 51(28), 3626-3628.

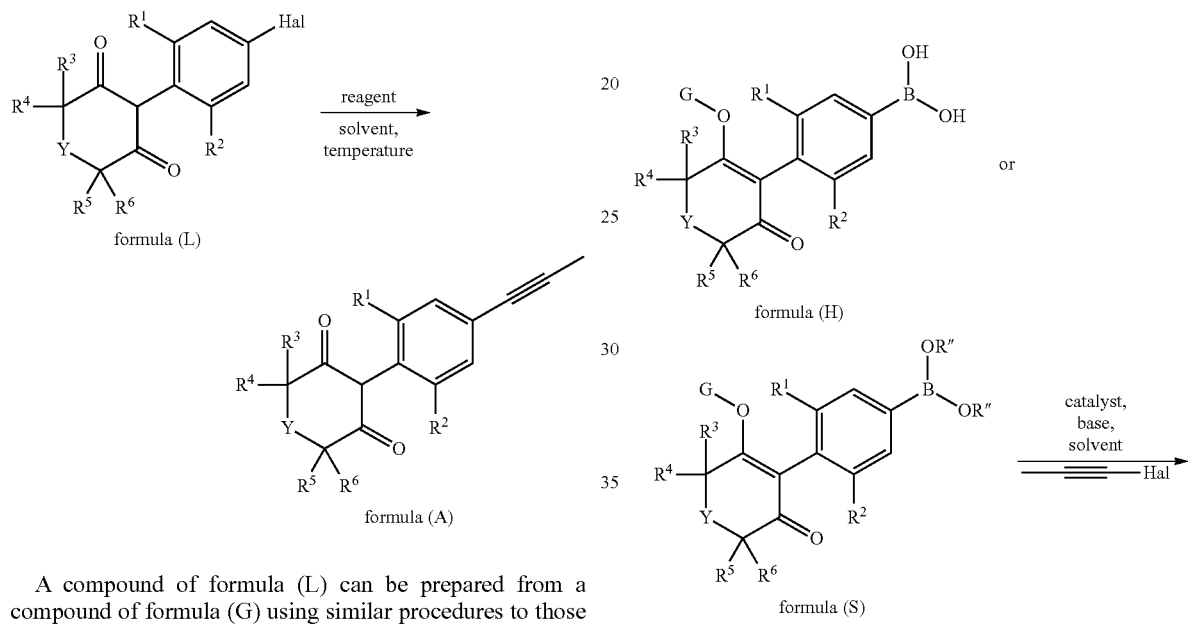

A compound of formula (L) can be prepared from a compound of formula (G) using similar procedures to those outlined previously.

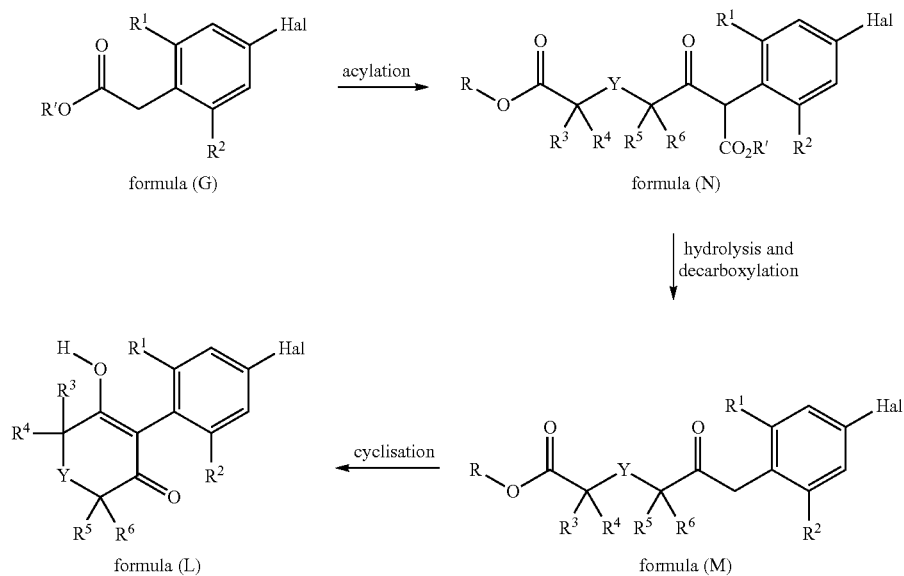

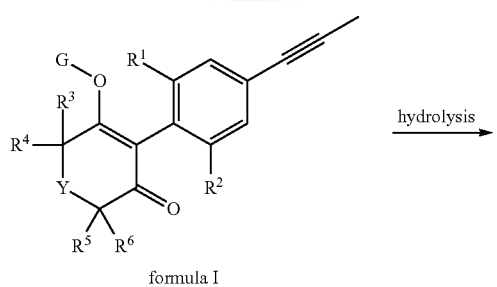

formula I

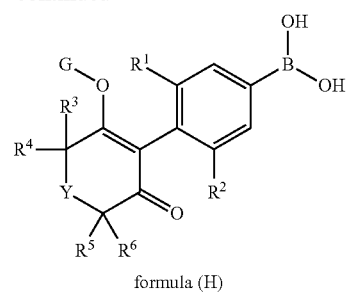

formula (H)

In an alternative approach a compound of formula (S) may be prepared from a compound of formula (V), wherein G is preferably methyl or ethyl, by C—H borylation with a suitable borylating agent, a suitable catalyst system, in a suitable solvent at a suitable temperature. Suitable catalysts include 1,5-cyclooctadiene)(methoxy)iridium(I) dimer in combination with 4,4'-di-tert-butyl-2,2'-dipyridyl, suitable borylating agents include bis(pinacolato)diboron or pinacol borane, and suitable solvents include hexane, octane, tetrahydrofuran and methyl tert-butyl ether. Similar examples are known in the literature (see for example J. F. Hartwig, Chemical Society Reviews (2011), 40(4), 1992-2002 and T. Ishiyama, N. Miyaura, Pure and Applied Chemistry (2006), 78(7), 1369-1375). Preferred conditions include treating a compound of formula (V) with 0.05-10% 1,5-cyclooctadiene)(methoxy)iridium(I) dimer (with respect to a compound of formula (V)), 0.05-10% 4,4'-di-tert-butyl-2,2'-dipyridyl (with respect to a compound of formula (V)), and 1-2 equivalents bis(pinacolato)diboron (with respect to a compound of formula (V)) in methyl tert-butyl ether at a temperature between 50° C.-150° C., optionally under microwave irradiation, as described by P. Harrisson, J. Morris, T. B. Marder, P. G. Steel, Organic Letters (2009), 11(16), 3586-3589.

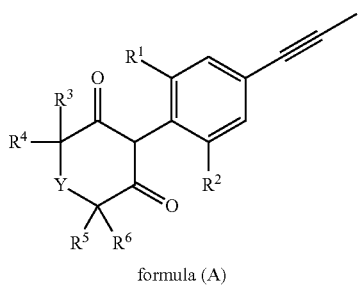

formula (A)

In one approach a compound of formula (S) may be prepared from a compound of formula (J), wherein Hal is preferably iodine or bromine, preferably by treatment with a suitable base (such as sodium hydride, potassium hydride or isopropylmagnesium chloride), in a suitable solvent (such as tetrahydrofuran or diethyl ether), followed by a metal-halogen exchange reaction (preferably by treatment with an alkyllithium reagent such as n-butyllithium, sec-butyllithium or tert-butyllithium, or an organomagnesium reagent such as isopropyl magnesium chloride) and subsequent treatment with a trialkylborate, B(OR")$_3$, (preferably trimethylborate) to give the corresponding boronate ester of formula (S). The boronic acid of formula (H) can be readily prepared form the boronate ester of formula (S) by known conditions.

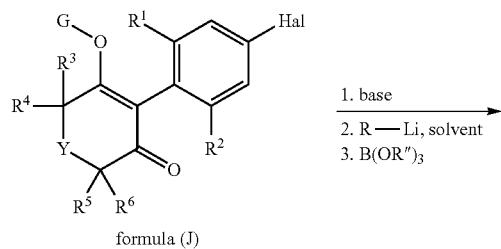

formula (J)

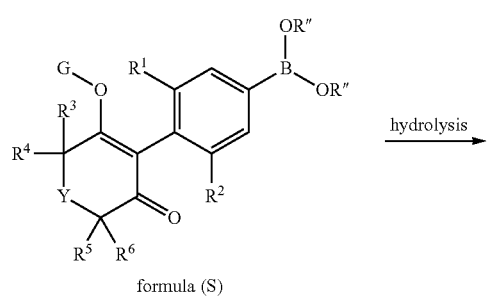

formula (S)

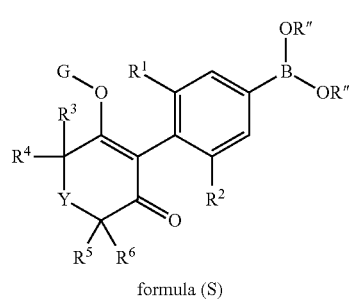

formula (V)

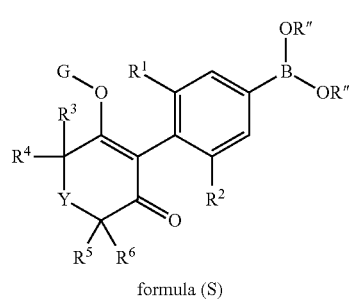

formula (S)

Compounds of formula (W) can be prepared from compounds of formula (X) using similar procedures described above, starting from compounds of formula (Z) which are known compounds.

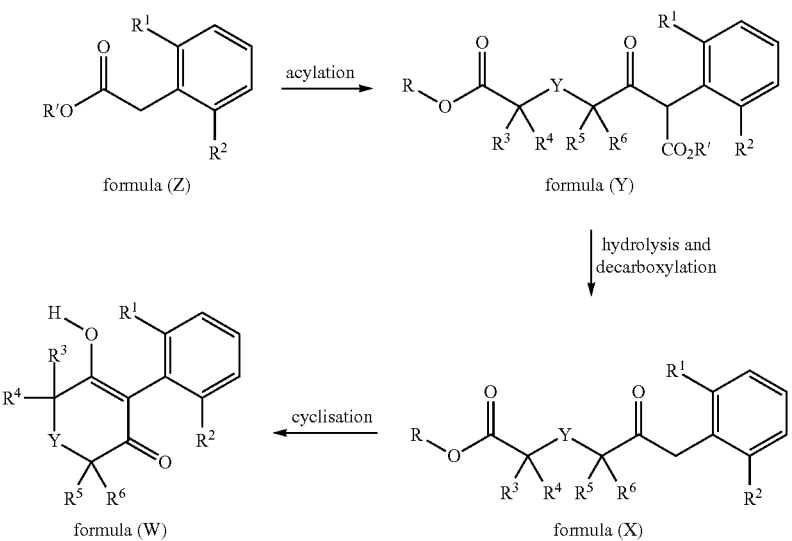

In a further approach a compound of formula (A) may be prepared via the rearrangement of a compound of formula (AA), in the presence of a reagent which promotes rearrangement, such as:

- a metal alkoxide (preferably in an amount equal to or greater than 100% with respect to compound of formula (AA), more preferably from 1 to 3 mole equivalents), preferably sodium methoxide or potassium methoxide; or
- a cyanide anion (for example 0.001 to 25 mole % potassium cyanide or 0.001 to 25 mol % sodium cyanide with respect to a compound of formula (AA)), or
- a cyanohydrin (preferably 0.001 to 25 mole % acetone cyanohydrin with respect to a compound of formula (AA)), or
- an acid, in particular:
  - a Brönsted acid (such as a mineral acid) or an organic acid, for example: Eaton's Reagent, sulfuric acid, hydrochloric acid, hydrogen chloride, p-toluenesulfonic acid, methanesulfonic acid, acetic acid or formic acid; or
  - a Lewis acid such as a metal halide, for example boron trifluoride, aluminium chloride, iron chloride, tin (IV) chloride, zinc chloride, zinc bromide, or lithium perchlorate, or a metal triflate such as scandium triflate or ytterbium triflate; or
  - a solid supported acid, such as silica- or resin-supported acids, for example Amberlyst 15; or
  - a mixture of any two or more of the above-mentioned acids.

This reaction (the rearrangement of a compound of formula (AA) to prepare a compound of formula (A)) is preferably performed in a suitable solvent (such as N,N-dimethylformamide) and/or at a suitable temperature (typically from 25 to 150° C., more particularly from 50 to 100° C.). Preferably, a compound of formula (AA) is treated with from 1 to 3 mole equivalents of sodium methoxide in N,N-dimethylformamide at a temperature of from 50° C. to 100° C.

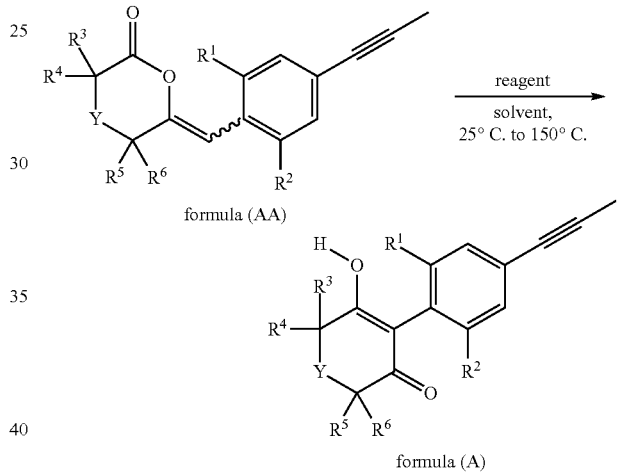

In one approach a compound of formula (AA) may be prepared from a compound of formula (AB) by treatment with a catalyst system which promotes lactonisation (such as palladium(II) dichloride, gold(I) chloride or silver carbonate), preferably 0.001-50% silver carbonate with respect to compound of formula (AB), in the presence of a suitable solvent (for example acetonitrile) at a suitable temperature (typically 25° C. to 150° C.), and optionally under microwave irradiation. Similar lactonisations are known in the literature (see for example WO 2008/071405, P. Huang and W. Zhou, Tetrahedron Asymmetry (1991), 2 (9), 875-878; and H. Harkat, J-M. Weibel, P. Pale, Tetrahedron Letters (2006), 47(35), 6273-6276).

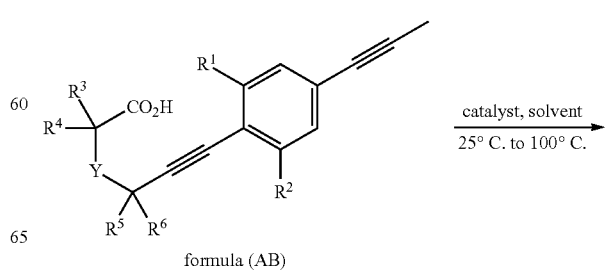

-continued

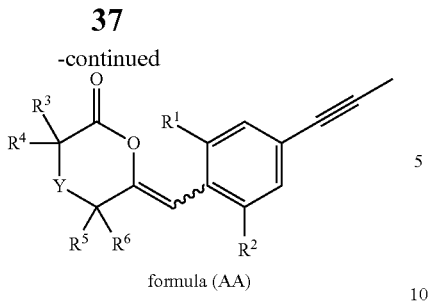

formula (AA)

Compounds of formula (AB) can be prepared from compounds of formula (AD) and compounds of formula (AE) (wherein R''' is preferably $C_1$-$C_4$alkyl), via compounds of formula (AC), by methods analogous to those described in WO 2008/071405. Alkynes of formula (AD) are known or can be prepared by known methods (see for example WO 2008/071405 and references therein, and J. P. Burke, M. Sabat, D. A. Iovan, W. H. Myers, J. J. Chruma, Organic Letters (2010), 12(14), 3192-3195). Compounds of formula (AE) are either known compounds or can be prepared from known reagents using known methods.

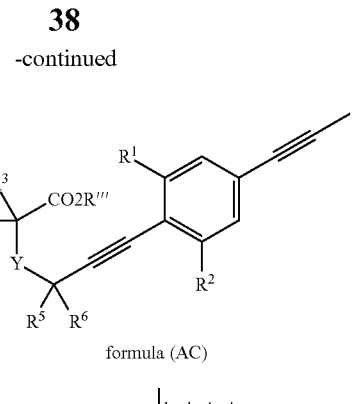

formula (AC)

↓ hydrolysis formula (AB)

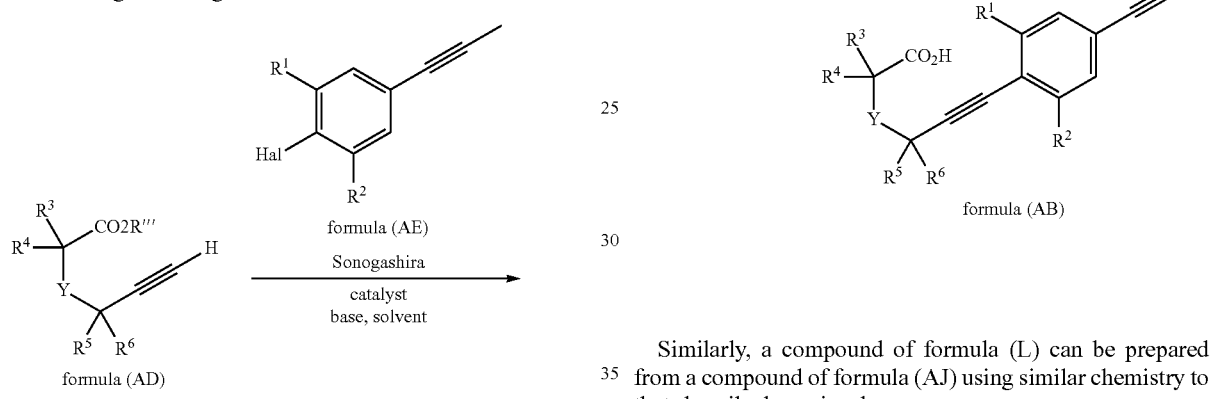

formula (AD)   formula (AE)
Sonogashira
catalyst
base, solvent

Similarly, a compound of formula (L) can be prepared from a compound of formula (AJ) using similar chemistry to that described previously.

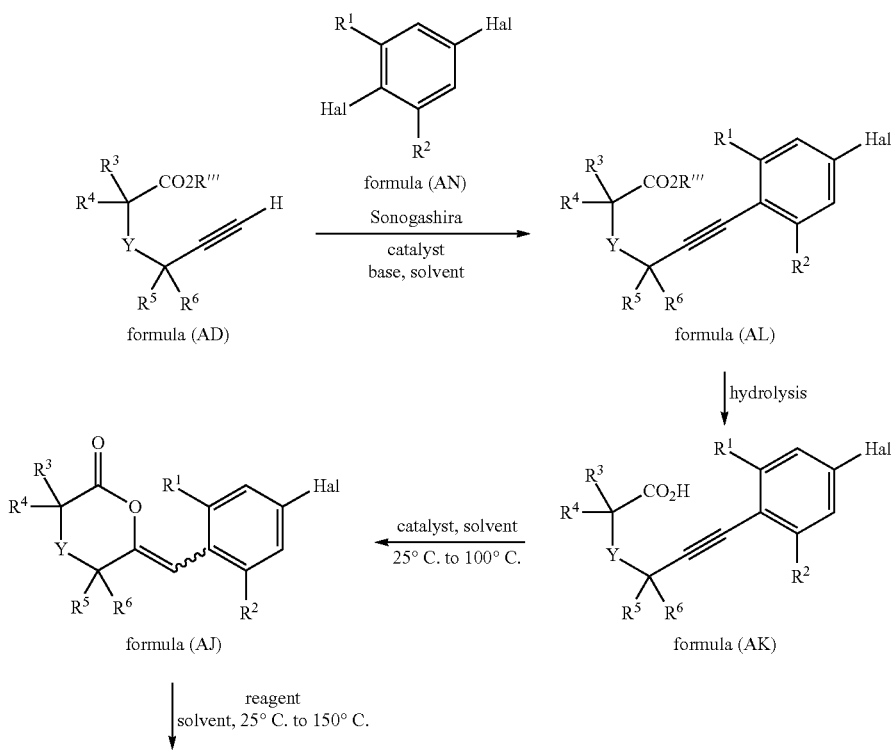

formula (AD)

formula (AN)
Sonogashira
catalyst
base, solvent formula (AL)

↓ hydrolysis formula (AK)

catalyst, solvent
25° C. to 100° C.

formula (AJ)

↓ reagent
solvent, 25° C. to 150° C.

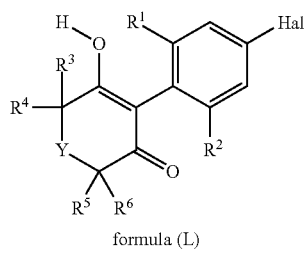

formula (L)

Similarly, a compound of formula (W) can be prepared from a compound of formula (AO) using similar chemistry to that described previously.

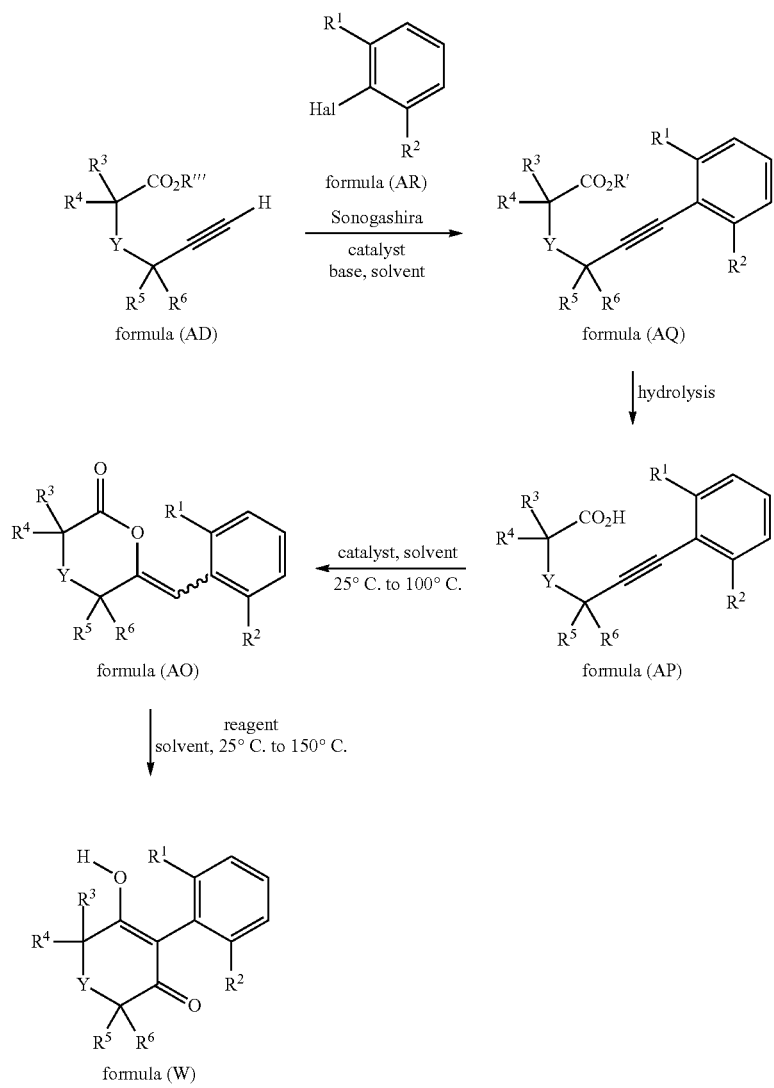

In a second approach a compound of formula (AA) may be prepared via the Baeyer-Villiger oxidation of a compound of formula (AS), preferably in a suitable solvent and/or at a suitable temperature (e.g. from 0° C. to 100° C.), and optionally in the presence of a suitable catalyst system. Suitable oxidants include peracetic acid and hydrogen peroxide. Preferred conditions are hydrogen peroxide and catalytic selenium dioxide (0.001-25 mol %) in tert-butanol at a temperature of from 0° C. to 100° C., as described by J. A. Guzman, V. Mendoza, E. Garcia, C. F. Garibay, L. Z. Olivares, L. A. Maldonado, Synthetic Communications (1995), 25(14), 2121-33.

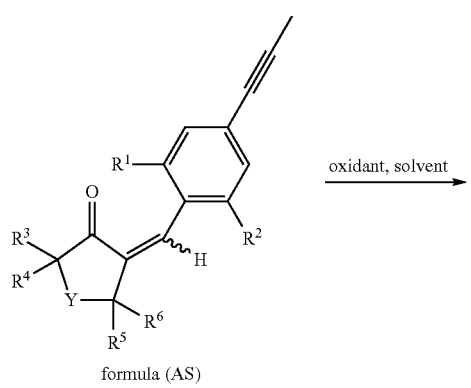

formula (AS)

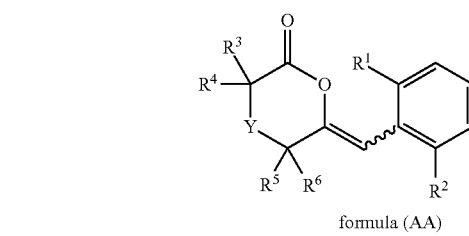

formula (AA)

A compound of formula (AS) may be prepared from a compound of formula (AU) by condensation with a benzaldehyde of formula (AT), in the presence of a suitable base and optionally in the presence of a suitable solvent (for similar examples see WO 2010136431; A. Lagrange, S. Forestier, G. Lang and B. Luppi, EP368717 A1; D. C. Rowlands, U.S. Pat. No. 2,776,239; E. Tamate, Journal of the Chemical Society of Japan, (1957), 78, 1293-7; R. Hernandez, D. Melian, T. Prange, E. Suarez, Heterocycles (1995), 41(3), 439-54; and J. Sotiropoulos, N. El Batouti, A. M. Lamazouere, Journal of Heterocyclic Chemistry (1987), 24(4), 907-12).

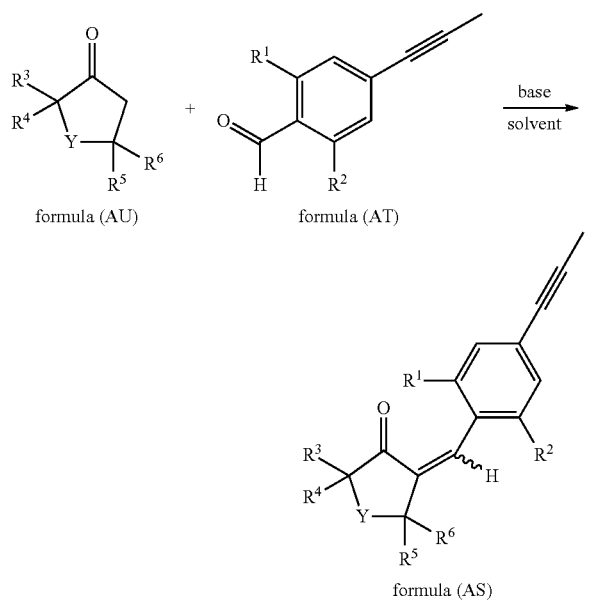

Preferably the base is a metal hydroxide, such as sodium hydroxide or potassium hydroxide, metal alkoxide such as sodium methoxide, sodium ethoxide or potassium tert-butoxide, or metal amide such as sodium amide. Preferably the solvent is dimethoxyethane, dioxane, tetrahydrofuran, diethyl ether or an alkyl alcohol, such as methanol, ethanol or isopropanol.

Compounds of formula (AU), wherein Y is O and or $CR^8R^9$, are known compounds (see for example X. Ye, M. D. Johnson, T. Diao, M. H. Yates, S. S. Stahl, Green Chemistry (2010), 12(7), 1180-1186; M. Newman and W. Reichle, Org. Synth. Coll. Vol. V., (1973), 1024; Y. Zal'kind, E. Venus-Danilova and V. Ryabtseva, Russian Journal of General Chemistry, (1950), 20, 2222-9; M. Bertrand, J. Dulcere, G. Gil, J. Grimaldi and P. Sylvestre-Panthet, Tetrahedron Letters (1976), (18), 1507-8), or may be prepared from known compounds by known methods.

Compounds of formula (AU), wherein Y is C(O), are known compounds (see for example N. J. Turro, D. R. Morton, E. Hedaya, M. E. Kent, P. D'Angelo, P. Schissel, Tetrahedron Letters (1971), (27), 2535-8; P. A. Krapcho, D. R. Rao, M. P. Silvon, B. Abegaz, Journal of Organic Chemistry (1971), 36(25), 3885-90; S. N. Crane, T. J. Jenkins, D. J. Burnell, Journal of Organic Chemistry (1997), 62(25), 8722-8729; S. N. Crane, D. J. Burnell, Journal of Organic Chemistry (1998), 63(4), 1352-1355; S. N. Crane, D. J. Burnell, Journal of Organic Chemistry (1998), 63(16), 5708-5710; C. E. Elliott, D. O. Miller, D. J. Burnell, Journal of the Chemical Society, Perkin Transactions 1 (2002), (2), 217-226), or may be prepared from known compounds by known methods.

Compounds of formula (AU), wherein Y is S, S(O) or $S(O)_2$ are known compounds (see for example E. R. Buchman, H. Cohen, Journal of the American Chemical Society (1944), 66, 847-8; A. W. D. Avison, F. Bergel, J. W. Haworth, U.S. Pat. No. 2,408,519: K. G. Mason, M. A. Smith, E. S. Stern, EJ. A. Elvidge, Journal of the Chemical Society [Section] C: Organic (1967), (21), 2171-6; T. A. Magee, Thomas A. DE 2033454; I. Tabushi, Y. Tamaru, Z. Yoshida, T. Sugimoto, Journal of the American Chemical Society (1975), 97(10), 2886-91; P. E. Aldrich, G. H. Berezin, B. I. Dittmar, I. Bruce, D E 2516554; I. Tabushi, Y. Tamaru, Z. Yoshida, Bulletin of the Chemical Society of Japan (1978), 51(4), 1178-82; D. N. Reinhoudt, J. Geevers, W. P. Trompenaars, S. Harkema, G. J. Van Hummel, Journal of Organic Chemistry (1981), 46(2), 424-34; F. Duus, Synthesis (1985), (6-7), 672-4; J. Schatz, Science of Synthesis (2002), 9, 287-422), or may be prepared from known compounds by known methods.

A compound of formula (AT) can be prepared from known compounds by known methods.

Similarly, a compound of formula (L) can also be prepared from a compound of formula (AJ) by rearrangement under similar conditions, as described previously. Compounds of formula (AY) are known compounds, or can be prepared from known reagents using known methods.

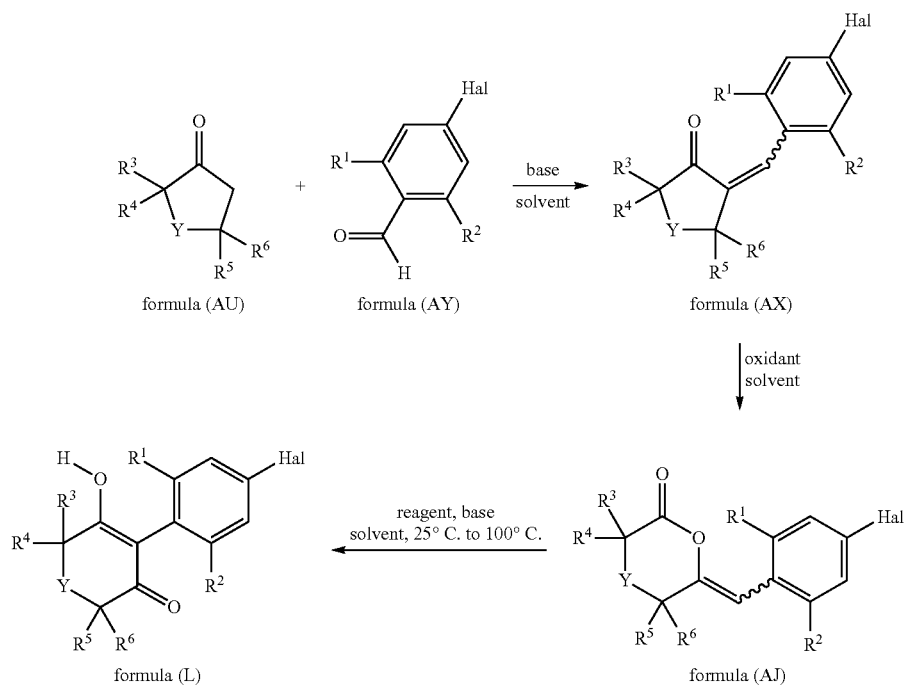

Similarly, a compound of formula (W) can also be prepared from a compound of formula (AO) by rearrangement under similar conditions, as described previously. Compounds of formula (AAA) are known compounds, or can be prepared from known reagents using known methods.

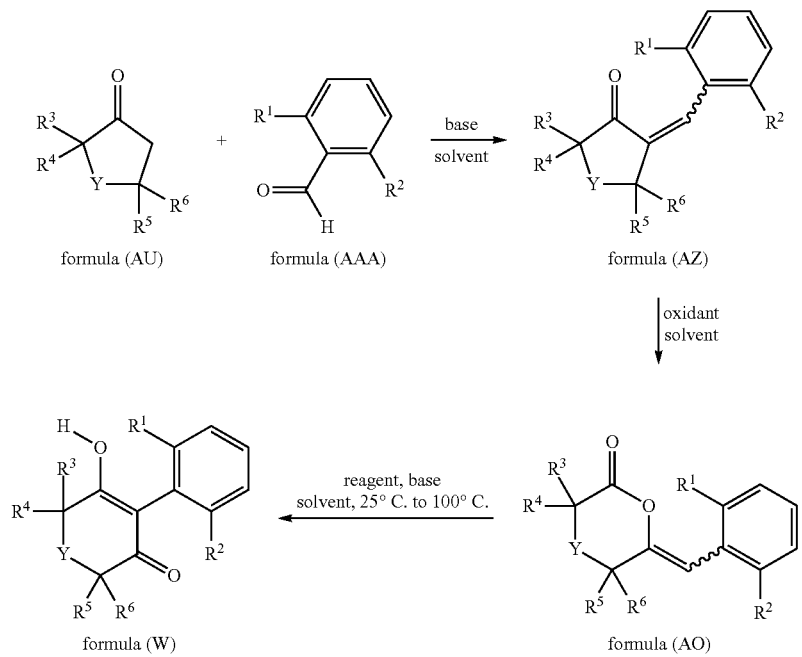

In a further approach, a compound of formula (A) can be prepared by a rearrangement of an epoxide of formula (AAB) catalysed by the presence of an acid, e.g. in the presence of a suitable solvent.

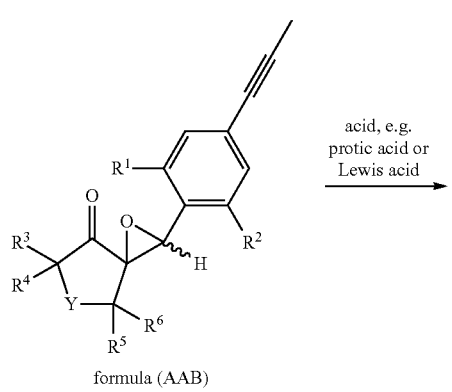

formula (AAB)

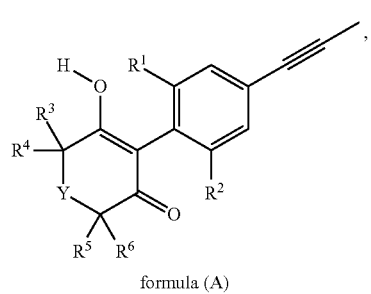

formula (A)

For the rearrangement of (AAB) to (A), suitable acids include a Brönsted acid such as a mineral acid or an organic acid, for example sulfuric acid, hydrochloric acid, hydrogen chloride, p-toluenesulfonic acid, methanesulfonic acid, acetic acid or formic acid, or a Lewis acid such as a metal halide, for example boron trifluoride, aluminium chloride, iron chloride, tin(IV) chloride, zinc chloride, zinc bromide, or lithium perchlorate, or a metal triflate such as scandium triflate or ytterbium triflate. Mixtures of such acids can also be used. The conversion of a compound of formula (AAB) into a compound of formula (A) may be considered to be an example of a semi-Pinacol rearrangement (see for example WO 2010136431; M. Paulson, M. Daliya and C. Asokan, Synth. Commun. (2007), 37(5), 661-665; S. Sankararaman and J. Nesakumar, J. Chem. Soc, Perkin Trans. 1, (1999), (21), 3173-3175; K. Rehse and R. Bienfait, Archiv der Pharmazie, (1984), 317(5), 385-93; H. Kamath, A. Sahasrabudhe, B. Bapat and S. Kulkarni, Indian J. Chem., Section B: (1981), 20B(12), 1094-6; G. Buchanan and D. Jhaveri, J. Org. Chem. (1961), 26 4295-9; and H. House, Richard L. Wasson, J. Am. Chem. Soc., (1956), 78, 4394-400). For the rearrangement of (AAB) to (A), a suitable solvent is generally a solvent chosen to be compatible with the acid used, and include a chlorinated hydrocarbon, an alcohol, an ether, an aromatic solvent or an organic acid, for example dichloromethane, dichloroethane, diethyl ether, acetic acid, formic acid, toluene, benzene, methanol, ethanol, isopropanol or tetrahydrofuran. Preferably the reaction is performed using methanesulfonic acid in toluene at a temperature between 25° C. and 150° C.

A compound of formula (AAB) can be prepared by the epoxidation of a compound of formula (AS). Epoxidation may be effected by treatment of a compound of formula (AS) with a suitable oxidising agent such as an organic peroxide or metal hyperchlorite, for example dimethyldioxirane, sodium hypochlorite, hydrogen peroxide, tert-butyl peroxide or trifluoroperacetic acid, optionally in combination with a suitable base (such as an alkali metal hydroxide or carbonate, alkaline earth metal hydroxide or carbonate, or an amine base such as 1,8-diazabicyclo[5.4.0]-undec-7-ene), optionally in a suitable solvent (such as an alcohol or halogenated hydrocarbon, for example methanol, ethanol or dichloromethane) and at a suitable temperature. The reaction can also be performed under biphasic conditions, in which a phase-transfer reagent is also typically used in 0.001-50 mol %. The phase transfer reagent is preferably a quaternary ammonium salt, a crown ether, a polyethylene glycol, or phosphonium salt. Similar reactions are known in the literature (see for example WO 2010136431; I. K. Korobitsyna, O. P. Studzinskii, The Russian Journal of Organic Chemistry (1969), 5(8), 1493-5; A. Halasz, Z. Jambor, A. Levai, C. Nemes, T. Patonay and G. Toth, J. Chem. Soc, Perkin Trans. 1, (1996), (4), 395-400; N. Yousif, F. Gad, A. Fahmy, M. Amine and H. Sayed, Phosphorus, Sulfur and Silicon and the Related Elements (1996), 117, 11-19; T. Ooi, D. Ohara, M. Tamura and K. Maruoka, J. Am. Chem. Soc., (2004), 126(22), 6844-6845; A. Amr, H. Hayam and M. Abdulla, Archiv der Pharmazie, (2005), 338(9), 433-440; K. Drauz, S. M. Roberts, T. Geller and A. Dhanda, U.S. Pat. No. 6,538,105 B1; and L. S. Chagonda and B. A. Marples, J. Chem. Soc. Perkin 1, 1988, 875-879). Preferably, epoxidation is carried out using hydrogen peroxide and a metal hydroxide (especially lithium hydroxide or sodium hydroxide), in methanol at a temperature of between −10° C. and 60° C.

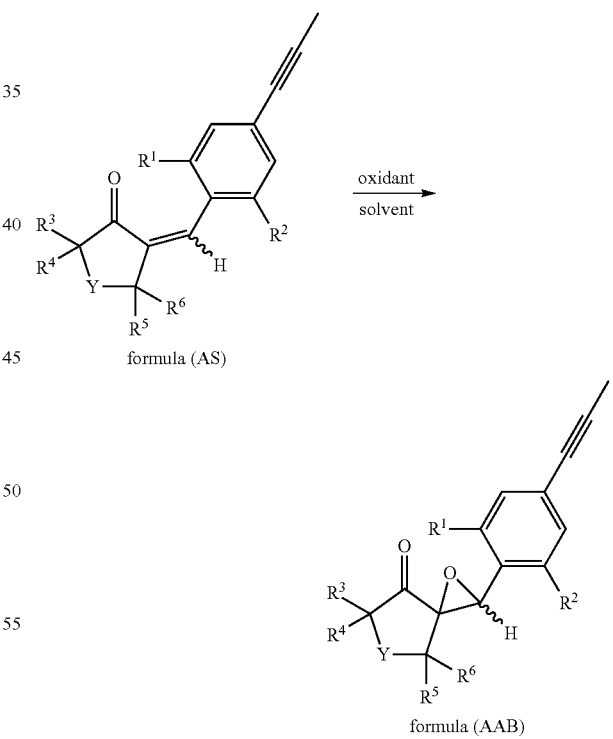

formula (AS)

formula (AAB)

Alternatively a compound of formula (AAB) may be prepared by reacting a compound of formula (AAC) (wherein halogen is chlorine, bromine or iodine, preferably chlorine or bromine) with a compound of formula (AT), in the presence of a suitable base, optionally in a suitable solvent, at a suitable temperature.

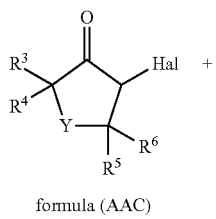

formula (AAC)

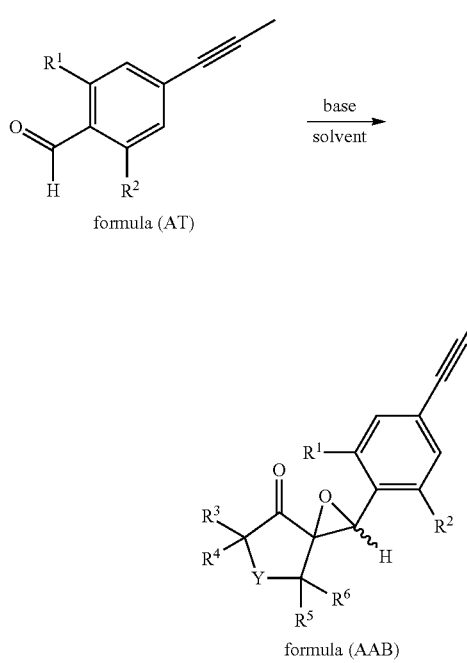

Suitable bases include alkali or alkali earth metal hydroxides (such as sodium hydroxide, lithium hydroxide or potassium hydroxide), alkali or alkali earth metal alkoxides (such as sodium methoxide, sodium ethoxide, potassium tert-butoxide or sodium tert-butoxide), alkali or alkali earth metal carbonates (such as potassium carbonate or sodium carbonate, or sodium bicarbonate), metal amides (such as lithium diisopropylamide, lithium hexamethyldisilazide or lithium 2,2,6,6-tetramethylpiperidide), organometallics (such as butyl lithium or ethylmagnesium bromide) or metal hydrides (such as sodium hydride or potassium hydride). Suitable solvents include chlorinated hydrocarbons, ethers, alcohols, aromatics and various polar aprotic solvents, for example 1,2-dimethoxyethane, tetrahydrofuran, 1,4-dioxane, diethyl ether, dibutyl ether, dichloromethane, dichloroethane, acetonitrile, dimethyl sulfoxide, N, N-dimethylformamide, benzene, toluene, methanol, ethanol, isopropanol or tert-butanol, and is chosen to be compatible with the base under the reaction conditions. The reaction can also be performed under biphasic conditions, in which a phase-transfer reagent is also typically used in 0.001-50 mol %. The phase transfer reagent is preferably a quaternary ammonium salt, a crown ether, a polyethylene glycol, or phosphonium salt. Most preferably the reaction is performed using lithium diisopropylamide in tetrahydrofuran at a temperature range of −100° C. to 60° C. The conversion of a compound of formula (AAC) into a compound of formula (AAB) may be considered to be an example of a Darzens condensation (see for example WO 2010136431; W. N. Wassef, M. M. EI-Barky, Journal of Chemical Research, Synopses (1990), (12), 402-3; J. Li, X. Liu, X. Li, Youji Huaxue (2007), 27(11), 1428-1431; Y. Tong, Y. Cheng, X. Guo, S. Wu, Hecheng Huaxue (2007), 15(1), 102-104; C. Parmenon, J. Guillard, D. Caignard, N. Hennuyer, B. Staels, V. Audinot-Bouchez, J. Boutin, C. Dacquet, A. Ktorza, M. Viaud-Massuard, Bioorganic & Medicinal Chemistry Letters (2008), 18(5), 1617-1622; H. Xiao, X. Han, J. Xiong, Faming Zhuanli Shenqing Gongkai Shuomingshu (2007), p 11; J. M. Concellon, E. Bardales, R. Llavona, Journal of Organic Chemistry (2003), 68(4), 1585-1588).

Compounds of formula (AAC), wherein Y is O or $CR^8R^9$ are either known compounds (see for example WO 2010136431; B. Sreedhar, P. S. Reddy, M. Madhavi, Synthetic Communications (2007), 37(23), 4149-4156; R. R. Agarwal, S. S. Deshapande, Journal of the Indian Chemical Society (1949), 26, 483-6; H. Richet, R. Dulou, R., G. Dupont, Bulletin de la Societe Chimique de France (1947), 693-9; H. Richet, Ann. Chim. [12] (1948), 3 317-54; I. K. Korobitsyna, Yu. K. Yur'ev, Yu. A. Cheburkov, E. M. Lukina, Russian Journal of General Chemistry (1955), 25, 734-8; I. K. Korobitsyna, Yu. K. Yur'ev, Yu. A. Cheburkov, E. M. Lukina, Russian Journal of General Chemistry (1955), 25, 690-702; F. Leonard, A. Wajngurt, H. Horn, Journal of Organic Chemistry (1956), 21, 1400-4; I. K. Korobitsyna, I. G. Zhukova, V. A. Kuvshinova, N. N. Gaidamovich, Yu. K. Yur'ev, Doklady Akademii Nauk SSSR (1957), 114, 327-30; I. K. Korobitsyna, I. G. Zhukova, I. G, Yu. K. Yur'ev, Russian Journal of General Chemistry (1959), 29, 2190-6; I. K. Korobitsyna, L. L. Rodina, L. M. Stashkova, Chemistry of Heterocyclic Compounds (1966), (6), 843-7; G. Hoehne, F. Marschner, K. Praefcke, P. Weyerstahl, Chem. Ber. (1975), 108(2), 673-82; H. Saimoto, T. Hiyama, H. Nozaki, Bull. Chem. Soc. Jpn., (1983), 56(10), 3078-87; A. M. Zvonok, N. M. Kuz'menok, I. G. Tishchenko, L. S. Stanishevskii, Russian Journal of General Chemistry (1985), 21(6), 1330-4) or can be prepared from compounds of formula (AU) under known conditions.

Compounds of formula (AAC), wherein Y is S, S(O) and $S(O)_2$, are either known compounds (see for example M. Polievka, L. Uhlar, V. Patek, Petrochemia (1973), 13(5-6), 156-60; N. N. Novitskaya, B. V. Flekhter, G. M. Prokhorov, A. S. Lukmanova, G. A. Tolstikov, G. V. Leplyanin, S. A. Lange, M. V. Strashnov, SU 468920 A1; P. H. McCabe, W. Routledge, Tetrahedron Letters (1976), (1), 85-6; T. S. Chou, C. Y. Tsai, Tetrahedron Letters (1992), 33(29), 4201-4), or can be prepared from compounds of formula (AU) under known conditions. Compounds of formula (AAC), wherein Y is C(O), can be prepared from compounds of formula (AU) under similar halogenation conditions.

Similarly, a compound of formula (L) can also be prepared from a compound of formula (AAE) using conditions as described previously. A compound of formula (AY) is known in the literature or can be prepared from known reagents using known methods.

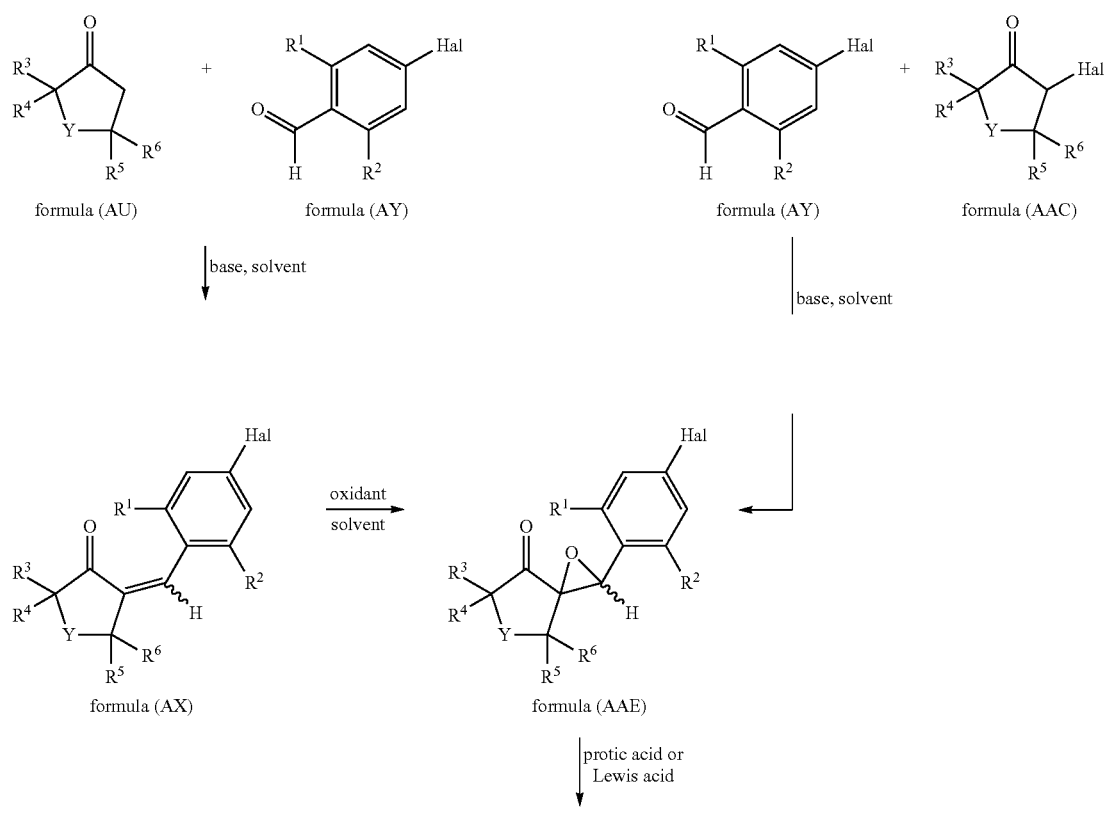
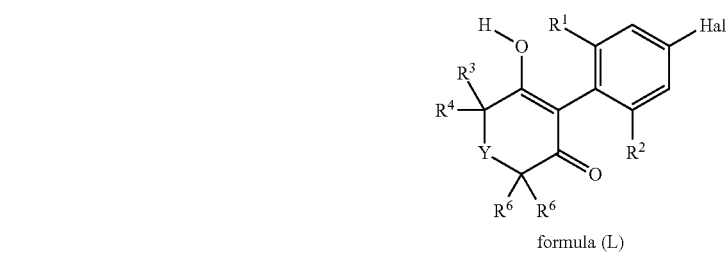
Similarly, a compound of formula (W) can also be prepared from a compound of formula (AAF), which can be prepared using similar chemistry to that described previously.
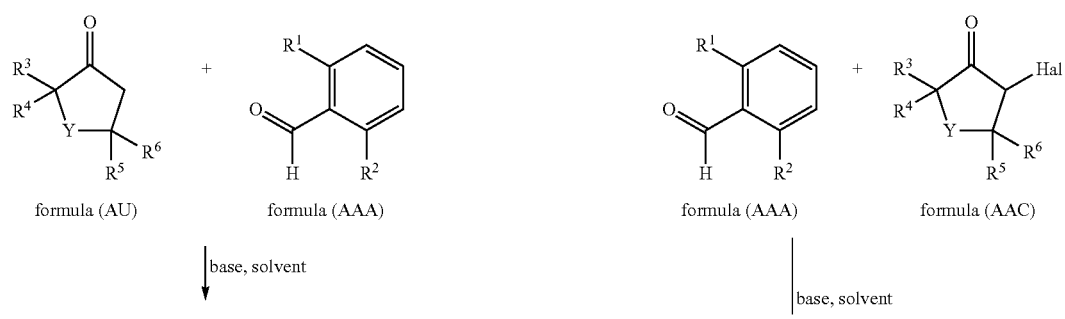

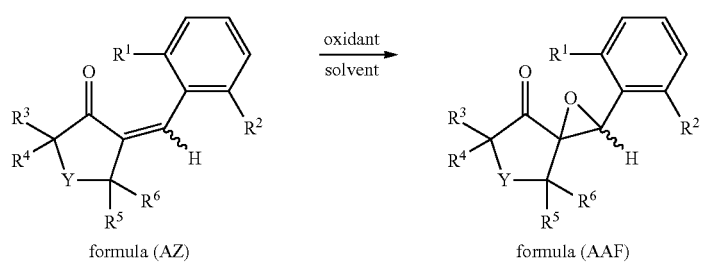

formula (AZ) → formula (AAF)

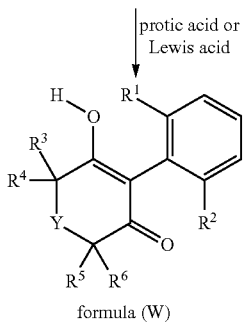

formula (W)

In a further approach, a compound of formula (A) may be prepared by reacting a compound of formula (AAH) with a with an aryllead tricarboxylate, in the presence of a suitable ligand and in a suitable solvent. Similar reactions are described in the literature (see for example M. Muehlebach et al., WO08/071405; J. Pinhey, B. Rowe, Aust. J. Chem., (1979), 32, 1561-6; J. Morgan, J. Pinhey, J. Chem. Soc. Perkin Trans. 1, (1990), 3, 715-20). Preferably the aryllead tricarboxylate is an aryllead triacetate of formula (AAG). Preferably the ligand is a nitrogen containing heterocycle such as N,N-dimethylaminopyridine, 1,10-phenanthroline pyridine, bipyridine, or imidazole, and one to ten equivalents of ligand with respect to a compound of formula (AAG) is preferably used. Most preferably the ligand is N,N-dimethylaminopyridine. The solvent is preferably chloroform, dichloromethane or toluene, most preferably chloroform, or a mixture of chloroform and toluene. Preferably the reaction is conducted at a temperature of −10° C. to 100° C., most preferably at 40-90° C.).

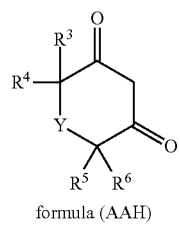

formula (AAH)

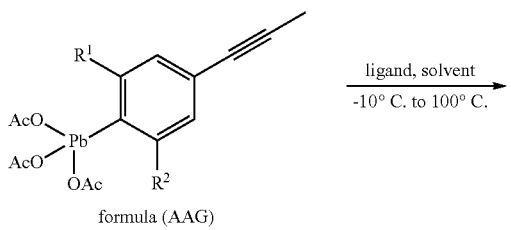

formula (AAG)

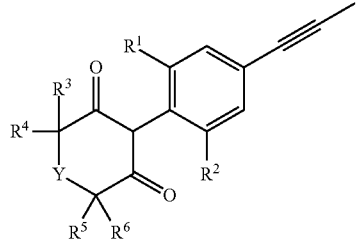

formula (A)

Compounds of formula (AAH), wherein Y is O, are known compounds or may be prepared by routes analogous to those described in the literature (see, for example, M. Muehlebach et al., WO08/071405; M. Morgan and E. Heyningen, J. Am. Chem Soc., (1957), 79, 422-424; I. Korobitsyna and K. Pivnitskii, Russian Journal of General Chemistry, (1960), 30, 4016-4023; T. Terasawa, and T. Okada, J. Org. Chem., (1977), 42 (7), 1163-1169; R. Anderson et al. U.S. Pat. No. 5,089,046; R. Altenbach, K. Agrios, I. Drizin and W. Carroll, Synth. Commun., (2004), 34 (4) 557-565; R. Beaudegnies et al., WO2005/123667; W. Li, G. Wayne, J. Lallaman, S. Chang, and S. Wittenberger, J. Org. Chem. (2006), 71, 1725-1727; R. Altenbach, M. Brune, S. Buckner, M. Coghlan, A. Daza, A. Fabiyi, M. Gopalakrishnan, R. Henry, A. Khilevich, M. Kort, I. Milicic, V. Scott, J. Smith, K. Whiteaker, and W. Carroll, J. Med. Chem, (2006), 49(23), 6869-6887; Carroll et al., WO 2001/083484 A1; J. K. Crandall, W. W. Conover, J. Org. Chem. (1978), 43(18), 3533-5; I. K. Korobitsyna, O. P. Studzinskii, Chemistry of Heterocyclic Compounds (1966), (6), 848-854).

Compounds of formula (AAH), wherein Y is S, are known compounds or may be prepared by routes analogous to those described in the literature (see, for example, E. Fehnel and A. Paul, J. Am. Chem Soc., (1955), 77, 4241-4244; E. Er and P. Margaretha, Helvetica Chimica Acta (1992), 75(7), 2265-69; H. Gayer et al., DE 3318648 A1).

Compounds of formula (AAH), wherein Y is C(O), are known compounds or may be prepared by routes analogous to those described in the literature (see, for example, R. Götz and N. Götz, WO2001/060776 R. Götz et al. WO 2000/

075095; M. Benbakkar et al., Synth. Commun. (1989) 19(18) 3241-3247; A. Jain and T. Seshadri, Proc. Indian Acad. Sci. Sect. A, (1955), 42, 279); N. Ahmad et al., J. Org. Chem., (2007), 72(13), 4803-4815); F. Effenberger et al., Chem. Ber., (1986), 119, 3394-3404 and references therein).

Compounds of formula (AAH), wherein Y is CR$^8$R$^9$ are known compounds or may be prepared by routes analogous to those described in the literature (see for example, M. Muehlebach et al., WO08/110307; M. Muehlebach et al., WO08/110308; S. Spessard and B. Stoltz, Organic Letters, (2002), Vol. 4, No. 11, 1943-1946; F. Effenberger et al., Chem. Ber., (1984), 117, 3280-3296; W. Childers et al., Tetrahedron Lett., (2006), 2217-2218; W. Childers et al., US2006/0004108; H. Schneider and C. Luethy, EP1352890; D. Jackson, A. Edmunds, M. Bowden and B. Brockbank, WO2005/105745 and WO2005/105717; R. Beaudegnies, C. Luethy, A. Edmunds, J. Schaetzer and S. Wendeborn, WO2005/123667; J-C. Beloeil, J-Y. Lallemand, T. Prange, Tetrahedron, (1986), Vol. 42. No. 13, 3491-3502; G. Stork and R. Danheiser, J. Org. Chem., (1973), 38 (9), 1775-1776; H. Favre et al., Can. J. Chem. (1956), 34 1329-39; R. Shriner and H. Todd, Org. Synth. Coll. Vol. II, (1943), 200-202).

A compound of formula (AAI) may be prepared from a compound of formula (AAJ) by treatment with lead tetraacetate in a suitable solvent (for example chloroform) at 25° C. to 100° C. (preferably 25-50° C.), and optionally in the presence of a catalyst such as mercury diacetate, according to procedures described in the literature (for example see, K. Shimi, G. Boyer, J-P. Finet and J-P. Galy, Letters in Organic Chemistry, (2005), 2, 407-409; J. Morgan and J. Pinhey, J. Chem. Soc. Perkin Trans. 1; (1990), 3, 715-720).

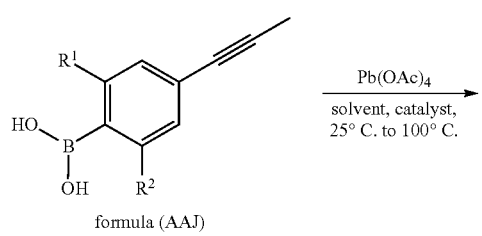

formula (AAJ)

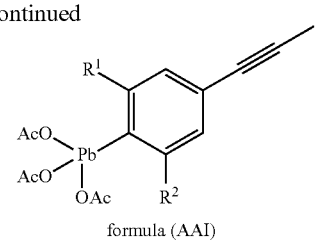

formula (AAI)

An aryl boronic acid of formula (AAJ) may be prepared from an aryl halide of formula (AE), wherein Hal is bromine or iodine by known methods (see, for example, W. Thompson and J. Gaudino, J. Org. Chem, (1984), 49, 5237-5243 and R. Hawkins et al., J. Am. Chem. Soc., (1960), 82, 3053-3059). Thus an aryl halide of formula (AE) may be treated with an alkyl lithium or alkyl magnesium halide at low temperature, and the aryl magnesium or aryl lithium reagent obtained is allowed to react with a trialkyl borate, B(OR")$_3$, preferably trimethylborate, to give an aryl dialkylboronate which may be hydrolysed to the desired boronic acid of formula (AAJ) under acidic conditions. Alternatively the same overall transformation of compound (AE) to compound (AAJ) may be achieved through a palladium-catalysed borylation reaction under known conditions using known reagents (see for example T. Ishiyama, M. Murata, N. Miyaura, J. Org. Chem. (1995), 60, 7508-7501; and K. L. Billingsley, T. E. Barder, S. L. Buchwald, Angew. Chem. Int. Ed. (2007), 46, 5359-5363), followed by hydrolysis of the intermediate boronate ester, compound (AAO).

In an alternative approach, a compound of formula (A) may be prepared by the reaction of a compound of formula (AAK), wherein Ar is an aryl moiety (preferably phenyl) with an arylboronic acid of formula (AAJ) in the presence of a suitable palladium catalyst, a suitable base, an optionally in the presence of a suitable ligand or additive, and in a suitable solvent.

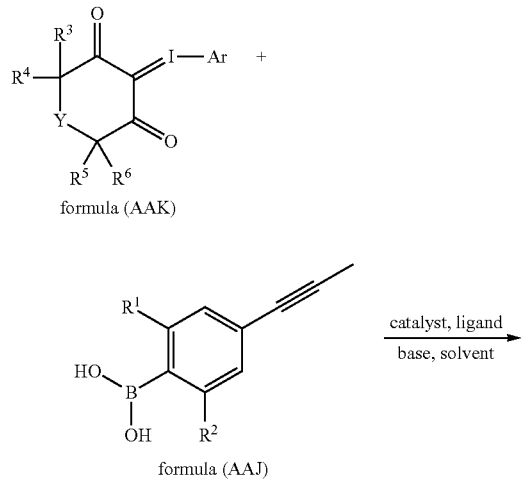

Suitable palladium catalysts include, for example palladium(II) dihalides, palladium(II) acetate and palladium(II) sulfate, and is preferably palladium(II) acetate. Suitable ligands include triphenylphosphine, tricyclopentylphosphine, tricyclohexylphosphine, 2-dicyclohexylphosphino-2', 6'-dimethoxybiphenyl, 2-dicyclohexylphosphino-2',4',6'-triisopropylbiphenyl, 1,1'-bis(diphenylphosphino)ferrocene and 1,2-bis(diphenylphosphino)ethane. The reaction may also be carried out in the presence of other additives, such as tetralkylammonium salts, for example, tetrabutylammonium bromide. Suitable bases include alkali metal hydroxides, especially lithium hydroxide. A suitable solvent is aqueous 1,2-dimethoxyethane.

A compound of formula (AAK), wherein Ar is phenyl, may be prepared from a compound of formula (AAH) by treatment with a hypervalent iodine reagent such as a (diacetoxy)iodobenzene or iodosylbenzene and a base such as aqueous sodium carbonate, lithium hydroxide or sodium hydroxide in a solvent such as water or an aqueous alcohol such as aqueous ethanol according to the procedures of K. Schank and C. Lick, Synthesis (1983), 392; R. Moriarty et al, J. Am. Chem. Soc, (1985), 107, 1375, or of Z. Yang et al., Org. Lett., (2002), 4 (19), 3333:

In a further approach, a compound of formula I may be prepared by reacting a compound of formula (AAL) (wherein G is preferably $C_{1-4}$ alkyl, and Hal is a halogen, preferably bromine or iodine), with an arylboronic acid of formula (AAJ) in the presence of a suitable palladium catalyst (for example 0.001-50% palladium(II) acetate with respect to compound (AAL)) and a base (for example 1 to 10 equivalents potassium phosphate with respect to compound (AAL)) and preferably in the presence of a suitable ligand (for example 0.001-50% (2-dicyclohexylphosphino)-2',6'-dimethoxybiphenyl with respect to compound (AAL)), and in a suitable solvent (for example toluene), preferably between 25° C. and 200° C. Similar couplings are known in the literature (see for example, Y. Song, B. Kim and J.-N. Heo, Tetrahedron Letters (2005), 46 (36), 5987-5990). A compound of formula I can be converted to a compound of formula (A) by hydrolysis of the enol ether under known conditions.

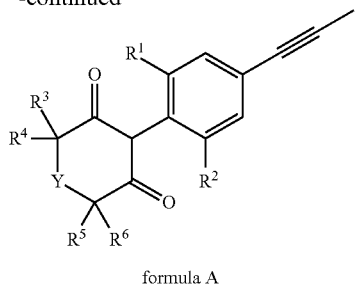

formula A

A compound of formula (AAL) may be prepared by halogenating a compound of formula (AAH), followed by reaction of the resulting halide of formula (AAN) with a $C_1$-$C_4$ alkyl halide or tri-$C_1$-$C_4$-alkylorthoformate under known conditions, for example by the procedures of R. Shepherd and A. White (J. Chem. Soc. Perkin Trans. 1 (1987), 2153-2155) and Y.-L. Lin et al. (Bioorg. Med. Chem. (2002), 10, 685-690). Alternatively, a compound of formula (AAL) may be prepared by reacting a compound of formula (AAH) with a $C_1$-$C_4$ alkyl halide or a tri-$C_1$-$C_4$-alkylorthoformate, and halogenating the resulting enol ether of formula (AAM) under known conditions (see for example Y. Song, B. Kim and J.-N. Heo, Tetrahedron Letters (2005), 46(36), 5987-5990).

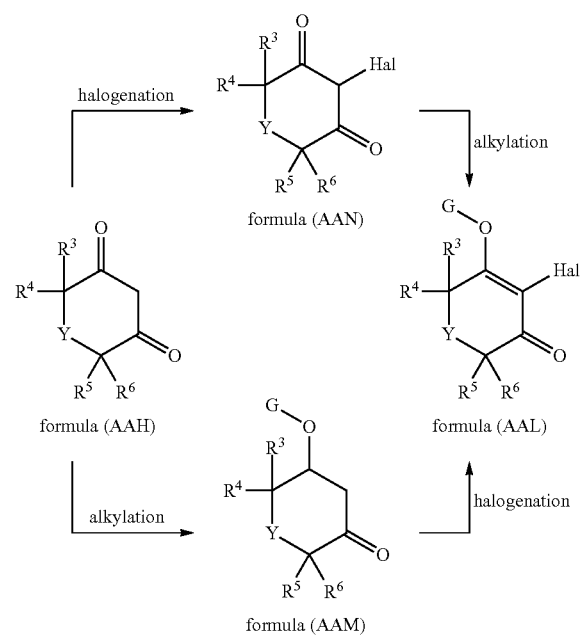

In a further approach, a compound of formula (A) may be prepared by reacting a compound of formula (AAH) with a compound of formula (AE) in the presence of a suitable palladium catalyst (for example 0.001-50% palladium(II) acetate with respect to compound (AAH)) and a base (for example 1 to 10 equivalents potassium phosphate with respect to compound (AAH)) and preferably in the presence of a suitable ligand (for example 0.001-50% (2-dicyclohexylphosphino)-2',4',6'-triisopropylbiphenyl with respect to compound (AAH)), and in a suitable solvent (for example dioxane), preferably between 25° C. and 200° C. and optionally under microwave heating.

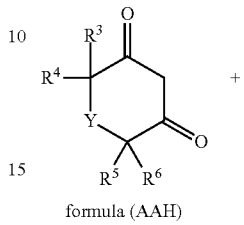

formula (AAH)

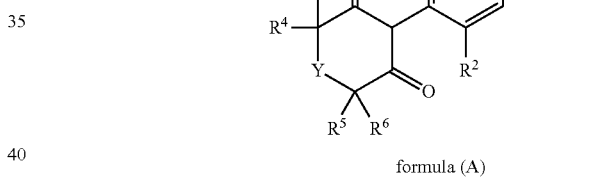

formula (AE)

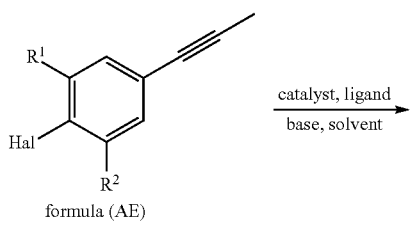

formula (A)

Similar couplings are known in the literature (see for example, S. Buchwald et al., J. Am. Chem. Soc. (2000), 122, 1360-1370; B. Hong et al. WO 2005/000233). Alternatively, a compound of formula (A) may be prepared by reacting a compound of formula (AAH) with a compound of formula (AE) in the presence of a suitable copper catalyst (for example 0.001-50% copper(I) iodide with respect to compound (AAH)) and a base (for example 1 to 10 equivalents cesium carbonate with respect to compound (AAH)) and preferably in the presence of a suitable ligand (for example 0.001-50% L-proline with respect to compound (AAH)), and in a suitable solvent (for example dimethylsulfoxide), preferably between 25° C. and 200° C. Similar couplings are known in the literature (see for example, Y. Jiang et al., Synlett, (2005), 18, 2731-2734, and X. Xie et al., Organic Letters (2005), 7(21), 4693-4695).

Similarly, a compound of formula (L) can also be prepared from suitable halogenated precursors, using similar methods to those described previously.

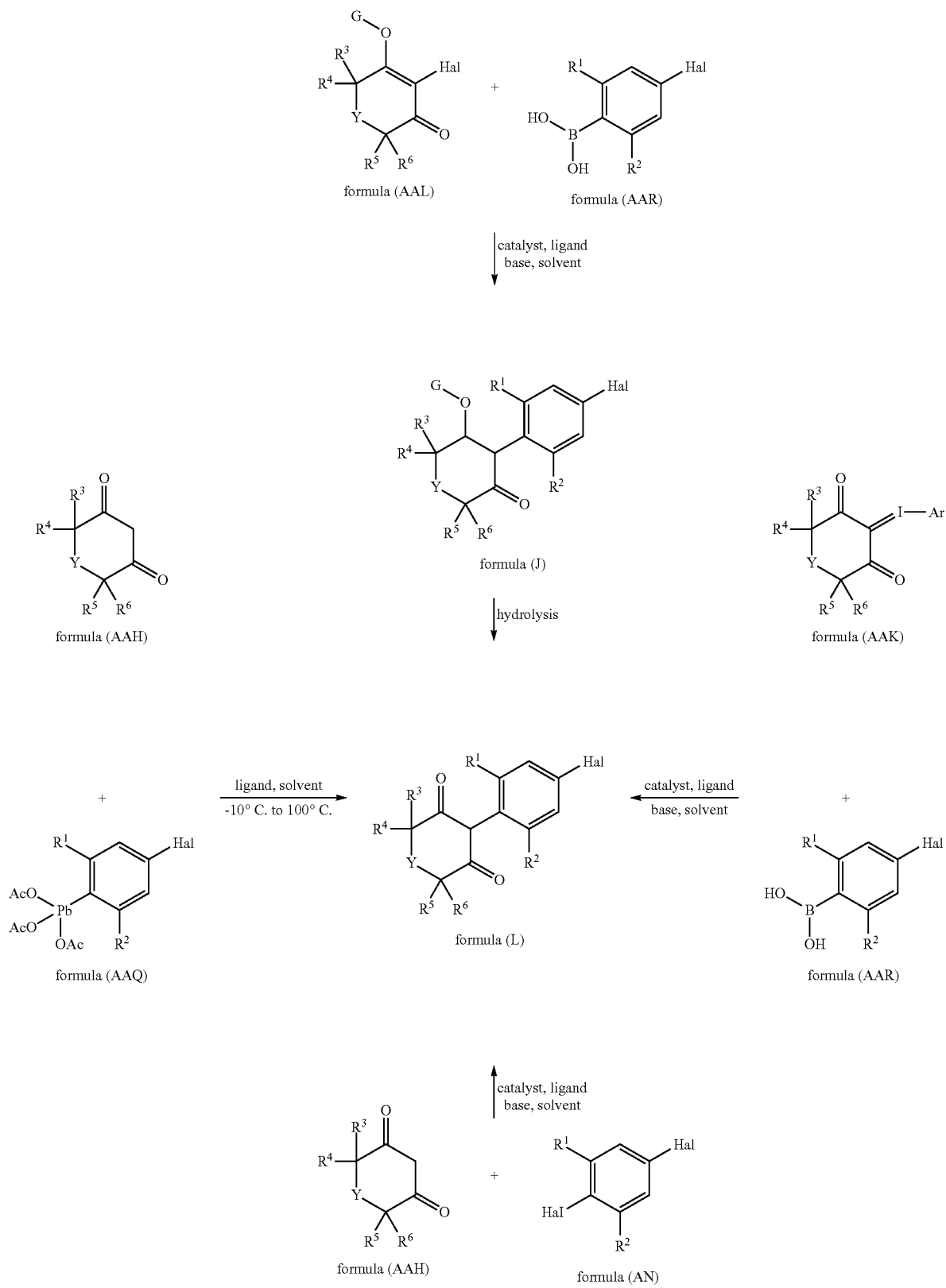
Similarly, a compound of formula (W) can also be prepared from suitable precursors, using similar methods to those described previously.

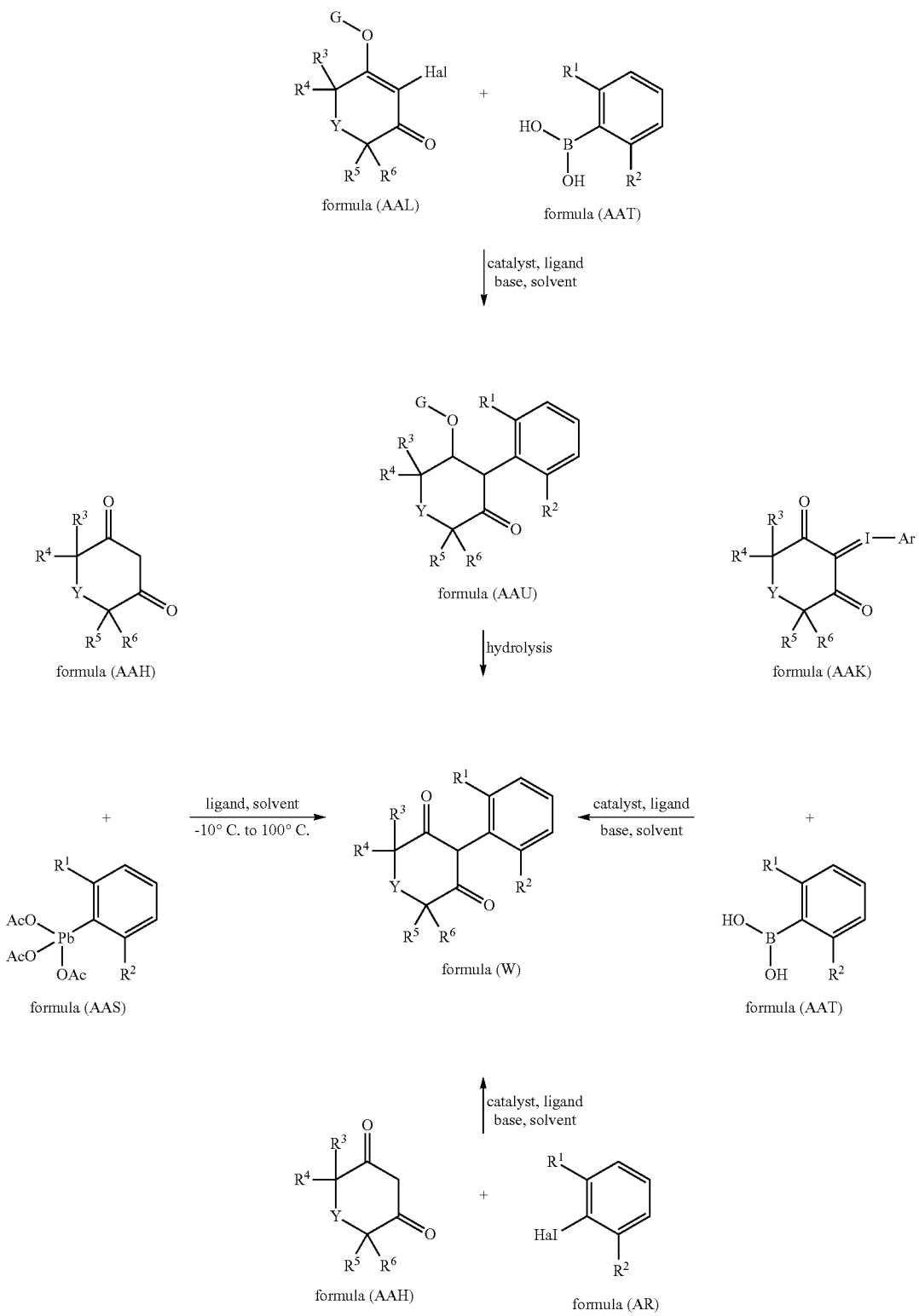

Furthermore, a compound of formula (L) can be prepared by reacting a compound of formula (AAH) with a halonitrobenzene of formula (AAX) (under conditions similar to those described for coupling a compound of formula (AAH) and a compound of formula (AE) to produce a compound of formula (A)), to produce a compound of formula (AAW) which is then reduced under standard conditions to give a compound of formula (AAV), for a similar example see T. N. Wheeler, CA1113959. The aniline (AAV) is then converted to the aryl halide (L) under Sandmeyer conditions (for a similar example see T. N. Wheeler, CA1113959).

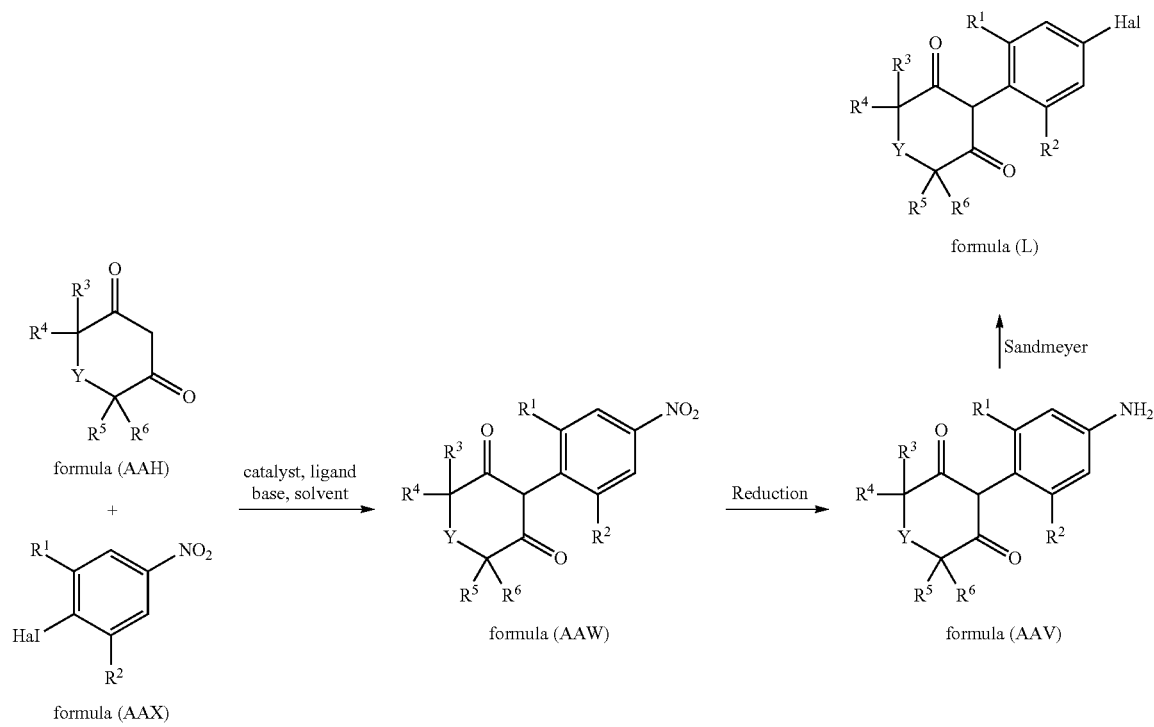

Herbicidal Compositions

In another aspect, the present invention provides a herbicidal composition, e.g. for use in a method of controlling weeds (e.g. monocotyledonous such as grassy monocotyledonous weeds) in crops of useful plants, which composition comprises a compound of formula (I) as defined herein (e.g. a herbicidally effective amount thereof), and a substantially-inert agriculturally acceptable substance (e.g. an agriculturally acceptable carrier, diluent and/or solvent, an agriculturally acceptable adjuvant, an an agriculturally acceptable emulsifier/surfactant/surface-active substance, and/or another agriculturally acceptable additive).

In a further aspect, the present invention provides a herbicidal composition, e.g. for use in a method of controlling weeds (e.g. monocotyledonous such as grassy monocotyledonous weeds) in crops of useful plants, comprising a compound of formula (I) as defined herein (e.g. a herbicidally effective amount thereof), and an agriculturally acceptable carrier, diluent and/or solvent.

In all aspects of the invention, the compound of the formula (I) is optionally present (e.g. where chemically possible) as an agriculturally acceptable salt (e.g. agriculturally acceptable metal, sulfonium or ammonium salt) thereof.

The compounds of formula (I) according to the invention can be used as crop protection agents in unmodified form, as obtained by synthesis, but, for use as herbicides, they are generally formulated into herbicidal compositions (formulations), e.g. in a variety of ways, containing one or more substantially-inert agriculturally acceptable substances (e.g. an agriculturally acceptable carrier, diluent and/or solvent, an agriculturally acceptable adjuvant, an an agriculturally acceptable emulsifier/surfactant/surface-active substance, and/or another agriculturally acceptable additive).

The formulations (herbicidal compositions) can be in various physical forms, for example in the form of dusting powders, gels, wettable powders, coated or impregnated granules for manual or mechanical distribution on target sites, water-dispersible granules, water-soluble granules, emulsifiable granules, water-dispersible tablets, effervescent compressed tablets, water-soluble tapes, emulsifiable concentrates, microemulsifiable concentrates, oil-in-water (EW) or water-in-oil (WO) emulsions, other multiphase systems such as oil/water/oil and water/oil/water products, oil flowables, aqueous dispersions, oily dispersions, suspoemulsions, capsule suspensions, soluble liquids, water-soluble concentrates (with water or a water-miscible organic solvent as carrier), impregnated polymer films or in other forms known, for example, from the Manual on Development and Use of FAO Specifications for Plant Protection Products, 5th Edition, 1999. The active ingredient may be incorporated into microfibers or micro-rods formed of polymers or polymerizable monomers and having diameter of about 0.1 to about 50 microns and aspect ratio of between about 10 and about 1000.

Such formulations can either be used directly or are diluted prior to use. They can then be applied through suitable ground or aerial application spray equipment or other ground application equipment such as central pivot irrigation systems or drip/trickle irrigation means. Diluted formulations can be prepared, for example, with water, liquid fertilisers, micronutrients, biological organisms, oil or solvents.

The formulations can be prepared, for example, by mixing the active ingredient with formulation adjuvants in order to obtain compositions in the form of finely divided solids, granules, solutions, dispersions or emulsions. The active ingredients can also be contained in fine microcapsules consisting of a core and a polymeric shell. Microcapsules usually have a diameter of from 0.1 to 500 microns. They contain active ingredients in an amount of about from 25 to 95% by weight of the capsule weight. The active ingredients can be present in the form of liquid technical material, in the form of a suitable solution, in the form of fine particles in solid or liquid dispersion or as a monolithic solid. The encapsulating membranes comprise, for example, natural and synthetic gums, cellulose, styrene-butadiene copolymers or other similar suitable membrane forming material, polyacrylonitrile, polyacrylate, polyester, polyamides, polyureas, polyurethane, aminoplast resins or chemically modified starch or other polymers that are known to the person skilled in the art in this connection.

Alternatively it is possible for fine so called "microcapsules" to be formed wherein the active ingredient is present in the form of finely divided particles in a solid matrix of a base substance, but in that case the microcapsule is not encapsulated with a diffusion limiting membrane as outlined in the preceding paragraph.

The active ingredients may be adsorbed on a porous carrier. This may enable the active ingredients to be released into their surroundings in controlled amounts (e.g. slow release). Other forms of controlled release formulations are granules or powders in which the active ingredient is dispersed or dissolved in a solid matrix consisting of a polymer, a wax or a suitable solid substance of lower molecular weight. Suitable polymers are polyvinyl acetates, polystyrenes, polyolefins, polyvinyl alcohols, polyvinyl pyrrolidones, alkylated polyvinyl pyrrolidones, copolymers of polyvinyl pyrrolidones and maleic anhydride and esters and half-esters thereof, chemically modified cellulose esters like carboxymethyl cellulose, methyl cellulose, hydroxyethyl cellulose, examples of suitable waxes are polyethylene wax, oxidized polyethylene wax, ester waxes like montan waxes, waxes of natural origin like carnauba wax, candelilla wax, bees wax etc. Other suitable matrix materials for slow release formulations are starch, stearin, lignin.

The formulation ingredients (e.g. inert ingredients) suitable for the preparation of the compositions according to the invention are generally known per se.

As a liquid carrier and/or solvent (e.g. organic solvent), e.g. for use in the herbicidal composition(s) according to the invention, there may be used: water, an aromatic solvent such as toluene, m-xylene, o-xylene, p-xylene or a mixture thereof, cumene, an aromatic hydrocarbon blend with a boiling range between 140 and 320° C. (e.g. known under various trademarks such as Solvesso®, Shellsol A®, Caromax®, Hydrosol®), a paraffinic or isoparaffinic carrier such as paraffin oil, mineral oil, a de-aromatized hydrocarbon solvent with a boiling range between 50 and 320° C. (e.g. known for instance under the trademark Exxsol®), a non-dearomatized hydrocarbon solvent with a boiling range between 100 and 320° C. (e.g. known under the tradename Varsol®), an isoparaffinic solvent with a boiling range between 100 and 320° C. (e.g. known under tradenames like Isopar® or Shellsol T®), a hydrocarbon such as cyclohexane, tetrahydronaphthalene (tetralin), decahydronaphthalene, alpha-pinene, d-limonene, hexadecane, isooctane; an ester solvent such as ethyl acetate, n- or iso-butyl acetate, amyl acetate, i-bornyl acetate, 2-ethylhexyl acetate, a $C_6$-$C_{18}$ alkyl ester of acetic acid (e.g. known under the tradename Exxate®), lactic acid ethylester, lactic acid propylester, lactic acid butylester, benzyl benzoate, benzyl lactate, dipropyleneglycol dibenzoate, or a dialkyl ester of succinic, maleic or fumaric acid; a polar solvent such as N-methyl pyrrolidone, N-ethyl pyrrolidone, $C_3$-$C_{18}$-alkyl pyrrolidones, gamma-butyrolactone, dimethylsulfoxide, N,N-dimethylformamide, N,N-dimethylacetamide, N,N-dimethyllactamide, a $C_4$-$C_{18}$ fatty acid dimethylamide, benzoic acid dimethylamide, acetonitrile, acetone, methyl ethyl ketone, methyl-isobutyl ketone, isoamyl ketone, 2-heptanone, cyclohexanone, isophorone, methyl isobutenyl ketone (mesityl oxide), acetophenone, ethylene carbonate, propylene carbonate, or butylene carbonate;

an alcoholic solvent or diluent such as methanol, ethanol, propanol, n- or iso-butanol, n- or iso-pentanol, 2-ethyl hexanol, n-octanol, tetrahydrofurfuryl alcohol, 2-methyl-2, 4-pentanediol, 4-hydroxy-4-methyl-2-pentanone, cyclohexanol, benzyl alcohol, ethylene glycol, ethylene glycol butyl ether, ethylene glycol methyl ether, diethylene glycol, diethylene glycol butyl ether, diethylene glycol monoethyl ether, diethylene glycol monomethyl ether, propylene glycol, dipropylene glycol, dipropylene glycol monomethyl ether, or another similar glycol monoether solvent based on a ethylene glycol, propylene glycol or butylene glycol feedstock, triethylene glycol, polyethylene glycol (e.g. PEG 400), a polypropylenglycol with a molecular mass of 400-4000, or glycerol;

glycerol acetate, glycerol diacetate, glycerol triacetate, 1,4-dioxane, diethylene glycol abietate, chlorobenzene, chlorotoluene; a fatty acid ester such as methyl octanoate, isopropyl myristate, methyl laurate, methyl oleate, a mixture of $C_8$-$C_{10}$ fatty acid methyl esters, rapeseed oil methyl ester, rapeseed oil ethyl ester, soybean oil methyl ester, soybean oil ethyl ester; a vegetable oil (e.g. rapeseed oil or soybean oil); a fatty acid such as oleic acid, linoleic acid, or linolenic acid; or an ester of phosphoric or phosphonic acid such as triethyl phosphate, a $C_3$-$C_{18}$-tris-alkyl phosphate, an alkylaryl phosphate, or bis-octyl-octyl phosphonate.

Water is generally the liquid carrier of choice for the dilution of the concentrates.

Suitable solid carriers are, for example, talc, titanium dioxide, pyrophyllite clay, silica (fumed or precipated silica and optionally functionalised or treated, for instance silanised), attapulgite clay, kieselguhr, limestone, calcium carbonate, bentonite, calcium montomorillonite, cottonseed husks, wheatmeal, soybean flour, pumice, wood flour, ground walnut shells, lignin and similar materials, as described, for example, in the EPA CFR 180.1001. (c) & (d). Powdered or granulated fertilisers can also be used as solid carriers.

A large number of surface-active substances can advantageously be used both in solid and in liquid formulations (herbicidal compositions), especially in those formulations (herbicidal compositions) which can be diluted with a carrier prior to use. Surface-active substances may be anionic, cationic, amphoteric, non-ionic or polymeric and they may be used as emulsifiying, wetting, dispersing or suspending agents or for other purposes. Typical surface-active substances include, for example, salts of alkyl sulfates, such as diethanolammonium lauryl sulfate; Sodium lauryl sulfate, salts of alkylarylsulfonates, such as calcium or sodium dodecylbenzenesulfonate; alkylphenol-alkylene oxide addition products, such as nonylphenol ethoxylates; alcohol-alkylene oxide addition products, such as tridecyl alcohol ethoxylate; soaps, such as sodium stearate; salts of alkyl-naphthalenesulfonates, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride, polyethylene glycol esters of fatty acids, such as polyethylene glycol stearate; block copolymers of ethylene oxide and propylene oxide; and salts of mono- and di-alkyl phosphate esters; and also further substances described e.g. in "McCutcheon's Detergents and Emulsifiers Annual", MC Publishing Corp., Ridgewood, N.J., 1981.

Further formulation ingredients (e.g. inert ingredients) which can typically be used in formulations (herbicidal compositions) include crystallisation inhibitors, viscosity-modifying substances, suspending agents, dyes, anti-oxidants, foaming agents, light absorbers, mixing aids, anti-foams, complexing agents, neutralising or pH-modifying substances and/or buffers, corrosion-inhibitors, fragrances, wetting agents, absorption improvers, micronutrients, plasticisers, glidants, lubricants, dispersants, thickeners, anti-freezes, microbiocides, compatibility agents and/or solubilisers; and/or also liquid and/or solid fertilisers.

The compositions (formulations) may also comprise additional active substances, for example further herbicides, herbicide safeners, plant growth regulators, fungicides and/or insecticides.

The compositions according to the invention can additionally include an additive (commonly referred to as an adjuvant), comprising a mineral oil, an oil of vegetable or animal origin, alkyl (e.g. $C_1$-$C_6$alkyl) esters of such oils, or mixtures of such oils and oil derivatives/oil esters. The amount of oil additive (oil adjuvant) used in the composition according to the invention is generally from 0.01 to 10%, based on the spray mixture. For example, the oil additive (oil adjuvant) can be added to the spray tank in the desired concentration after the spray mixture has been prepared. Preferred oil additives (oil adjuvants) comprise mineral oils or an oil of vegetable origin, for example rapeseed oil, olive oil or sunflower oil, emulsifiable vegetable oil, such as AMIGO® (Loveland Products Inc.), $C_1$-$C_6$alkyl esters of oils of vegetable origin, for example the methyl esters, or an oil of animal origin, such as fish oil or beef tallow. A preferred oil additive (oil adjuvant) contains methylated rapeseed oil (rapeseed oil methyl ester). Another preferred oil additive (oil adjuvant) contains, for example, as active components essentially 80% by weight alkyl esters of fish oils and 15% by weight methylated rapeseed oil (rapeseed oil methyl ester), and also 5% by weight of customary emulsifiers and pH modifiers. Especially preferred oil additives (oil adjuvants) comprise $C_1$-$C_6$alkyl ester(s) of $C_8$-$C_{22}$ fatty acid(s), especially the methyl ester(s) of $C_8$-$C_{22}$ (especially $C_{12}$-$C_{18}$) fatty acid(s); preferably the methyl ester of lauric acid, of palmitic acid, or of oleic acid. Those esters are known as methyl laurate (CAS-111-82-0), methyl palmitate (CAS-112-39-0) and methyl oleate (CAS-112-62-9) respectively. A preferred fatty acid methyl ester derivative is AGNIQUE ME 18 RD-F® (e.g. available from Cognis). Those and other oil derivatives are also known from the Compendium of Herbicide Adjuvants, 5th Edition, Southern Illinois University, 2000.

The application and action of the above-mentioned oil additives (oil adjuvants) can be further improved by combining them with surface-active substances, such as non-ionic, anionic, cationic or amphoteric surfactants. Examples of suitable (e.g. agriculturally acceptable) anionic, non-ionic, cationic or amphoteric surfactants, e.g. for this purpose, are listed on pages 7 and 8 of WO97/34485. Preferred surface-active substances are anionic surfactants of the dodecylbenzylsulfonate type, especially the calcium salts thereof, and also non-ionic surfactants of the fatty alcohol ethoxylate type. As non-ionic sufactants, special preference is given to ethoxylated $C_{12}$-$C_{22}$ fatty alcohols preferably having a degree of ethoxylation of from 5 to 40. Examples of commercially available surfactants are the Genapol types (Clariant). Also preferred are silicone surfactants, especially polyalkyl-oxide-modified heptamethyltrisiloxanes, which are commercially available e.g. as SILWET L-77®, and also perfluorinated surfactants. The concentration of surface-active substances in relation to the total oil additive (oil adjuvant) is generally from 1 to 50% by weight of the oil additive (oil adjuvant). Examples of oil additives (oil adjuvants) that consist of mixtures of oils and/or mineral oils and/or derivatives thereof with surfactants are TURBOCHARGE®, ADIGOR® (both Syngenta Crop Protection AG), ACTIPRON® (BP Oil UK Limited), AGRI-DEX® (Helena Chemical Company).

The above-mentioned surface-active substances may also be used in the formulations alone, that is to say without oil additives (oil adjuvants).

Furthermore, the addition of an organic solvent to the oil additive (oil adjuvant)/surfactant mixture can contribute to a further enhancement of action. Suitable solvents are, for example, heavy aromatic hydrocarbon solvents such as SOLVESSO® or AROMATIC® solvents (Exxon Corporation). The concentration of such solvents can e.g. be from 10 to 80% by weight of the oil additive (oil adjuvant). Such oil additives (oil adjuvants), which may be in admixture with solvents, are described, for example, in U.S. Pat. No. 4,834,908. A commercially available oil additive disclosed therein is known by the name MERGE® (BASF). Further such oil additives (oil adjuvants) that are preferred according to the invention are SCORE® and ADIGOR® (both Syngenta Crop Protection AG).

In addition to the oil additives (oil adjuvants) listed above, in order to enhance the activity of the compositions according to the invention it is also possible for formulations of alkylpyrrolidones, (e.g. AGRIMAX® from ISP) to be added to the spray mixture. Formulations of synthetic latices, such as, for example, polyacrylamide, polyvinyl compounds or poly-1-p-menthene (e.g. BOND®, COURIER® or EMERALD®) can also be used.

A particularly preferred oil adjuvant (oil additive), e.g. for use in the herbicidal compositionas of the invention, is an emulsifiable concentrate which consists of:

(i) ethoxylated alcohols, which preferably includes ethoxylated $C_{12}$-$C_{22}$ fatty alcohols (preferably having a degree of ethoxylation of from 5 to 40); and (ii) a mixture of heavy aromatic hydrocarbons, which preferably includes (or more preferably includes 50% or more by weight of the heavy aromatic hydrocarbons of) a mixture of naphthalenes each of which is substituted by one or more alkyls wherein the alkyl(s) in total have 1-4 carbon atoms per naphthalene molecule (e.g. Solvesso 200 ND™); and (iii) methylated rapeseed oil (rapeseed oil methyl ester) (e.g. Agnique ME 18 RD-F™), as an adjuvant; preferably present at about 47% w/w and/or about 45% w/v of the oil adjuvant/oil additive/emulsifiable concentrate. One example of such a emulsifiable concentrate oil adjuvant (oil additive) is ADIGOR™, currently available in many countries from Syngenta.

When the above emulsifiable concentrate oil adjuvant is used, it is preferably added to the herbicidal composition after dilution (e.g. with water and/or in a spray tank), typically before application to weeds and/or to crops of useful plants and/or to the locus thereof. In one particular embodiment, the herbicidal composition, e.g. after dilution (e.g. with water and/or in a spray tank), contains the above emulsifiable concentrate oil adjuvant, and additionally ammonium sulphate and/or isopropyl alcohol.

Such adjuvant oils as described in the preceding paragraphs may be employed as a or the carrier liquid in which an active compound is dissolved, emulsified or dispersed as appropriate to the physical form of the active compound.

In an alternative particular embodiment, the herbicidal composition of the invention comprises an agriculturally acceptable adjuvant comprising 1,2-cyclohexane dicarboxylic acid di-isononyl ester (e.g. CAS Registry no. 166412-78-8), e.g. as available from BASF as Hexamoll™ DINCH™. "Isononyl" in this context is thought to mean one or more, preferably a mixture of two or more, branched isomers of $C_9H_{19}$. In one particular embodiment, the herbicidal composition, e.g. after dilution (e.g. with water and/or in a spray tank), contains 1,2-cyclohexane dicarboxylic acid di-isononyl ester, and additionally ammonium sulphate and/or isopropyl alcohol.

In an alternative particular embodiment, the herbicidal composition of the invention comprises an agriculturally acceptable adjuvant comprising an organic phosphate and/or organic phosphonate adjuvant. Preferably, the phosphate adjuvant is a tris-[$C_4$-$C_{12}$alkyl or 2-($C_2$-$C_6$alkoxy)ethyl-] ester of phosphoric acid, or more preferably is tris-(2-ethylhexyl) phosphate, tris-n-octyl phosphate and/or tris-[2-(n-butoxy)ethyl] phosphate, or most preferably is tris-(2-ethylhexyl) phosphate. Preferably, the phosphonate adjuvant is a bis-($C_3$-$C_{12}$alkyl) ester of a $C_3$-$C_{12}$alkyl-phosphonic acid, or more preferably is bis-(2-ethylhexyl) (2-ethylhexyl) phosphonate, bis-(2-ethylhexyl) (n-octyl)phosphonate and/or di-n-butyl (n-butyl)phosphonate.

The formulations (herbicidal compositions) generally contain from 0.1 to 99% by weight, especially from 0.1 to 95% by weight, of a compound of formula I and from 1 to 99.9% by weight of a substantially-inert agriculturally acceptable substance, which preferably includes a formulation adjuvant and/or from 0 to 30% or from 0 to 25% (preferably from 0.5 to 30% or from 0.5 to 25%) by weight of a surface-active substance. Whereas herbicidal compositions (especially commercial products) will preferably be formulated as concentrates, the end user will normally employ dilute formulations (compositions), e.g. formulations (compositions) diluted with water, in particular when applying the herbicidal composition to weeds and/or to crops of useful plants and/or to the locus thereof.

The rate of application of the compounds of formula I may vary within wide limits and depends upon the nature of the soil, the method of application (pre- or post-emergence; seed dressing; application to the seed furrow; no tillage application etc.), the crop plant, the weed or grass to be controlled, the prevailing climatic conditions, and other factors governed by the method of application, the time of application and the target crop. The compounds of formula I according to the invention are generally applied (preferably post-emergence) at a rate of from 1 to 2000 g/ha, preferably from 1 to 1000 g/ha and most preferably at from 1 to 500 g/ha or from 5 to 500 g/ha.

Preferred formulations/compositions have especially the following representative compositions:
(%=percent by weight of the composition):
Emulsifiable Concentrates:
  active ingredient: 0.3 to 95%, preferably 0.5 to 60% such as 1 to 40%
  surface-active agents: 1 to 30%, preferably 3 to 20% such as 5 to 15%
  solvents as liquid carrier: 1 to 80%, preferably 1 to 60% such as 1 to 40%
Dusts:
  active ingredient: 0.1 to 10%, preferably 0.1 to 5%
  solid carriers: 99.9 to 90%, preferably 99.9 to 99%
Suspension Concentrates:
  active ingredient: 1 to 75%, preferably 3 to 50% or 10 to 50%
  water: 98 to 24%, preferably 95 to 30% or 88 to 30%
  surface-active agents: 1 to 40%, preferably 2 to 30%
Wettable Powders:
  active ingredient: 0.5 to 90%, preferably 1 to 80%
  surface-active agents: 0.5 to 20%, preferably 1 to 15%
  solid carriers: 5 to 95%, preferably 15 to 90%
Granules:
  active ingredient: 0.1 to 30%, preferably 0.1 to 15%
  solid carriers: 99.5 to 70%, preferably 97 to 85%
Waterdispersible Granules:
  active ingredient: 1 to 90%, preferably 10 to 80%
  surface-active agents: 0.5 to 80%, preferably 5 to 30%
  solid carriers: 90 to 10%, preferably 70 to 30%

The following Examples further illustrate, but do not limit, the invention.

F1. Emulsifiable Concentrates

|  | a) | b) | c) | d) |
|---|---|---|---|---|
| active ingredient | 5% | 10% | 25% | 50% |
| calcium dodecylbenzene-sulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | — | 4% | — | 2% |
| NMP (N-methyl-2-pyrrolidone) | — | 10% | — | 20% |
| aromatic hydrocarbon mixture $C_9$-$C_{12}$ | 85% | 68% | 65% | 16% |

Emulsions of any desired concentration can be prepared from such concentrates by dilution with water.

F2. Solutions

|  | a) | b) | c) | d) |
|---|---|---|---|---|
| active ingredient | 5% | 10% | 50% | 90% |
| 1-methoxy-3-(3-methoxy-propoxy)-propane | 40% | 50% | — | — |
| polyethylene glycol MW 400 | 20% | 10% | — | — |
| NMP (N-methyl-2-pyrrolidone) | — | — | 50% | 10% |
| aromatic hydrocarbon mixture $C_9$-$C_{12}$ | 35% | 30% | — | — |

The solutions are suitable for application undiluted or after dilution with water.

F3. Wettable Powders

|  | a) | b) | c) | d) |
|---|---|---|---|---|
| active ingredient | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | — | 1% | 2% | — |
| highly disperse silicic acid | 1% | 3% | 5% | 10% |
| kaolin | 88% | 62% | 35% | — |

The active ingredient is thoroughly mixed with the adjuvants and the mixture is thoroughly ground in a suitable mill, yielding wettable powders which can be diluted with water to give suspensions of any desired concentration.

F4. Coated Granules

|  | a) | b) | c) |
|---|---|---|---|
| active ingredient | 0.1% | 5% | 15% |
| highly dispersed silica | 0.9% | 2% | 2% |
| inorganic carrier (diameter 0.1-1 mm) e.g. CaCO$_3$ or SiO$_2$ | 99.0% | 93% | 83% |

The active ingredient is dissolved in methylene chloride, the solution is sprayed onto the carrier and the solvent is subsequently evaporated off in vacuo.

F5. Coated Granules

|  | a) | b) | c) |
|---|---|---|---|
| active ingredient | 0.1% | 5% | 15% |
| polyethylene glycol MW 200 | 1.0% | 2% | 3% |
| highly dispersed silica | 0.9% | 1% | 2% |
| inorganic carrier (diameter 0.1-1 mm) e.g. CaCO$_3$ or SiO$_2$ | 98.0% | 92% | 80% |

The finely ground active ingredient is applied uniformly, in a mixer, to the carrier moistened with polyethylene glycol. Non-dusty coated granules are obtained in this manner.

F6. Extruded Granules

|  | a) | b) | c) | d) |
|---|---|---|---|---|
| active ingredient | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97.0% | 93% | 90% | 79% |

The active ingredient is mixed and ground with the adjuvants and the mixture is moistened with water. The resulting mixture is extruded and then dried in a stream of air.

F7. Water-Dispersible Granules

|  | a) | b) | c) | d) |
|---|---|---|---|---|
| active ingredient | 5% | 10% | 40% | 90% |
| sodium lignosulfonate | 20% | 20% | 15% | 7% |
| dibutyl naphthalene sulfonate | 5% | 5% | 4% | 2% |
| Gum arabic | 2% | 1% | 1% | 1% |
| Diatomaceous earth | 20% | 30% | 5% | — |
| Sodium sulfate | — | 4% | 5% | — |
| kaolin | 48% | 30% | 30% | — |

The active ingredient is mixed and ground with the adjuvants and the mixture is moistened with water. The resulting mixture is extruded and then dried in a stream of air.

F8. Dusts

|  | a) | b) | c) |
|---|---|---|---|
| active ingredient | 0.1% | 1% | 5% |
| talcum | 39.9% | 49% | 35% |
| kaolin | 60.0% | 50% | 60% |

Ready-to-use dusts are obtained by mixing the active ingredient with the carriers and grinding the mixture in a suitable mill.

F9. Suspension Concentrates

|  | a) | b) | c) | d) |
|---|---|---|---|---|
| active ingredient | 3% | 10% | 25% | 50% |
| propylene glycol | 5% | 5% | 5% | 5% |
| nonylphenol polyglycol ether (15 mol of ethylene oxide) | — | 1% | 2% | — |
| sodium lignosulfonate | 3% | 3% | 7% | 6% |
| heteropolysacharide (Xanthan) | 0.2% | 0.2% | 0.2% | 0.2% |
| 1,2-benzisothiazolin-3-one | 0.1% | 0.1% | 0.1% | 0.1% |
| silicone oil emulsion | 0.7% | 0.7% | 0.7% | 0.7% |
| water | 88% | 80% | 60% | 38% |

The finely ground active ingredient is intimately mixed with the adjuvants, yielding a suspension concentrate from which suspensions of any desired concentration can be prepared by dilution with water.

Herbicidal Uses—Crops of Useful Plants, Weeds, Application Rates, et al.

In a further aspect, the present invention provides a method of controlling weeds (preferably monocotyledonous weeds such as more preferably grassy monocotyledonous weeds) in crops of useful plants, which comprises applying a compound of the formula (I), or a herbicidal composition comprising such a compound, to the weeds and/or to the plants and/or to the locus thereof. (Preferably, in this further aspect, the herbicidal composition can be as described hereinabove or hereinbelow, e.g. as described in the "Herbicidal compositions", "Herbicidal uses", "Combinations and mixtures" and/or Claims sections hereinabove or hereinbelow.)

In a further aspect, the present invention provides a herbicidal composition, in particular for use in a method of controlling weeds (preferably monocotyledonous weeds such as more preferably grassy monocotyledonous weeds) in crops of useful plants, comprising a compound of formula (I) as defined herein (e.g. a herbicidally effective amount thereof), and an agriculturally acceptable carrier, diluent and/or solvent.

In all aspects of the invention, the compound of the formula (I) is optionally present (e.g. where chemically possible) as an agriculturally acceptable salt (e.g. agrochemically acceptable metal, sulfonium or ammonium salt) thereof.

In one embodiment, the herbicidal composition also comprises one or more further herbicides, e.g. as mixture partner(s) for the compound of formula (I), and/or a safener. See the combinations and mixtures section herein for more details of examples of these.

In all aspects of the invention (e.g. the methods of use of the invention), crops of useful plants, e.g. on or in which or at the locus of which the compounds or compositions according to the invention can be used, comprise (e.g. are), in particular: cereals (e.g. non-oat cereals, in particular non-oat non-sorghum non-millet cereals, more particularly wheat, barley, rye and/or triticale), rice, corn (maize), sugarcane, leguminous crops [preferably soybean, peanut, and/or pulse crops; more preferably soybean; wherein typically the pulse crops comprise dry beans (e.g. kidney or haricot or pinto bean which is *Phaseolus vulgaris*, or mung bean which is *Vigna radiata*), chickpea, blackeye bean (i.e. black-eyed pea, *Vigna unguiculata*), lentil, dry broad beans, and/or dry peas such as garden peas], cotton, rape (in particular oilseed rape or canola), sunflower, linseed, sugarbeet, fodder beet, potato, vegetables (preferably dicotyledonous vegetables), flax, tobacco, plantation crops (such as conifer trees, olives and/or olive trees, oil palms, coffee, or vines), and/or fruit crops (in particular dicotyledonous and/or broadleaved fruit, and/or in particular pome fruit, stone fruit, bush fruit, citrus fruit, pineapple, banana, and/or strawberry); and/or turf and/or pastureland grass.

Preferably, in all aspects of the invention, the crops of useful plants, e.g. on or in which or at the locus of which the compounds or compositions according to the invention can be used, comprise (e.g. are): cereals (in particular non-oat cereals, more particularly non-oat non-sorghum non-millet cereals, even more particularly wheat, barley, rye and/or triticale), rice, sugarcane, leguminous crops [preferably soybean, peanut, and/or pulse crops (more preferably soybean)], cotton, rape (in particular oilseed rape or canola), sunflower, linseed, sugarbeet, fodder beet, potato, and/or vegetables (preferably dicotyledonous vegetables).

More preferably, in all aspects of the invention, the crops of useful plants, e.g. on or in which or at the locus of which the compounds or compositions according to the invention can be used, comprise (e.g. are): wheat (e.g. winter wheat, spring wheat, or durum wheat), barley (e.g. winter or spring barley), rye, triticale, sugarcane, leguminous crops [preferably soybean, peanut, and/or pulse crops (more preferably soybean)], cotton, rape (in particular oilseed rape or canola), sunflower, linseed, sugarbeet, fodder beet, potato, and/or vegetables (preferably dicotyledonous vegetables).

Even more preferably, in all aspects of the invention, the crops of useful plants, e.g. on or in which or at the locus of which the compounds or compositions according to the invention can be used, comprise (e.g. are): leguminous crops [preferably soybean, peanut, and/or pulse crops; more preferably soybean; wherein typically the pulse crops comprise dry beans (e.g. kidney or haricot or pinto bean which is *Phaseolus vulgaris*, or mung bean which is *Vigna radiata*), chickpea, blackeye bean (i.e. black-eyed pea, *Vigna unguiculata*), lentil, dry broad beans, and/or dry peas such as garden peas], cotton, rape (in particular oilseed rape or canola), sunflower, sugarbeet, fodder beet, potato, and/or vegetables (preferably dicotyledonous vegetables).

Certain compounds of formula (I) according to the present invention are particularly efficacious against grassy (e.g. warm-climate grassy) monocotyledonous weeds and appear to be selective for grassy (e.g. warm-climate grassy) monocotyledonous weed control in crops of soybean (e.g. see Biological Examples herein).

The term "crops" is to be understood as also including crops that have been rendered tolerant to herbicides or classes of herbicides (for example ALS, GS, EPSPS, PPO and HPPD inhibitors, and/or 2,4-D or dicamba) as a result of conventional methods of breeding or genetic engineering. Examples of crops that have been rendered tolerant e.g. to imid-azolinones (which are ALS inhibitors), such as imazamox, by conventional methods of breeding include Clearfield® summer rape (canola) and/or Clearfield® wheat and/or Clearfield® rice (all from BASF). Examples of crops that have been rendered tolerant to herbicides by genetic engineering methods include e.g. glyphosate-tolerant or glufosinate-tolerant maize or soybean varieties, in particular those commercially available under the trade name RoundupReady® or RoundupReady® 2 (both from Monsanto, both glyphosate-tolerant) or LibertyLink® (from Bayer, glufosinate-tolerant). Glufosinate-resistant rice (LibertyLink®) also has been published.

Other crops of useful plants include 2,4-D-tolerant soybean, e.g. soybean genetically-modified to be tolerant to the herbicide 2,4-D, or dicamba-tolerant soybean, e.g. soybean genetically-modified to be tolerant to the herbicide dicamba. Such 2,4-D-tolerant or dicamba-tolerant soybean crops can also, in particular, be tolerant to glyphosate or glufosinate. For example, crops of useful plants include soybeans containing a dicamba-tolerance trait combined (stacked) with a glyphosate-tolerance trait, such that these soybeans have tolerance to the herbicides glyphosate and dicamba (for example Genuity® Roundup Ready® 2 Xtend soybeans, currently under development by Monsanto).

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt-176 maize hybrids of NK® (Syngenta Seeds). The Bt toxin is a protein that is formed naturally by *Bacillus thuringiensis* soil bacteria. Examples of toxins and transgenic plants able to synthesise such toxins are described in EP-A-451 878, EP-A-374 753, WO 93/07278, WO 95/34656, WO 03/052073 and EP-A-427 529. Examples of transgenic plants that contain one or more genes which code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops and their seed material can be resistant to herbicides and at the same time also to insect feeding ("stacked" transgenic events). Seed can, for example, have the ability to express an insecticidally active Cry3 protein and at the same time be glyphosate-tolerant. The term "crops" is to be understood as also including crops obtained as a result of conventional methods of breeding or genetic engineering which contain so-called output traits (e.g. improved flavour, storage stability, nutritional content).

In all aspects of the invention, the weeds, e.g. to be controlled and/or growth-inhibited, may be either monocotyledonous (e.g. grassy) and/or dicotyledonous weeds. Preferably the weeds, e.g. to be controlled and/or growth-inhibited, comprise or are monocotyledonous weeds, more preferably grassy monocotyledonous weeds.

In all aspects of the invention, typically, the monocotyledonous (preferably grassy) weeds, e.g. to be controlled and/or growth-inhibited, comprise (e.g. are): weeds from the genus *Agrostis, Alopecurus, Apera, Avena, Brachiaria, Bromus, Cenchrus, Cyperus* (a genus of sedges), *Digitaria, Echinochloa, Eleusine, Eriochloa, Fimbristylis* (a genus of sedges), *Juncus* (a genus of rushes), *Leptochloa, Lolium, Monochoria, Ottochloa, Panicum, Pennisetum, Phalaris, Poa, Rottboellia, Sagittaria, Scirpus* (a genus of sedges), *Setaria* and/or *Sorghum*, and/or volunteer corn (volunteer maize) weeds; in particular: *Alopecurus myosuroides* (ALOMY, English name "blackgrass"), *Apera spica*-venti, *Avena fatua* (AVEFA, English name "wild oats"), *Avena ludoviciana, Avena sterilis, Avena sativa* (English name "oats" (volunteer)), *Brachiaria decumbens, Brachiaria plantaginea, Brachiaria platyphylla* (BRAPP), *Bromus tectorum, Digitaria horizontalis, Digitaria insularis, Digitaria sanguinalis* (DIGSA), *Echinochloa crus-galli* (English name "common barnyard grass", ECHCG), *Echinochloa oryzoides, Echinochloa colona* or *colonum, Eleusine indica, Eriochloa villosa* (English name "woolly cupgrass"), *Leptochloa chinensis, Leptochloa panicoides, Lolium perenne* (LOLPE, English name "perennial ryegrass"), *Lolium multiflorum* (LOLMU, English name "Italian ryegrass"), *Lolium persicum* (English name "Persian darnel"), *Lolium rigidum, Panicum dichotomiflorum* (PANDI), *Panicum miliaceum* (English name "wild proso millet"), *Phalaris minor, Phalaris paradoxa, Poa annua* (POAAN, English name "annual bluegrass"), *Scirpus maritimus, Scirpus juncoides, Setaria viridis* (SETVI, English name "green foxtail"), *Setaria faberi* (SETFA, English name "giant foxtail"), *Setaria glauca, Setaria lutescens* (English name "yellow foxtail"), *Sorghum bicolor*, and/or *Sorghum halepense* (English name "Johnson grass"), and/or *Sorghum vulgare*; and/or volunteer corn (volunteer maize) weeds.

In one preferred embodiment of all aspects of the invention, the monocotyledonous weeds, e.g. to be controlled and/or growth-inhibited, are grassy monocotyledonous weeds; in which case they typically comprise (e.g. are): weeds from the genus *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum*, and/or volunteer corn (volunteer maize) weeds; in particular: weeds from the genus *Agrostis, Alopecurus, Apera, Avena, Brachiaria, Bromus, Cenchrus, Digitaria, Echinochloa, Eleusine, Eriochloa, Leptochloa, Lolium, Panicum, Phalaris, Poa, Rottboellia, Setaria* and/or *Sorghum*, and/or volunteer corn (volunteer maize) weeds.

In one preferred embodiment of all aspects of the invention, the grassy monocotyledonous weeds, e.g. to be controlled and/or growth-inhibited, are "warm-season" (warm climate) grassy weeds; in which case they preferably comprise (e.g. are): weeds from the genus *Brachiaria, Cenchrus, Digitaria, Echinochloa, Eleusine, Eriochloa, Leptochloa, Ottochloa, Panicum, Pennisetum, Phalaris, Rottboellia, Setaria* and/or *Sorghum*, and/or volunteer corn (volunteer maize) weeds. More preferably, the grassy monocotyledonous weeds, e.g. to be controlled and/or growth-inhibited, are "warm-season" (warm climate) grassy weeds comprising (e.g. being): weeds from the genus *Brachiaria, Cenchrus, Digitaria, Echinochloa, Eleusine, Eriochloa, Panicum, Setaria* and/or *Sorghum*, and/or volunteer corn (volunteer maize) weeds.

In another particular embodiment of all aspects of the invention, the grassy monocotyledonous weeds, e.g. to be controlled and/or growth-inhibited, are "cool-season" (cool climate) grassy weeds; in which case they typically comprise (e.g. are) weeds from the genus *Agrostis, Alopecurus, Apera, Avena, Bromus, Lolium* and/or *Poa*.

In non-oat cereal crops such as wheat and/or barley, control and/or growth inhibition of weeds from the genus *Alopecurus, Apera, Avena*, especially *Avena fatua, Bromus, Lolium, Phalaris*, and/or *Setaria* is preferred; in particular *Alopecurus, Avena* (especially *Avena fatua*), *Lolium* and/or *Setaria* (especially *Setaria viridis, Setaria lutescens, Setaria faberi* and/or *Setaria glauca*).

In all aspects of the invention, in a particular embodiment, the weeds, e.g. to be controlled and/or growth-inhibited e.g. by applying a compound of formula (I), may be grassy monocotyledonous weeds (e.g. *Agrostis, Alopecurus, Apera, Avena, Brachiaria, Bromus, Cenchrus, Digitaria, Echinochloa, Eleusine, Eriochloa, Leptochloa, Lolium, Ottochloa, Panicum, Pennisetum, Phalaris, Poa, Rottboellia, Setaria* and/or *Sorghum* weeds), which are resistant to one or more ACCase inhibitor herbicides (ACCase=acetyl-coenzyme A carboxylase) selected from the group consisting of pinoxaden, clodinafop-propargyl, fenoxaprop-P-ethyl, diclofop-methyl, fluazifop-P-butyl, haloxyfop-P-methyl, quizalofop-P-ethyl, propaquizafop, cyhalofop-butyl, clethodim, sethoxydim, cycloxydim, tralkoxydim and butroxydim;

and/or which are resistant to glyphosate;

and/or which are resistant to one or more ALS inhibitor herbicides (ALS=acetolactate synthase), such as one or more sulfonyl urea herbicides (e.g. iodosulfuron-methyl, mesosulfuron-methyl, tribenuron-methyl, triasulfuron, prosulfuron, sulfosulfuron, pyrazosulfuron-ethyl, bensulfuron-methyl, nicosulfuron, flazasulfuron, iofensulfuron, metsulfuron-methyl, or any other sulfonyl urea herbicide disclosed in The Pesticide Manual, 15th edition (2009) or 16th Edition (2012), ed. C. D. S. Tomlin, British Crop Protection Council) and/or one or more triazolopyrimidine herbicides (e.g. florasulam, pyroxsulam or penoxsulam) and/or one or more pyrimidinyl-(thio or oxy)-benzoate herbicides (e.g. bispyribac-sodium or pyriftalid) and/or one or more sulfonylamino-carbonyl-triazolinone herbicides (e.g. thiencarbazone-methyl, propoxycarbazone-sodium or flucarbazone-sodium) and/or one or more imidazolinone herbicides (e.g. imazamox).

Such resistant (in particular ACCase-inhibitor-resistant, glyphosate-resistant, and/or ALS-inhibitor-resistant) grassy weeds can more particularly comprise *Alopecurus myosuroides, Apera spica-venti, Avena fatua, Avena sterilis, Brachiaria decumbens, Brachiaria plantaginea, Digitaria horizontalis, Digitaria insularis, Digitaria sanguinalis, Echinochloa colona, Echinochloa crus-galli, Eleusine indica, Lolium multiflorum, Lolium rigidum, Lolium perenne, Phalaris minor, Phalaris paradoxa, Setaria viridis, Setaria faberi, Setaria glauca*, and/or *Sorghum halepense*.

In an even more particular embodiment of the invention, the compound of formula (I) can be applied to grassy monocotyledonous weeds (e.g. selected from one of the above-mentioned list(s) of grassy weeds):

(a1) which are resistant to one or more ACCase inhibitor herbicides (e.g. selected from the above-mentioned list of ACCase inhibitor herbicides) at least partly by means of mutation (e.g. substitution) of one or more amino acids on the ACCase target site in the weed (e.g. see S. B. Powles and Qin Yu, "Evolution in Action: Plants Resistant to Herbicides", *Annu. Rev. Plant Biol.*, 2010, 61, pp. 317-347, e.g. see pages 325-327 therein in particular Table 3, incorporated herein by reference, for examples of such resistant weeds and/or amino acid substitutions); and/or (a2) which are resistant to glyphosate at least partly by means of mutation (e.g. substitution) of one or more amino acids on the EPSPS target site in the weed targeted by glyphosate (e.g. see above-mentioned S. B. Powles and Qin Yu article, pp. 327-329); and/or (a3) which are resistant to one or more ALS inhibitor herbicides (e.g. selected from the above-mentioned list of ALS inhibitor herbicides) at least partly by mutation (e.g. substitution) of one or more amino acids on the ALS target site in the weed (e.g. see S. B. Powles and Qin Yu, "Evolution in Action: Plants Resistant to Herbicides", *Annu. Rev. Plant Biol.*, 2010, 61, pp. 317-347, e.g. see pages 322-324 therein in particular Table 2, incorporated herein by reference, for examples of such resistant weeds and/or amino acid substitutions); and/or (b) which are resistant to: one or more ACCase inhibitor herbicides (e.g. selected from the above-mentioned list), and/or glyphosate, and/or one or more ALS inhibitor herbicides (e.g. selected from the above-mentioned list); at least partly by metabolic-type herbicidal resistance e.g. at least partly by cytochrome P450-mediated herbicide metabolism (e.g. see S. B. Powles and Qin Yu, "Evolution in Action: Plants Resistant to Herbicides", *Annu. Rev. Plant Biol.*, 2010, 61, pp. 317-347, e.g. see Table 4 on page 328 therein, incorporated herein by reference, for examples of such resistant weeds).

In one embodiment of the invention, dicotyledonous weeds, e.g. to be controlled, comprise (e.g. are) *Abutilon, Amaranthus, Chenopodium, Chrysanthemum, Galium, Ipomoea, Kochia, Nasturtium, Polygonum, Sida, Sinapsis, Solanum, Stellaria, Viola*, Veronica and/or *Xanthium*.

Areas under cultivation, and/or the locus (e.g. of weeds and/or of crops of useful plants), are to be understood as including land where the crop plants are already growing as well as land intended for the cultivation of those crop plants.

In all aspects of the invention, the rate of application (typically to the weeds and/or to the crops of useful plants and/or to the locus thereof) of the compound of formula (I) (which optionally may be an agriculturally acceptable salt thereof) is generally from 1 to 2000 g of the compound of formula (I) per hectare (ha) (measured as the salt-free compound, i.e. excluding the weight of any associated salt counterion(s)), in particular from 5 to 1000 g/ha or from 5 to 500 g/ha or from 10 to 500 g/ha, preferably from 10 to 400 g/ha or from 20 to 300 g/ha, of the compound of formula (I) (measured as the salt-free compound, i.e. excluding the weight of any associated salt counterion(s)). In a preferred embodiment, the above rates of application are for post-emergence application of the compound of formula (I) (which optionally may be an agriculturally acceptable salt thereof).

In all aspects of the invention, the compound of formula (I) can be applied (typically to the weeds and/or to the crops of useful plants and/or to the locus thereof) pre- and/or post-emergence, but preferably is applied post-emergence.
Other Possible Uses—e.g. Possible Insecticidal and/or Acaricidal Uses The main use and purpose of the compounds of formula (I) according to the invention is their herbicidal use. However, at least some of the compounds of formula (I) may have activity against one or more types of pest (in particular pests associated with agriculture and/or food storage). For example, at least some of the compounds of formula (I) may have at least some insecticidal, acaricidal, molluscicidal and/or nematicidal activity.

At least some of the compounds of formula (I) may have activity against (and/or may help to control and/or combat) insect pests, such as one or more of: Coleoptera, Dictyoptera, Diptera, Hemiptera (including Homoptera), Hymenoptera, Isoptera, Lepidoptera, Orthoptera, Siphonaptera and/or Thysanoptera.

At least some of the compounds of formula (I) may have activity against (and/or may help to control and/or combat) acarine pests and/or pests from the order Acarina, such as one or more of: *Acalitus* spp, *Aculus* spp, *Acaricalus* spp, *Aceria* spp, *Acarus siro, Amblyomma* spp., *Argas* spp., *Boophilus* spp., *Brevipalpus* spp., *Bryobia* spp., *Calipitrimerus* spp., *Chorioptes* spp., *Dermanyssus gallinae, Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus, Panonychus* spp., *Phyllocoptruta oleivora*, Phytonemus spp, *Polyphagotarsonemus* spp, *Psoroptes* spp., *Rhipicephalus* spp., *Rhizoglyphus* spp., *Sarcoptes* spp., *Steneotarsonemus* spp, *Tarsonemus* spp. and/or *Tetranychus* spp.

At least some of the compounds of formula (I) may have activity against (and/or may help to control and/or combat) other (i.e. non-insect, non-acarine) invertebrate pests, for example, nematode and/or mollusc pests.

Insects, acarines, nematodes and/or molluscs are hereinafter collectively referred to as pests.

Examples of pest species, on and/or to which the compounds of formula (I) can be tried and/or applied, include one or more of: *Myzus* spp. such as *Myzus persicae* (aphid), *Aphis* spp. such as *Aphis gossypii* (aphid) or *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (*thrips*), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta_migratoria* (locust), *Chortiocetes terminifera* (locust), *Diabrotica* spp. (rootworms), *Panonychus ulmi* (European red mite), *Panonychus citri* (citrus red mite), *Tetranychus* spp. such as *Tetranychus urticae* (two-spotted spider mite) or *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), of the Kalotermitidae (for example Neotermes spp.), of the Rhinotermitidae (for example *Coptotermes formosanus, Reticulitermes flavipes, R. speratu, R. virginicus, R. hesperus*, or *R. santonensis*) or of the Termitidae (for example *Globitermes sulphureus*), *Solenopsis geminata* (fire ant), *Monomorium pharaonis* (pharaoh's ant), *Damalinia* spp. or *Linognathus* spp. (biting lice or sucking lice), *Meloidogyne* spp. (root knot nematodes), *Globodera* spp. or *Heterodera* spp. (cyst nematodes), *Pratylenchus* spp. (lesion nematodes), Rhodopholus spp. (banana burrowing nematodes), *Tylenchulus* spp. (citrus nematodes), *Haemonchus contortus* (barber pole worm), *Caenorhabditis elegans*_(vinegar eelworm), *Trichostrongylus* spp. (gastro intestinal nematodes) and/or *Deroceras reticulatum* (slug).
Combinations and Mixtures In a further aspect, the present invention provides a herbicidal composition, e.g. for use in a method of controlling weeds (preferably monocotyledonous such as grassy monocotyledonous weeds) in crops of useful plants, comprising a compound of formula (I) as defined herein (e.g. a herbicidally effective amount thereof), and an agriculturally acceptable carrier, diluent and/or solvent, and also comprising one or more further herbicides, and/or a safener.

In all aspects of the invention, the compound of the formula (I) is optionally present (e.g. where chemically possible) as an agriculturally acceptable salt (e.g. agriculturally acceptable metal, sulfonium or ammonium salt) thereof.

Examples of these mixtures/compositions, comprising one or more further herbicides and/or a safener, follow.

The compounds of formula (I) according to the invention can be used in combination with one or more further herbicides, e.g. as mixture partner(s) for the compound of formula (I). Preferably, in these mixtures (in particular in the specific mixtures disclosed hereinbelow), the compound of the formula (I) is one of those compounds listed in Table 1 and/or one of the exemplified compounds (e.g. A1, A2, A3, A4, A5, or A6) as disclosed herein e.g. hereinbelow, present either as a free compound and/or as an agriculturally acceptable salt thereof.

In particular, the following mixtures of the compound of formula (I) with one or more further herbicides are particularly disclosed:

compound of formula I+acetochlor, compound of formula I+acifluorfen, compound of formula I+acifluorfen-sodium, compound of formula I+aclonifen, compound of formula I+acrolein, compound of formula I+alachlor, compound of formula I+alloxydim, compound of formula I+allyl alcohol, compound of formula I+ametryn, compound of formula I+amicarbazone, compound of formula I+amidosulfuron, compound of formula I+aminopyralid, compound of formula I+amitrole, compound of formula I+ammonium sulfamate, compound of formula I+anilofos, compound of formula I+asulam, compound of formula I+atraton, compound of formula I+atrazine, compound of formula I+azimsulfuron, compound of formula I+BCPC, compound of formula I+beflubutamid, compound of formula I+benazolin, compound of formula I+benfluralin, compound of formula I+benfuresate, compound of formula I+bensulfuron, compound of formula I+bensulfuron-methyl, compound of formula I+bensulide, compound of formula I+bentazone, compound of formula I+benzfendizone, compound of formula I+benzobicyclon, compound of formula I+benzofenap, compound of formula I+bifenox, compound of formula I+bilanafos, compound of formula I+bispyribac, compound of formula I+bispyribac-sodium, compound of formula I+borax, compound of formula I+bromacil, compound of formula I+bromobutide, compound of formula I+bromoxynil, compound of formula I+bromoxynil heptanoate, compound of formula I+bromoxynil octanoate, compound of formula I+bromoxynil heptanoate+bromoxynil octanoate, compound of formula I+butachlor, compound of formula I+butafenacil, compound of formula I+butamifos, compound of formula I+butralin, compound of formula I+butroxydim, compound of formula I+butylate, compound of formula I+cacodylic acid, compound of formula I+calcium chlorate, compound of formula I+cafenstrole, compound of formula I+carbetamide, compound of formula I+carfentrazone, compound of formula I+carfentrazone-ethyl, compound of formula I+CDEA, compound of formula I+CEPC, compound of formula I+chloransulam, compound of formula I+chloransulam-methyl, compound of formula I+chlorflurenol, compound of formula I+chlorflurenol-methyl, compound of formula I+chloridazon, compound of formula I+chlorimuron, compound of formula I+chlorimuron-ethyl, compound of formula I+chloroacetic acid, compound of formula I+chlorotoluron, compound of formula I+chlorpropham, compound of formula I+chlorsulfuron, compound of formula I+chlorthal, compound of formula I+chlorthal-dimethyl, compound of formula I+cinidon-ethyl, compound of formula I+cinmethylin, compound of formula I+cinosulfuron, compound of formula I+cisanilide, compound of formula I+clethodim, compound of formula I+clodinafop, compound of formula I+clodinafop-propargyl, compound of formula I+clomazone, compound of formula I+clomeprop, compound of formula I+clopyralid, compound of formula I+cloransulam, compound of formula I+cloransulam-methyl, compound of formula I+CMA, compound of formula I+4-CPB, compound of formula I+CPMF, compound of formula I+4-CPP, compound of formula I+CPPC, compound of formula I+cresol, compound of formula I+cumyluron, compound of formula I+cyanamide, compound of formula I+cyanazine, compound of formula I+cycloate, compound of formula I+cyclosulfamuron, compound of formula I+cycloxydim, compound of formula I+cyhalofop, compound of formula I+cyhalofop-butyl, compound of formula I+2,4-D, compound of formula I+2,4-D-dimethylammonium, compound of formula I+2,4-D-2-ethylhexyl, compound of formula I+a choline salt of 2,4-D (see e.g. Examples 2 and 3 of WO2010/123871A1), compound of formula I+2,4-D+glyphosate, compound of formula I+2,4-D-dimethylammonium+glyphosate, compound of formula I+2,4-D-2-ethylhexyl+glyphosate, compound of formula I+a choline salt of 2,4-D+glyphosate (see e.g. Examples 2 and 3 of WO2010/123871A1), compound of formula I+3,4-DA, compound of formula I+daimuron, compound of formula I+dalapon, compound of formula I+dazomet, compound of formula I+2,4-DB, compound of formula I+3,4-DB, compound of formula I+2,4-DEB, compound of formula I+desmedipham, compound of formula I+dicamba, compound of formula I+dicamba-dimethylammonium, compound of formula I+dicamba-potassium, compound of formula I+dicamba-sodium, compound of formula I+dicamba-diglycolamine, compound of formula I+a N,N-bis-[aminopropyl]methylamine salt of dicamba (see e.g. US2012/0184434A1), compound of formula I+dicamba+glyphosate, compound of formula I+dicamba-dimethylammonium+glyphosate, compound of formula I+dicamba-potassium+glyphosate, compound of formula I+dicamba-sodium+glyphosate, compound of formula I+dicamba-diglycolamine+glyphosate, compound of formula I+a N,N-bis-[aminopropyl]methylamine salt of dicamba+glyphosate (see e.g. US2012/0184434A1), compound of formula I+dichlobenil, compound of formula I+ortho-dichlorobenzene, compound of formula I+para-dichlorobenzene, compound of formula I+dichlorprop, compound of formula I+dichlorprop-P, compound of formula I+diclofop, compound of formula I+diclofop-methyl, compound of formula I+diclosulam, compound of formula I+difenzoquat, compound of formula I+difenzoquat metilsulfate, compound of formula I+diflufenican, compound of formula I+diflufenzopyr, compound of formula I+dimefuron, compound of formula I+dimepiperate, compound of formula I+dimethachlor, compound of formula I+dimethametryn, compound of formula I+dimethenamid, compound of formula I+dimethenamid-P, compound of formula I+dimethipin, compound of formula I+dimethylarsinic acid, compound of formula I+dinitramine, compound of formula I+dinoterb, compound of formula I+diphenamid, compound of formula I+diquat, compound of formula I+diquat dibromide, compound of formula I+dithiopyr, compound of formula I+diuron, compound of formula I+DNOC, compound of formula I+3,4-DP, compound of formula I+DSMA, compound of formula I+EBEP, compound of formula I+endothal, compound of formula I+EPTC, compound of formula I+esprocarb, compound of formula I+ethalfluralin, compound of formula I+ethametsulfuron, compound of formula I+ethametsulfuron-methyl, compound of formula I+ethofumesate, compound of formula I+ethoxyfen, compound of formula I+ethoxysulfuron, compound of formula I+etobenzanid, compound of formula (I)+fenoxaprop, compound of formula (I)+fenoxaprop-ethyl, compound of formula I+fenoxaprop-P, compound of formula I+fenoxaprop-P-ethyl, compound of formula I+fenoxasulfone (CAS Reg. No. 639826-16-7), compound of formula I+fentrazamide, compound of formula I+ferrous sulfate, compound of formula I+flamprop-M, compound of formula I+flazasulfuron, compound of formula I+florasulam, compound of formula I+fluazifop, compound of formula I+fluazifop-butyl, compound of formula I+fluazifop-P, compound of formula I+fluazifop-P-butyl, compound of formula I+flucarbazone, compound of formula I+flucarbazone-sodium, compound of formula I+flucetosulfuron, compound of formula I+fluchloralin, compound of formula I+flufenacet, compound of formula I+flufenpyr, compound of formula I+flufenpyr-ethyl, compound of formula I+flumetsulam, compound of formula I+flumiclorac, compound of formula I+flumiclorac-pentyl, compound of formula I+flumioxazin, compound of formula I+fluometuron, compound of formula I+fluoroglycofen, compound of formula I+fluoroglycofen-ethyl, compound of formula I+flupropanate, compound of formula I+flupyrsulfuron, compound of formula I+flupyrsulfuron-methyl-sodium, compound of formula I+flurenol, compound of formula I+fluridone, compound of formula I+flurochloridone, compound of formula I+fluroxypyr, compound of formula I+fluroxypyr-meptyl, compound of formula I+fluroxypyr-butometyl, compound of formula I+flurtamone, compound of formula I+fluthiacet, compound of formula I+fluthiacet-methyl, compound of formula I+fomesafen, compound of formula I+foramsulfuron, compound of formula I+fosamine, compound of formula I+glufosinate, compound of formula I+glufosinate-ammonium, compound of formula I+glufosinate-P, compound of formula I+glyphosate, compound of formula I+glyphosate-diammonium, compound of formula I+glyphosate-isopropylammonium, compound of formula I+glyphosate-potassium, compound of formula I+halosulfuron, compound of formula I+halosulfuron-methyl, compound of formula I+haloxyfop, compound of formula I+haloxyfop-P, compound of formula (I)+haloxyfop-methyl, compound of formula (I)+haloxyfop-P-methyl, compound of formula I+HC-252, compound of formula I+hexazinone, compound of formula I+imazamethabenz, compound of formula I+imazamethabenz-methyl, compound of formula I+imazamox, compound of formula I+imazapic, compound of formula I+imazapyr, compound of formula I+imazaquin, compound of formula I+imazethapyr, compound of formula I+imazosulfuron, compound of formula I+indanofan, compound of formula I+iodomethane, compound of formula I+iodosulfuron, compound of formula I+iodosulfuron-methyl-sodium, compound of formula I+ioxynil, compound of formula I+ipfencarbazone (CAS Reg. No. 212201-70-2), compound of formula I+isoproturon, compound of formula I+isouron, compound of formula I+isoxaben, compound of formula I+isoxachlortole, compound of formula I+isoxaflutole, compound of formula I+karbutilate, compound of formula I+lactofen, compound of formula I+lenacil, compound of formula I+linuron, compound of formula I+MAA, compound of formula I+MAMA, compound of formula I+MCPA, compound of formula I+MCPA-thioethyl, compound of formula I+MCPB, compound of formula I+mecoprop, compound of formula I+mecoprop-P, compound of formula I+mefenacet, compound of formula I+mefluidide, compound of formula I+mesosulfuron, compound of formula I+mesosulfuron-methyl, compound of formula I+mesotrione, compound of formula I+metam, compound of formula I+metamifop, compound of formula I+metamitron, compound of formula I+metazachlor, compound of formula I+metazosulfuron (NC-620, CAS Reg. No. 868680-84-6), compound of formula I+methabenzthiazuron, compound of formula I+methylarsonic acid, compound of formula I+methyldymron, compound of formula I+methyl isothiocyanate, compound of formula I+metobenzuron, compound of formula I+metolachlor, compound of formula I+S-metolachlor, compound of formula I+metosulam, compound of formula I+metoxuron, compound of formula I+metribuzin, compound of formula I+metsulfuron, compound of formula I+metsulfuron-methyl, compound of formula I+MK-616, compound of formula I+molinate, compound of formula I+monolinuron, compound of formula I+MSMA, compound of formula I+naproanilide, compound of formula I+napropamide, compound of formula I+naptalam, compound of formula I+neburon, compound of formula I+nicosulfuron, compound of formula I+nonanoic acid, compound of formula I+norflurazon, compound of formula I+oleic acid (fatty acids), compound of formula I+orbencarb, compound of formula I+orthosulfamuron, compound of formula I+oryzalin, compound of formula I+oxadiargyl, compound of formula I+oxadiazon, compound of formula I+oxasulfuron, compound of formula I+oxaziclomefone, compound of formula I+oxyfluorfen, compound of formula I+paraquat, compound of formula I+paraquat dichloride, compound of formula I+pebulate, compound of formula I+pendimethalin, compound of formula I+penoxsulam, compound of formula I+pentachlorophenol, compound of formula I+pentanochlor, compound of formula I+pentoxazone, compound of formula I+pethoxamid, compound of formula I+petrolium oils, compound of formula I+phenmedipham, compound of formula I+phenmedipham-ethyl, compound of formula I+picloram, compound of formula I+picolinafen, compound of formula I+pinoxaden, compound of formula I+piperophos, compound of formula I+potassium arsenite, compound of formula I+potassium azide, compound of formula I+pretilachlor, compound of formula I+primisulfuron, compound of formula I+primisulfuron-methyl, compound of formula I+prodiamine, compound of formula I+profluazol, compound of formula I+profoxydim, compound of formula I+prometon, compound of formula I+prometryn, compound of formula I+propachlor, compound of formula I+propanil, compound of formula I+propaquizafop, compound of formula I+propazine, compound of formula I+propham, compound of formula I+propisochlor, compound of formula I+propoxycarbazone, compound of formula I+propoxycarbazone-sodium, compound of formula I+propyrisulfuron (TH-547, CAS Reg. No. 570415-88-2), compound of formula I+propyzamide, compound of formula I+prosulfocarb, compound of formula I+prosulfuron, compound of formula I+pyraclonil, compound of formula I+pyraflufen, compound of formula I+pyraflufen-ethyl, compound of formula I+pyrazolynate, compound of formula I+pyrazosulfuron, compound of formula I+pyrazosulfuron-ethyl, compound of formula I+pyrazoxyfen, compound of formula I+pyribenzoxim, compound of formula I+pyributicarb, compound of formula I+pyridafol, compound of formula I+pyridate, compound of formula I+pyriftalid, compound of formula I+pyriminobac, compound of formula I+pyriminobac-methyl, compound of formula I+pyrimisulfan, compound of formula I+pyrithiobac, compound of formula I+pyrithiobac-sodium, compound of formula I+quinclorac, compound of formula I+quinmerac, compound of formula I+quinoclamine, compound of formula I+quizalofop, compound of formula I+quizalofop-ethyl, compound of formula I+quizalofop-P, compound of formula I+quizalofop-P-ethyl, compound of formula I+quizalofop-P-tefuryl, compound of formula I+rimsulfuron, compound of formula I+sethoxydim, compound of formula I+siduron, compound of formula I+simazine, compound of formula I+simetryn, compound of formula I+SMA, compound of formula I+sodium arsenite, compound of formula I+sodium azide, compound of formula I+sodium chlorate, compound of formula I+sulcotrione, compound of formula I+sulfentrazone, compound of formula I+sulfometuron, compound of formula I+sulfometuron-methyl, compound of formula I+sulfosate, compound of formula I+sulfosulfuron, compound of formula I+sulfuric acid, compound of formula I+tar oils, compound of formula I+2,3,6-TBA, compound of formula I+TCA, compound of formula I+TCA-sodium, compound of formula I+tebuthiuron, compound of formula I+tepraloxydim, compound of formula I+terbacil, compound of formula I+terbumeton, compound of formula I+terbuthylazine, compound of formula I+terbutryn, compound of formula I+thenylchlor, compound of formula I+thiazopyr, compound of formula I+thifensulfuron, compound of formula I+thifensulfuron-methyl, compound of formula I+thiobencarb, compound of formula I+tiocarbazil, compound of formula I+topramezone, compound of formula I+tralkoxydim, compound of formula I+tri-allate, compound of formula I+triasulfuron, compound of formula I+triaziflam, compound of formula I+tribenuron, compound of formula I+tribenuron-methyl, compound of formula I+tricamba, compound of formula I+triclopyr, compound of formula I+trietazine, compound of formula I+trifloxysulfuron, compound of formula I+trifloxysulfuron-sodium, compound of formula I+trifluralin, compound of formula I+triflusulfuron, compound of formula I+triflusulfuron-methyl, compound of formula I+trihydroxytriazine, compound of formula I+tritosulfuron, compound of formula I+[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetic acid ethyl ester (CAS Reg. No. 353292-31-6), compound of formula I+4-[(4,5-dihydro-3-methoxy-4-methyl-5-oxo)-1H-1,2,4-triazol-1-ylcarbonylsulfamoyl]-5-methylthiophene-3-carboxylic acid (BAY636), compound of formula I+BAY747 (CAS Reg. No. 335104-84-2), compound of formula I+topramezone (CAS Reg. No. 210631-68-8), compound of formula I+4-hydroxy-3-[[2-[(2-methoxyethoxy)-methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula I+4-hydroxy-3-[[2-(3-methoxypropyl)-6-(difluoromethyl)-3-pyridinyl]carbonyl]-bicyclo[3.2.1]oct-3-en-2-one, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9, and which is also compound A-13 disclosed in pages 4, 5, 7 and 11 of WO 2011/073616 A2, these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9, and which is also compound A-12 disclosed in page 10 of WO 2011/073616 A2, these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1, and which is also compound A-4 disclosed on page 7 of WO 2011/073615 A2, these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1, and which is also the compound of Example P10 disclosed on pages 41 and 45 of WO 2010/136431 A9, and which is also compound A-7 disclosed on page 7 of WO 2011/073615 A2, these parts of these publications being incorporated herein by reference), compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1, and which is also compound A-9 disclosed on page 8 of WO 2011/073615 A2, these parts of these publications being incorporated herein by reference), compound of formula (I)+one of the specific herbicidal compounds disclosed in WO 2010/059676 (e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (e.g. as defined in one of the examples therein and/or e.g. can be plus cloquintocet-mexyl or another safener) these parts of which are incorporated herein by reference, and compound of formula (I)+one of the specific herbicidal compounds disclosed in WO 2010/059671 (e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+aminocyclopyrachlor (which is 6-amino-5-chloro-2-cyclopropylpyrimidine-4-carboxylic acid, CAS Reg. No. 858956-08-8), compound of formula I+aminocyclopyrachlor-methyl (which is methyl 6-amino-5-chloro-2-cyclopropylpyrimidine-4-carboxylate, CAS Reg. No. 858954-83-3), compound of formula I+aminocyclopyrachlor-potassium (which is potassium 6-amino-5-chloro-2-cyclopropylpyrimidine-4-carboxylate, CAS Reg. No. 858956-35-1), compound of formula I+saflufenacil (which is N'-{2-chloro-4-fluoro-5-[1,2,3,6-tetrahydro-3-methyl-2,6-dioxo-4-(trifluoromethyl)pyrimidin-1-yl]benzoyl}-N-isopropyl-N-methylsulfamide, CAS Reg. No. 372137-35-4), compound of formula I+iofensulfuron (which is 1-(2-iodophenylsulfonyl)-3-(4-methoxy-6-methyl-1,3,5-triazin-2-yl) urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), compound of formula I+clacyfos (which is dimethyl [(1RS)-1-(2,4-dichlorophenoxyacetoxy)ethyl]phosphonate, also named Ivxiancaolin or lxiancaolin, CAS Reg. No. 215655-76-8), compound of formula I+cyclopyrimorate (which is 6-chloro-3-(2-cyclopropyl-6-methylphenoxy)pyridazin-4-yl morpholine-4-carboxylate, CAS Reg. No. 499231-24-2), or compound of formula I+triafamone (which is N-[2-[(4,6-dimethoxy-1,3,5-triazin-2-yl)carbonyl]-6-fluorophenyl]-N-methyl-1, 1-difluoromethanesulfonamide, CAS Reg. No. 874195-61-6).

The mixture partners for the compound of formula (I) are optionally in the form of an ester (in particular an agriculturally acceptable ester) or a salt (in particular an agriculturally acceptable salt) thereof (e.g. where chemically possible). The above-mentioned mixture partners for the compound of formula (I), are generally mentioned e.g. in The Pesticide Manual, 15th Edition (2009) or 16th Edition (2012), ed. C. D. S. Tomlin, British Crop Production Council.

In the present patent specification, "CAS Reg. No." or "CAS RN" means the Chemical Abstracts Service Registry Number of the stated compound.

For applications in cereals, the following mixtures are preferred: compound of formula I+aclonifen, compound of formula I+amidosulfuron, compound of formula I+aminopyralid, compound of formula I+beflubutamid, compound of formula I+benfluralin, compound of formula I+bifenox, compound of formula I+bromoxynil, compound of formula I+bromoxynil heptanoate, compound of formula I+bromoxynil octanoate, compound of formula I+bromoxynil heptanoate+bromoxynil octanoate, compound of formula I+butafenacil, compound of formula I+carbetamide, compound of formula I+carfentrazone, compound of formula I+carfentrazone-ethyl, compound of formula I+chlorotoluron, compound of formula I+chlorpropham, compound of formula I+chlorsulfuron, compound of formula I+cinidon-ethyl, compound of formula I+clodinafop, compound of formula I+clodinafop-propargyl, compound of formula I+clopyralid, compound of formula I+2,4-D, compound of formula I+2,4-D-dimethylammonium, compound of formula I+2,4-D-2-ethylhexyl, compound of formula I+a choline salt of 2,4-D (see e.g. Examples 2 and 3 of WO2010/123871A1), compound of formula I+dicamba, compound of formula I+dicamba-dimethylammonium, compound of formula I+dicamba-potassium, compound of formula I+dicamba-sodium, compound of formula I+dicamba-diglycolamine, compound of formula I+a N,N-bis-[aminopropyl]methylamine salt of dicamba (see e.g. US2012/0184434A1), compound of formula I+dichlobenil, compound of formula I+dichlorprop, compound of formula I+diclofop, compound of formula I+diclofop-methyl, compound of formula I+difenzoquat, compound of formula I+difenzoquat metilsulfate, compound of formula I+diflufenican, compound of formula I+diquat, compound of formula I+diquat dibromide, compound of formula (I)+fenoxaprop, compound of formula (I)+fenoxaprop-ethyl, compound of formula I+fenoxaprop-P, compound of formula I+fenoxaprop-P-ethyl, compound of formula I+flamprop-M, compound of formula I+florasulam, compound of formula I+fluazifop-P-butyl, compound of formula I+flucarbazone, compound of formula I+flucarbazone-sodium, compound of formula I+flufenacet, compound of formula I+flupyrsulfuron, compound of formula I+flupyrsulfuron-methyl-sodium, compound of formula I+flurochloridone, compound of formula I+fluroxypyr, compound of formula I+fluroxypyr-meptyl, compound of formula I+fluroxypyr-butometyl, compound of formula I+flurtamone, compound of formula I+imazamethabenz-methyl, compound of formula I+imazamox, compound of formula I+iodosulfuron, compound of formula I+iodosulfuron-methyl-sodium, compound of formula I+ioxynil, compound of formula I+isoproturon, compound of formula I+linuron, compound of formula I+MCPA, compound of formula I+mecoprop, compound of formula I+mecoprop-P, compound of formula I+mesosulfuron, compound of formula I+mesosulfuron-methyl, compound of formula I+mesotrione, compound of formula I+metribuzin, compound of formula I+metsulfuron, compound of formula I+metsulfuron-methyl, compound of formula I+pendimethalin, compound of formula I+picolinafen, compound of formula I+pinoxaden, compound of formula I+prodiamine, compound of formula I+propanil, compound of formula I+propoxycarbazone, compound of formula I+propoxycarbazone-sodium, compound of formula I+prosulfocarb, compound of formula I+pyrasulfotole, compound of formula I+pyridate, compound of formula I+pyroxasulfone (KIH-485), compound of formula I+pyroxsulam compound of formula I+sulfosulfuron, compound of formula 1+tembotrione, compound of formula I+terbutryn, compound of formula I+thifensulfuron, compound of formula I+thiencarbazone, compound of formula I+thifensulfuron-methyl, compound of formula I+topramezone, compound of formula I+tralkoxydim, compound of formula I+tri-allate, compound of formula I+triasulfuron, compound of formula I+tribenuron, compound of formula I+tribenuron-methyl, compound of formula I+trifluralin, compound of formula I+trinexapac-ethyl and compound of formula I+tritosulfuron, compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula (I)+one of the specific herbicidal compounds disclosed in WO 2010/059676 (e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (e.g. as defined in one of the examples therein and/or e.g. can be plus cloquintocet-mexyl or another safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), or compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2);

wherein the mixture partners for the compound of formula (I) may optionally be in the form of an ester (in particular an agriculturally acceptable ester) or a salt (in particular an agriculturally acceptable salt) thereof (e.g. where chemically possible).

For applications in cereals, more preferred is a mixture comprising: a compound of formula (I)+amidosulfuron, compound of formula (I)+aminopyralid, compound of formula (I)+beflubutamid, compound of formula (I)+bromoxynil, compound of formula (I)+bromoxynil heptanoate, compound of formula (I)+bromoxynil octanoate, compound of formula (I)+bromoxynil heptanoate+bromoxynil octanoate, compound of formula (I)+carfentrazone, compound of formula (I)+carfentrazone-ethyl, compound of formula (I)+chlorotoluron, compound of formula (I)+chlorsulfuron, compound of formula (I)+clodinafop, compound of formula (I)+clodinafop-propargyl, compound of formula (I)+clopyralid, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+dicamba, compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+difenzoquat, compound of formula (I)+difenzoquat metilsulfate, compound of formula (I)+diflufenican, compound of formula (I)+fenoxaprop-P, compound of formula (I)+fenoxaprop-P-ethyl, compound of formula (I)+florasulam, compound of formula (I)+flucarbazone, compound of formula (I)+flucarbazone-sodium, compound of formula (I)+flufenacet, compound of formula (I)+flupyrsulfuron, compound of formula (I)+flupyrsulfuron-methyl-sodium, compound of formula (I)+fluroxypyr, compound of formula I+fluroxypyr-meptyl, compound of formula I+fluroxypyr-butometyl, compound of formula (I)+flurtamone, compound of formula (I)+iodosulfuron, compound of formula (I)+iodosulfuron-methyl-sodium, compound of formula (I)+MCPA, compound of formula (I)+mesosulfuron, compound of formula (I)+mesosulfuron-methyl, compound of formula (I)+metsulfuron, compound of formula (I)+metsulfuron-methyl, compound of formula (I)+pendimethalin, compound of formula (I)+picolinafen, compound of formula (I)+pinoxaden, compound of formula (I)+prosulfocarb, compound of formula (I)+pyrasulfotole, compound of formula (I)+pyroxasulfone (KIH-485), compound of formula (I)+pyroxsulam, compound of formula (I)+sulfosulfuron, compound of formula (I)+thifensulfuron, compound of formula (I)+thifensulfuron-methyl, compound of formula I+topramezone, compound of formula (I)+tralkoxydim, compound of formula (I)+triasulfuron, compound of formula (I)+tribenuron, compound of formula (I)+tribenuron-methyl, compound of formula (I)+trifluralin, compound of formula (I)+trinexapac-ethyl, compound of formula (I)+tritosulfuron, compound of formula I+4-hydroxy-3-[[2-[(2-methoxyethoxy)methyl]-6-(trifluoromethyl)-3-pyridinyl]carbonyl]-bicyclo[3.2.1]oct-3-en-2-one (which is bicyclopyrone, CAS Reg. No. 352010-68-5), compound of formula (I)+one of the specific herbicidal compounds disclosed in WO 2010/059676 (e.g. as defined in one of the examples therein and/or e.g. can be plus cloquintocet-mexyl as safener) these parts of which are incorporated herein by reference, compound of formula (I)+one of the specific herbicidal compounds disclosed in WO 2010/059680 (e.g. as defined in one of the examples therein and/or e.g. can be plus cloquintocet-mexyl or another safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), or compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2);

wherein the mixture partners for the compound of formula (I) may optionally be in the form of an ester (in particular an agriculturally acceptable ester) or a salt (in particular an agriculturally acceptable salt) thereof (e.g. where chemically possible).

For applications in rice, the following mixtures are preferred: compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+butachlor, compound of formula (I)+cafenstrole, compound of formula (I)+cinosulfuron, compound of formula (I)+clomazone, compound of formula (I)+clomeprop, compound of formula (I)+cyclosulfamuron, compound of formula (I)+cyhalofop, compound of formula (I)+cyhalofop-butyl, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+daimuron, compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+diquat, compound of formula (I)+diquat dibromide, compound of formula (I)+esprocarb, compound of formula (I)+ethoxysulfuron, compound of formula (I)+fenoxaprop, compound of formula (I)+fenoxaprop-ethyl, compound of formula (I)+fenoxaprop-P, compound of formula (I)+fenoxaprop-P-ethyl, compound of formula I+fenoxasulfone (CAS Reg. No. 639826-16-7), compound of formula (I)+fentrazamide, compound of formula (I)+florasulam, compound of formula (I)+glufosinate-ammonium, compound of formula (I)+glyphosate, compound of formula (I)+glyphosate-diammonium, compound of formula (I)+glyphosate-isopropylammonium, compound of formula (I)+glyphosate-potassium, compound of formula (I)+halosulfuron, compound of formula (I)+halosulfuron-methyl, compound of formula (I)+imazosulfuron, compound of formula I+ipfencarbazone (CAS Reg. No. 212201-70-2), compound of formula (I)+MCPA, compound of formula (I)+mefenacet, compound of formula (I)+mesotrione, compound of formula (I)+metamifop, compound of formula I+metazosulfuron (NC-620, CAS Reg. No. 868680-84-6), compound of formula (I)+metsulfuron, compound of formula (I)+metsulfuron-methyl, compound of formula (I)+n-methyl glyphosate, compound of formula (I)+orthosulfamuron, compound of formula (I)+oryzalin, compound of formula (I)+oxadiargyl, compound of formula (I)+oxadiazon, compound of formula (I)+paraquat dichloride, compound of formula (I)+pendimethalin, compound of formula (I)+penoxsulam, compound of formula (I)+pretilachlor, compound of formula (I)+profoxydim, compound of formula (I)+propanil, compound of formula I+propyrisulfuron (TH-547, CAS Reg. No. 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9, and which is also compound A-13 disclosed in pages 4, 5, 7 and 11 of WO 2011/073616 A2, these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9, and which is also compound A-12 disclosed in page 10 of WO 2011/073616 A2, these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1, and which is also compound A-4 disclosed on page 7 of WO 2011/073615 A2, these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1, and which is also the compound of Example P10 disclosed on pages 41 and 45 of WO 2010/136431 A9, and which is also compound A-7 disclosed on page 7 of WO 2011/073615 A2, these parts of these publications being incorporated herein by reference), compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1, and which is also compound A-9 disclosed on page 8 of WO 2011/073615 A2, these parts of these publications being incorporated herein by reference), compound of formula (I)+one of the specific herbicidal compounds disclosed in WO 2010/059671 (e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), or compound of formula I+triafamone (which is N-[2-[(4,6-dimethoxy-1,3,5-triazin-2-yl)carbonyl]-6-fluorophenyl]-N-methyl-1,1-difluoromethanesulfonamide, CAS Reg. No. 874195-61-6); wherein the mixture partners for the compound of formula (I) may optionally be in the form of an ester (in particular an agriculturally acceptable ester) or a salt (in particular an agriculturally acceptable salt) thereof (e.g. where chemically possible).

For applications in rice, more preferred is a mixture comprising: a compound of formula (I)+azimsulfuron, compound of formula (I)+bensulfuron, compound of formula (I)+bensulfuron-methyl, compound of formula (I)+benzobicyclon, compound of formula (I)+benzofenap, compound of formula (I)+bispyribac, compound of formula (I)+bispyribac-sodium, compound of formula (I)+clomazone, compound of formula (I)+clomeprop, compound of formula (I)+cyhalofop, compound of formula (I)+cyhalofop-butyl, compound of formula (I)+2,4-D, compound of formula (I)+2,4-D-dimethylammonium, compound of formula (I)+2,4-D-2-ethylhexyl, compound of formula (I)+a choline salt of 2,4-D (see e.g. Examples 2 and 3 of WO2010/123871A1), compound of formula (I)+daimuron, compound of formula (I)+dicamba, compound of formula (I)+dicamba-dimethylammonium, compound of formula (I)+dicamba-potassium, compound of formula (I)+dicamba-sodium, compound of formula (I)+dicamba-diglycolamine, compound of formula (I)+a N,N-bis-[aminopropyl]methylamine salt of dicamba (see e.g. US2012/0184434A1), compound of formula (I)+esprocarb, compound of formula (I)+ethoxysulfuron, compound of formula (I)+fenoxaprop-P, compound of formula (I)+fenoxaprop-P-ethyl, compound of formula I+fenoxasulfone (CAS Reg. No. 639826-16-7), compound of formula (I)+fentrazamide, compound of formula (I)+florasulam, compound of formula (I)+halosulfuron, compound of formula (I)+halosulfuron-methyl, compound of formula (I)+imazosulfuron, compound of formula I+ipfencarbazone (CAS Reg. No. 212201-70-2), compound of formula (I)+MCPA, compound of formula (I)+mefenacet, compound of formula (I)+mesotrione, compound of formula I+metazosulfuron (NC-620, CAS Reg. No. 868680-84-6), compound of formula (I)+metsulfuron, compound of formula (I)+metsulfuron-methyl, compound of formula (I)+orthosulfamuron, compound of formula (I)+oxadiargyl, compound of formula (I)+oxadiazon, compound of formula (I)+pendimethalin, compound of formula (I)+penoxsulam, compound of formula (I)+pretilachlor, compound of formula I+propyrisulfuron (TH-547, CAS Reg. No. 570415-88-2), compound of formula (I)+pyrazolynate, compound of formula (I)+pyrazosulfuron, compound of formula (I)+pyrazosulfuron-ethyl, compound of formula (I)+pyrazoxyfen, compound of formula (I)+pyribenzoxim, compound of formula (I)+pyriftalid, compound of formula (I)+pyriminobac, compound of formula (I)+pyriminobac-methyl, compound of formula (I)+pyrimisulfan, compound of formula (I)+quinclorac, compound of formula (I)+tefuryltrione, compound of formula (I)+triasulfuron and compound of formula (I)+trinexapac-ethyl, compound of formula (I)+4-(4'-chloro-4-cyclopropyl-2'-fluorobiphenyl-3-yl)-2,2,6,6-tetramethyl-2H-pyran-3,5 (4H,6H)-dione (which is the compound of Example P8 disclosed on pages 31-32 and 35-36 of WO 2010/136431 A9, and which is also compound A-13 disclosed in pages 4, 5, 7 and 11 of WO 2011/073616 A2, these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9, and which is also compound A-12 disclosed in page 10 of WO 2011/073616 A2, these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1, and which is also compound A-4 disclosed on page 7 of WO 2011/073615 A2, these parts of these publications being incorporated herein by reference), compound of formula (I)+4-(2',4'-dichloro-4-ethylbiphenyl-3-yl)-2,2,6,6-tetramethyl-2H-pyran-3,5(4H, 6H)-dione (which is compound A-45 disclosed on page 93 of WO 2008/071405 A1, and which is also the compound of Example P10 disclosed on pages 41 and 45 of WO 2010/136431 A9, and which is also compound A-7 disclosed on page 7 of WO 2011/073615 A2, these parts of these publications being incorporated herein by reference), compound of formula (I)+4-(2',4'-dichloro-4-ethylbiphenyl-3-yl)-5-(methoxycarbonyloxy)-2,2,6,6-tetramethyl-2H-pyran-3 (6H)-one (which is compound D-26 disclosed on page 231 of WO 2008/071405 A1, and which is also compound A-9 disclosed on page 8 of WO 2011/073615 A2, these parts of these publications being incorporated herein by reference), compound of formula (I)+one of the specific herbicidal compounds disclosed in WO 2010/059671 (e.g. as defined in one of the examples therein and/or e.g. can be plus a safener) these parts of which are incorporated herein by reference, compound of formula I+halauxifen (which is 4-amino-3-chloro-6-(4-chloro-2-fluoro-3-methoxyphenyl)pyridine-2-carboxylic acid, CAS Reg. No. 943832-60-8), compound of formula I+halauxifen-methyl (which is methyl 4-amino-3-chloro-6-(4-chloro-2-fluoro-3-methoxyphenyl)pyridine-2-carboxylate, CAS Reg. No. 943831-98-9), compound of formula I+iofensulfuron (which is 1-(2-iodophenylsulfonyl)-3-(4-methoxy-6-methyl-1,3,5-triazin-2-yl)urea, CAS Reg. No. 1144097-22-2), compound of formula I+iofensulfuron-sodium (which is sodium N-(2-iodophenylsulfonyl)-N'-(4-methoxy-6-methyl-1,3,5-triazin-2-yl)carbamimidate, CAS Reg. No. 1144097-30-2), or compound of formula I+triafamone (which is N-[2-[(4,6-dimethoxy-1,3,5-triazin- 2-yl)carbonyl]-6-fluorophenyl]-N-methyl-1, 1-difluoromethanesulfonamide, CAS Reg. No. 874195-61-6);

wherein the mixture partners for the compound of formula (I) may optionally be in the form of an ester (in particular an agriculturally acceptable ester) or a salt (in particular an agriculturally acceptable salt) thereof (e.g. where chemically possible).

For applications in soybean, the following mixtures are preferred:

compound of formula (I)+acifluorfen, compound of formula (I)+acifluorfen-sodium, compound of formula (I)+ametryn, compound of formula (I)+atrazine, compound of formula (I)+bentazone, compound of formula (I)+bicyclopyrone, compound of formula (I)+bromoxynil, compound of formula (I)+bromoxynil heptanoate, compound of formula (I)+bromoxynil octanoate, compound of formula (I)+bromoxynil heptanoate+bromoxynil octanoate, compound of formula (I)+carfentrazone, compound of formula (I)+carfentrazone-ethyl, compound of formula (I)+chloransulam, compound of formula (I)+chloransulam-methyl, compound of formula (I)+chlorimuron, compound of formula (I)+chlorimuron-ethyl, compound of formula (I)+clethodim, compound of formula (I)+clomazone, compound of formula (I)+cyanazine, compound of formula (I)+2,4-D (especially for applications to 2,4-D-tolerant soybean, e.g. genetically-modified), compound of formula (I)+2,4-D-dimethylammonium (especially for applications to 2,4-D-tolerant soybean, e.g. genetically-modified), compound of formula (I)+2,4-D-2-ethylhexyl (especially for applications to 2,4-D-tolerant soybean, e.g. genetically-modified), compound of formula (I)+a choline salt of 2,4-D (see e.g. Examples 2 and 3 of WO2010/123871A1) (especially for applications to 2,4-D-tolerant soybean, e.g. genetically-modified), compound of formula (I)+2,4-D+glyphosate (especially for applications to 2,4-D-tolerant and/or glyphosate-tolerant soybean, e.g. genetically-modified), compound of formula (I)+2,4-D-dimethylammonium+glyphosate (especially for applications to 2,4-D-tolerant and/or glyphosate-tolerant soybean, e.g. genetically-modified), compound of formula (I)+2,4-D-2-ethylhexyl+glyphosate (especially for applications to 2,4-D-tolerant and/or glyphosate-tolerant soybean, e.g. genetically-modified), compound of formula I+a choline salt of 2,4-D+glyphosate (see e.g. Examples 2 and 3 of WO2010/123871A1) (especially for applications to dicamba-tolerant and/or glyphosate-tolerant soybean, e.g. genetically-modified), compound of formula (I)+dicamba (especially for applications to dicamba-tolerant soybean, e.g. genetically-modified), compound of formula (I)+dicamba-dimethylammonium (especially for applications to dicamba-tolerant soybean, e.g. genetically-modified), compound of formula (I)+dicamba-potassium (especially for applications to dicamba-tolerant soybean, e.g. genetically-modified), compound of formula (I)+dicamba-sodium (especially for applications to dicamba-tolerant soybean, e.g. genetically-modified), compound of formula (I)+dicamba-diglycolamine (especially for applications to dicamba-tolerant soybean, e.g. genetically-modified), compound of formula (I)+a N,N-bis-[aminopropyl]methylamine salt of dicamba (see e.g. US2012/0184434A1) (especially for applications to dicamba-tolerant soybean, e.g. genetically-modified), compound of formula (I)+dicamba+glyphosate (especially for applications to dicamba-tolerant and/or glyphosate-tolerant soybean, e.g. genetically-modified), compound of formula (I)+dicamba-dimethylammonium+glyphosate (especially for applications to dicamba-tolerant and/or glyphosate-tolerant soybean, e.g. genetically-modified), compound of formula (I)+dicamba-potassium+glyphosate (especially for applications to dicamba-tolerant and/or glyphosate-tolerant soybean, e.g. genetically-modified), compound of formula (I)+dicamba-sodium+glyphosate (especially for applications to dicamba-tolerant and/or glyphosate-tolerant soybean, e.g. genetically-modified), compound of formula (I)+dicamba-diglycolamine+glyphosate (especially for applications to dicamba-tolerant and/or glyphosate-tolerant soybean, e.g. genetically-modified), compound of formula (I)+a N,N-bis-[aminopropyl]methylamine salt of dicamba+glyphosate (see e.g. US2012/0184434A1) (especially for applications to dicamba-tolerant and/or glyphosate-tolerant soybean, e.g. genetically-modified), compound of formula (I)+diclosulam, compound of formula (I)+dimethenamid, compound of formula (I)+dimethenamid-P, compound of formula (I)+diquat, compound of formula (I)+diquat dibromide, compound of formula (I)+diuron, compound of formula (I)+fenoxaprop, compound of formula (I)+fenoxaprop-ethyl, compound of formula (I)+fenoxaprop-P, compound of formula (I)+fenoxaprop-P-ethyl, compound of formula (I)+fluazifop, compound of formula (I)+fluazifop-butyl, compound of formula (I)+fluazifop-P, compound of formula (I)+fluazifop-P-butyl, compound of formula (I)+flufenacet, compound of formula (I)+flumetsulam, compound of formula (I)+flumioxazin, compound of formula (I)+fluthiacet, compound of formula (I)+fluthiacet-methyl, compound of formula (I)+fomesafen, compound of formula (I)+glufosinate, compound of formula (I)+glufosinate-ammonium, compound of formula (I)+glyphosate, compound of formula (I)+glyphosate-diammonium, compound of formula (I)+glyphosate-isopropylammonium, compound of formula (I)+glyphosate-potassium, compound of formula (I)+imazethapyr, compound of formula (I)+lactofen, compound of formula (I)+mesotrione, compound of formula (I)+metolachlor, compound of formula (I)+S-metolachlor, compound of formula (I)+metribuzin, compound of formula (I)+oxyfluorfen, compound of formula (I)+paraquat, compound of formula (I)+paraquat dichloride, compound of formula (I)+pendimethalin, compound of formula (I)+pyroxasulfone, compound of formula I+quizalofop, compound of formula I+quizalofop-ethyl, compound of formula I+quizalofop-P, compound of formula I+quizalofop-P-ethyl, compound of formula I+quizalofop-P-tefuryl, compound of formula (I)+saflufenacil, compound of formula (I)+sethoxydim, compound of formula (I)+sulfentrazone, compound of formula (I)+thifensulfuron, compound of formula (I)+thifensulfuron-methyl, compound of formula (I)+tribenuron, compound of formula (I)+tribenuron-methyl, compound of formula (I)+trifluralin, compound of formula (I)+4-(4'-chloro-4-cyclopropyl-2'-fluorobiphenyl-3-yl)-2,2,6,6-tetramethyl-2H-pyran-3,5(4H,6H)-dione (which is the compound of Example P8 disclosed on pages 31-32 and 35-36 of WO 2010/136431 A9, and which is also compound A-13 disclosed in pages 4, 5, 7 and 11 of WO 2011/073616 A2, these parts of these publications being incorporated herein by reference), compound of formula (I)+4-(2',4'-dichloro-4-cyclopropylbiphenyl-3-yl)-2,2,6,6-tetramethyl-2H-pyran-3,5(4H,6H)-dione (which is the compound of Example P9 disclosed on pages 36-37 and 40-41 of WO 2010/136431 A9, and which is also compound A-12 disclosed in page 10 of WO 2011/073616 A2, these parts of these publications being incorporated herein by reference), compound of formula (I)+4-(4'-chloro-4-ethyl-2'-fluorobiphenyl-3-yl)-2,2,6,6-tetramethyl-2H-pyran-3,5(4H,6H)-dione (which is compound A-66 disclosed on page 95 of WO 2008/071405 A1, and which is also compound A-4 disclosed on page 7 of WO 2011/073615 A2, these parts of these publications being incorporated herein by reference), compound of formula (I)+4-(2',4'-dichloro-4-ethylbiphenyl-3-yl)-2,2,6,6-tetramethyl-2H-pyran-3,5(4H,6H)-dione (which is compound A-45 disclosed on page 93 of WO 2008/071405 A1, and which is also the compound of Example P10 disclosed on pages 41 and 45 of WO 2010/136431 A9, and which is also compound A-7 disclosed on page 7 of WO 2011/073615 A2, these parts of these publications being incorporated herein by reference), or compound of formula (I)+4-(2',4'-dichloro-4-ethylbiphenyl-3-yl)-5-(methoxycarbonyloxy)-2,2,6,6-tetramethyl-2H-pyran-3(6H)-one (which is compound D-26 disclosed on page 231 of WO 2008/071405 A1, and which is also compound A-9 disclosed on page 8 of WO 2011/073615 A2, these parts of these publications being incorporated herein by reference);

wherein the mixture partners for the compound of formula (I) may optionally be in the form of an ester (in particular an agriculturally acceptable ester) or a salt (in particular an agriculturally acceptable salt) thereof (e.g. where chemically possible).

In the above-mentioned compositions or mixtures comprising a compound of formula (I) (in particular, one of the specific compounds disclosed herein, e.g. any of compounds A1 to A6 and/or any of the compounds disclosed in Table 1 herein, present either as a free compound and/or as an agriculturally acceptable salt thereof) and one or more further herbicides, the weight ratio of the compound of formula (I) to each further herbicide can vary over a large range and is, typically, from 500:1 to 1:500 or from 300:1 to 1:500 or from 500:1 to 1:200, especially from 200:1 to 1:200 or from 150:1 to 1:200 or from 200:1 to 1:100, more especially from 100:1 to 1:100 or from 100:1 to 1:50, even more especially from 30:1 to 1:30. Typically, these weight ratios are measured as the free compound(s), i.e. excluding the weight of any associated salt counterion(s).

The compounds of formula I according to the invention can be used in combination with a safener. Preferably, in these mixtures, the compound of the formula I is one of those compounds listed (disclosed) in Table 1 herein and/or one of the exemplified compounds (e.g. A1 to A6) disclosed herein, present either as a free compound and/or as an agriculturally acceptable salt thereof. The following mixtures with safeners, especially, come into consideration:

compound of formula I+cloquintocet-mexyl, compound of formula I+cloquintocet acid or an agriculturally acceptable salt thereof, compound of formula I+fenchlorazole-ethyl, compound of formula I+fenchlorazole acid or an agriculturally acceptable salt thereof, compound of formula I+mefenpyr-diethyl, compound of formula I+mefenpyr diacid, compound of formula I+isoxadifen-ethyl, compound of formula I+isoxadifen acid, compound of formula I+furilazole, compound of formula I+furilazole R isomer, compound of formula (I)+N-(2-methoxybenzoyl)-4-[(methylaminocarbonyl)amino]benzenesulfonamide, compound of formula I+benoxacor, compound of formula I+dichlormid, compound of formula I+AD-67, compound of formula I+oxabetrinil, compound of formula I+cyometrinil, compound of formula I+cyometrinil Z-isomer, compound of formula I+fenclorim, compound of formula I+cyprosulfamide, compound of formula I+naphthalic anhydride, compound of formula I+flurazole, compound of formula I+CL 304,415, compound of formula I+dicyclonon, compound of formula I+fluxofenim, compound of formula I+DKA-24, compound of formula I+R-29148 and compound of formula I+PPG-1292.

The above-mentioned safeners and herbicides are described, for example, in the Pesticide Manual, 14th Edition, British Crop Protection Council, 2006; or The Pesticide Manual 15th edition (2009) or 16th Edition (2012), ed. C. D. S. Tomlin, British Crop Production Council. R-29148 is described, for example by P. B. Goldsbrough et al., *Plant Physiology*, (2002), Vol. 130 pp. 1497-1505 and references therein. PPG-1292 is known from WO 2009/211761. N-(2-methoxybenzoyl)-4-[(methylaminocarbonyl)amino]benzenesulfonamide is known inter alia from EP365484.

Especially preferably, in a composition or mixture comprising a compound of formula (I) (in particular, one of the specific compounds disclosed herein, e.g. any of compounds A1 to A6 herein and/or any of the compounds disclosed in Table 1 herein, present either as a free compound and/or as an agriculturally acceptable salt thereof) and a safener, the safener comprises (e.g. is) benoxacor, cloquintocet-mexyl, cloquintocet acid or an agriculturally acceptable salt thereof, cyprosulfamide, mefenpyr-diethyl, isoxadifen-ethyl and/or N-(2-methoxybenzoyl)-4-[(methylaminocarbonyl)amino]-benzenesulfonamide. In one particular embodiment, the safener comprises (e.g. is) cloquintocet-mexyl, cloquintocet acid or an agriculturally acceptable salt thereof, mefenpyr-diethyl and/or isoxadifen-ethyl; in particular for use on non-oat cereals such as wheat, barley, rye and/or triticale. Cloquintocet-mexyl is particularly valuable and is the most preferred safener, especially for use on non-oat cereals such as wheat, barley, rye and/or triticale.

In the above-mentioned compositions or mixtures comprising a compound of formula (I) (in particular, one of the specific compounds disclosed herein, e.g. any of compounds A1 to A6 herein and/or any of the compounds disclosed in Table 1 herein, present either as a free compound and/or as an agriculturally acceptable salt thereof) with a safener, the weight ratio of the compound of formula (I) to the safener can vary over a large range and is, typically, from 200:1 to 1:200, especially from 50:1 to 1:50 such as from 50:1 to 1:20, more especially from 20:1 to 1:20, even more especially from 20:1 to 1:10. Preferably, the safener comprises (e.g. is) benoxacor, cloquintocet-mexyl, cloquintocet acid or an agriculturally acceptable salt thereof, cyprosulfamide, mefenpyr-diethyl, isoxadifen-ethyl and/or N-(2-methoxybenzoyl)-4-[(methylaminocarbonyl)amino]-benzenesulfonamide; in which case, more preferably, the weight ratio of the compound of formula (I) to the safener is from 50:1 to 1:20 or from 20:1 to 1:10, even more preferably from 15:1 to 1:2. Typically, these weight ratios are measured as the free compound(s), i.e. excluding the weight of any associated salt counterion(s).

Application rates of compound of formula (I) and/or safener:

The rate of application of safener relative to the compound of formula (I) is largely dependent upon the mode of application. In the case of field and/or soil and/or plant treatment (e.g. in a field or glasshouse): for example from 0.5 to 1000 g or from 1 to 500 g of safener per ha, or preferably from 1 to 250 g or from 2 to 200 g or from 5 to 200 g of safener per ha, are applied; and/or generally from 1 to 2000 g or from 5 to 1000 g of compound of formula (I) per ha, or preferably from 5 to 500 g or from 10 to 400 g or from 10 to 300 g or from 20 to 200 g of compound of formula (I) per ha, are applied. ha=hectare. Typically, these application rates are measured as the free compound, i.e. excluding the weight of any associated salt counterion(s). In field and/or plant treatment, the application of the compound of formula (I) is preferably post-emergence.

In one particular embodiment, the herbicidal composition or mixture comprising the compound of formula (I) and one or more further herbicides (in particular as mentioned hereinabove) can be applied together with a safener (in particular one of the safeners mentioned herein, e.g. hereinabove).

In a further aspect, the present invention provides a herbicidal composition, e.g. for use in a method of controlling weeds (in particular monocotyledonous such as grassy monocotyledonous weeds) in crops of useful plants, comprising a compound of formula (I) as defined herein (in particular, one of the specific compounds disclosed herein, e.g. any of compounds A1 to A6, or any of the compounds disclosed in Table 1, present either as a free compound and/or as an agrochemically acceptable salt thereof) (e.g. a herbicidally effective amount thereof), and an agrochemically acceptable carrier, diluent and/or solvent, and also comprising a plant growth regulator, and optionally one or more further herbicides (e.g. as described herein, e.g. glyphosate or a salt and/or dicamba or a salt or ester and/or 2,4-D or a salt or ester) and optionally a safener (e.g. as described herein).

Preferably, the plant growth regulator is: abscisic acid, acibenzolar-S-methyl, a brassinosteroid plant growth regulator, 24-epi brassinolide, 28-homobrassinolide, chlormequat, a cytokinin plant growth regulator, ethephon, ethylene, flurprimidol, gibberellic acid, a gibberellin plant growth regulator (in particular gibberellin A3, gibberellin A4, or gibberellin A7, or gibberellin A4 and gibberellin A7), GR24, indole-3-acetic acid (IAA), indole-3-butyric acid (IBA), jasmonic acid, methyl jasmonate, a karrikin plant growth regulator, maleic hydrazide, mefluidide, mepiquat, methylcyclopropene such as 1-methylcyclopropene, 1-naphthaleneacetic acid (NAA), paclobutrazol, prohexadione, prohexadione-calcium, salicylic acid, a strigolactone plant growth regulator (such as strigol or orobanchol or a derivative of one of these, or the synthetic strigolactone GR-24) (see e.g. K. Yoneyma et al, "Strigolactones as a new plant growth regulator", http://www.niaes.affrc.go.jp/marco/marco2009/english/program/W3-04_Yoneyama_Koichi.pdf), trinexapac-ethyl and/or uniconzole, or an agrochemically acceptable salt e.g. acid addition salt or metal or ammonium salt e.g. alkali metal salt of any of these. More preferably, the plant growth regulator is: gibberellic acid, or a gibberellin plant growth regulator (in particular gibberellin A3, gibberellin A4, or gibberellin A7, or gibberellin A4 and gibberellin A7), or an agrochemically acceptable salt e.g. metal or ammonium salt e.g. alkali metal salt of any of these. Most preferably, the plant growth regulator is gibberellic acid or an agrochemically acceptable salt e.g. metal or ammonium salt e.g. alkali metal salt thereof. Gibberellic acid is preferred because WO 2014/071110 A1 (Valent USA Corp.) discloses that gibberelic acid, when mixed with clethodim, increased clethodim's control and/or speed of control of Johnsongrass (*Sorghum halepense*) and volunteer corn; and increased the control of glyphosate-tolerant (Roundup-Ready™) volunteer corn at 21 days after the application of a mixture of clethodim+dicamba-glycolamine+glyphosate+gibberellic acid (compared to clethodim+dicamba-glycolamine+glyphosate+ammonium sulfate).

In the above-mentioned herbicidal compositions comprising a compound of formula (I), an agrochemically acceptable carrier, diluent and/or solvent, and a plant growth regulator (e.g. gibberellic acid or a salt thereof), and optionally one or more further herbicides and optionally a safener, the weight ratio of the compound of formula (I) to the plant growth regulator (e.g. gibberellic acid or an agrochemically acceptable salt e.g. metal salt e.g. alkali metal salt thereof) can vary over a large range and is, typically, from 500:1 to 1:500, especially from 200:1 to 1:200, more especially from 100:1 to 1:100, even more especially from 30:1 to 1:30. Typically, these weight ratios are measured as the free compound(s), i.e. excluding the weight of any associated salt counterion(s).

The compounds and/or herbicidal compositions according to the invention are suitable for all methods of application customary in agriculture, such as, for example, pre-emergence application, post-emergence application and seed dressing. Post-emergence application is preferred. Depending upon the intended use, the safeners can be used for pretreating the seed material of the crop plant (dressing the seed or seedlings) or introduced into the soil before or after sowing, followed by the application of the (unsafened) compound of the formula (I), optionally in combination with a co-herbicide. It can, however, also be applied alone or together with the herbicide before or after emergence of the plants. The treatment of the plants or the seed material with the safener can therefore take place in principle independently of the time of application of the herbicide. The treatment of the plant by simultaneous application of herbicide and safener (e.g. in the form of a tank mixture) is generally preferred. The rate of application of safener relative to herbicide is largely dependent upon the mode of application. In the case of field and/or soil and/or plant treatment (e.g. in a field or glasshouse), generally from 0.001 to 5.0 kg of safener/ha, preferably from 0.001 to 0.5 kg of safener/ha, are applied. In the case of seed dressing, generally from 0.001 to 10 g of safener/kg of seed, preferably from 0.05 to 2 g of safener/kg of seed, are applied. When the safener is applied in liquid form, with seed soaking, shortly before sowing, it is advantageous to use safener solutions which contain the active ingredient in a concentration of from 1 to 10 000 ppm, preferably from 100 to 1000 ppm.

In the invention, in the case of field and/or soil and/or plant treatment (e.g. post-emergence application), generally from 1 to 2000 g of herbicide (in particular compound of formula (I))/ha, but preferably from 5 to 1000 g of herbicide (in particular compound of formula (I))/ha, more preferably from 10 to 400 g of herbicide (in particular compound of formula (I))/ha, is applied. If a safener is used, in the case of field and/or soil and/or plant treatment (e.g. post-emergence application), generally from 0.5 to 1000 g of safener/ha, preferably from 2 to 500 g of safener/ha, more preferably from 5 to 200 g of safener/ha, is applied.

The following Examples illustrate the invention further but do not limit the invention.

PREPARATION EXAMPLES

Those skilled in the art will appreciate that certain compounds described below are 3-ketoenols, and as such may exist as a single tautomer or as a mixture of keto-enol and diketone tautomers, as described, for example by J. March, Advanced Organic Chemistry, third edition, John Wiley and Sons. The compounds shown below, and in Table T1 are drawn as an arbitrary single enol tautomer, but it should be inferred that this description covers both the diketone form and any possible enols which could arise through tautomerism. Where more than one tautomer is observed in proton NMR, the data shown are for the mixture of tautomers. Furthermore, some of the compounds shown below are drawn as single enantiomers for the purposes of simplicity, but unless specified as single enantiomers, these structures should be construed as representing a mixture of enantiomers. Additionally, some of the compounds can exist as diastereoisomers, and it should be inferred that these can be present as a mixture of diastereoisomers or as any possible single diastereoisomer. Within the detailed experimental section the diketone tautomer is chosen for naming purposes, even if the predominant tautomer is the enol form.

As used herein, room (ambient) temperature is typically about 15-30° C. (e.g. 15-25° C.). Herein, d4 MeOD means tetradeutero-methanol (CD₃OD).

Example 1: Preparation of 3-(2-methoxy-4-prop-1-ynyl-phenyl)bicyclo[3.2.1]octane-2,4-dione (Compound A1)

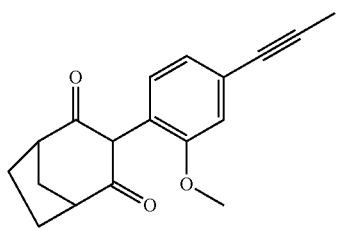 [SMILES: CC#Cc1ccc(C2C(=O)C3CCC(C3)C2=O)c(OC)c1]

Step 1: Preparation of 3-[(4-bromo-2-methoxy-phenyl)methylene]norbornan-2-one

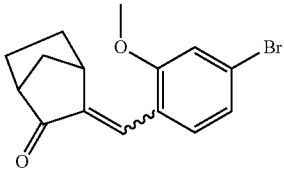 [SMILES: COc1cc(Br)ccc1C=C1C(=O)C2CCC1C2]

To a mixture of norcamphor (3.7 g) and 4-bromo-2-methoxy-benzaldehyde (9 g) in ethanol (100 mL) under nitrogen atmosphere was cautiously added potassium hydroxide (4.7 g) and the mixture heated to reflux for 18 hours. The reaction mixture was cooled to 0° C. and water (50 mL) cautiously added drop wise followed by 2M hydrochloric acid (500 mL). The mixture was partitioned with ethyl acetate and the aqueous layer extracted further with ethyl acetate (2×). The combined organic extracts were washed with brine, dried with magnesium sulfate, concentrated under reduced pressure and purified by chromatography on silica eluting with ethyl acetate in iso-hexane to give 3-[(4-bromo-2-methoxy-phenyl)methylene]norbornan-2-one (4.61 g) as a brown gum. The compound was used as is in the next step.

Step 2: Preparation of 2-[(4-bromo-2-methoxy-phenyl)methylene]-3-oxabicyclo[3.2.1]octan-4-one

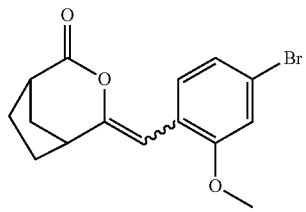 [SMILES: COc1cc(Br)ccc1C=C1OC(=O)C2CCC1C2]

To a solution of 3-[(4-bromo-2-methoxy-phenyl)methylene]norbornan-2-one (400 mg) in t-butyl alcohol (1.6 mL) was added selenium dioxide (6 mg) followed by hydrogen peroxide (0.4 mL, 50% in water) in one portion. The solution was stirred at room temperature for 24 hours then partitioned between chloroform and water. The aqueous layer was extracted with further chloroform and the combined organic extracts washed with water until no more peroxide was present. The organic extract was dried with magnesium sulfate, concentrated and purified by chromatography on silica eluting with ethyl acetate in iso-hexane to give (2E/Z)-2-[(4-bromo-2-methoxy-phenyl)methylene]-3-oxabicyclo[3.2.1]octan-4-one (90 mg) as a colourless gum.

LC/MS 1.06 min, MH+323 (2 min run)

Step 3: Preparation of 3-(4-bromo-2-methoxy-phenyl)bicyclo[3.2.1]octane-2,4-dione

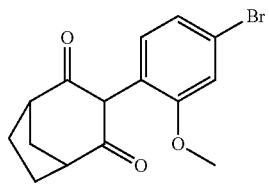 [SMILES: COc1cc(Br)ccc1C1C(=O)C2CCC(C2)C1=O]

To a solution of 2-[(4-bromo-2-methoxy-phenyl)methylene]-3-oxabicyclo[3.2.1]octan-4-one (1 g) in toluene (20 mL) at room temperature under nitrogen atmosphere was added 7.7% phosphorus pentoxide in methane sulfonic acid (Eaton's Reagent, CAS 39394-84-8, 4.1 mL) drop wise over 20 seconds. The mixture was heated to 70° C. for 140 minutes. The mixture was cooled and added to 2M sodium hydroxide (5 mL) at 0° C. and stirred for 15 minutes. Ethyl acetate (20 mL) was added followed by water (10 mL) and the phases separated. The aqueous phase was washed with further ethyl acetate (20 mL). The aqueous phase was acidified to pH1 with conc. hydrochloric acid and extracted with dichloromethane. The organic layer was concentrated to give 3-(4-bromo-2-methoxy-phenyl)bicyclo[3.2.1]octane-2,4-dione (650 mg) as a beige solid.

LC/MS 0.65 min, MH+323 (2 min run)

Step 4: Preparation of 3-(4-bromo-2-methoxy-phenyl)-2-methoxy-bicyclo[3.2.1]oct-2-en-4-one

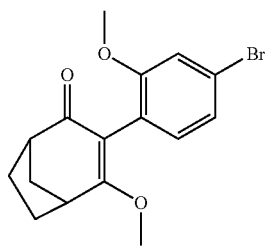 [SMILES: COC1=C(c2ccc(Br)cc2OC)C(=O)C2CCC1C2]

To a solution of 3-(4-bromo-2-methoxy-phenyl)bicyclo[3.2.1]octane-2,4-dione (1 g) in acetone (30 mL) was added potassium carbonate (1 g), followed by iodomethane (0.9 mL) and water (0.2 mL). The mixture was stirred at room temperature overnight. The mixture was partitioned between dichloromethane and water and the organic layer was concentrated to give 3-(4-bromo-2-methoxy-phenyl)-2-methoxy-bicyclo[3.2.1]oct-2-en-4-one (0.93 g) as a brown gum. This was used as is in the next step.

Step 5: Preparation of 2-methoxy-3-(2-methoxy-4-prop-1-ynyl-phenyl)bicyclo[3.2.1]oct-2-en-4-one

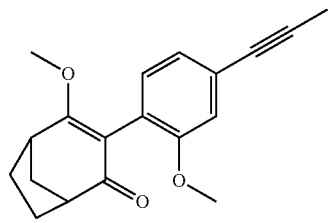 [SMILES: CC#Cc1ccc(C2=C(OC)C3CCC(C3)C2=O)c(OC)c1]

To a mixture of 3-(4-bromo-2-methoxy-phenyl)-2-methoxy-bicyclo[3.2.1]oct-2-en-4-one (600 mg), 2-butynoic acid (CAS 590-93-2, 180 mg), bis(triphenylphosphine)palladium(II) dichloride (CAS 13965-03-2, 63 mg) and 1,4-bis-(diphenylphosphino)butane (CAS 7688-25-7, 76 mg) in methyl sulfoxide (16 mL) under nitrogen atmosphere was added tetrabutylammonium fluoride (CAS 429-41-4, 1M in tetrahydrofuran, 5.3 mL). The reaction was heated to 110° C. for 1 hour. The reaction mixture was quenched with water and extracted twice with dichloromethane. The combined organics were concentrated and purified by chromatography on silica eluting with ethyl acetate in iso-hexane to give 2-methoxy-3-(2-methoxy-4-prop-1-ynyl-phenyl)bicyclo[3.2.1]oct-2-en-4-one (600 mg) as a white solid.

LC/MS 0.90 min, MH+297 (2 min run)

Step 6: Preparation of 3-(2-methoxy-4-prop-1-ynyl-phenyl)bicyclo[3.2.1]octane-2,4-dione (Compound A1)

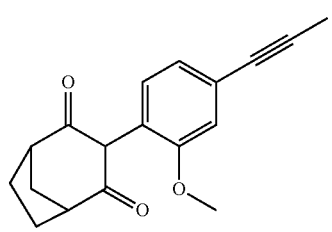 [SMILES: CC#Cc1ccc(C2C(=O)C3CCC(C3)C2=O)c(OC)c1]

A mixture of 2-methoxy-3-(2-methoxy-4-prop-1-ynyl-phenyl)bicyclo[3.2.1]oct-2-en-4-one (5.57 g), acetone (50 mL) and 2M hydrochloric acid (50 mL) was heated to 60° C. for 1 hour. The reaction mixture was concentrated under reduced pressure and partitioned between water and dichloromethane. The organic layer was concentrated under reduced pressure to give 3-(2-methoxy-4-prop-1-ynyl-phenyl)bicyclo[3.2.1]octane-2,4-dione (Compound A1, 5.1 g) as a cream solid.

$^1$H NMR (400 MHz, CD$_3$OD) δ ppm 6.84-6.96 (m, 3H) 3.66-3.75 (m, 3H) 2.92-3.00 (m, 2H) 2.12-2.25 (m, 3H) 1.98-2.07 (m, 3H) 1.78-1.88 (m, 2H) 1.66 (dt, 1H)

Example 2: Preparation of 4-(2,6-Dimethoxy-4-prop-1-ynyl-phenyl)-2,2,6,6-tetramethyl-tetrahydro-pyran-3,5-dione (Compound A2)

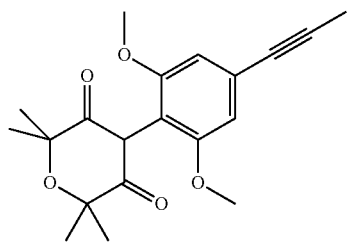 [SMILES: CC#Cc1cc(OC)c(C2C(=O)C(C)(C)OC(C)(C)C2=O)c(OC)c1]

Step 1: Preparation of 4-[(4-bromo-2,6-dimethoxy-phenyl)methylene]-2,2,5,5-tetramethyl-tetrahydro-furan-3-one

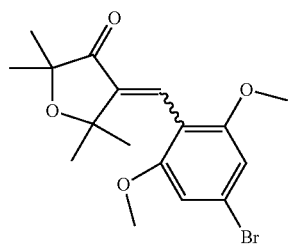

To a mixture of 4-bromo-2,6-dimethoxy-benzaldehyde (CAS 1354050-38-6, 5 g) and 2,2,5,5-tetramethyltetrahydrofuran-3-one (CAS 5455-94-7, 2.90 g) in ethanol (75 mL) was added a solution of potassium hydroxide (0.445 g) in ethanol (5 ml) drop wise over 5 minutes. The mixture was stirred for 3 hours then left to stand overnight. The reaction mixture was concentrated, diluted with water and acidified with 2M hydrochloric acid. The suspension was extracted twice with dichloromethane. The combined organics were washed with water, brine, dried with magnesium sulfate, concentrated, triturated with ice-cold isohexane and filtered and dried to give a mixture of isomers 4-[(4-bromo-2,6-dimethoxy-phenyl)methylene]-2,2,5,5-tetramethyl-tetrahydrofuran-3-one (6.834 g) as a pale yellow solid.

LC/MS 1.10 min, MH+369 (2 min run)

Step 2: Preparation of 1-(4-bromo-2,6-dimethoxy-phenyl)-5,5,7,7-tetramethyl-2,6-dioxaspiro[2.4]heptan-4-one

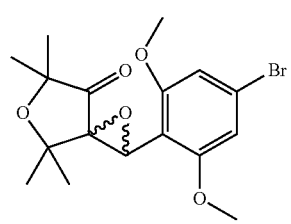

A solution of 4-[(4-bromo-2,6-dimethoxy-phenyl)methylene]-2,2,5,5-tetramethyl-tetrahydrofuran-3-one (1.5 g) in methanol (67 mL) was heated to 35° C. and hydrogen peroxide (0.35 mL, 50% in water) was added in one portion, immediately followed by lithium hydroxide hydrate (2M in water, 0.41 mL). After stirring the mixture at 35° C. for 3 hours the same amount of hydrogen peroxide and lithium hydroxide hydrate were added and the reaction stirred for a further 2 hours then allowed to cool overnight. To this was added 10% sodium metabisulfite solution until the mixture was negative to starch iodide paper. Water was added and mixture extracted with ether (×3). The combined organics were washed with saturated sodium bicarbonate solution, brine, dried with magnesium sulphate and concentrated to give a pale orange gum. This can be purified by chromatography on silica eluting with ethyl acetate in iso-hexane to separate the isomers, if necessary, though the sample can be taken through the next step as a mixture.

(1 S,3S)-1-(4-bromo-2,6-dimethoxy-phenyl)-5,5,7,7-tetramethyl-2,6-dioxaspiro[2.4]heptan-4-one (0.419 g) as a pale yellow solid LC/MS 1.12 min, MH+385 (2 min run)

(1R,3S)-1-(4-bromo-2,6-dimethoxy-phenyl)-5,5,7,7-tetramethyl-2,6-dioxaspiro[2.4]heptan-4-one (0.247 g) as a cream solid LC/MS 1.06 min, MH+385 (2 min run)

Step 3: Preparation of 4-(4-bromo-2,6-dimethoxyphenyl)-2,2,6,6-tetramethyl-tetrahydropyran-3,5-dione

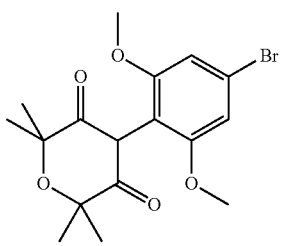 [SMILES: COc1cc(Br)cc(OC)c1C1C(=O)C(C)(C)OC(C)(C)C1=O]

A solution of 1-(4-bromo-2,6-dimethoxy-phenyl)-5,5,7,7-tetramethyl-2,6-dioxaspiro[2.4]heptan-4-one (2.206 g) in dichloromethane (22.06 mL) was added drop wise at 0° C. to cooled conc sulfuric acid (3.053 mL) over 0.5 hour with vigorous stirring. The emulsion was stirred vigorously at 0° C. for 1.5 hours then quenched onto iced water. The emulsion was extracted with dichloromethane (×3). The combined organics were washed with brine, dried with magnesium sulfate and concentrated. Triturated the resulting solid with ice-cold iso-hexane and ether, filtered and air-dried to give 4-(4-bromo-2,6-dimethoxy-phenyl)-2,2,6,6-tetramethyl-tetrahydropyran-3,5-dione (1.913 g) as a lilac solid.

$^1$H NMR (400 MHz, CDCl$_3$) δ ppm 6.78 (s, 2H) 5.80 (brs, 1H) 3.75 (s, 6H) 1.57 (s, 6H) 1.45 (s, 6H)

Step 4: Preparation of 4-(2,6-Dimethoxy-4-prop-1-ynyl-phenyl)-2,2,6,6-tetramethyl-tetrahydropyran-3,5-dione (Compound A2)

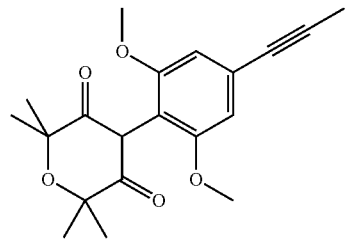 [SMILES: CC#Cc1cc(OC)c(C2C(=O)C(C)(C)OC(C)(C)C2=O)c(OC)c1]

To a mixture of 4-(4-bromo-2,6-dimethoxy-phenyl)-2,2,6,6-tetramethyl-tetrahydropyran-3,5-dione (500 mg), 2-butynoic acid (CAS 590-93-2, 130 mg), bis(triphenylphosphine)palladium(II) dichloride (CAS 13965-03-2, 46 mg) and 1,4-bis-(diphenylphosphino)butane (CAS 7688-25-7, 55 mg) in methyl sulfoxide (16 mL) under nitrogen atmosphere was added tetrabutylammonium fluoride (CAS 429-41-4, 1M in tetrahydrofuran, 3.9 mL). The reaction was heated to 110° C. for 1 hour. The reaction mixture was quenched with 2M hydrochloric acid and extracted twice with ethyl acetate. The combined organics were washed with water, brine, dried with magnesium sulfate, concentrated and purified by chromatography on silica eluting with ethyl acetate in iso-hexane to give 4-(2,6-dimethoxy-4-prop-1-ynyl-phenyl)-2,2,6,6-tetramethyl-tetrahydropyran-3,5-dione (354 mg) as a cream solid.

$^1$H NMR (400 MHz, CDCl$_3$+2 drops CD$_3$OD) δ ppm 6.62-6.66 (m, 2H), 3.68-3.76 (m, 6H), 2.02-2.12 (m, 3H), 1.42-1.59 (m, 12H)

Example 3: Preparation of 3-[2-methoxy-4-prop-1-ynyl-6-(trifluoromethyl)phenyl]bicyclo[3.2.1]octane-2,4-dione (Compound A3)

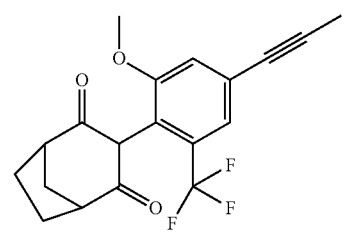 [SMILES: CC#Cc1cc(OC)c(C2C(=O)C3CCC(C3)C2=O)c(C(F)(F)F)c1]

Step 1: Preparation of 2-methoxy-6-(trifluoromethyl)benzaldehyde

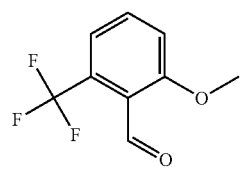

Suspended powdered potassium hydroxide (0.482 g) and 2-fluoro-6-(trifluoromethyl)benzaldehyde (CAS 60611-24-7, 1.5 g) in methanol (10 mL) and heated to 60° C. for 2.5 hours. The mixture was cooled, diluted with water and extracted with ether (×2). The combined organics were washed with water and concentrated to give 2-methoxy-6-(trifluoromethyl)benzaldehyde (1.051 g) as a colourless oil which crystallised on standing.

$^1$H NMR (400 MHz, CDCl$_3$) δ ppm 10.52 (d, 1H) 7.60 (t, 1H) 7.37 (d, 1H) 7.22 (d, 1H) 3.95 (s, 3H)

Step 2: Preparation of 3'-[2-methoxy-6-(trifluoromethyl)phenyl]spiro[norbornane-3,2'-oxirane]-2-one

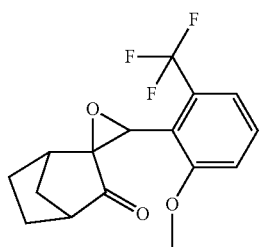 [SMILES: COc1cccc(C(F)(F)F)c1C1OC12C(=O)C1CCC2C1]

Potassium tert-butoxide (1M in tetrahydrofuran, 6.054 mL) was added drop wise to a solution of 2-methoxy-6-(trifluoromethyl)benzaldehyde (1.030 g) and 3-bromonorbornan-2-one (CAS 89856-55-3, 1.145 g) in anhydrous methylsulfoxide (25.23 mL) at room temperature. The reaction was stirred for 4 hours and partitioned between saturated aqueous ammonium chloride and ethyl acetate. The aqueous was extracted with further ethyl acetate and the combined organics were dried with magnesium sulfate and concentrated to give 3'-[2-methoxy-6-(trifluoromethyl)phenyl]spiro[norbornane-3,2'-oxirane]-2-one which was used crude in the next step.

Step 3: Preparation of 3-[2-methoxy-6-(trifluoromethyl)phenyl]bicyclo[3.2.1]octane-2,4-dione

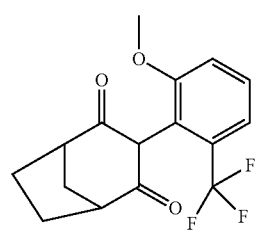 [SMILES: COc1cccc(C(F)(F)F)c1C1C(=O)C2CCC(C2)C1=O]

To a solution of crude 3'-[2-methoxy-6-(trifluoromethyl)phenyl]spiro[norbornane-3,2'-oxirane]-2-one in toluene (25.23 mL) at room temperature and under nitrogen atmosphere was added 7.7% phosphorus pentoxide in methane sulfonic acid (Eaton's Reagent, CAS 39394-84-8, 3.532 mL) drop wise. The mixture was heated to 65° C. for 2.5 hours. The mixture was cooled and partitioned between ethyl acetate and water. The aqueous phase was extracted with further ethyl acetate and the combined organics were dried with magnesium sulfate, concentrated and purified by chromatography on silica eluting with ethyl acetate in iso-hexane to give 3-[2-methoxy-6-(trifluoromethyl)phenyl]bicyclo[3.2.1]octane-2,4-dione (532 mg) as a brown solid.

$^1$H NMR (400 MHz, DMSO-d$_6$) δ ppm 7.38-7.45 (m, 1H) 7.18-7.26 (m, 2H) 3.64-3.71 (m, 3H) 2.72-3.00 (m, 2H) 2.02-2.09 (m, 2H) 1.89-2.02 (m, 1H) 1.61-1.80 (m, 2H) 1.52-1.63 (m, 1H)

Step 4: Preparation of 2-methoxy-3-[2-methoxy-6-(trifluoromethyl)phenyl]bicyclo[3.2.1]oct-2-en-4-one

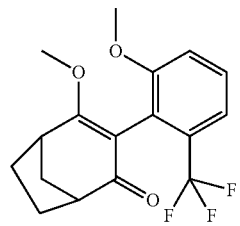 [SMILES: COC1=C(c2c(OC)cccc2C(F)(F)F)C(=O)C2CCC1C2]

To a solution of 3-[2-methoxy-6-(trifluoromethyl)phenyl]bicyclo[3.2.1]octane-2,4-dione (499 mg) in acetone (20 mL) was added potassium carbonate (0.331 g), followed by iodomethane (0.497 mL) and water (0.2 mL). The mixture was stirred at room temperature for 5.5 hours. The mixture was partitioned between ethyl acetate and 2M hydrochloric acid and the organic layer was dried with magnesium sulfate and concentrated to give 2-methoxy-3-[2-methoxy-6-(trifluoromethyl)phenyl]bicyclo[3.2.1]oct-2-en-4-one (0.535 g) as a brown solid.

$^1$H NMR (400 MHz, CDCl$_3$) δ ppm 7.34-7.39 (m, 1H) 7.25-7.30 (m, 1H) 7.05 (t, 1H) 3.76 (d, 3H) 3.56-3.66 (m, 3H) 3.21 (d, 1H) 3.00-3.06 (m, 1H) 2.06-2.19 (m, 3H) 1.92 (s, 2H) 1.61-1.75 (m, 1H)

Step 5: Preparation of 2-methoxy-3-[2-methoxy-4-(4,4,5,5-tetramethyl-1,3,2-dioxaborolan-2-yl)-6-(trifluoromethyl)phenyl]bicyclo[3.2.1]oct-2-en-4-one

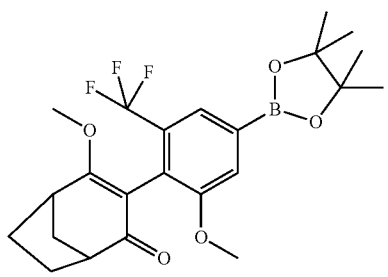 [SMILES: COC1=C(c2c(OC)cc(B3OC(C)(C)C(C)(C)O3)cc2C(F)(F)F)C(=O)C2CCC1C2]

A mixture of 2-methoxy-3-[2-methoxy-6-(trifluoromethyl)phenyl]bicyclo[3.2.1]oct-2-en-4-one (532 mg), bis(pinacolato)diboron (CAS 73183-34-3, 591 mg), (1,5-cyclooctadiene)(methoxy)iridium(I) dimer (CAS 12148-71-9, 49 mg) and 4,4'-di-t-butyl-2,2'-bipyridine (CAS 72914-19-3, 40 mg) in 2-methoxy-2-methyl-propane (11.2 mL) under nitrogen atmosphere was heated at 80° C. for 4 hours.

The mixture was cooled and partitioned between ethyl acetate and water. The aqueous phase was extracted with further ethyl acetate and the combined organics were dried with magnesium sulfate, concentrated and purified by chromatography on silica eluting with ethyl acetate in iso-hexane to give 2-methoxy-3-[2-methoxy-4-(4,4,5,5-tetramethyl-1,3,2-dioxaborolan-2-yl)-6-(trifluoromethyl)phenyl]bicyclo[3.2.1]oct-2-en-4-one (687 mg) as a gum.

¹H NMR (400 MHz, CDCl₃) δ ppm 7.73 (s, 1H) 7.44 (s, 1H) 3.78-3.82 (m, 3H) 3.54 (s, 3H) 3.15-3.21 (m, 1H) 2.97-3.05 (m, 1H) 2.07-2.21 (m, 2H) 1.92 (s, 3H) 1.59-1.67 (m, 1H) 1.24 (s, 12H)

Step 6: Preparation of 3-[4-bromo-2-methoxy-6-(trifluoromethyl)phenyl]-2-methoxy-bicyclo[3.2.1]oct-2-en-4-one

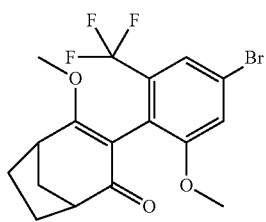 [SMILES: COC1=C(c2c(OC)cc(Br)cc2C(F)(F)F)C(=O)C2CCC1C2]

To a solution of 2-methoxy-3-[2-methoxy-4-(4,4,5,5-tetramethyl-1,3,2-dioxaborolan-2-yl)-6-(trifluoromethyl)phenyl]bicyclo[3.2.1]oct-2-en-4-one (313 mg) in methanol (6.92 mL) under nitrogen atmosphere was added a solution of copper dibromide (464 mg) in water (6.92 mL). The mixture was refluxed for 2 hours. The mixture was cooled, concentrated and partitioned between ethyl acetate and water. The aqueous phase was extracted with further ethyl acetate and the combined organics were washed with brine, dried with magnesium sulfate and concentrated to give crude 3-[4-bromo-2-methoxy-6-(trifluoromethyl)phenyl]-2-methoxy-bicyclo[3.2.1]oct-2-en-4-one (285 mg) as a yellow gum which crystallised on standing.

¹H NMR (400 MHz, CDCl₃) δ ppm 7.38-7.44 (m, 1H) 7.13-7.19 (m, 1H) 3.75-3.80 (m, 3H) 3.60-3.69 (m, 3H) 3.23 (d, 1H) 2.99-3.06 (m, 1H) 2.28 (d, 1H) 2.08-2.17 (m, 2H) 1.89-2.01 (m, 1H) 1.82 (d, 1H) 1.71 (dt, 1H)

Step 7: 3-[2-methoxy-4-prop-1-ynyl-6-(trifluoromethyl)phenyl]bicyclo[3.2.1]octane-2,4-dione (Compound A3)

( 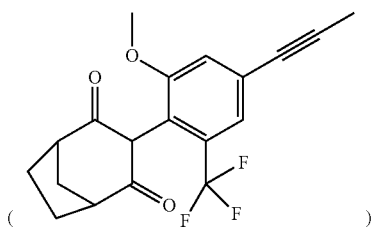 [SMILES: CC#Cc1cc(OC)c(C2C(=O)C3CCC(C3)C2=O)c(C(F)(F)F)c1] )

can be prepared using chemistry described in other examples.

Example 4: Preparation of 4-bromo-2-(2,2,2-trifluoroethoxy)benzaldehyde

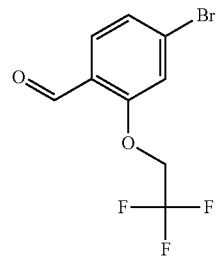 [SMILES: O=Cc1ccc(Br)cc1OCC(F)(F)F]

To a solution of 4-bromo-2-hydroxy-benzaldehyde (CAS 22532-62-3, 1 g) in N,N-dimethylformamide (20 mL) at room temperature under nitrogen atmosphere was added sodium hydride (60% in mineral oil, 0.24 g). This mixture was stirred for 30 minutes. A solution of 2,2,2-trifluoroethyl trifluoromethanesulfonate (CAS 6226-25-1, 1.39 g) in N,N-dimethylformamide (10 mL) was added drop wise and then the reaction was heated to 65° C. for 4 hours. Iced water was added to the reaction mixture and extracted with ethyl acetate (×2). The combined organics were dried with magnesium sulfate, concentrated and purified by chromatography on silica eluting with ethyl acetate in iso-hexane to give 4-bromo-2-(2,2,2-trifluoroethoxy)benzaldehyde (1.21 g) as a cream solid ¹H NMR (400 MHz, CDCl₃) δ ppm 10.42 (d, 1H) 7.76 (d, 1H) 7.29-7.35 (m, 1H) 7.14 (d, 1H) 4.49 (q, 2H)

Example 5: Preparation of 4-bromo-2-(difluoromethoxy)benzaldehyde

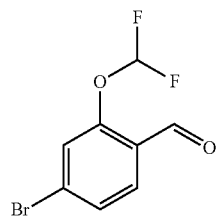

A mixture of 4-bromo-2-hydroxy-benzaldehyde (CAS 22532-62-3, 7 g) and caesium carbonate (15.884 g) in N,N-dimethylformamide (60 mL) was stirred for 5 minutes at room temperature. To this was added sodium 2-chloro-2,2-difluoro-acetic acid (CAS 1895-39-2, 12.3 g) and water (10 mL). The mixture was heated at 85-90° C. (internal temperature) for 5 hours then allowed to cool overnight. Poured the mixture onto ice-water and extracted with diethyl ether (×2). The combined organics were washed with brine, dried with magnesium sulfate, concentrated and purified by chromatography on silica eluting with ethyl acetate in iso-hexane to give 4-bromo-2-(difluoromethoxy)benzaldehyde (4.9 g)

¹H NMR (400 MHz, CDCl₃) δ ppm 10.33 (s, 1H) 7.81 (d, 1H) 7.47-7.53 (m, 1H) 7.45 (d, 1H) 6.44-6.87 (m, 1H)

Example 6: Preparation of 3-[2-(2-methoxyethoxy)-4-prop-1-ynyl-phenyl]bicyclo[3.2.1]octane-2,4-dione (Compound A15)

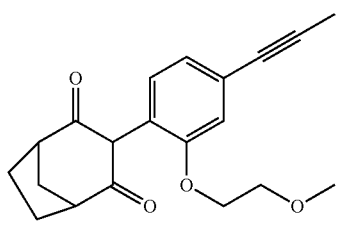 [SMILES: CC#Cc1ccc(C2C(=O)C3CCC(C3)C2=O)c(OCCOC)c1]

Step 1: Preparation of 3-(4-bromo-2-hydroxy-phenyl)bicyclo[3.2.1]octane-2,4-dione

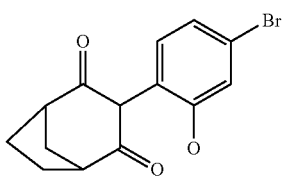 [SMILES: O=C1C2CCC(C2)C(=O)C1c1ccc(Br)cc1O]

Potassium tert-butoxide (1M in tetrahydrofuran, 30.5 mL) was added drop wise to a solution of 4-bromo-2-(difluoromethoxy)benzaldehyde (Example 5, 6.39 g) and 3-bromonorbornan-2-one (CAS 89856-55-3, 7.2 g) in anhydrous methylsulfoxide (130 mL) at room temperature.

The reaction was stirred for 30 minutes and partitioned between saturated aqueous ammonium chloride and ethyl acetate. The aqueous was extracted with further ethyl acetate and the combined organics were dried with magnesium sulphate and concentrated to give 3'-[4-bromo-2-(difluoromethoxy)phenyl]spiro[norbornane-3,2'-oxirane]-2-one as a brown gum which was used crude in the next step.

The crude 3'-[4-bromo-2-(difluoromethoxy)phenyl]spiro[norbornane-3,2'-oxirane]-2-one was stirred in toluene (127 mL) at room temperature under nitrogen atmosphere and 7.7% phosphorus pentoxide in methane sulfonic acid (Eaton's Reagent, CAS 39394-84-8, 17.8 mL) was added drop wise. The mixture was heated to 60° C. for 3 hours. The mixture was cooled and basified to pH14 using 2M potassium hydroxide and washed twice with dichloromethane. The aqueous phase was acidified to pH1 using conc. hydrochloric acid and this was extracted with dichloromethane (×2). The combined organics were concentrated and purified by chromatography on silica eluting with ethyl acetate in iso-hexane to give 3-(4-bromo-2-hydroxy-phenyl)bicyclo[3.2.1]octane-2,4-dione (0.59 g) as a white solid.

LC/MS 0.63 min, MH+309 (2 min run)

Step 2: Preparation of 3-[4-bromo-2-(2-methoxyethoxy)phenyl]-2-(2-methoxyethoxy)bicyclo[3.2.1]oct-2-en-4-one

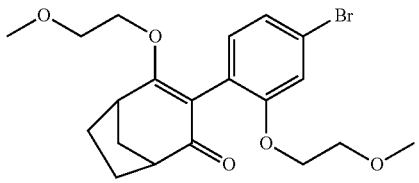

To a mixture of 3-(4-bromo-2-hydroxy-phenyl)bicyclo[3.2.1]octane-2,4-dione (0.59 g) and potassium carbonate (290 mg) in N,N-dimethylformamide (9.5 mL) was added drop wise 1-bromo-2-methoxy-ethane (0.23 ml). The reaction mixture was stirred at room temperature for 2 hours then heated to 70° C. for 2 hours. The reaction mixture was partitioned between 2M hydrochloric acid and ethyl acetate. The organic layer was concentrated and purified by chromatography on silica eluting with ethyl acetate in iso-hexane to give 3-[4-bromo-2-(2-methoxyethoxy)phenyl]-2-(2-methoxyethoxy)bicyclo[3.2.1]oct-2-en-4-one (320 mg).

LC/MS 0.91 min, MH+425 (2 min run)

Step 3: 3-[2-(2-methoxyethoxy)-4-prop-1-ynyl-phenyl]bicyclo[3.2.1]octane-2,4-dione (Compound A15)

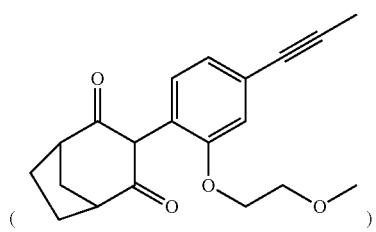 [SMILES: CC#Cc1ccc(C2C(=O)C3CCC(C3)C2=O)c(OCCOC)c1]

can be prepared using chemistry described in other examples.

Example 7: Preparation of [3-(2-methoxy-4-prop-1-ynyl-phenyl)-4-oxo-2-bicyclo[3.2.1]oct-2-enyl] acetate Compound P1

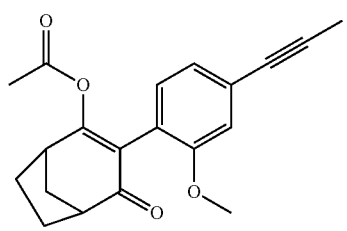 [SMILES: CC#Cc1ccc(C2=C(OC(C)=O)C3CCC(C3)C2=O)c(OC)c1]

To a solution of 3-(2-methoxy-4-prop-1-ynyl-phenyl)bicyclo[3.2.1]octane-2,4-dione (Compound A1, 200 mg) in dichloromethane (7.084 mL) at room temperature was added triethylamine (108 mg) and acetyl chloride (83 mg). This mixture was stirred at room temperature overnight.

Methanol (1 mL) was added to the reaction mixture and stirred for one hour, then concentrated and purified by chromatography on silica eluting with ethyl acetate in iso-hexane to give [3-(2-methoxy-4-prop-1-ynyl-phenyl)-4-oxo-2-bicyclo[3.2.1]oct-2-enyl] acetate (175 mg) as a yellow gum.

$^1$H NMR (400 MHz, CDCl$_3$) δ ppm 6.78-7.03 (m, 3H) 3.67-3.77 (m, 3H) 2.91-3.17 (m, 2H) 2.28-2.43 (m, 1H) 1.94-2.23 (m, 9H) 1.63-1.91 (m, 2H)

Example 8: Preparation of 3-(2-methoxy-4-prop-1-ynyl-phenyl)-2-prop-2-ynoxy-bicyclo[3.2.1]oct-2-en-4-one (Compound P2)

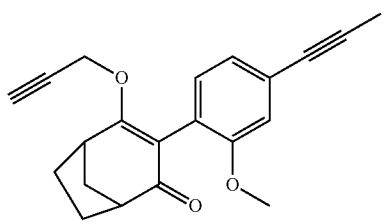 [SMILES: C#CCOC1=C(c2ccc(C#CC)cc2OC)C(=O)C2CCC1C2]

To a solution of 3-(2-methoxy-4-prop-1-ynyl-phenyl)bicyclo[3.2.1]octane-2,4-dione (Compound A1, 200 mg) in acetone (5 mL) was added potassium carbonate (201 mg) followed by 3-bromoprop-1-yne (80% in Toluene, 0.158 mL). The mixture was stirred at room temperature for 6 hours. The mixture was partitioned between dichloromethane and water and the organic layer concentrated to give 3-(2-methoxy-4-prop-1-ynyl-phenyl)-2-prop-2-ynoxy-bicyclo[3.2.1]oct-2-en-4-one (203 mg) as a brown gum.

$^1$H NMR (400 MHz, CDCl$_3$) δ ppm 6.82-7.03 (m, 3H) 4.20-4.52 (m, 2H) 3.68-3.75 (m, 3H) 3.23 (d, 3H) 3.17-3.30 (m, 1H) 2.94-3.07 (m, 1H) 2.45-2.56 (m, 1H) 1.55-2.28 (m, 6H)

Example 9: Preparation of 2-(2,6-dimethoxy-4-prop-1-ynyl-phenyl)cyclohexane-1,3-dione (Compound A11)

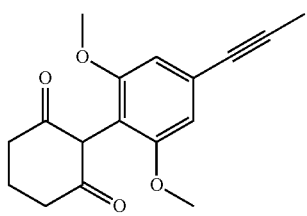 [SMILES: CC#Cc1cc(OC)c(C2C(=O)CCCC2=O)c(OC)c1]

Step 1: Preparation of [diacetoxy-(2,6-dimethoxyphenyl)plumbyl] acetate

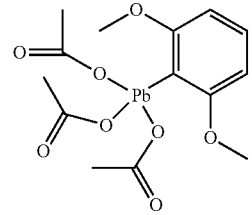

A nitrogen flushed mixture of mercury (II) acetate (0.438 g) and lead (IV) acetate (14.6 g) in chloroform (50 mL) was warmed to 40° C. with stirring. The heat source was removed and (2,6-dimethoxyphenyl)boronic acid (CAS 23112-96-1, 5 g) was added in portions over 1 minute. This mixture was heated at 40° C. for 4 hours and left to cool. Chloroform (25 mL) was added and the mixture cooled in an ice bath with stirring. Potassium carbonate (34 g) was added gradually and the mixture stirred for 10 minutes under nitrogen. The resulting dark orange suspension was filtered through chloroform-washed Celite and washed through with further chloroform (40 ml). The filtrate was concentrated to leave a yellow solid which was triturated with iso-Hexane and chloroform and filtered, washed with a little cold iso-Hexane and air-dried to give

[diacetoxy-(2,6-dimethoxyphenyl)plumbyl] acetate (10.9 g) as a yellow solid.

Used as is in the next step.

Step 2: Preparation of 2-(2,6-dimethoxyphenyl)cyclohexane-1,3-dione

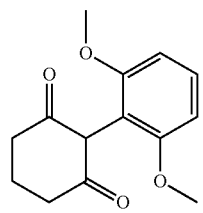 [SMILES: COc1cccc(OC)c1C1C(=O)CCCC1=O]

To a mixture of cyclohexane-1,3-dione (0.66 g) and 4-(dimethylamino)pyridine (3.6 g) in chloroform (32 mL) under nitrogen atmosphere was added toluene (8 mL) followed by [diacetoxy-(2,6-dimethoxyphenyl)plumbyl] acetate (3.7 g). This mixture was heated at 80° C. for 3 hours. Diluted the reaction with chloroform (50 mL) and cooled with an ice-water-bath. Gradually acidified the mixture with aqueous 2M hydrochloric acid (20 mL) then stirred the mixture vigorously for 10 minutes. Filtered the mixture through water-washed 'Celite' then washed through with chloroform. The organic layer was separated, concentrated under reduced pressure and purified by chromatography on silica eluting with methanol in dichloromethane to give 2-(2,6-dimethoxyphenyl)cyclohexane-1,3-dione (1.4 g) as a yellow gum.

LC/MS 0.28 min, MH+249 (2 min run)

Step 3: 2-(2,6-dimethoxy-4-prop-1-ynyl-phenyl)cyclohexane-1,3-dione (Compound A11)

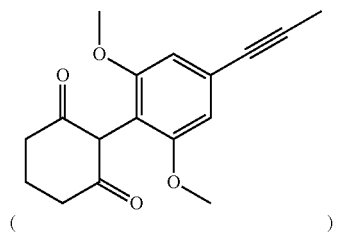

can be prepared using chemistry described in other examples.

Example 10: Preparation of 2-(2,6-dimethoxy-4-prop-1-ynyl-phenyl)-5-(2-methylsulfanylethyl)cyclohexane-1,3-dione (Compound A13)

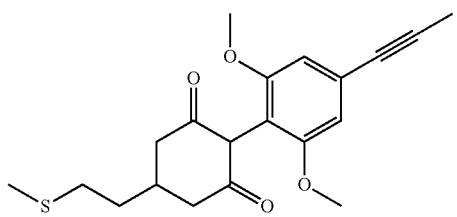 [SMILES: CC#Cc1cc(OC)c(C2C(=O)CC(CCSC)CC2=O)c(OC)c1]

Step 1: Preparation of 5-bromo-2-iodo-1,3-dimethoxy-benzene

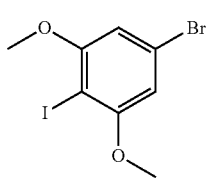

Methanol (338 mL) was cooled to 5° C. and potassium hydroxide (29.3 g) was added portion wise over 15 minutes maintaining the temperature below 10° C. This solution was added over 15 minutes to a solution of 5-bromo-1,3-difluoro-2-iodo-benzene (CAS 160976-02-3, 15 g) in methanol (9 mL) at 60° C. under nitrogen atmosphere. The mixture was heated at 60° C. for 168 hours. The reaction was concentrated and partitioned between ethyl acetate and water. The aqueous phase was extracted with further ethyl acetate and the combined organic phases were washed with brine, dried over magnesium sulfate and concentrated to give 5-bromo-2-iodo-1,3-dimethoxy-benzene (10.83 g) as a white solid.

$^1$H NMR (500 MHz, CDCl$_3$) δ ppm 6.65 (s, 2H), 3.88 (s, 6H)

Step 2: Preparation of (4-bromo-2,6-dimethoxy-phenyl)boronic acid

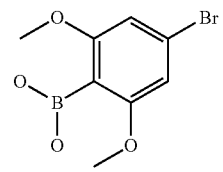

A solution of 5-bromo-2-iodo-1,3-dimethoxy-benzene (8.5 g) in tetrahydrofuran (99 mL) was cooled to −78° C. under nitrogen atmosphere. A solution of i-propyl magnesium chloride (25 mL) was added drop wise over 1 hour, maintaining the temperature below −65° C. The reaction mixture was stirred at −78° C. for 25 minutes and then allowed to warm to room temperature and stirred for 1.25 hours.

After this time, the solution was cooled back to −78° C. and trimethyl borate (8.8 mL) was added drop wise over 5 minutes, maintaining the temperature below −65° C. On completion of the addition the cooling was removed and the solution was stirred for 2.5 hours. The reaction mixture was diluted with water and acidified with 2M hydrochloric acid and stirred for 2 hours. Ethyl acetate was added and the layers separated. The aqueous was extracted with further ethyl acetate (×2) and the combined organic phases were washed with brine, dried over magnesium sulfate and concentrated. The residue was triturated with iso-hexane and air dried to give (4-bromo-2,6-dimethoxy-phenyl)boronic acid (5.85 g) as an off-white solid.

$^1$H NMR (500 MHz, CDCl$_3$) δ ppm 7.00-7.05 (m, 2H), 6.78-6.82 (m, 2H), 3.91 (s, 6H)

Step 3: Preparation of (E)-6-Methylsulfanylhex-3-en-2-one

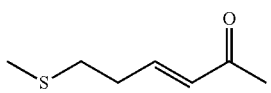

To a solution of 3-methylsulfanylpropanal (CAS 3268-49-3, 5.6 g) in dichloromethane (120 mL) was added 1-(triphenylphosphoranylidene)-2-propanone (CAS 1439-36-7, 17 g) in a single portion. The reaction mixture was heated and stirred at reflux for 5 hours. The cooled reaction mixture was concentrated to leave a pale yellow solid which was triturated with a 1:1 mixture of ether:iso-hexane (100 mL). The resulting solid was collected by filtration and washed with further 1:1 ether:iso-hexane (50 mL). The filtrate was concentrated to a yellow oil and purified by chromatography on silica eluting with ethyl acetate in iso-hexane to give (E)-6-methylsulfanylhex-3-en-2-one (5.890 g) as a colourless liquid.

$^1$H NMR (400 MHz, CDCl$_3$) 6.81 (dt, 1H), 6.08-6.15 (m, 1H), 2.61-2.67 (m, 2H), 2.49-2.58 (m, 2H), 2.24-2.27 (m, 3H), 2.10-2.15 (m, 3H)

Step 4: Preparation of Ethyl 2-(2-methylsulfanyl-ethyl)-4,6-dioxo-cyclohexanecarboxylate

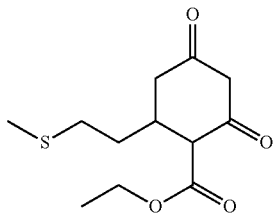 [SMILES: CCOC(=O)C1C(=O)CC(=O)CC1CCSC]

To ice cooled ethanol (50 mL) was added sodium metal (1.249 g) in small portions under nitrogen and the resulting solution was stirred for 15 minutes. Diethyl propanedioate (7.901 g) in ethanol (25 mL) was added drop wise to this cooled solution over 20 minutes. The reaction was allowed to warm to ambient temperature and stirred for a further 2 hours. The mixture was cooled in an ice bath and a solution of (E)-6-methylsulfanylhex-3-en-2-one (5.890 g) in ethanol (25 mL) was added drop wise. The reaction was allowed to warm to ambient temperature, stirred for 4 hours and then left to stand overnight. The reaction was concentrated to a yellow slurry which was poured into a cooled solution of 2M hydrochloric acid and stirred for 5 minutes. This was extracted with dichloromethane (×2) and the combined organic layers dried over anhydrous magnesium sulfate and concentrated to give ethyl 2-(2-methylsulfanylethyl)-4,6-dioxo-cyclohexanecarboxylate (11.446 g) as a yellow oil.

$^1$H NMR (400 MHz, CDCl$_3$) 5.48-5.56 (m, 1H), 4.13-4.33 (m, 2H), 3.38-3.48 (m, 1H), 3.11-3.21 (m, 1H), 2.44-2.75 (m, 3H), 2.17-2.26 (m, 1H), 2.09 (s, 3H), 1.63-1.86 (m, 2H), 1.30 (t, 3H)

Step 5: Preparation of 5-(2-Methylsulfanylethyl)cyclohexane-1,3-dione

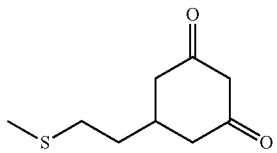

A solution of ethyl 2-(2-methylsulfanylethyl)-4,6-dioxo-cyclohexanecarboxylate (11.446 g) in propan-2-ol (32 mL) was stirred with 2M sodium hydroxide solution (115.2 mL) for 4 hours. The reaction was concentrated to remove the propan-2-ol and the remaining aqueous solution was taken to pH 1 by the addition of conc. hydrochloric acid. This solution was heated to 70° C. for 1.5 hours, then left to cool overnight. The resulting solid was collected by filtration and washed with water then iso-hexane and air dried to leave a pale yellow powder. The powder was washed further with water (×4) and air dried to give 5-(2-methylsulfanylethyl) cyclohexane-1,3-dione (6.583 g) as a yellow solid 1H NMR (400 MHz, CDCl$_3$) 5.48 (s, 1H), 3.41 (d, 1H), 2.77 (dd, 3H), 2.45-2.61 (m, 2H), 2.25-2.43 (m, 2H), 2.08-2.18 (m, 3H), 1.63-1.74 (m, 2H)

Step 6: 2-(2,6-dimethoxy-4-prop-1-ynyl-phenyl)-5-(2-methylsulfanylethyl)cyclohexane-1,3-dione (Compound A13)

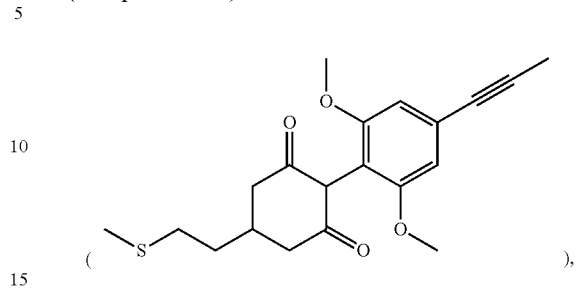

can be prepared using chemistry described in other examples.

LC-MS Analysis

Note: Compounds characterised by HPLC-MS were analysed using an Agilent 1100 Series HPLC equipped with a Waters Atlantis dC18 column (column length 20 mm, internal diameter of column 3 mm, particle size 3 micron, temperature 40° C.), Waters photodiode array and Micromass ZQ2000. The analysis was conducted using either a two or five minute run time, using a solvent gradient between Solvent A: H$_2$O with 0.1% HCOOH and Solvent B: 0.1% HCOOH in CH$_3$CN. The characteristic values obtained for each compound were the retention time (RT, recorded in minutes) and the molecular ion, typically the cation MH+.

Example 11: Preparation of 3-(2-butyl-4-prop-1-ynyl-phenyl)bicyclo[3.2.1]octane-2,4-dione (Compound A18)

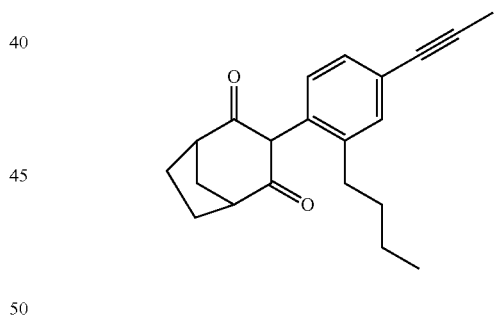

Step 1: Preparation of 4-bromo-2-butyl-aniline

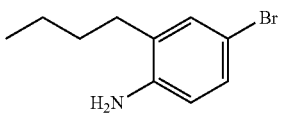

A solution of 2-butylaniline (CAS 2696-85-7, 5 g) in acetonitrile (100 mL) was cooled to 0° C. To this was added N-bromosuccinimde (6 g) portion wise over 25 minutes. The reaction was stirred for 1 hour at 0° C. The reaction was partitioned between water (200 mL) and ethyl acetate (200 mL) and extracted with further ethyl acetate. The combined organic layers were washed with aqueous sodium thiosulfate solution, concentrated and purified by chromatography on silica eluting with ethyl acetate in iso-hexane to give 4-bromo-2-butyl-aniline as a pale brown liquid (1.37 g)

$^1$H NMR (400 MHz, CDCl$_3$) δ ppm 7.14 (d, 1H) 7.10 (dd, 1H) 6.54 (d, 1H) 3.60 (brs, 2H) 2.40-2.47 (m, 2H) 1.53-1.62 (m, 2H) 1.40 (dq, 2H) 0.95 (t, 3H)

Step 2: Preparation of 4-bromo-2-butyl-1-iodo-benzene

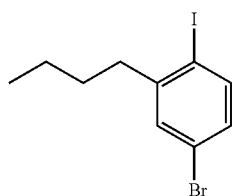

To a solution of 4-methylbenzenesulfonic acid (3.10 g) in acetonitrile (41.1 mL) was added 4-bromo-2-butyl-aniline (1.37 g). This mixture was stirred for 10 minutes at room temperature and then cooled to 5-10° C. To this suspension was added, portion wise over 10 minutes, a solution of sodium nitrite (0.829 g) and potassium iodide (2.49 g) in water (4.80 mL). On completion of addition, the reaction mixture was stirred at 5° C. for 20 minutes and then the cooling removed and the mixture stirred at room temperature for 1 hour. The reaction mixture was adjusted to pH 9/10 by addition of aqueous sodium hydrogen carbonate solution. The mixture was partitioned between 10% aqueous sodium metabisulfite solution (100 mL) was then added followed by ethyl acetate (100 mL). The layers were separated and the aqueous extracted with further ethyl acetate (2×100 mL). The combined organic phases were washed with 10% aqueous sodium metabisulfite solution (100 mL), water (100 mL) and brine (100 mL), then dried with magnesium sulfate, concentrated and purified by chromatography on silica eluting with ethyl acetate in iso-hexane to give 4-bromo-2-butyl-1-iodo-benzene as a colourless gum (0.99 g).

$^1$H NMR (400 MHz, CDCl$_3$) δ ppm 7.64 (d, 1H) 7.33 (d, 1H) 7.00 (dd, 1H) 2.62-2.69 (m, 2H) 1.50-1.60 (m, 2H) 1.41 (dq, 2H) 0.92-0.99 (m, 3H)

Step 3: Preparation of 4-bromo-2-butyl-benzaldehyde

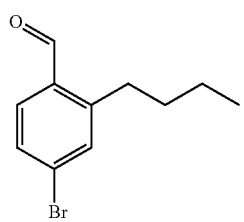

A solution of 4-bromo-2-butyl-1-iodo-benzene (0.99 g) in anhydrous tetrahydrofuran (8 mL) was cooled to −78° C. under nitrogen atmosphere. A solution of i-propyl magnesium chloride (2M in tetrahydrofuran, 2.9 mL) was added drop wise over 5 minutes. The reaction mixture was stirred at −78° C. for 25 minutes and then allowed to warm to room temperature and stirred for 45 minutes. After this time, the reaction mixture was cooled to −78° C. and a solution of 4-formyl morpholine (1.2 g) in anhydrous tetrahydrofuran (4 mL) was added drop wise. On completion of addition the cooling was removed and solution was stirred at room temperature for 18 hours. To the reaction mixture was added 2M hydrochloric acid (20 mL) and the mixture stirred for 30 minutes. Ethyl acetate (20 mL) and water (20 mL) were added and the phases separated. The aqueous phase was extracted with further ethyl acetate (×2) and the combined organics were washed with brine, dried over magnesium sulphate, concentrated and purified by chromatography on silica eluting with ethyl acetate in iso-hexane to give 4-bromo-2-butyl-benzaldehyde as a yellow oil (0.42 g).

$^1$H NMR (400 MHz, CDCl$_3$) δ ppm 10.23 (s, 1H) 7.69 (d, 1H) 7.49 (dd, 1H) 7.44 (d, 1H) 2.96-3.02 (m, 2H) 1.55-1.68 (m, 2H) 1.36-1.46 (m, 2H) 0.92-0.98 (m, 3H)

Step 4: Preparation of 3'-(4-bromo-2-butyl-phenyl)spiro[norbornane-3,2'-oxirane]-2-one

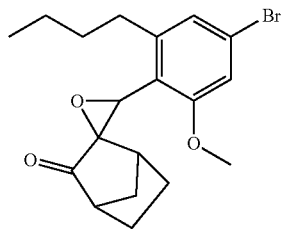 [SMILES: CCCCc1cc(Br)cc(OC)c1C1OC12C(=O)C1CCC2C1]

Potassium tert-butoxide (1M in tetrahydrofuran, 29 ml) was added drop wise to a solution of 3-bromonorbornan-2-one (CAS 89856-55-3, 5.42 g) and 4-bromo-2-butyl-benzaldehyde (5.77 g) in anhydrous methyl sulfoxide (120 mL) at room temperature. The reaction was stirred for 1 hour, quenched with saturated aqueous ammonium chloride and extracted twice with ethyl acetate. The combined organics were washed with water, brine, dried over magnesium sulfate and concentrated to give 3'-(4-bromo-2-butyl-phenyl)spiro[norbornane-3,2'-oxirane]-2-one as a brown gum which solidified on standing.

This compound was used crude in the next step.

Step 5: Preparation of 3-(4-bromo-2-butyl-phenyl)bicyclo[3.2.1]octane-2,4-dione

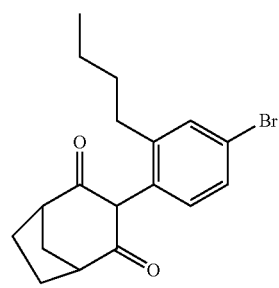 [SMILES: CCCCc1cc(Br)ccc1C1C(=O)C2CCC(C2)C1=O]

Crude 3'-(4-bromo-2-butyl-phenyl)spiro[norbornane-3,2'-oxirane]-2-one (0.32 g) was dissolved in acetonitrile (3 mL) and dry Amberlyst 15 resin (CAS 39389-20-3, 320 mg) was added. This mixture was stirred and heated at 75° C. overnight. The resin is removed by filtration and the filtrate concentrated and purified by chromatography on silica eluting with ethyl acetate in iso-hexane to give 3-(4-bromo-2-butyl-phenyl)bicyclo[3.2.1]octane-2,4-dione (120 mg) as a brown gum.

$^1$H NMR (400 MHz, CDCl$_3$) δ ppm 7.39-7.46 (m, 1H) 7.31-7.38 (m, 1H) 6.78-6.92 (m, 1H) 3.03 (brs, 2H) 2.33-2.52 (m, 1H) 2.02-2.30 (m, 4H) 1.83-2.00 (m, 1H) 1.61-1.83 (m, 2H) 1.24-1.52 (m, 4H) 0.82-0.97 (m, 3H)

Step 6: Preparation of 3-(2-butyl-4-prop-1-ynyl-phenyl)bicyclo[3.2.1]octane-2,4-dione Compound A3

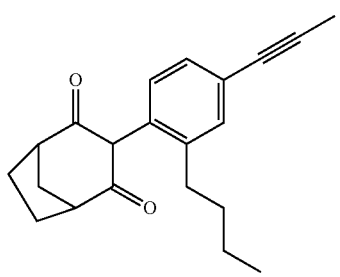 [SMILES: CC#Cc1ccc(C2C(=O)C3CCC(C3)C2=O)c(CCCC)c1]

To a mixture of 3-(4-bromo-2-butyl-phenyl)bicyclo[3.2.1]octane-2,4-dione (500 mg), 2-butynoic acid (CAS 590-93-2, 144 mg), bis(triphenylphosphine)palladium(II) dichloride (CAS 13965-03-2, 51 mg) and 1,4-bis-(diphenylphosphino)butane (CAS 7688-25-7, 61 mg) in methyl sulfoxide (10 mL) under nitrogen atmosphere was added tetrabutylammonium fluoride (CAS 429-41-4, 1M in tetrahydrofuran, 4.3 mL). The reaction was heated to 110° C. for 3 hours. The reaction contents were transferred to a microwave vial and subjected to microwave heating at 160° C. for 1 hr. The reaction mixture was quenched with 2M hydrochloric acid and extracted twice with dichloromethane. The combined organics were concentrated and purified by chromatography on silica eluting with ethyl acetate in iso-hexane to give a yellow gum. The gum was partitioned between 0.5M potassium carbonate solution and dichloromethane. The aqueous phase was acidified with conc. hydrochloric acid and extracted with dichloromethane (2×). The combined organics were concentrated to give 3-(2-butyl-4-prop-1-ynyl-phenyl)bicyclo[3.2.1]octane-2,4-dione as a colourless gum $^1$H NMR (400 MHz, CDCl$_3$) δ=7.34-7.28 (m, 1H), 7.23 (dd, 1H), 6.9-6.81 (m, 1H), 5.92 (brs, 1H), 3.12-2.83 (m, 2H), 2.43-2.09 (m, 5H), 2.07-2.01 (m, 3H), 1.98-1.58 (m, 3H), 1.49-1.14 (m, 4H), 0.94-0.78 (m, 3H)

Example 12: Preparation of 3-(2-propyl-4-prop-1-ynyl-phenyl)bicyclo[3.2.1]octane-2,4-dione (Compound A16)

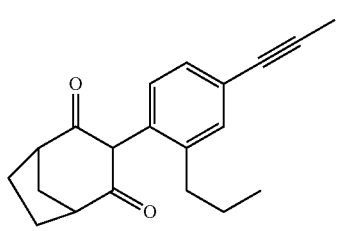 [SMILES: CC#Cc1ccc(C2C(=O)C3CCC(C3)C2=O)c(CCC)c1]

Step 1: Preparation of 3-(4-bromo-2-propyl-phenyl)-2-methoxy-bicyclo[3.2.1]oct-2-en-4-one

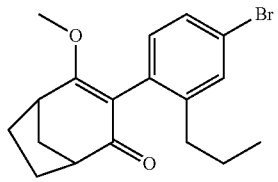 [SMILES: CCCc1cc(Br)ccc1C1=C(OC)C2CCC(C2)C1=O]

To a solution of 3-(4-bromo-2-propyl-phenyl)bicyclo[3.2.1]octane-2,4-dione (0.96 g) in acetone (30 mL) was added potassium carbonate (0.93 g) followed by iodomethane (0.89 mL). The reaction was stirred at room temperature overnight. The mixture was partitioned between dichloromethane and water and the organics were concentrated to give 3-(4-bromo-2-propyl-phenyl)-2-methoxy-bicyclo[3.2.1]oct-2-en-4-one (0.97 g) as a brown gum.

LC-MS (2 min run) 1.08 min MH+349

Step 2: Preparation of 2-methoxy-3-(2-propyl-4-prop-1-ynyl-phenyl)bicyclo[3.2.1]oct-2-en-4-one

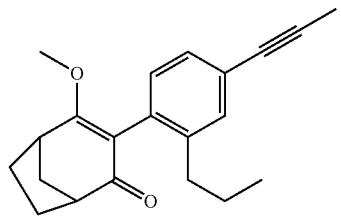 [SMILES: CC#Cc1ccc(C2=C(OC)C3CCC(C3)C2=O)c(CCC)c1]

To a mixture of 3-(4-bromo-2-propyl-phenyl)-2-methoxy-bicyclo[3.2.1]oct-2-en-4-one (300 mg), 2-butynoic acid (CAS 590-93-2, 87 mg), bis(triphenylphosphine)palladium (II) dichloride (CAS 13965-03-2, 30 mg) and 1,4-bis-(diphenylphosphino)butane (CAS 7688-25-7, 37 mg) in methyl sulfoxide (8 mL) under nitrogen atmosphere was added tetrabutylammonium fluoride (CAS 429-41-4, 1M in tetrahydrofuran, 2.4 mL). The reaction was heated to 110° C. for 1 hour. The reaction mixture was quenched with water and extracted twice with dichloromethane. The combined organics were concentrated and purified by chromatography on silica eluting with ethyl acetate in iso-hexane to give 2-methoxy-3-(2-propyl-4-prop-1-ynyl-phenyl)bicyclo[3.2.1]oct-2-en-4-one (100 mg) as a yellow gum.

LC-MS (2 min run) 1.08 min MH+309

Step 3: Preparation of 3-(2-propyl-4-prop-1-ynyl-phenyl)bicyclo[3.2.1]octane-2,4-dione Compound A1

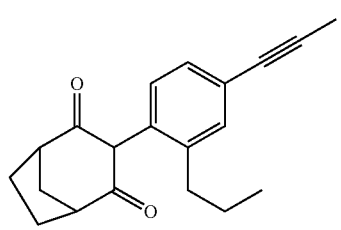 [SMILES: CC#Cc1ccc(C2C(=O)C3CCC(C3)C2=O)c(CCC)c1]

To a solution of 2-methoxy-3-(2-propyl-4-prop-1-ynyl-phenyl)bicyclo[3.2.1]oct-2-en-4-one (100 mg) in acetone (1 mL) was added 2M hydrochloric acid (1 mL) and the mixture heated to 60° C. for 1 hour. The reaction mixture was concentrated and partitioned between water and dichloromethane. The organic layer was concentrated to give 3-(2-propyl-4-prop-1-ynyl-phenyl)bicyclo[3.2.1]octane-2,4-dione (100 mg) as a gum.

$^1$H NMR (400 MHz, CDCl$_3$) δ ppm 7.30-7.36 (m, 1H) 7.21-7.27 (m, 1H) 6.85-6.99 (m, 1H) 2.99-3.09 (m, 2H) 2.32-2.42 (m, 1H) 2.09-2.30 (m, 4H) 1.99-2.07 (m, 3H) 1.87 (brs, 2H) 1.30-1.73 (m, 3H) 0.88 (q, 3H)

LC-MS Analysis

Note: Compounds characterised by HPLC-MS were analysed using an Agilent 1100 Series HPLC equipped with a Waters Atlantis dC18 column (column length 20 mm, internal diameter of column 3 mm, particle size 3 micron, temperature 40° C.), Waters photodiode array and Micromass ZQ2000. The analysis was conducted using either a two or five minute run time, using a solvent gradient between Solvent A: H$_2$O with 0.1% HCOOH and Solvent B: 0.1% HCOOH in CH$_3$CN. The characteristic values obtained for each compound were the retention time (RT, recorded in minutes) and the molecular ion, typically the cation MH+. Additional compounds in Tables T1 and P1 below illustrate the present invention, and are particular embodiments of the compounds of formula (I) according to the present invention. For the most part, these compounds can generally be prepared by methods similar to those shown in the Examples and/or shown in the process section hereinabove using appropriate starting materials.

TABLE T1

| Compound Number | Structure | $^1$H NMR 400 MHz (CDCl$_3$ solvent unless stated otherwise) δ (delta) |
| --- | --- | --- |
| A1 | 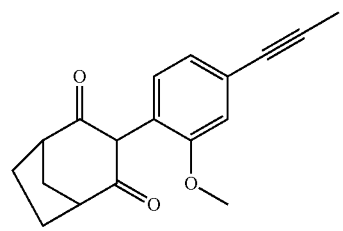 [SMILES: CC#Cc1ccc(C2C(=O)C3CCC(C3)C2=O)c(OC)c1] | (CD$_3$OD) 6.84-6.96 (m, 3H) 3.66-3.75 (m, 3H) 2.92-3.00 (m, 2H) 2.12-2.25 (m, 3H) 1.98-2.07 (m, 3H) 1.78-1.88 (m, 2H) 1.66 (dt, 1H) |
| A2 | 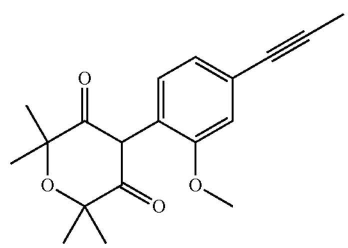 [SMILES: CC#Cc1ccc(C2C(=O)C(C)(C)OC(C)(C)C2=O)c(OC)c1] | (+2 drops CD$_3$OD) 6.62-6.66 (m, 2H) 3.68-3.76 (m, 6H) 2.02-2.12 (m, 3H) 1.42-1.59 (m, 12H) |
| A3 | 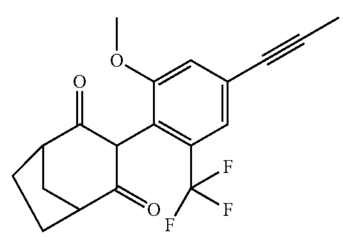 [SMILES: CC#Cc1cc(OC)c(C2C(=O)C3CCC(C3)C2=O)c(C(F)(F)F)c1] | (CD$_3$OD) 7.25 (s, 1H) 7.13-7.19 (m, 1H) 3.72-3.79 (m, 3H) 2.95 (brs, 2H) 2.15-2.27 (m, 3H) 2.07-2.08 (m, 1H) 2.06 (s, 3H) 1.84 (d, 2H) 1.71 (d, 1H) |
| A4 | 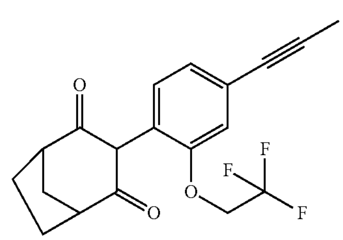 [SMILES: CC#Cc1ccc(C2C(=O)C3CCC(C3)C2=O)c(OCC(F)(F)F)c1] | 7.11-7.18 (m, 1H) 7.02-7.09 (m, 1H) 6.88-6.96 (m, 1H) 5.93 (s, 1H) 4.18-4.34 (m, 2H) 3.01 (m, 2H) 1.59-2.24 (m, 9H) |

TABLE T1-continued

| Compound Number | Structure | $^1$H NMR 400 MHz (CDCl$_3$ solvent unless stated otherwise) δ (delta) |
|---|---|---|
| A5 | 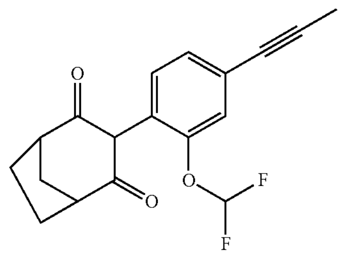 [SMILES: CC#Cc1ccc(C2C(=O)C3CCC(C3)C2=O)c(OC(F)F)c1] | 7.19-7.31 (m, 3H) 7.07 (d, 1H) 6.95-7.14 (m, 1H) 6.01-6.50 (m, 1H) ) 2.96-3.07 (m, 1H) 1.79-2.28 (m, 7H) 1.65 (dt, 1H) |
| A6 | 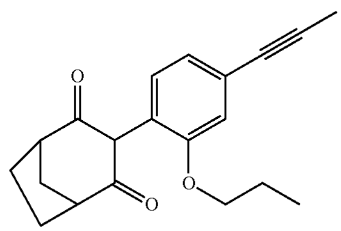 [SMILES: CC#Cc1ccc(C2C(=O)C3CCC(C3)C2=O)c(OCCC)c1] | (CD$_3$OD) 6.99-7.08 (m, 1H) 6.82-6.94 (m, 2H) 3.82 (t, 2H) 3.30 (s, 3H) 2.95 (brs, 2H) 2.16 (d, 3H) 1.82 (d, 2H) 1.62-1.76 (m, 3H) 0.98 (t, 3H) |
| A7 | 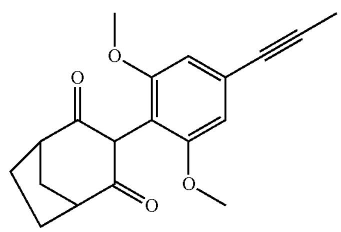 [SMILES: CC#Cc1cc(OC)c(C2C(=O)C3CCC(C3)C2=O)c(OC)c1] | (+2 drops CD$_3$OD) 6.58-6.66 (m, 2H) 3.66-3.76 (d, 6H) 2.98 (m, 2H) 1.75-2.25 (m, 8H) 1.56-1.64 (m, 1H) |
| A8 | 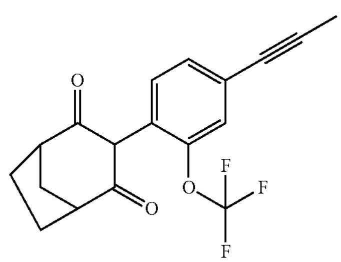 [SMILES: CC#Cc1ccc(C2C(=O)C3CCC(C3)C2=O)c(OC(F)(F)F)c1] | (CD$_3$OD) 7.25-7.35 (m, 1H) 7.20-7.25 (m, 1H) 7.04-7.16 (m, 1H) 2.96-3.06 (m, 2H) 2.02-2.7 (m, 6H) 1.82 (d, 2H) 1.64-1.77 (m, 1H) |
| A9 | 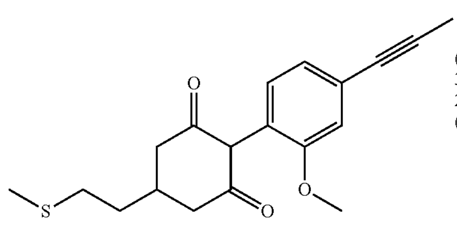 | (500 MHz, CD$_3$OD) 6.91-6.97 (m, 3H) 3.73 (s, 3H) 2.57-2.67 (m, 4H) 2.32-2.43 (m, 3H) 2.13 (s, 3H) 2.02-2.06 (m, 3H) 1.74-1.82 (m, 2H) |
| A10 | 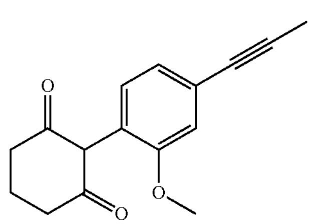 [SMILES: CC#Cc1ccc(C2C(=O)CCCC2=O)c(OC)c1] | 6.98-7.07 (m, 3H) 6.37 (brs, 1H) 3.78 (s, 3H) 2.60 (t, 2H) 2.48 (t, 2H) 2.01-2.11 (m, 5H) |

TABLE T1-continued

| Compound Number | Structure | ¹H NMR 400 MHz (CDCl₃ solvent unless stated otherwise) δ (delta) |
|---|---|---|
| A11 | 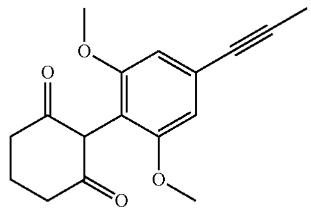 [SMILES: CC#Cc1cc(OC)c(C2C(=O)CCCC2=O)c(OC)c1] | (500 MHz) 6.66 (s, 2H) 5.76 (s, 1H) 3.71-3.77 (m, 6H) 2.55-2.67 (m, 2H) 2.38-2.51 (m, 2H) 1.98-2.12 (m, 5H) |
| A12 | 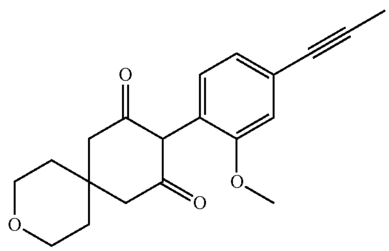 [SMILES: CC#Cc1ccc(C2C(=O)CC3(CCOCC3)CC2=O)c(OC)c1] | 7.05 (d, 1H) 7.03 (d, 1H) 6.99 (s, 1H) 6.23 (brs, 1H) 3.79 (s, 3H) 3.72 (m, 4H) 2.62 (s, 2H) 2.54 (s, 2H) 2.06 (s, 3H) 1.68 (m, 4H) |
| A13 | 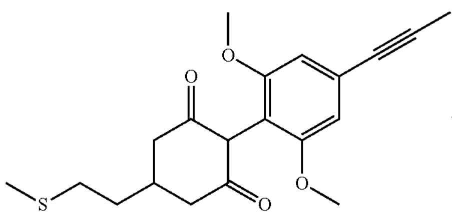 [SMILES: CC#Cc1cc(OC)c(C2C(=O)CC(CCSC)CC2=O)c(OC)c1] | (500 MHz, CD₃OD) 6.66 (d, 2H) 3.71 (d, 6H) 2.59-2.64 (m, 3H) 2.30-2.40 (m, 3H) 2.13 (s, 3H) 2.03-2.07 (m, 4H) 1.76-1.83 (m, 2H) |
| A14 | 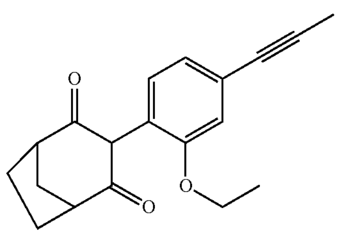 [SMILES: CC#Cc1ccc(C2C(=O)C3CCC(C3)C2=O)c(OCC)c1] | (CD₃OD) 6.98-7.11 (m, 1H) 6.82-6.95 (m, 2H) 3.91 (d, 2H) 2.95 (brs, 2H) 2.15 (d, 3H) 2.00 (s, 2H) 1.82 (d, 2H) 1.52-1.75 (m, 1H) 1.18-1.37 (m, 4H) |
| A15 | 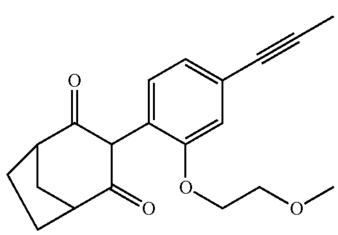 [SMILES: CC#Cc1ccc(C2C(=O)C3CCC(C3)C2=O)c(OCCOC)c1] | 7.03-7.11 (m, 2H) 6.93-6.98 (m, 1H) 4.09 (brs, 2H) 3.64 (m, 2H) 3.29-3.42 (m, 3H) 2.96-3.06 (m, 2H) 1.52-2.23 (m, 9H) |
| A16 | 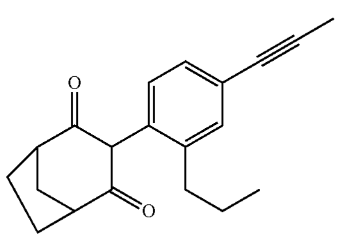 [SMILES: CC#Cc1ccc(C2C(=O)C3CCC(C3)C2=O)c(CCC)c1] | 1H NMR (400 MHz, CDCl3) δ ppm 7.30-7.36 (m, 1H) 7.21-7.27 (m, 1H) 6.85-6.99 (m, 1H) 2.99-3.09 (m, 2H) 2.32-2.42 (m, 1H) 2.09-2.30 (m, 4H) 1.99-2.07 (m, 3H) 1.87 (brs, 2H) 1.30-1.73 (m, 3H) 0.88 (q, 3H) |

TABLE T1-continued

| Compound Number | Structure | $^1$H NMR 400 MHz (CDCl$_3$ solvent unless stated otherwise) δ (delta) |
|---|---|---|
| A17 | 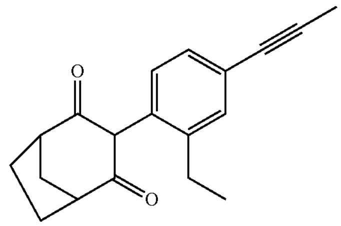 [SMILES: CC#Cc1ccc(C2C(=O)C3CCC(C3)C2=O)c(CC)c1] | 1H NMR (500 MHz, CD3OD) δ ppm 7.20-7.30 (m, 1H) 7.10-7.19 (m, 1H) 6.76-6.92 (m, 1H) 3.01 (d, 2H) 2.44 (q, 1H) 2.32 (q, 1H) 2.13-2.26 (m, 3H) 1.98-2.07 (m, 3H) 1.80-1.91 (m, 2H) 1.72 (dt, 1H) 1.01-1.17 (m, 3H) |
| A18 | 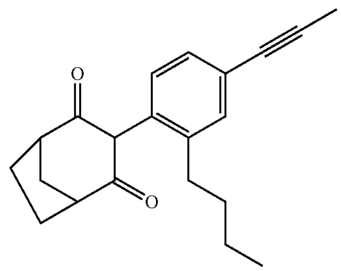 [SMILES: CC#Cc1ccc(C2C(=O)C3CCC(C3)C2=O)c(CCCC)c1] | 1H NMR (400 MHz, CDCl3) δ = 7.34-7.28 (m, 1H), 7.23 (dd, 1H), 6.9-6.81 (m, 1H), 5.92 (brs, 1H), 3.12-2.83 (m, 2H), 2.43-2.09 (m, 5H), 2.07-2.01 (m, 3H), 1.98-1.58 (m, 3H), 1.49-1.14 (m, 4H), 0.94-0.78 (m, 3H) |
| A19 | 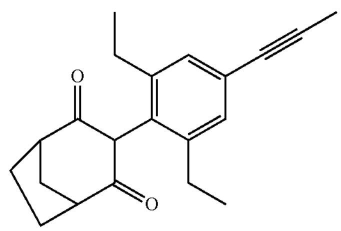 [SMILES: CC#Cc1cc(CC)c(C2C(=O)C3CCC(C3)C2=O)c(CC)c1] | |

Note:
1H missing in some cases because of exchange of the cyclic dione proton between the two C(O) groups in the cyclic dioine

TABLE P1

| Compound Number | Structure | $^1$H NMR 400 MHz δ (delta) CDCl$_3$ (unless stated) |
|---|---|---|
| P1 | 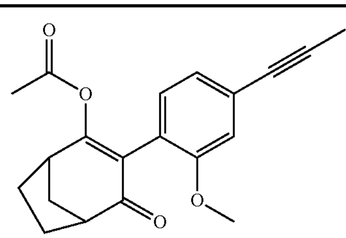 | 6.78-7.03 (m, 3H) 3.67-3.77 (m, 3H) 2.91-3.17 (m, 2H) 2.28-2.43 (m, 1H) 1.94-2.23 (m, 9H) 1.63-1.91 (m, 2H) |
| P2 | 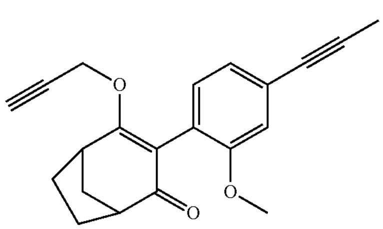 [SMILES: C#CCOC1=C(c2ccc(C#CC)cc2OC)C(=O)C2CCC1C2] | 6.82-7.03 (m, 3H) 4.20-4.52 (m, 2H) 3.68-3.75 (m, 3H) 3.23 (d, 3H) 3.17-3.30 (m, 1H) 2.94-3.07 (m, 1H) 2.45-2.56 (m, 1H) 1.55-2.28 (m, 6H) |

TABLE P1-continued

| Compound Number | Structure | ¹H NMR 400 MHz δ (delta) CDCl₃ (unless stated) |
|---|---|---|
| P3 | 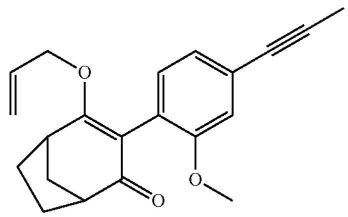 [SMILES: C=CCOC1=C(c2ccc(C#CC)cc2OC)C(=O)C2CCC1C2] | (500 MHz) 6.86-7.00 (m, 3H) 5.72-5.85 (m, 1H) 5.10-5.24 (m, 2H) 4.22-4.37 (m, 2H) 3.66-3.77 (m, 3H) 3.09-3.23 (m, 1H) 2.96-3.06 (m, 1H) 1.69-2.24 (m, 7H) 1.56-1.68 (m, 2H) |
| P4 | 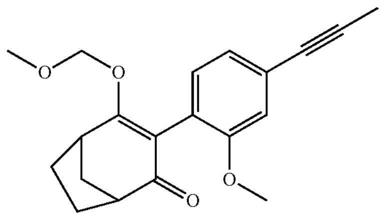 [SMILES: CC#Cc1ccc(C2=C(OCOC)C3CCC(C3)C2=O)c(OC)c1] | (500 MHz) 6.94-7.02 (m, 1H) 6.84-6.92 (m, 2H) 4.85-4.99 (m, 2H) 3.64-3.76 (m, 3H) 3.31-3.41 (m, 3H) 2.95-3.08 (m, 1H) 1.60-2.27 (m, 10H) |
| P5 | 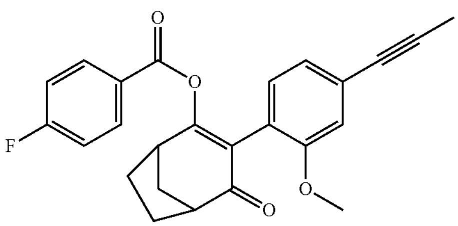 [SMILES: CC#Cc1ccc(C2=C(OC(=O)c3ccc(F)cc3)C3CCC(C3)C2=O)c(OC)c1] | (500 MHz, CD₃CN) 7.18-7.22 (m, 4H) 7.00-7.06 (m, 2H) 6.92-6.98 (m, 1H) 3.70-3.78 (m, 3H) 3.24-3.42 (m, 1H) 3.02-3.10 (m, 1H) 2.10-2.34 (m, 7H) 1.70-1.86 (m, 2H) |
| P6 | 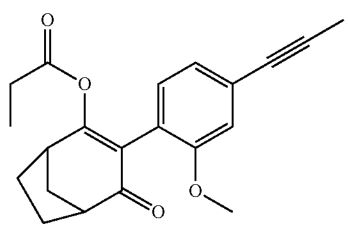 [SMILES: CC#Cc1ccc(C2=C(OC(=O)CC)C3CCC(C3)C2=O)c(OC)c1] | (500 MHz, CD₃CN) 6.94-6.99 (m, 2H) 6.82-6.88 (m, 1H) 3.68-3.76 (m, 3H) 2.96-3.18 (m, 2H) 2.04-2.34 (m, 9H) 1.74-1.81 (m, 2H) 0.99 (t, 3H) |
| P7 | 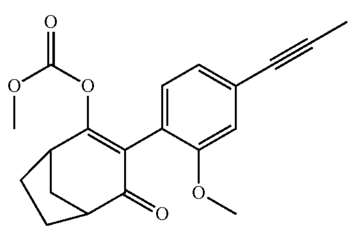 [SMILES: CC#Cc1ccc(C2=C(OC(=O)OC)C3CCC(C3)C2=O)c(OC)c1] | (500 MHz, CD₃CN) 6.88-7.02 (m, 3H) 3.68-3.82 (m, 6H) 2.98-3.32 (m, 2H) 2.04-2.30 (m, 7H) 1.66-1.82 (m, 2H) |
| P8 | 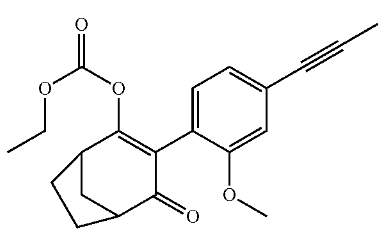 [SMILES: CC#Cc1ccc(C2=C(OC(=O)OCC)C3CCC(C3)C2=O)c(OC)c1] | (500 MHz, CD₃CN) 6.86-7.00 (m, 3H) 4.16-4.24 (m, 2H) 3.68-3.78 (m, 3H) 2.98-3.01 (m, 2H) 2.04-2.30 (m, 7H) 1.66-1.82 (m, 2H) 1.20-1.30 (m, 3H) |
| P9 | 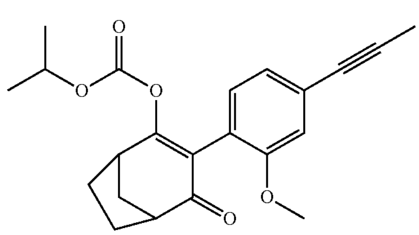 [SMILES: CC#Cc1ccc(C2=C(OC(=O)OC(C)C)C3CCC(C3)C2=O)c(OC)c1] | (500 MHz, CD₃CN) 6.86-7.00 (m, 3H) 4.81-4.88 (m, 1H) 3.68-3.74 (m, 3H) 3.11-3.38 (m, 1H) 2.98-3.04 (m, 1H) 2.04-2.30 (m, 7H) 1.66-1.92 (m, 2H) 1.20-1.26 (m, 6H) |

TABLE P1-continued

| Compound Number | Structure | $^1$H NMR 400 MHz δ (delta) CDCl$_3$ (unless stated) |
|---|---|---|
| P10 | 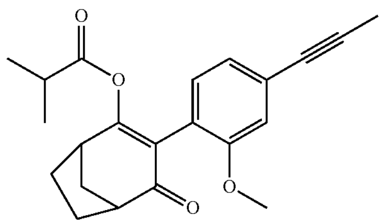 [SMILES: CC#Cc1ccc(C2=C(OC(=O)C(C)C)C3CCC(C3)C2=O)c(OC)c1] | (500 MHz, CD$_3$CN) 6.80-6.98 (m, 3H) 3.71 (s, 3H) 2.98-3.10 (m, 2H) 2.46-2.59 (m, 1H) 2.03-2.31 (m, 7H) 1.64-1.79 (m, 2H) 0.90-1.02 (m, 6H) |
| P11 | 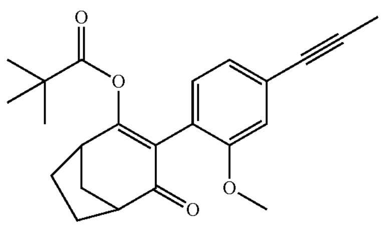 [SMILES: CC#Cc1ccc(C2=C(OC(=O)C(C)(C)C)C3CCC(C3)C2=O)c(OC)c1] | (500 MHz, CD$_3$CN) 6.82-6.97 (m, 3H) 3.71 (s, 3H) 2.98-3.09 (m, 2H) 2.04-2.32 (m, 7H) 1.64-1.78 (m, 2H) 1.00-1.04 (m, 9H) |
| P12 | 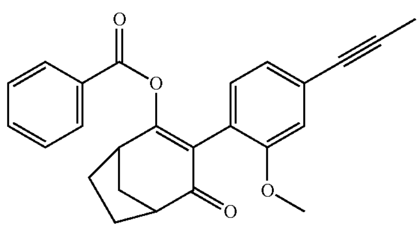 [SMILES: CC#Cc1ccc(C2=C(OC(=O)c3ccccc3)C3CCC(C3)C2=O)c(OC)c1] | (500 MHz, CD$_3$CN) 7.31-7.48 (m, 3H) 6.92-7.16 (m, 5H) 3.68-3.76 (m, 3H) 3.22-3.40 (m, 1H) 2.98-3.08 (m, 1H) 2.08-2.34 (m, 7H) 1.68-1.84 (m, 2H) |
| P13 | 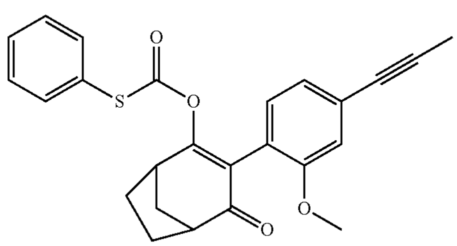 [SMILES: CC#Cc1ccc(C2=C(OC(=O)Sc3ccccc3)C3CCC(C3)C2=O)c(OC)c1] | (500 MHz, CD$_3$CN) 7.42-7.54 (m, 5H) 6.86-7.04 (m, 3H) 3.70-3.76 (m, 3H) 3.12-3.28 (m, 1H) 2.98-3.04 (m, 1H) 2.04-2.28 (m, 7H) 1.66-1.80 (m, 2H) |
| P14 | 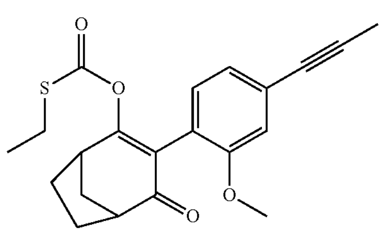 [SMILES: CC#Cc1ccc(C2=C(OC(=O)SCC)C3CCC(C3)C2=O)c(OC)c1] | (500 MHz, CD$_3$CN) 6.72-6.84 (m, 3H) 3.56-3.62 (m, 3H) 2.76-3.12 (m, 2H) 2.70-2.78 (m, 2H) 1.92-2.18 (m, 7H) 1.52-1.68 (m, 2H) 1.09-1.18 (m, 3H) |
| P15 | 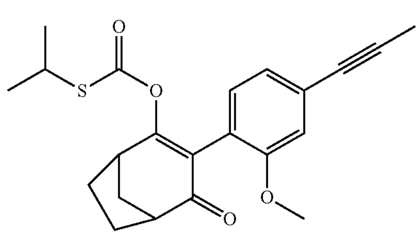 [SMILES: CC#Cc1ccc(C2=C(OC(=O)SC(C)C)C3CCC(C3)C2=O)c(OC)c1] | (500 MHz, CD$_3$CN) 6.86-6.98 (m, 3H) 3.69-3.76 (m, 3H) 3.42-3.51 (m, 1H) 2.98-3.24 (m, 2H) 2.02-2.30 (m, 7H) 1.64-1.70 (m, 2H) 1.26-1.34 (m, 6H) |

TABLE P1-continued

| Compound Number | Structure | $^1$H NMR 400 MHz δ (delta) CDCl$_3$ (unless stated) |
|---|---|---|
| P16 | 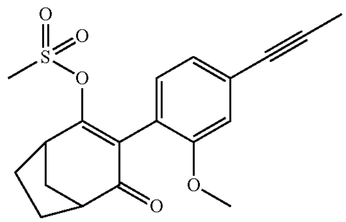 [SMILES: CC#Cc1ccc(C2=C(OS(C)(=O)=O)C3CCC(C3)C2=O)c(OC)c1] | (500 MHz, CD$_3$CN) 6.94-7.02 (m, 3H) 3.72-3.78 (m, 3H) 3.36-3.42 (m, 1H) 3.00-3.08 (m, 1H) 2.86-2.92 (m, 3H) 2.10-2.32 (m, 7H) 1.64-1.84 (m, 2H) |
| P17 | 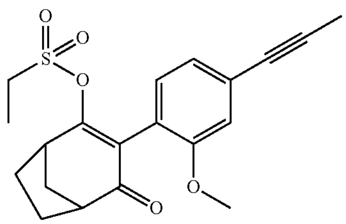 [SMILES: CC#Cc1ccc(C2=C(OS(=O)(=O)CC)C3CCC(C3)C2=O)c(OC)c1] | (500 MHz, CD$_3$CN) 6.94-7.02 (m, 3H) 3.72-3.78 (m, 3H) 3.36-3.44 (m, 1H) 2.96-3.08 (m, 3H) 2.12-2.31 (m, 7H) 1.62-1.82 (m, 2H) 0.98-1.06 (m, 3H) |
| P18 | 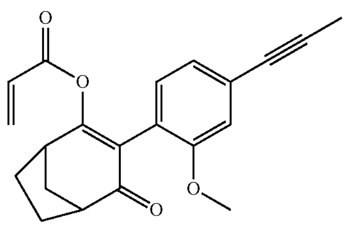 [SMILES: C=CC(=O)OC1=C(c2ccc(C#CC)cc2OC)C(=O)C2CCC1C2] | (500 MHz, CD$_3$CN) 6.82-6.96 (m, 3H) 6.28-6.34 (m, 1H) 6.02-6.12 (m, 1H) 5.90-5.98 (m, 1H) 3.66-3.72 (m, 3H) 2.98-3.24 (m, 2H) 2.04-2.32 (m, 7H) 1.68-1.82 (m, 2H) |

Compounds of Tables 1 to 22

The compounds of the following Tables 1 to 22 also illustrate the present invention, and are also particular embodiments of the compounds of formula (I) according to the present invention. For the most part, these compounds can generally be prepared by methods similar or analogous to those shown in the Examples and/or in the process section hereinabove using appropriate starting materials.

Table 1 covers 22 compounds of the following type

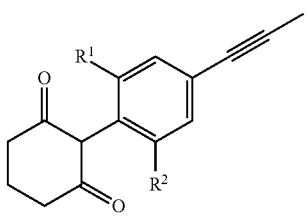

wherein R$^1$ and R$^2$ are as defined in Table 1.

TABLE 1

| Compound Number | R$^1$ | R$^2$ |
|---|---|---|
| 1.01 | methoxy | hydrogen |
| 1.02 | methoxy | methoxy |
| 1.03 | methoxy | n-propyl |
| 1.04 | methoxy | trifluoromethoxy |
| 1.05 | methoxy | difluoromethoxy |
| 1.06 | methoxy | ethyl |
| 1.07 | trifluoromethoxy | hydrogen |
| 1.08 | trifluoromethoxy | trifluoromethoxy |
| 1.09 | trifluoromethoxy | difluoromethoxy |

TABLE 1-continued

| Compound Number | R$^1$ | R$^2$ |
|---|---|---|
| 1.10 | trifluoromethoxy | ethyl |
| 1.11 | trifluoromethoxy | n-propyl |
| 1.12 | difluoromethoxy | n-propyl |
| 1.13 | difluoromethoxy | hydrogen |
| 1.14 | difluoromethoxy | difluoromethoxy |
| 1.15 | difluoromethoxy | ethyl |
| 1.16 | ethoxy | ethoxy |
| 1.17 | ethoxy | methoxy |
| 1.18 | ethoxy | n-propyl |
| 1.19 | ethoxy | ethyl |
| 1.20 | ethoxy | trifluoromethoxy |
| 1.21 | ethoxy | hydrogen |
| 1.22 | ethoxy | difluoromethoxy |
| 1.23 | ethyl | hydrogen |
| 1.24 | ethyl | ethyl |
| 1.25 | ethyl | n-propyl |
| 1.26 | n-propyl | hydrogen |
| 1.27 | n-propyl | n-propyl |

Table 2 covers 27 compounds of the following type

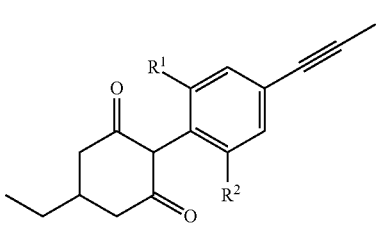

wherein R$^1$ and R$^2$ are as defined in Table 1.

Table 3 covers 27 compounds of the following type

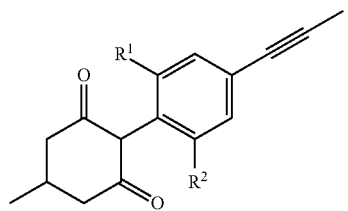

wherein R¹ and R² are as defined in Table 1.
Table 4 covers 27 compounds of the following type

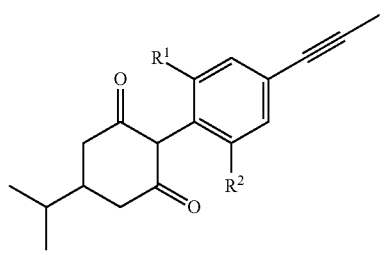

wherein R¹ and R² are as defined in Table 1.
Table 5 covers 27 compounds of the following type

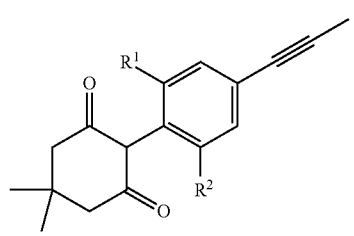

wherein R¹ and R² are as defined in Table 1.
Table 6 covers 27 compounds of the following type

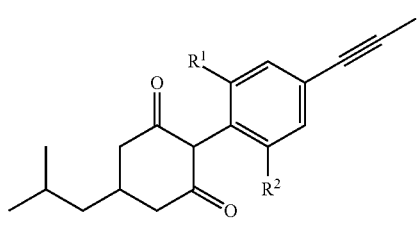

wherein R¹ and R² are as defined in Table 1.

Table 7 covers 27 compounds of the following type

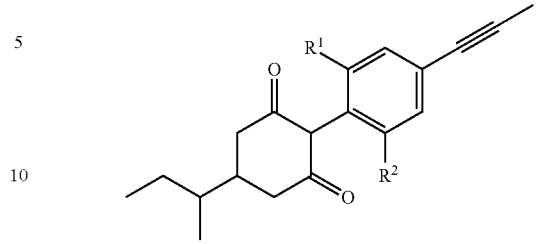

wherein R¹ and R² are as defined in Table 1.
Table 8 covers 27 compounds of the following type

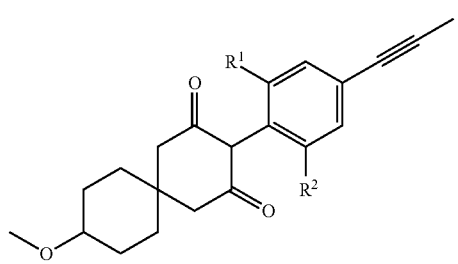

wherein R¹ and R² are as defined in Table 1.
Table 9 covers 27 compounds of the following type

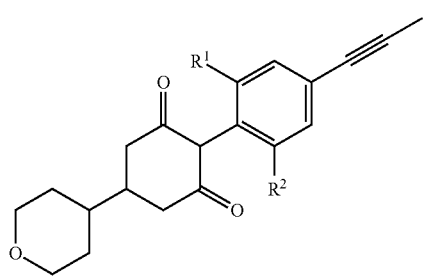

wherein R¹ and R² are as defined in Table 1.
Table 10 covers 27 compounds of the following type

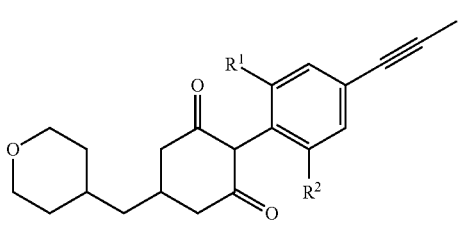

wherein R¹ and R² are as defined in Table 1.

Table 11 covers 27 compounds of the following type

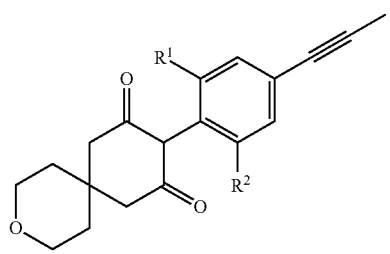

wherein $R^1$ and $R^2$ are as defined in Table 1.
Table 12 covers 27 compounds of the following type

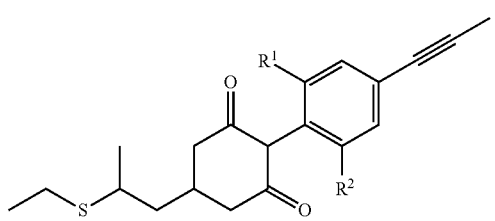

wherein $R^1$ and $R^2$ are as defined in Table 1.
Table 13 covers 27 compounds of the following type

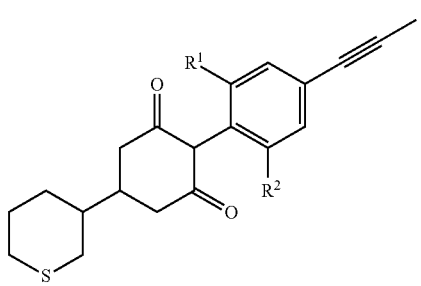

wherein $R^1$ and $R^2$ are as defined in Table 1.
Table 14 covers 27 compounds of the following type

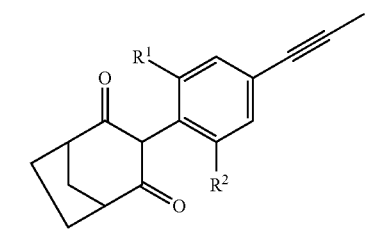

wherein $R^1$ and $R^2$ are as defined in Table 1.

Table 15 covers 27 compounds of the following type

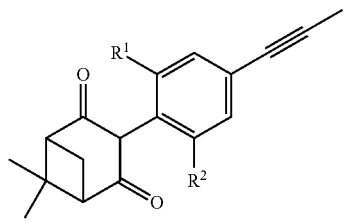

wherein $R^1$ and $R^2$ are as defined in Table 1.
Table 16 covers 27 compounds of the following type

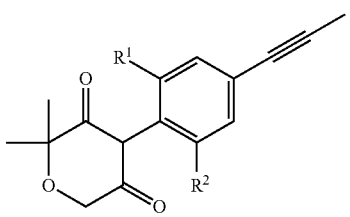

wherein $R^1$ and $R^2$ are as defined in Table 1.
Table 17 covers 27 compounds of the following type

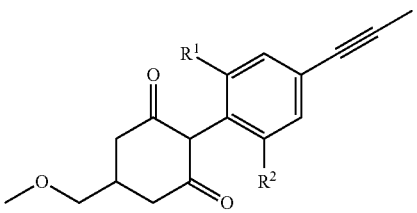

wherein $R^1$ and $R^2$ are as defined in Table 1.
Table 18 covers 27 compounds of the following type

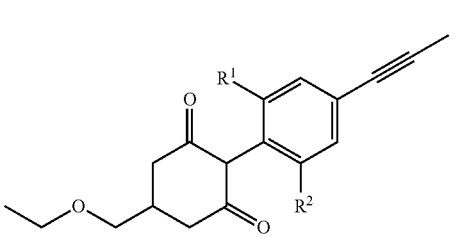

wherein $R^1$ and $R^2$ are as defined in Table 1.
Table 19 covers 27 compounds of the following type Table 20 covers 27 compounds of the following type

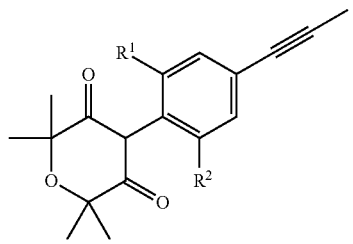

wherein $R^1$ and $R^2$ are as defined in Table 1.

Table 21 covers 27 compounds of the following type

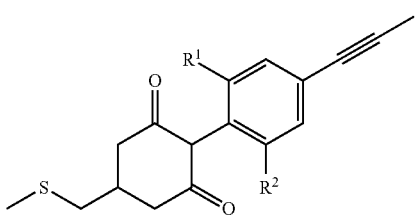

wherein $R^1$ and $R^2$ are as defined in Table 1.

Table 22 covers 27 compounds of the following type

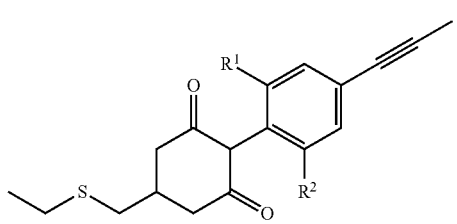

wherein $R^1$ and $R^2$ are as defined in Table 1.

BIOLOGICAL EXAMPLES

Biological Example 1—Glasshouse Assay for Herbicidal Activity

Seeds of a variety of test plant species were sown in standard soil ** in pots. After cultivation for one day (pre-emergence) or after 8 days cultivation (post-emergence) under controlled conditions in a glasshouse (at 24/16° C., day/night; 14 hours light; 65% humidity), the plants were sprayed with an aqueous spray solution derived from the formulation of the technical active ingredient (the test herbicide) in acetone/water (50:50) solution containing 0.5% Tween 20 (polyoxyethylene sorbitan monolaurate, CAS Reg. No. 9005-64-5). The test plants were then grown on under controlled conditions in a glasshouse (at 24/16° C., day/night; 14 hours light; 65% humidity) and watered twice daily. 13 Days after application of the test herbicide, for pre- and post-emergence, the test was evaluated visually for percentage phytotoxicity to each plant (where 100%=total damage to plant; 0%=no damage to plant). Generally, each test herbicide is only tested on 1 plant per plant species for each application rate tested and for each application timing.

The "standard soil" in Biological Example 1 is usually a "sand" or "sandy loam" type of soil.

Biological Example 1—Pre-Emergence Application—Herbicidal Activity Results (Percentage Phytotoxicity)

Test Plants:

Dicotyledonous weeds: ABUTH=*Abutilon theophrasti*; AMARE=*Amaranthus retroflexus*. Grassy monocotyledonous weeds: SETFA=*Setaria faberi*; ALOMY=*Alopecurus myosuroides*; ECHCG=*Echinochloa crus-galli*; ZEAMX=*Zea mays* (corn, maize, e.g. volunteer corn).

Biological Example 1—Post-Emergence Application—Herbicidal Activity Results (Percentage Phytotoxicity)

Test Plants:

Dicotyledonous weeds: ABUTH=*Abutilon theophrasti*; AMARE=*Amaranthus retroflexus*. Grassy monocotyledonous weeds: SETFA=*Setaria faberi*; ALOMY=*Alopecurus myosuroides*; ECHCG=*Echinochloa crus-galli*; ZEAMX=*Zea mays* (corn, maize, e.g. volunteer corn).

| Compound Number | Application Rate g/ha | ABUTH | AMARE | SETFA | ALOMY | ECHCG | ZEAMX |
|---|---|---|---|---|---|---|---|
| A1 | 250 | 20 | 50 | 100 | 100 | 100 | 100 |
| A1 | 30 | 10 | 30 | 90 | 100 | 100 | 100 |
| A2 | 250 | 10 | 0 | 90 | 90 | 70 | 70 |
| A3 | 250 | 0 | 0 | 90 | 70 | 100 | 90 |
| A3 | 30 | 0 | 0 | 70 | 40 | 70 | 90 |
| A4 | 250 | 0 | 0 | 70 | 30 | 40 | 60 |
| A4 | 30 | 0 | 0 | 40 | 10 | 20 | 30 |
| A5 | 250 | 0 | 0 | 90 | 80 | 100 | 100 |
| A5 | 30 | 0 | 0 | 60 | 50 | 90 | 100 |
| A6 | 250 | 0 | 0 | 50 | - | 70 | 80 |
| A6 | 30 | 0 | 0 | 10 | - | 40 | 40 |
| A7 | 250 | 10 | 0 | 100 | 100 | 100 | 100 |
| A7 | 30 | 0 | 0 | 100 | 90 | 100 | 100 |
| A8 | 250 | 80 | 10 | 100 | 100 | 100 | 100 |
| A9 | 250 | 40 | 20 | 90 | 90 | 90 | 100 |

-continued

| Compound Number | Application Rate g/ha | ABUTH | AMARE | SETFA | ALOMY | ECHCG | ZEAMX |
|---|---|---|---|---|---|---|---|
| A9 | 30 | 20 | 0 | 80 | 30 | 80 | 90 |
| A10 | 250 | 10 | 20 | 70 | 70 | 30 | 90 |
| A10 | 30 | 0 | 10 | 60 | 0 | 20 | 90 |
| A11 | 250 | 0 | 30 | 100 | 90 | 100 | 100 |
| A11 | 30 | 0 | 10 | 100 | 70 | 100 | 100 |
| A12 | 250 | 20 | 30 | 100 | 100 | 100 | 100 |
| A12 | 30 | 0 | 0 | 100 | 90 | 100 | 100 |
| A14 | 250 | 0 | 0 | 90 | - | 100 | 90 |
| A14 | 30 | 0 | 0 | 50 | - | 70 | 70 |
| A15 | 250 | 0 | 0 | 80 | 20 | 40 | 80 |
| A15 | 30 | 0 | 0 | 50 | 10 | 10 | 40 |
| A16 | 250 | 0 | 0 | 100 | 100 | 100 | 100 |
| A17 | 250 | 50 | 0 | 90 | 100 | 100 | 100 |
| P1 | 250 | 10 | 20 | 90 | 100 | 100 | 100 |
| P2 | 250 | 0 | 0 | 80 | 70 | 90 | 100 |
| P3 | 250 | 0 | 10 | 90 | 70 | 100 | 100 |
| P4 | 250 | 10 | 0 | 100 | 100 | 100 | 100 |
| P5 | 250 | 50 | 30 | 90 | 90 | 100 | 100 |
| P6 | 250 | 60 | 40 | 90 | 90 | 100 | 100 |
| P7 | 250 | 40 | 30 | 90 | 90 | 100 | 100 |
| P8 | 250 | 60 | 20 | 90 | 90 | 100 | 100 |
| P10 | 250 | 70 | 40 | 90 | 90 | 100 | 100 |
| P11 | 250 | 70 | 20 | 100 | 90 | 100 | 100 |
| P12 | 250 | 70 | 20 | 90 | 100 | 100 | 100 |
| P13 | 250 | 40 | 60 | 100 | 90 | 100 | 100 |
| P14 | 250 | 70 | 20 | 100 | 90 | 100 | 100 |
| P15 | 250 | 70 | 10 | 100 | 90 | 100 | 100 |
| P16 | 250 | 40 | 40 | 70 | 80 | 90 | 100 |
| P17 | 250 | 70 | 0 | 80 | 90 | 90 | 100 |
| P18 | 250 | 70 | 30 | 90 | 90 | 100 | 100 |

Note:
a hyphen (-) in the table above indicates that no measurement was made.

The invention claimed is:
1. A compound of formula (I):

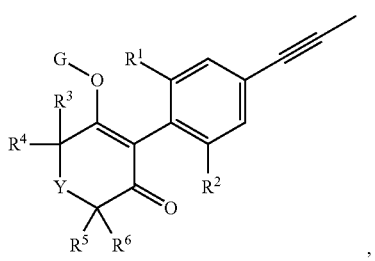

(I)

wherein:

$R^1$ is methoxy;

$R^2$ is selected from the group consisting of hydrogen, ethyl, n-propyl, cyclopropyl, vinyl, ethynyl, methoxy, ethoxy and fluoromethoxy;

provided that when $R^1$ is ethyl, n-propyl, n-butyl, cyclopropyl or ethynyl, then $R^2$ is hydrogen, ethyl, n-propyl, cyclopropyl, vinyl or ethynyl; and $R^3$, $R^4$, $R^5$ and $R^6$, independently of each other, are hydrogen, $C_1$-$C_5$alkyl, $C_2$-$C_4$alkenyl, $C_2$-$C_4$alkynyl, $C_1$-$C_2$fluoroalkyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, $C_1$-$C_3$alkylsulfonyl$C_1$-$C_3$alkyl; $C_3$-$C_4$cycloalkyl; or an unsubstituted 4, 5 or 6 membered monocyclic heterocyclyl having one ring heteroatom independently selected from oxygen, sulfur and nitrogen, and attached at a ring carbon atom within the heterocyclyl; provided that no more than one of $R^3$, $R^4$, $R^5$ and $R^6$ is alkenyl, alkynyl, alkoxyalkyl, alkylthioalkyl, alkylsulfinylalkyl, alkylsulfonylalkyl, cycloalkyl or heterocyclyl;

or $R^3$ and $R^4$ taken together are —$(CH_2)_{n1}$— or —$(CH_2)_{n2}$—$X^1$—$(CH_2)_{n3}$— and $R^5$ and $R^6$ are as defined herein, or $R^5$ and $R^6$ taken together are —$(CH_2)_{n1}$— or —$(CH_2)_{n2}$—$X^1$—$(CH_2)_{n3}$— and $R^3$ and $R^4$ are as defined herein;

wherein $X^1$ is O, S, S(O), S(O)$_2$, NH, N($C_1$-$C_2$alkyl), N($C_1$-$C_2$alkoxy), C(H)($C_1$-$C_2$alkyl), C($C_1$-$C_2$alkyl)$_2$ or C(H)($C_1$-$C_2$alkoxy);

n1 is 2, 3, 4 or 5; and n2 and n3 are independently 1, 2 or 3 provided that n2+n3 is 2, 3 or 4;

or $R^4$ and $R^5$ taken together are —$(CH_2)_{n4}$— or —$(CH_2)_{n5}$—C($R^{7a}$)($R^{7b}$)—$(CH_2)_{n6}$— or —C($R^{7c}$)=C($R^{7d}$)—;

wherein $R^{7a}$ is $C_1$-$C_2$alkyl or $C_1$-$C_2$alkoxy; and $R^{7b}$ is hydrogen or $C_1$-$C_2$alkyl provided that $R^{7b}$ is hydrogen when $R^{7a}$ is $C_1$-$C_2$alkoxy;

n4 is 1, 2 or 3; and n5 and n6 are independently 0, 1 or 2 provided that n5+n6 is 0, 1 or 2;

and $R^{7c}$ and $R^{7d}$ independently are hydrogen or $C_1$-$C_2$alkyl; and

Y is O, S, S(O), S(O)$_2$, N($C_1$-$C_2$alkyl), N($C_1$-$C_2$alkoxy), C(O), $CR^8R^9$ or —$CR^{10}R^{11}CR^{12}R^{13}$—; and $R^8$ and $R^9$ are, independently of each other:
hydrogen, $C_1$-$C_6$alkyl, $C_2$-$C_4$alkenyl, $C_2$-$C_4$alkynyl, $C_1$-$C_2$fluoroalkyl, $C_1$-$C_3$alkoxy$C_1$-$C_3$alkyl, $C_1$-$C_3$alkylthio$C_1$-$C_3$alkyl, $C_1$-$C_3$alkylsulfinyl$C_1$-$C_3$alkyl, or $C_1$-$C_3$alkylsulfonyl$C_1$-$C_3$alkyl;

$C_3$-$C_6$cycloalkyl or $C_3$-$C_6$cycloalkyl substituted by one or two substituents which independently are $C_1$-$C_3$alkyl or $C_1$-$C_2$fluoroalkyl; and in which one ring $CH_2$ moiety of a $C_4$-$C_6$cycloalkyl is optionally replaced by an oxygen or sulfur atom or by a S(O), $S(O)_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety;

$C_3$-$C_6$cycloalkyl substituted by one substituent being $C_1$-$C_3$alkoxy and optionally further substituted by one substituent being $C_1$-$C_2$alkyl;

$C_5$-$C_6$cycloalkenyl or $C_5$-$C_6$cycloalkenyl substituted by one or two $C_1$-$C_3$alkyl substituents;

$C_3$-$C_6$cycloalkyl$C_1$-$C_2$alkyl- or $C_3$-$C_6$cycloalkyl$C_1$-$C_2$alkyl- substituted by one or two ring substituents which independently are $C_1$-$C_3$alkyl or $C_1$-$C_2$fluoroalkyl; and in which one ring $CH_2$ moiety of a $C_4$-$C_6$cycloalkyl$C_1$-$C_2$alkyl- is optionally replaced by an oxygen or sulfur atom or by a S(O), $S(O)_2$, NH, N($C_1$-$C_2$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety;

$C_3$-$C_6$cycloalkyl$C_1$-$C_2$alkyl- substituted by one ring substituent being $C_1$-$C_3$alkoxy and optionally further substituted by one ring substituent being $C_1$-$C_2$alkyl; or Het or Het-$CH_2$—, wherein Het is a heteroaryl, attached at a ring-carbon, which is optionally substituted by 1, 2 or 3 ring-carbon substituents independently being $C_1$-$C_3$alkyl, $C_1$-$C_2$fluoroalkyl, $C_1$-$C_3$alkyl-C(O)—, $C_1$-$C_2$fluoroalkyl-C(O)—, hydroxy (including any oxo tautomer), $C_2$-$C_3$alkenyl, $C_2$-$C_3$alkynyl, $C_1$-$C_3$alkoxy, $C_1$-$C_2$fluoroalkoxy, halogen, cyano or nitro, provided that any non-fluorine halogen, alkoxy or fluoroalkoxy is not substituted at any ring-carbon bonded directly to a ring-nitrogen of the heteroaryl; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-$S(O)_2$— substituent;

provided that no more than one of $R^8$ and $R^9$ is an optionally substituted cycloalkyl; an optionally substituted cycloalkyl in which one ring $CH_2$ moiety has been replaced by an oxygen or sulfur atom or by a S(O), $S(O)_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; an optionally substituted cycloalkenyl; an optionally substituted cycloalkyl-alkyl-; an optionally substituted cycloalkyl-alkyl- in which one ring $CH_2$ moiety has been replaced by an oxygen or sulfur atom or by a S(O), $S(O)_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl] or N($C_1$-$C_2$alkoxy) moiety; or Het or Het-$CH_2$—;

or $R^8$ is hydrogen or $C_1$-$C_2$alkyl, and $R^9$ is $C_1$-$C_2$alkoxy;
or $R^8$ and $R^9$ taken together are —$(CH_2)_{n7}$— or —$(CH_2)_{n8}$—$X^2$—$(CH_2)_{n9}$—;

wherein $X^2$ is O, S, S(O), $S(O)_2$, NH, N($C_1$-$C_3$alkyl), N($C_1$-$C_2$fluoroalkyl), N[C(O)$C_1$-$C_3$alkyl], N[C(O)$C_1$-$C_2$fluoroalkyl], N($C_1$-$C_2$alkoxy), C(H)($C_1$-$C_3$alkyl), C($C_1$-$C_2$alkyl)$_2$ or C(H)($C_1$-$C_3$alkoxy);

n7 is 2, 3, 4, 5 or 6; and n8 and n9 are independently 0, 1, 2 or 3 provided that n8+n9 is 2, 3, 4 or 5; and $R^{10}$, $R^{11}$, $R^{12}$ and $R^{13}$ are independently of each other hydrogen or $C_1$-$C_4$alkyl provided that no more than one of $R^{10}$, $R^{11}$, $R^{12}$ and $R^{13}$ is $C_3$-$C_4$alkyl; and and wherein:

G is hydrogen; an agriculturally acceptable metal, or an agriculturally acceptable sulfonium or ammonium group; or G is —C($X^a$)—$R^a$, —C($X^b$)—$X^c$—$R^b$, —C($X^d$)—N($R^c$)—$R^d$, —$SO_2$—$R^e$, —P($X^e$)($R^f$)—$R^g$, —$CH_2$—$X^f$—$R^h$; or phenyl-$CH_2$— or phenyl-CH($C_1$-$C_2$alkyl)- (in each of which the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or heteroaryl-$CH_2$— or heteroaryl-CH($C_1$-$C_2$alkyl)- (in each of which the heteroaryl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro), or phenyl-C(O)—$CH_2$— (wherein the phenyl is optionally substituted by 1, 2 or 3 of, independently, $C_1$-$C_2$alkyl, $C_1$fluoroalkyl, $C_1$-$C_2$alkoxy, $C_1$fluoroalkoxy, fluorine, chlorine, bromine, cyano or nitro); or $C_1$-$C_6$alkoxy-C(O)—$CH_2$—, $C_1$-$C_6$alkoxy-C(O)—CH=CH—, $C_2$-$C_7$alken-1-yl-$CH_2$—, $C_2$-$C_7$alken-1-yl-CH($C_1$-$C_2$alkyl)-, $C_2$-$C_4$fluoroalken-1-yl-$CH_2$—, $C_2$-$C_7$alkyn-1-yl-$CH_2$—, or $C_2$-$C_7$alkyn-1-yl-CH($C_1$-$C_2$alkyl)-;

wherein $X^a$, $X^b$, $X^c$, $X^d$, $X^e$ and $X^f$ are independently of each other oxygen or sulfur; and wherein $R^a$ is H, $C_1$-$C_{21}$alkyl, $C_2$-$C_{21}$alkenyl, $C_2$-$C_{18}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_5$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro;

$R^b$ is $C_1$-$C_{18}$alkyl, $C_3$-$C_{18}$alkenyl, $C_3$-$C_{18}$alkynyl, $C_2$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino ($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_5$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl$C_1$-$C_5$alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkyl-thio, $C_1$-$C_3$alkylsulfinyl, $C_1$-$C_3$alkylsulfonyl, halogen, cyano, or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; and $R^c$ and $R^d$ are each independently of each other hydrogen, $C_1$-$C_{10}$alkyl, $C_3$-$C_{10}$alkenyl, $C_3$-$C_{10}$alkynyl, $C_2$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_5$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_5$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or by nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino or $C_3$-$C_7$cycloalkoxy;

or $R^c$ and $R^d$, together with the nitrogen to which they are bonded, to form an unsubstituted 4, 5, 6 or 7 membered ring, optionally containing one heteroatom selected from 0 or S; and $R^e$ is $C_1$-$C_{10}$alkyl, $C_2$-$C_{10}$alkenyl, $C_2$-$C_{10}$alkynyl, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$)alkyl, $C_3$-$C_5$alkenyloxy($C_1$-$C_5$)alkyl, $C_3$-$C_5$alkynyloxy($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl($C_1$-$C_5$)alkyl, $C_2$-$C_5$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-05fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$alkoxy, $C_1$-$C_{10}$fluoroalkoxy, $C_1$-$C_5$alkylamino or di($C_1$-$C_4$alkyl)amino;

$R^f$ and $R^g$ are each independently of each other $C_1$-$C_{10}$alkyl, $C_2$-$C_{10}$alkenyl, $C_2$-$C_{10}$alkynyl, $C_1$-$C_{10}$alkoxy, $C_1$-$C_{10}$fluoroalkyl, $C_1$-$C_{10}$cyanoalkyl, $C_1$-$C_{10}$nitroalkyl, $C_1$-$C_{10}$aminoalkyl, $C_1$-$C_5$alkylamino ($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$) alkyl, $C_3$-$C_5$alkenyloxy($C_1$-$C_5$)alkyl, $C_3$-$C_5$alkynyloxy ($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl ($C_1$-$C_5$)alkyl, $C_2$-$C_5$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_5$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_2$-$C_5$)alkylaminoalkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$alkylsulfonyl, halogen, cyano, or nitro), $C_2$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; heteroaryl or heteroaryl substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; heteroarylamino or heteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro; diheteroarylamino or diheteroarylamino substituted by 1, 2 or 3 of, independently, $C_1$-$C_3$ alkyl, $C_1$-$C_3$fluoroalkyl, $C_1$-$C_3$alkoxy, $C_1$-$C_3$fluoroalkoxy, halogen, cyano or nitro;

phenylamino or phenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; diphenylamino or diphenylamino substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or $C_3$-$C_7$cycloalkylamino, di($C_3$-$C_7$cycloalkyl)amino, $C_3$-$C_7$cycloalkoxy, $C_1$-$C_{10}$fluoroalkoxy, $C_1$-$C_5$alkylamino or di($C_1$-$C_4$alkyl)amino; or benzyloxy or phenoxy, wherein the benzyl and phenyl groups are in turn optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; and $R^h$ is $C_1$-$C_{10}$alkyl, $C_3$-$C_{10}$alkenyl, $C_3$-$C_{10}$alkynyl, $C_1$-$C_{10}$fluoroalkyl, $C_1$-$C_{10}$cyanoalkyl, $C_1$-$C_{10}$nitroalkyl, $C_2$-$C_{10}$aminoalkyl, $C_1$-$C_5$alkylamino ($C_1$-$C_5$)alkyl, $C_2$-$C_8$dialkylamino($C_1$-$C_5$)alkyl, $C_3$-$C_7$cycloalkyl($C_1$-$C_5$)alkyl, $C_1$-$C_5$alkoxy($C_1$-$C_5$) alkyl, $C_3$-$C_5$alkenyloxy($C_1$-$C_5$)alkyl, $C_3$-$C_5$alkynyloxy ($C_1$-$C_5$)alkyl, $C_1$-$C_5$alkylthio($C_1$-$C_5$)alkyl, $C_1$-$C_5$alkylsulfinyl($C_1$-$C_5$)alkyl, $C_1$-$C_5$alkylsulfonyl ($C_1$-$C_5$)alkyl, $C_2$-$C_5$alkylideneaminoxy($C_1$-$C_5$)alkyl, $C_1$-$C_5$alkylcarbonyl($C_1$-$C_5$)alkyl, $C_1$-$C_5$alkoxycarbonyl($C_1$-$C_5$)alkyl, aminocarbonyl($C_1$-$C_5$)alkyl, $C_1$-$C_5$alkylaminocarbonyl($C_1$-$C_5$)alkyl, $C_2$-$C_8$dialkylaminocarbonyl($C_1$-$C_5$)alkyl, $C_1$-$C_5$alkylcarbonylamino($C_1$-$C_5$)alkyl, N—($C_1$-$C_5$)alkylcarbonyl-N—($C_1$-$C_5$)alkylamino($C_1$-$C_5$)alkyl, $C_3$-$C_6$trialkylsilyl($C_1$-$C_5$)alkyl, phenyl($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkyl sulfonyl, halogen, cyano or nitro), heteroaryl($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), phenoxy($C_1$-$C_5$)alkyl (wherein the phenyl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), heteroaryloxy($C_1$-$C_5$)alkyl (wherein the heteroaryl is optionally substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, $C_1$-$C_3$alkylthio, $C_1$-$C_3$alkylsulfinyl, $C_1$-$C_3$ alkylsulfonyl, halogen, cyano or nitro), $C_3$-$C_5$fluoroalkenyl, $C_3$-$C_8$cycloalkyl; phenyl or phenyl substituted by 1, 2 or 3 of, independently, $C_1$-$C_3$alkyl, $C_1$-$C_3$fluoroalkyl, $C_1$-$C_3$alkoxy, $C_1$-$C_3$fluoroalkoxy, halogen, cyano or nitro; or heteroaryl or heteroaryl substituted by 1, 2 or 3 of, independently, $C_1$-$C_3$alkyl, $C_1$-$C_1$fluoroalkyl, $C_1$-$C_3$alkoxy, $C_1$-$C_1$fluoroalkoxy, halogen, cyano or nitro; $C_1$-$C_6$alkyl-C(O)—; or phenyl-C(O)— wherein the phenyl is optionally substituted by 1 or 2 of, independently, $C_1$-$C_2$alkyl, $C_1$fluoroalkyl, $C_1$-$C_2$alkoxy, $C_1$fluoroalkoxy, fluorine, chlorine, bromine, cyano or nitro;

wherein "heteroaryl" means an aromatic ring system containing at least one ring heteroatom and consisting either of a single ring or of two fused rings;

and wherein the compound of formula (I) is optionally present as an agrochemically acceptable salt thereof.

2. The compound as claimed in claim 1, wherein when G is —C($X^a$)—$R^a$ or —C($X^b$)—$X^c$—$R^b$, then $X^a$, $X^b$ and $X^c$ are oxygen, $R^a$ is $C_1$-$C_{10}$alkyl, $C_2$-$C_6$alkenyl, $C_2$-$C_6$alkynyl, $C_3$-$C_6$cycloalkyl or $C_1$-$C_4$alkoxy$C_1$-$C_4$alkyl; and $R^b$ is $C_1$-$C_{10}$alkyl, $C_2$-$C_5$alkenyl-CH$_2$—, $C_2$-$C_4$alkenyl-CH(Me)-, $C_2$-$C_5$alkynyl-CH$_2$—, $C_2$-$C_4$alkynyl-CH(Me)-, $C_3$-$C_6$cycloalkyl or $C_1$-$C_4$alkoxy$C_1$-$C_4$alkyl.

3. The compound as claimed in claim 1, wherein $R^2$ is hydrogen, or methoxy.

4. The compound as claimed in claim 1, wherein $R^3$, $R^4$, $R^5$ and $R^6$, independently of each other, are hydrogen, $C_1$-$C_3$alkyl or $C_1$-$C_2$alkoxy$C_1$-$C_2$alkyl; provided that no more than one of $R^3$, $R^4$, $R^5$ and $R^6$ is alkoxyalkyl;

or $R^4$ and $R^5$ taken together are —(CH$_2$)$_{n4}$— or —(CH$_2$)$_{n5}$—C($R^{7a}$)($R^{7b}$)—(CH$_2$)$_{n6}$—;

wherein $R^{7a}$ is $C_1$-$C_2$alkyl; $R^{7b}$ is hydrogen or $C_1$-$C_2$alkyl;

n4 is 2 or 3; and n5 and n6 are independently 0, 1 or 2 provided that n5+n6 is 1 or 2.

5. The compound as claimed in claim 1, wherein:

$R^8$ is hydrogen or $C_1$-$C_2$alkyl; and $R^9$ is:

$C_1$-$C_2$alkoxy;

$C_2$-$C_3$alkynyl-CH$_2$—;

$C_1$-$C_3$alkoxy$C_1$-$C_3$alkyl;

$C_1$-$C_3$alkylthio$C_1$-$C_3$alkyl;

$C_1$-$C_3$alkylsulfinyl$C_1$-$C_3$alkyl;

$C_1$-$C_3$alkylsulfonyl$C_1$-$C_3$alkyl;

$C_3$-$C_6$cycloalkyl or $C_3$-$C_6$cycloalkyl substituted by one or two substituents which independently are $C_1$-$C_3$alkyl or $C_1$-$C_2$fluoroalkyl; and in which one ring $CH_2$ moiety of a $C_4$-$C_6$cycloalkyl is optionally replaced by an oxygen or sulfur atom or by a S(O), $S(O)_2$, NH, $N(C_1$-$C_3$alkyl), $N(C_1$-$C_2$fluoroalkyl), $N[C(O)C_1$-$C_3$alkyl]$, $N[C(O)C_1$-$C_2$fluoroalkyl] or $N(C_1$-$C_2$alkoxy) moiety;

$C_3$-$C_6$cycloalkyl substituted by one substituent being $C_1$-$C_3$alkoxy and optionally further substituted by one substituent being $C_1$-$C_2$alkyl;

$C_3$-$C_6$cycloalkylmethyl- or $C_3$-$C_6$cycloalkylmethyl- substituted by one or two ring substituents which independently are $C_1$-$C_3$alkyl or $C_1$-$C_2$fluoroalkyl; and in which one ring $CH_2$ moiety of a $C_4$-$C_6$cycloalkylmethyl- is optionally replaced by an oxygen or sulfur atom or by a S(O), $S(O)_2$, NH, $N(C_1$-$C_2$alkyl), $N(C_1$-$C_2$fluoroalkyl), $N[C(O)C_1$-$C_3$alkyl]$, $N[C(O)C_1$-$C_2$fluoroalkyl] or $N(C_1$-$C_2$alkoxy) moiety;

$C_3$-$C_6$cycloalkylmethyl- substituted by one ring substituent being $C_1$-$C_3$ alkoxy and optionally further substituted by one ring substituent being $C_1$-$C_2$alkyl; or Het or Het-$CH_2$—, wherein Het is a heteroaryl, attached at a ring-carbon, which is optionally substituted by 1, 2 or 3 ring-carbon substituents independently being $C_1$-$C_3$alkyl, $C_1$-$C_2$fluoroalkyl, $C_1$-$C_3$alkyl-C(O)—, $C_1$-$C_2$fluoroalkyl-C(O)—, hydroxy (including any oxo tautomer), $C_2$-$C_3$alkenyl, $C_2$-$C_3$alkynyl, $C_1$-$C_3$alkoxy, $C_1$-$C_2$fluoroalkoxy, halogen, cyano or nitro, provided that any non-fluorine halogen, alkoxy or fluoroalkoxy is not substituted at any ring-carbon bonded directly to a ring-nitrogen of the heteroaryl; and/or, in the case of a 5-membered heteroaryl ring containing a ring-nitrogen atom not partaking in a C=N ring double bond, the heteroaryl is optionally substituted on the ring-nitrogen atom not partaking in a C=N ring double bond by one $C_1$-$C_3$alkyl, $C_1$-$C_2$fluoroalkyl, $C_1$-$C_3$alkyl-C(O)—, $C_1$-$C_2$fluoroalkyl-C(O)— or $C_1$-$C_2$alkyl-$S(O)_2$— substituent;

or $R^8$ and $R^9$ taken together are —$(CH_2)_{n7}$— or —$(CH_2)_{n8}$—$X^2$—$(CH_2)_{n9}$—.

6. The compound as claimed in claim 1, wherein $R^8$ and $R^9$ are, independently of each other, hydrogen or $C_1$-$C_3$alkyl.

7. The compound as claimed in claim 1, wherein Y is O, S, S(O), $S(O)_2$, C(O), $CR^8R^9$ or —$CR^{10}R^{11}CR^{12}R^{13}$—.

8. The compound as claimed in claim 1, wherein Y is $CR^8R^9$; and $R^4$ and $R^5$ are taken together and are —$(CH_2)_{n4}$— or —$(CH_2)_{n5}$—$C(R^{7a})(R^{7b})$—$(CH_2)_{n6}$—;

wherein $R^{7a}$ is $C_1$-$C_2$alkyl; $R^{7b}$ is hydrogen or $C_1$-$C_2$alkyl;

n4 is 2 or 3; and n5 and n6 are independently 0, 1 or 2 provided that n5+n6 is 1 or 2.

9. The compound as claimed in claim 8, wherein Y is $CH_2$.

10. The compound as claimed in claim 8 or 9, wherein $R^3$ and $R^6$, independently of each other, are hydrogen or $C_1$-$C_2$alkyl; and $R^4$ and $R^5$ taken together are —$(CH_2)_{n4}$— wherein n4 is 2 or 3.

11. A herbicidal composition which comprises a compound of formula (I), as defined in claim 1, and an agrochemically acceptable carrier, diluent or solvent.

12. The herbicidal composition according to claim 11, which comprises one or more further herbicides or a safener.

13. A method of controlling grassy monocotyledonous weeds in crops of useful plants, comprising applying a compound of formula (I), as defined in claim 1, or a herbicidal composition comprising such a compound, to the weeds and/or to the plants and/or to the locus thereof.

14. The method as claimed in claim 13, wherein the grassy monocotyledonous weeds comprise volunteer corn and/or one or more weeds selected from the genera *Brachiaria, Cenchrus, Digitaria, Echinochloa, Eleusine, Eriochloa, Leptochloa, Ottochloa, Panicum, Pennisetum, Phalaris, Rottboellia, Setaria* and *Sorghum*.

* * * * *